United States Patent
Schein et al.

(10) Patent No.: US 8,003,692 B2
(45) Date of Patent: Aug. 23, 2011

(54) METHODS AND COMPOSITIONS TO INHIBIT EDEMA FACTOR AND ADENYLYL CYCLASE

(75) Inventors: Catherine H. Schein, Friendswood, TX (US); Johnny W. Peterson, Dickinson, TX (US); Scott R. Gilbertson, Galveston, TX (US); Deliang Chen, League City, TX (US); Maria Estrella-Jimenez, Lawrenceville, NJ (US); Mary A. Walter, Fair Oaks Ranch, TX (US); Jian Gao, Helotes, TX (US)

(73) Assignees: Board of Regents, The University of Texas System, Austin, TX (US); Mission Pharmacal Co., San Antonio, TX (US)

( * ) Notice: Subject to any disclaimer, the term of this patent is extended or adjusted under 35 U.S.C. 154(b) by 247 days.

(21) Appl. No.: 12/139,212

(22) Filed: Jun. 13, 2008

(65) Prior Publication Data

US 2009/0093519 A1    Apr. 9, 2009

Related U.S. Application Data

(60) Provisional application No. 60/944,375, filed on Jun. 15, 2007, provisional application No. 61/035,269, filed on Mar. 10, 2008.

(51) Int. Cl.
| | |
|---|---|
| A61K 31/195 | (2006.01) |
| A61K 31/192 | (2006.01) |
| A61K 31/381 | (2006.01) |
| A61K 31/343 | (2006.01) |
| A61K 31/403 | (2006.01) |

(52) U.S. Cl. ........ 514/468; 514/443; 514/441; 514/563; 514/615

(58) Field of Classification Search .................. None
See application file for complete search history.

(56) References Cited

U.S. PATENT DOCUMENTS

| | | | |
|---|---|---|---|
| 4,066,834 A | 1/1978 | Woessner et al. | |
| 4,222,944 A | 9/1980 | Berger et al. | |
| 6,294,674 B1 | 9/2001 | Picard et al. | |
| 7,495,103 B2 * | 2/2009 | Hadida-Ruah et al. | 546/156 |
| 2002/0188016 A9 | 12/2002 | Peterson et al. | |
| 2003/0224403 A1 | 12/2003 | Popov et al. | |
| 2005/0075367 A1 * | 4/2005 | Hagiwara et al. | 514/319 |
| 2006/0178418 A1 | 8/2006 | Balasubramanian et al. | |
| 2006/0205800 A1 | 9/2006 | Donde et al. | |

FOREIGN PATENT DOCUMENTS

WO  WO-2000/56341    9/2000

OTHER PUBLICATIONS

Ippolitti, C., Am. J. Health Syst. Pharm. (Aug. 1, 1998), 55(15):1573-80 (abstract).*
Sonawane et al., FASEB J. (Jan., 2006), 20(1):130-2 (abstract).*
International Search Report issued May 19, 2009 during the prosecution of International Application No. PCT/US2008/066898.
Written Opinion issued May 19, 2009 during the prosecution of International Application No. PCT/US2008/066898.
International Preliminary Report on Patentability, issued Dec. 30, 2009 (published Dec. 30, 2009) during the prosecution of International Application No. PCT/US2008/066898.

* cited by examiner

Primary Examiner — Phyllis G. Spivack
(74) Attorney, Agent, or Firm — Fulbright & Jaworski L.L.P.

(57) ABSTRACT

Fluorene-based molecules and their derivatives are described in compositions for the treatment of intestinal fluid loss.

12 Claims, 91 Drawing Sheets

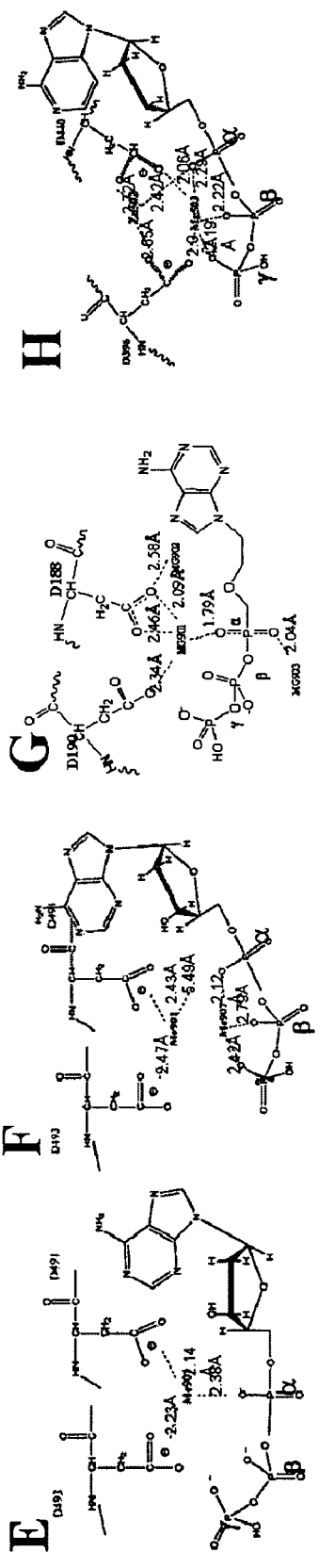
FIG 3

Top: CTA1
Bottom ARF

NAD+ — Active site of CTA1, fragments were docked to this site to build fragment based pharmacophore

FIG. 9

Selected zinc compounds have better scores than known inhibitors and substrate analogues

| Compound | BE_EF [1] (kcal/mol) | BE_AC [2] (kcal/mol) | BE_EF-BE_AC (kcal/mol) |
|---|---|---|---|
| *Controls* | | | |
| FIII-1 | -20.6 | -17.8 | -2.8 |
| DC02 | -20.6 | -16.1 | -4.5 |
| DC03 | -20.4 | -17.8 | -2.6 |
| DC04 | -20.1 | -15.5 | -4.6 |
| FIV-50 | -19.2 | -17.5 | -1.7 |
| DC06 | -18.8 | -14.1 | -4.7 |
| DC07 | -18.6 | -15.4 | -3.2 |
| FII-1 | -18.1 | -16.2 | -1.9 |

| Compound | BE_EF [1] (kcal/mol) | BE_AC [2] (kcal/mol) | BE_EF-BE_AC (kcal/mol) |
|---|---|---|---|
| DC09 | -17.1 | -13.7 | -3.4 |
| DC10 | -17.0 | -14.6 | -2.3 |
| DC11 | -16.8 | -14.1 | -2.7 |
| DC12 | -16.7 | -13.3 | -3.4 |
| DC13 | -16.7 | -13.5 | -3.2 |
| DC14 | -16.6 | -14.3 | -2.3 |
| DC15 | -16.5 | -14.2 | -2.3 |
| DC16 | -16.4 | -16.1 | -0.3 |
| DC17 | -16.3 | -13.6 | -2.7 |
| DC18 | -16.2 | -14.7 | -1.5 |
| DC19 | -16.0 | -13.5 | -2.4 |
| *Previously identified inhibitors* [3] | | | |
| Soelaiman7 (25 μM) | -10.7 | -10.7 | 0.0 |
| Soelaiman6 (60 μM) | -11.4 | -10.8 | -0.6 |
| Soelaiman2 (70 μM) | -11.0 | -10.3 | -0.7 |

[1] BE_EF: AutoDock binding energies for anthrax EF
[2] BE_AC:

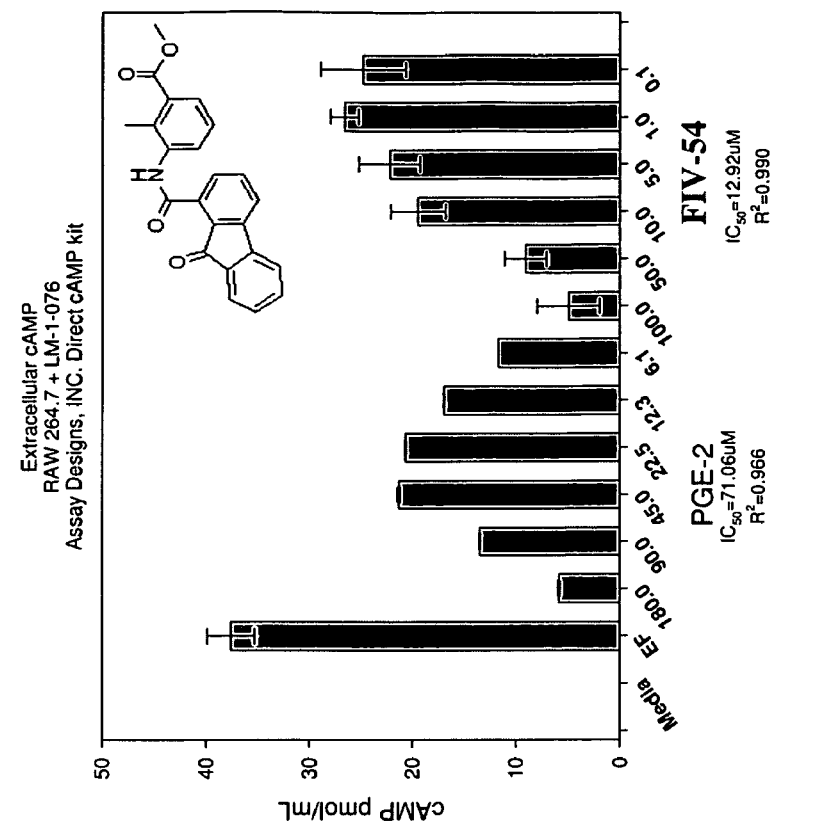
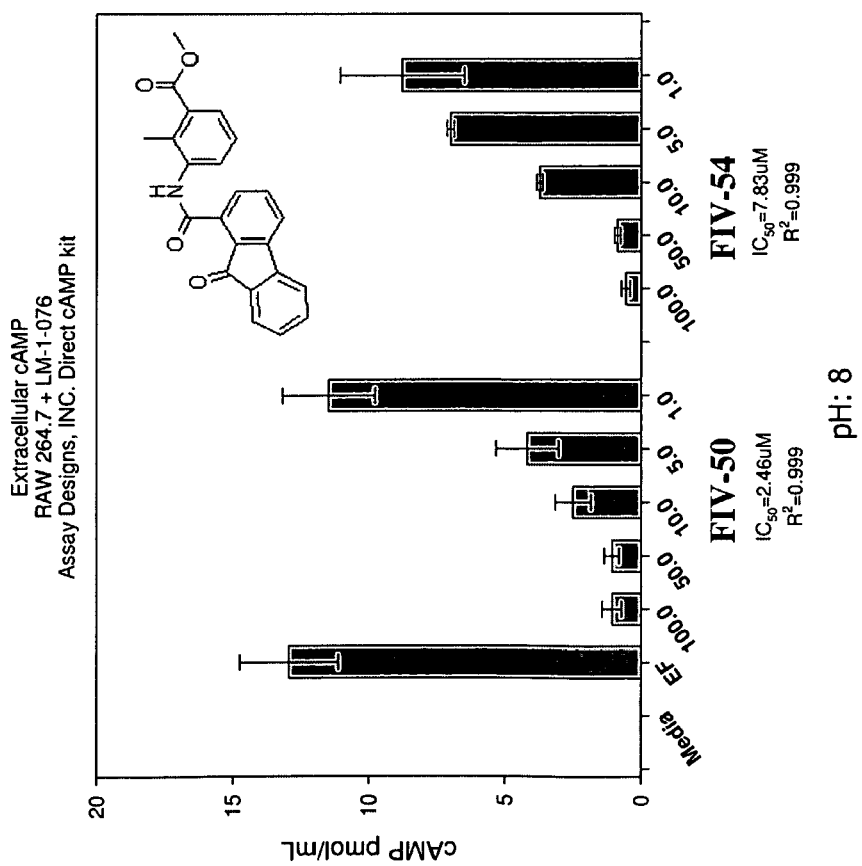
FIG. 15I

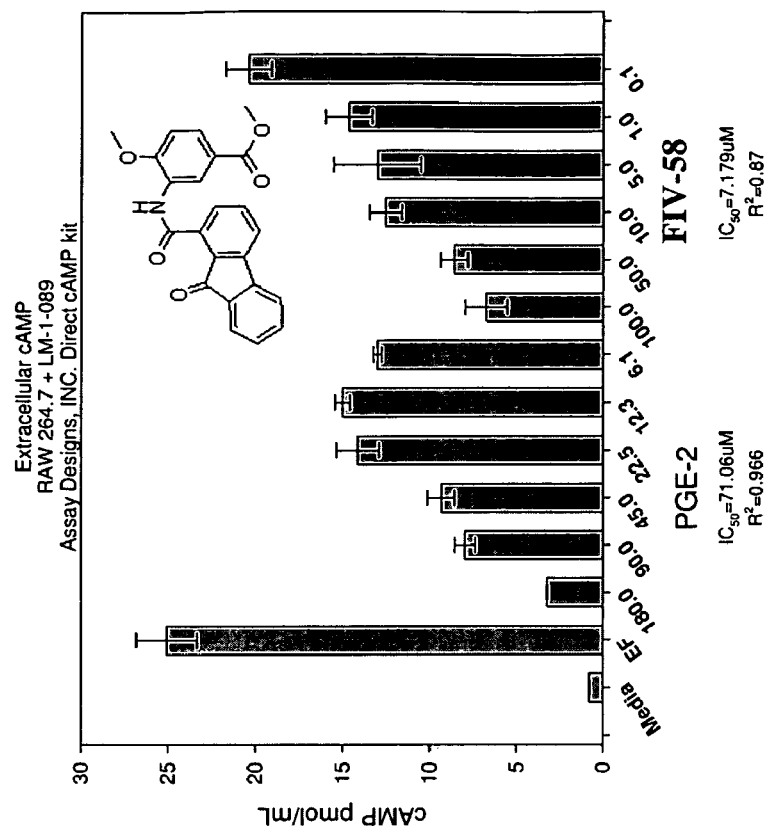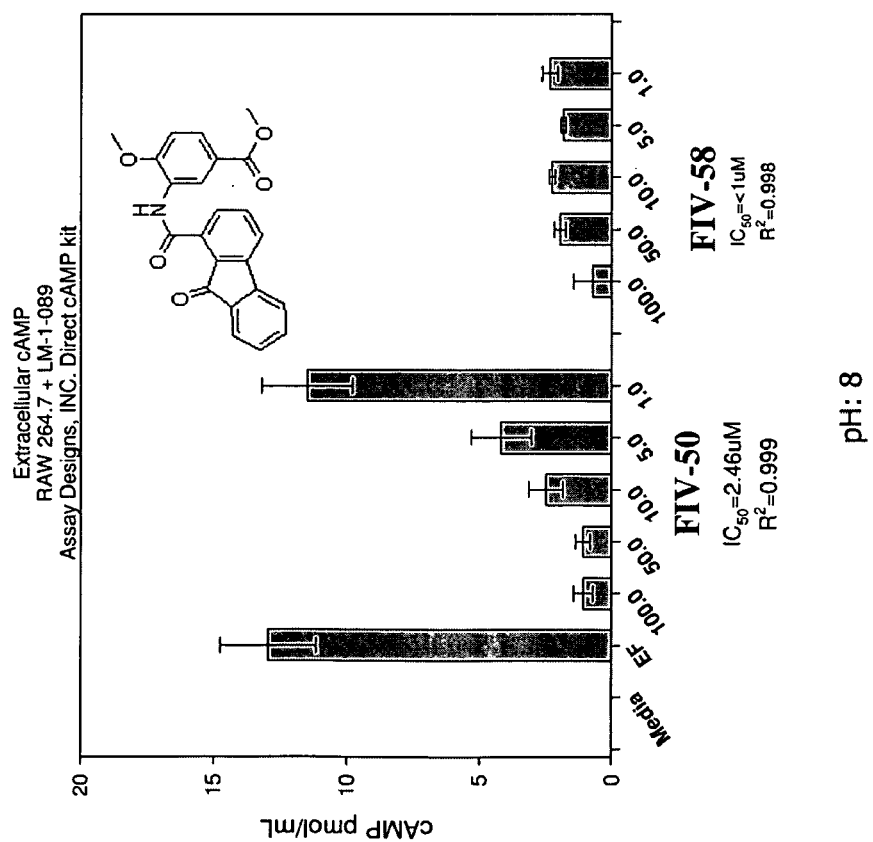
FIG. 15M

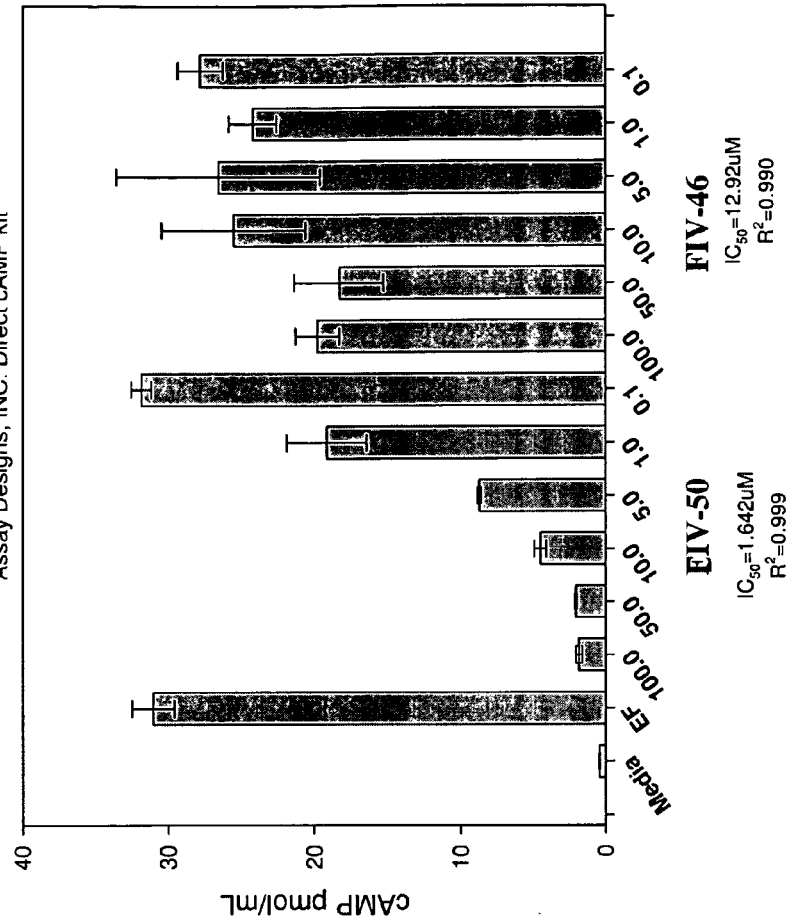
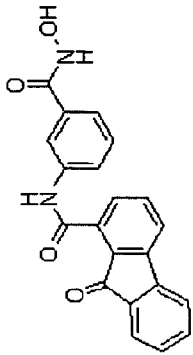
FIG. 16A

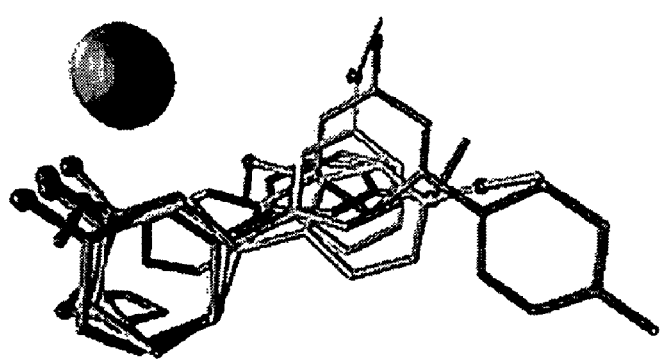
FIG. 23

| 72 Hour Mouse Set | | | | | | |
|---|---|---|---|---|---|---|
| | | CFU x 10⁻² | CFU x 10⁻³ | CFU x 10⁻⁴ | CFU x 10⁻⁵ | Average |
| ETEC | M9 | TNTC | TNTC | TNTC | 260 | |
| ETEC | M10 | TNTC | TNTC | TNTC | 58 | |
| ETEC | M11 | TNTC | TNTC | 57 | 13 | |
| ETEC | M12 | TNTC | TNTC | TNTC | 105 | 1.09E+08 |
| | | CFU x 10⁻¹ | CFU x 10⁻² | CFU x 10⁻³ | Average | |
| FIV-50 | M13 | TNTC | TNTC | 1760 | | |
| FIV-50 | M14 | TNTC | TNTC | 768 | | |
| FIV-50 | M15 | TNTC | TNTC | 1424 | | |
| FIV-50 | M16 | TNTC | TNTC | 1440 | 1.35E+06 | |

(TNTC = To numerous to count) (M9, M10, etc. = Mouse number)

FIG. 46

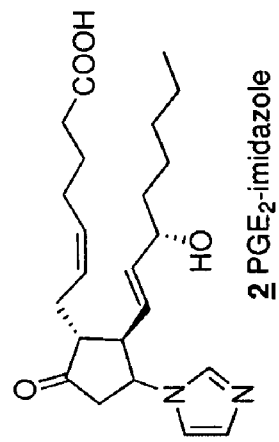
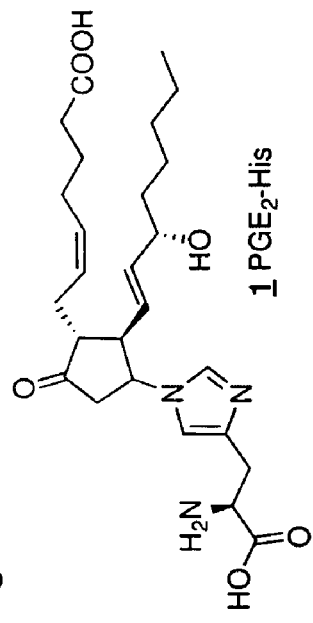
Figure 1
FIG. 70

METHODS AND COMPOSITIONS TO INHIBIT EDEMA FACTOR AND ADENYLYL CYCLASE

CROSS-REFERENCE TO RELATED APPLICATIONS

This application claims priority to U.S. Provisional Application No. 60/944,375 filed on Jun. 15, 2007, and U.S. Provisional Application No. 61/035,269 filed on Mar. 10, 2008, both of which are incorporated herein by reference in their entirety.

STATEMENT REGARDING FEDERALLY SPONSORED RESEARCH OR DEVELOPMENT

The present invention was developed with funds from the United States Government grants number NIAID U01AI5385802 and DAMD 170210699. Therefore, the United States Government has certain rights in the invention.

TECHNICAL FIELD

The present invention relates generally to treatment of biological conditions and/or chemical compounds. The present invention also relates to a method of treating conditions caused by increased 3',5'-adenosine monophosphate levels and compositions used to treat such conditions. Additionally, the invention relates to a method of treating intestinal fluid loss.

BACKGROUND OF THE INVENTION

The pathogenesis of several diseases involve factors that increase the concentration of 3'5'-adenosine monophosphate (cAMP) in the tissues of humans and nonhuman animals. In mammalian cells this important intracellular mediator is formed by the conversion of adenosine triphosphate (ATP) to cAMP; the latter reaction is catalyzed by adenylyl cyclase. Bacterial cells also form cAMP catalyzed by a prokaryotic version of adenylyl cyclase.

An increase in tissue cAMP concentration is the key factor in numerous bacterial infections. For example, the bacterial toxins produced by *Vibrio cholerae* and many strains of enterotoxinogenic *Escherichia coli* (ETEC) stimulate intestinal epithelial cell adenylyl cyclase, evoking an increase in the intracellular and extracellular levels of cAMP (FIG. 1). The physiological consequence of this effect is the stimulatory impact of cAMP on the chloride, potassium, and sodium channels in the membranes of cells lining the lumen of the small intestine. The hypersecretion of chloride and other ions culminate in the accumulation of water and electrolytes in the intestinal lumen that ultimately becomes diarrhea. This is also known as cholera, in the case of *V. cholerae* and Tourista or Travelers diarrhea in the case of *Escherichia coli*.

Other bacteria that evoke increases in tissue cAMP include *Bordetella pertussis*, the causative agent of whooping cough or Pertussis. These bacteria secrete two bacterial proteins that increase cAMP levels in the respiratory tract. One virulence factor is a bacterial adenylyl cyclase that is taken up by respiratory cells and converts respiratory ATP to cAMP. In addition, *B. pertussis* secretes pertussis toxin, which binds to respiratory cells and stimulates mammalian adenylyl cyclase in cells of the respiratory tract (Young and Collier, 2007). The physiological significance of these bacteria needing to increase cAMP in the respiratory tract is not entirely clear, but it is known that cAMP inhibits phagocytosis of bacteria by macrophages (mφ) and polymorphonuclear neutrophils (PMNs), which would limit the protection of the body against bacteria. Drugs that increase lung cAMP levels cause dilatation of the airways, which could facilitate the access to and colonization of the alveolar sacs. Since cAMP stimulates the expression of many mammalian cell genes, proteins thus formed could enhance the synthesis of tissue receptors for bacteria and their toxins.

Much of the tissue edema in patients infected with *B. anthracis* is attributed to the *B. anthracis* edema toxin, which is a combination of edema factor (EF) and protective antigen (PA). The latter protein binds the anthrax toxins to receptors on target cells in the lungs and many other tissues throughout the body (Firoved et al., 2005; Milne et al., 1995). Although all these examples are bacterial infections, some tumor types are known to hypersecrete prostaglandins (e.g., $PGE_2$) that stimulate adenylyl cyclase in epithelial cells along the intestinal tract to form excessive amounts of cAMP. These patients have virtually continuous diarrhea. All possible uses of small molecules that inhibit adenylyl cyclase may not yet be obvious; however, many drugs used in the treatment of asthma patients work by increasing cAMP levels to open the airways. In patients over medicated with drugs like theophyline, a small molecule inhibitor of adenylyl cyclase could be used to neutralize excessive levels of cAMP. There may be multiple clinical uses for small molecules that inhibit adenylyl cyclase.

As described above, many pathogenic bacteria, regardless of their cellular morphology and grouping, produce toxins with similar functions that are often plasmid encoded. For example, *Bacillus anthracis*, a Gram-positive, spore-forming, rod-shaped bacterium, produces two types of factors that enhance its lethality, a polysaccharide capsule (Drysdale et al., 2005) and two protein toxins, lethal toxin (LT) and edema toxin (ET). Both toxins are lethal when injected into mice, and they suppress the functions of macrophages, polymorphopneutrophils, and lymphocytes. Thus, there is a need for toxin inhibitors as an adjunct to antibiotic treatment. One component of both toxins is protective antigen (PA), which enables the cell entry of the enzymatic toxin components lethal factor (LF) and edema factor (EF) (Abrami et al., 2005). LF contains metalloprotease activity that is specific for the MAP kinase proteins. An inhibitor of LF has been identified, and shown to be an effective adjunct to antibiotic therapy in animal studies (Xiong et al., 2006). This inhibitor does not affect the activity of EF, which is an adenylyl cyclase analogous to that produced by *Bordetella pertussis* (the causative agent of whooping cough) (Munier et al., 1992; Hewlett et al., 1979; Hewlett et al., 1976). These "adenylyl cyclase" toxins (Drum et al., 2002; Shen et al., 2005) catalyze the intracellular production of cAMP from ATP (Leppla, 1982; de Rooij et al., 1998; Lacy et al., 2002; Lacy et al., 2002). High levels of cAMP perturb the water homeostasis of the cell leading to abnormalities in the intracellular signaling pathways and chloride channel stimulation (Ajuha et al., 2004; Ascenzi et al., 2002; Peterson et al. 2001), This contributes to edema (and widening) of the mediastinum located between the lobes of the lungs of patients with inhalation anthrax. Patients with cutaneous anthrax often display tissue edema near the lesion. Inhibitors that would bind to EF and prevent its intracellular enzymatic activity could reduce the severity of infections by *B. anthracis* and other bacteria that produce similar toxins. Currently known cAMP inhibitors in the art are toxic (Soelaiman et al., 2003), demonstrating a need for the current invention.

BRIEF SUMMARY OF THE INVENTION

An embodiment of the invention is a method of treating and/or preventing intestinal fluid loss in a subject. In a general embodiment the composition comprises a therapeutically effective amount of a compound or a pharmaceutically acceptable salt thereof that is administered to a subject. In a specific embodiment the general formula of the compound is selected from the group consisting of:

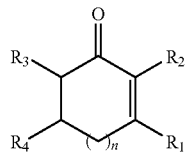

Formula I

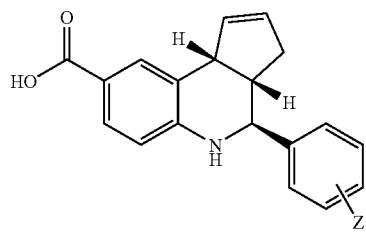

Formula II

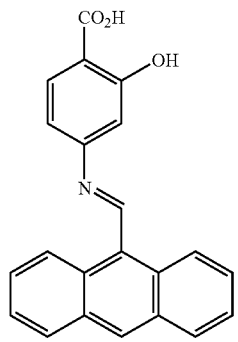

Formula III

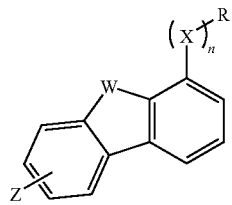

Formula IV

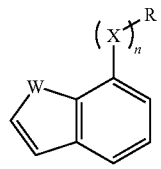

Formula V

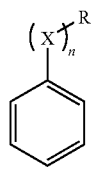

Formula VI

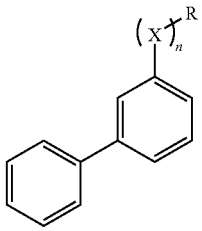

Formula VII

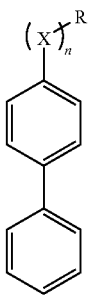

Formula VIII

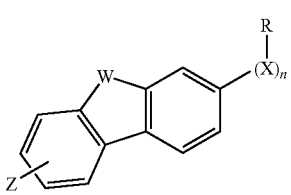

Formula and any combination thereof. In specific embodiments of the invention, the R group of the general formula is cyclic or bicyclic ring structure; $R_1$ is a cyclic or bicyclic ring structure; $R_1'$ is a hydrogen, cyclic or bicyclic ring structure; Z is selected from the group consisting of hydrogen, alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, isopropyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate; W is selected from the group consisting of CO, NH, methylene, sulfur atom, oxygen atom and thionyl; X is alkyl, oxygen, an ester, an amine, or an amide; and, m and n are the same or different and are 0 or 1. In another specific embodiment of the invention, R is substituted or unsubstituted and selected from the group consisting of phenyl, pyranonyl, pyridyl, imidazolyl, 1,8-napthyridinyl, and N-oxide pyridyl. In a further embodiment of the invention, R is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, isopropyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. In another embodiment of the invention, $R_1$ is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. In a specific embodiment of the invention, $R_4$ is a cyclic or bicyclic ring structure, substituted or unsubstituted and selected from the group consisting of phenyl, pyridyl, and furanyl. In a further embodiment of the invention, $R_4$ is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof.

An embodiment of the invention is a method of treating or preventing a condition associated with increased 3'-5'-adenosine monophosphate levels in a subject. In a general embodiment the composition comprises a therapeutically effective amount of a compound or a pharmaceutically acceptable salt thereof is administered to a subject. In a specific embodiment the general formula of the compound is selected from the group consisting of:

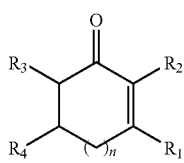

Formula I

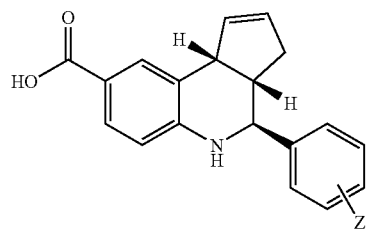

Formula II

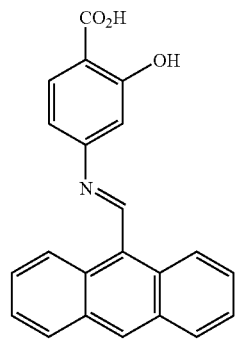

Formula III

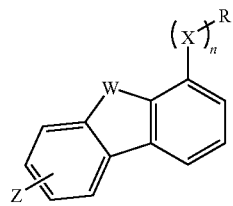

Formula IV

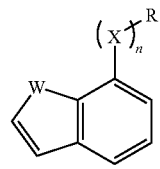

Formula V

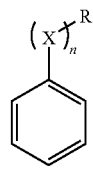

Formula VI

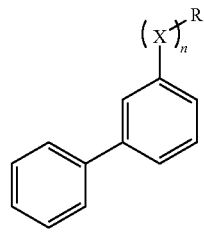

Formula VII

-continued

Formula VIII

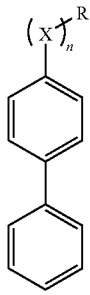

Formula

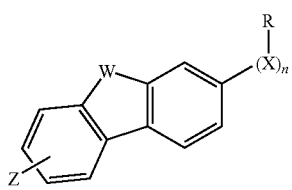

and any combination thereof. In specific embodiments of the invention, the R group of the general formula is cyclic or bicyclic ring structure; $R_1$ is a cyclic or bicyclic ring structure; $R_1'$ is a hydrogen, cyclic or bicyclic ring structure; X is alkyl, oxygen, an ester, an amine, or an amide; Z is selected from the group consisting of hydrogen, alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate; W is selected from the group consisting of CO, NH, methylene, sulfur atom, oxygen atom and thionyl; and, m and n are the same or different and are 0 or 1. In another specific embodiment of the invention, R is substituted or unsubstituted and selected from the group consisting of phenyl, pyranonyl, pyridyl, imidazolyl, 1,8-napthyridinyl, and N-oxide pyridyl. In a further embodiment of the invention, R is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. In another embodiment of the invention, $R_1$ is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. In a specific embodiment of the invention, $R_4$ is a cyclic or bicyclic ring structure, substituted or unsubstituted and selected from the group consisting of phenyl, pyridyl, and furanyl. In a further embodiment of the invention, $R_4$ is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof.

In an embodiment of the invention, the compound used in the general embodiment is from the group consisting of FIV-50, FIV-1, FIV-29, FIV-31, FIV-34, FIV-35, FIV-39, FIV-40, FIV-46, FIII-1, FII-1, FI-3, FI-1, FI-2, FIV-54, FIV-58, FIV-55, FIV-53, FIV-67, FIV-70, FIV-65, FIV-68, FIV-66, FIV-61, FIV-60, FIV-64, FIV-71, FIV-46, FIV-72, FIV-73, FIV-49, FIV-75, and any combination thereof.

In a specific embodiment of the invention, the method of treating intestinal fluid loss comprises inhibiting adenylyl cyclase, edema factor, CTA1, or any combination thereof. In another embodiment, the intestinal fluid loss is the result of infection of one or more pathogens. In a specific embodiment, the pathogen is *B. anthracis, V. cholerae, E. coli, Pertussis, Y. pestis*, or any combination thereof. In a further specific embodiment, when the pathogen is *B. anthracis*, the method may further comprise administration of a LT inhibitory drug. In another specific embodiment, the LT inhibitory drug is selected from the group consisting of bestatin, captopril, adefovir, and any combination thereof. In a general embodiment of the invention the intestinal fluid loss is caused by an increase in 3',5'-adenosine monophosphate levels in the subject's tissue. In a specific embodiment of the invention, the intestinal fluid loss is caused by cancer.

In another embodiment of the invention, the composition is administered in combination with one or more other drugs. In a further embodiment of the invention, the drug is an antibiotic or an anti-inflammatory. In another embodiment, the composition comprises a pharmaceutically acceptable carrier. In another embodiment of the invention, the composition is administered through a route selected from the group consisting of alimentary, parenteral, topical, mucosal, inhalation and any combination thereof. In a specific embodiment of the invention, the compound is delivered at dosages between 0.01 mM and 10 mM. In a further specific embodiment of the invention, the compound is delivered at dosages between 0.1 mM and 1 mM. In another embodiment of the invention, the subject is a human.

Another embodiment of the invention is a composition comprising a compound selected from the group consisting of FIV-50, FIV-1, FIV-29, FIV-31, FIV-34, FIV-35, FIV-39, FIV-40, FIV-46, FIII-1, FII-1, FI-3, FI-1, FI-2, FIV-54, FIV-58, FIV-55, FIV-53, FIV-67, FIV-70, FIV-65, FIV-68, FIV-66, FIV-61, FIV-60, FIV-64, FIV-71, FIV-46, FIV-72, FIV-73, FIV-49, FIV-75 and any combination thereof. The invention may also comprise any one or more of the above compounds individually or combinations thereof.

Another embodiment of the invention is a kit for treating and/or preventing a medical condition directly or indirectly, the treatment intestinal fluid loss caused by 3',5'-adenosine monophosphate increased levels in a subject. In a general embodiment the kit comprises a therapeutically effective amount of a compound or a pharmaceutically acceptable salt thereof is administered to a subject. In a specific embodiment the general formula of the compound is selected from the group consisting of:

Formula I

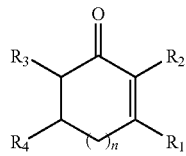

Formula II

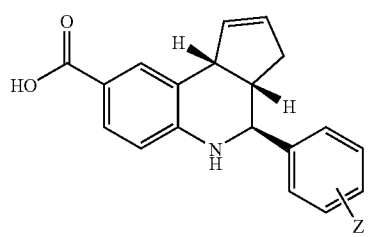

Formula III

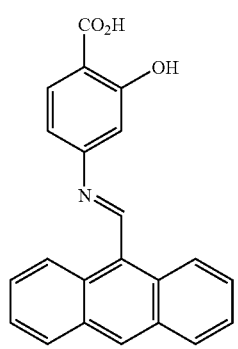

Formula IV

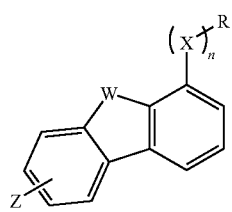

-continued

Formula V

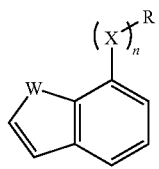

Formula VI

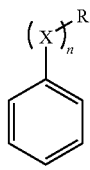

Formula VII

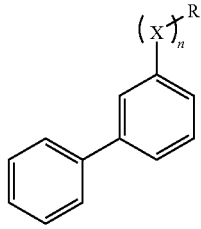

Formula VIII

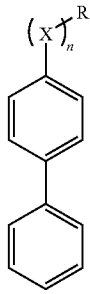

Formula

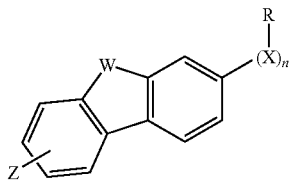

and any combination thereof. In specific embodiments of the invention, the R group of the general formula is cyclic or bicyclic ring structure; $R_1$ is a cyclic or bicyclic ring structure; $R_1'$ is a hydrogen, cyclic or bicyclic ring structure; X is alkyl, oxygen, an ester, an amine, or an amide; Z is selected from the group consisting of hydrogen, alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate; W is selected from the group consisting of CO, NH, methylene, sulfur atom, oxygen atom and thionyl; and, m and n are the same or different and are 0 or 1. In another specific embodiment of the invention, R is substituted or unsubstituted and selected from the group consisting of phenyl, pyranonyl, pyridyl, imidazolyl, 1,8-napthyridinyl, and N-oxide pyridyl. In a further embodiment of the invention, R is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. In another embodiment of the invention, $R_1$ is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. In a specific embodiment of the invention, $R_4$ is a cyclic or bicyclic ring structure, substituted or unsubstituted and selected from the group consisting of phenyl, pyridyl, and furanyl. In a further embodiment of the invention, $R_4$ is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. The R, $R_1$, $R_4$ and Z groups can be embodied as described above in other embodiments. In a specific embodiment the kit further comprises a drug selected from the group consisting of an antibiotic, an antidiarrheal, and a LT inhibitory drug. In another general embodiment, the kit further comprises a pharmaceutically acceptable carrier.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1 shows a scheme for the mechanism of pathogenic action of *B. anthracis.*

FIG. 2 shows a scheme for the mechanism of action of cholera toxin from *Vibrio cholerae.*

FIG. 3 demonstrates a comparison of the metal sites in two crystal structures of *B. anthracis* anthrax EF (Protein Database (PDB) designations: 1K90, 1XFV), in crystal structure of *B. Pertussis* (1ZOT) and in crystal structure of the mammalian AC (1CJV): FIGS. 3A & E shows the active site of EF (from 1K90) with 1 metal ($Yb^{3+}$). Residues Asp491, Asp493, His577 of EF and the α-phosphate of 3'-dATP chelate the metal ion. FIGS. 3B & F shows the active site of EF (from 1XFV) which shows two Mg ions 4.32 Å apart. Mg901 chelate residues Asp491, Asp493 and His577 of EF, while Mg101 chelate the oxygen atoms from the three phosphates of 3'-dATP. 3C & G) The active site of *B. Pertussis* (from 1ZOT) which shows three Mg ions. Mg902 interacts with Asp188. Mg902 interacts with the α-phosphate of EMA. M9901 chelates with residues Asp188 Asp190, and the α-phosphate EMA. FIGS. 3D & H show the active site of mammalian adenylyl cyclase(from 1CJV) with two metal (Zn and Mg) ions. The Mg ion chelates the α, β, γ phosphates of 2'3'-ddATP, Asp396 and Asp440. The Zn ion chelates the α-phosphates of 2'3'-ddATP, Asp396 and Asp440.

FIG. 4 shows the structures of 3'dATP, 2'3'-ddATP, EMA and $PGE_2$-imidazole, FIG. 5 shows an example of a fragment based pharmacophore that may be used with the UNITY program in Sybyl to do a 3-D search of the over 250,000 compounds in the NCI database.

FIG. 6A shows lead compounds obtained by screening the NCI database with UNITY (the numbers below the structure represent NCI code/FlexX score). FIG. 6 B shows examples of fragments based on these lead compounds. Such fragments were used for 2-D ZINC database searches.

FIG. 7 demonstrates the scheme for screening of compound libraries to select novel inhibitors of EF.

FIG. 8 shows CTA1 (top domain) and ARG (bottom domain) for designing selective cholera toxin inhibitors. NAD is shown docked into CTA and GTP is shown docked into ARF in the active sites.

FIG. 9 shows NAD+ docked into the active site of CTA1.

FIG. 10 shows the active site of anthrax EF (PDB 1K90) and fragments used for UNITY search of the NCI database. FIG. 10A. shows the active site of EF and hydrogen bond interactions between the residues in the active site and the substrate 3'dATP. FIG. 10B. shows the location of the best binding fragments in the active site. F1: phenyl ring; F2, F3, and F4: carboxyl groups; F5: ammonium group. FIG. 10C. overlays the fragments and the substrate analogue in the crystal structure, 3'dATP. FIG. 10D demonstrates an example of the fragment combination, containing two carboxyl groups (F2 and F3) and a phenyl ring (F1), for a pharmacophore used in a UNITY search.

FIG. 12 shows the AutoDock results for known inhibitors and substrates of edema factor, including three from a previous report of nucleotide based inhibitors (Soleiman) in comparison to a selected 19 compounds. Note that, consistent with their mediocre docking scores, the Soleiman compounds have relatively low ability to inhibit EF.

Figure 14:
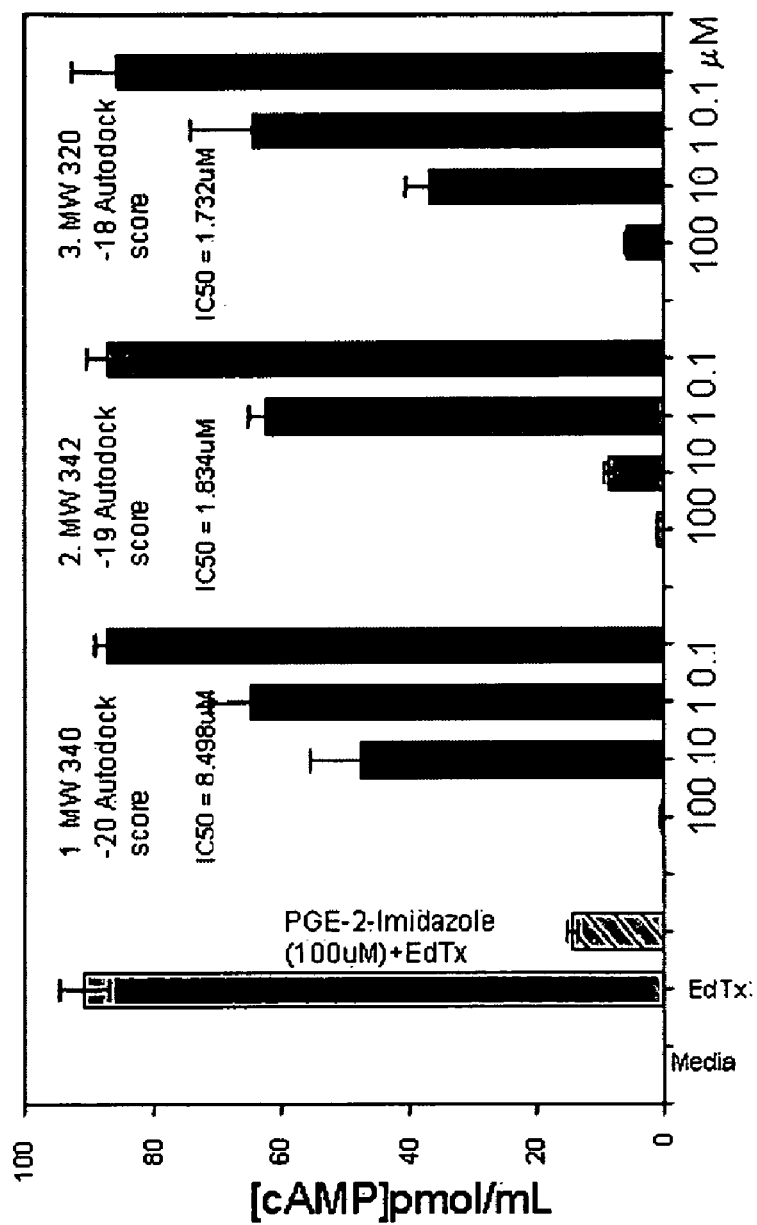
Figure 15A:
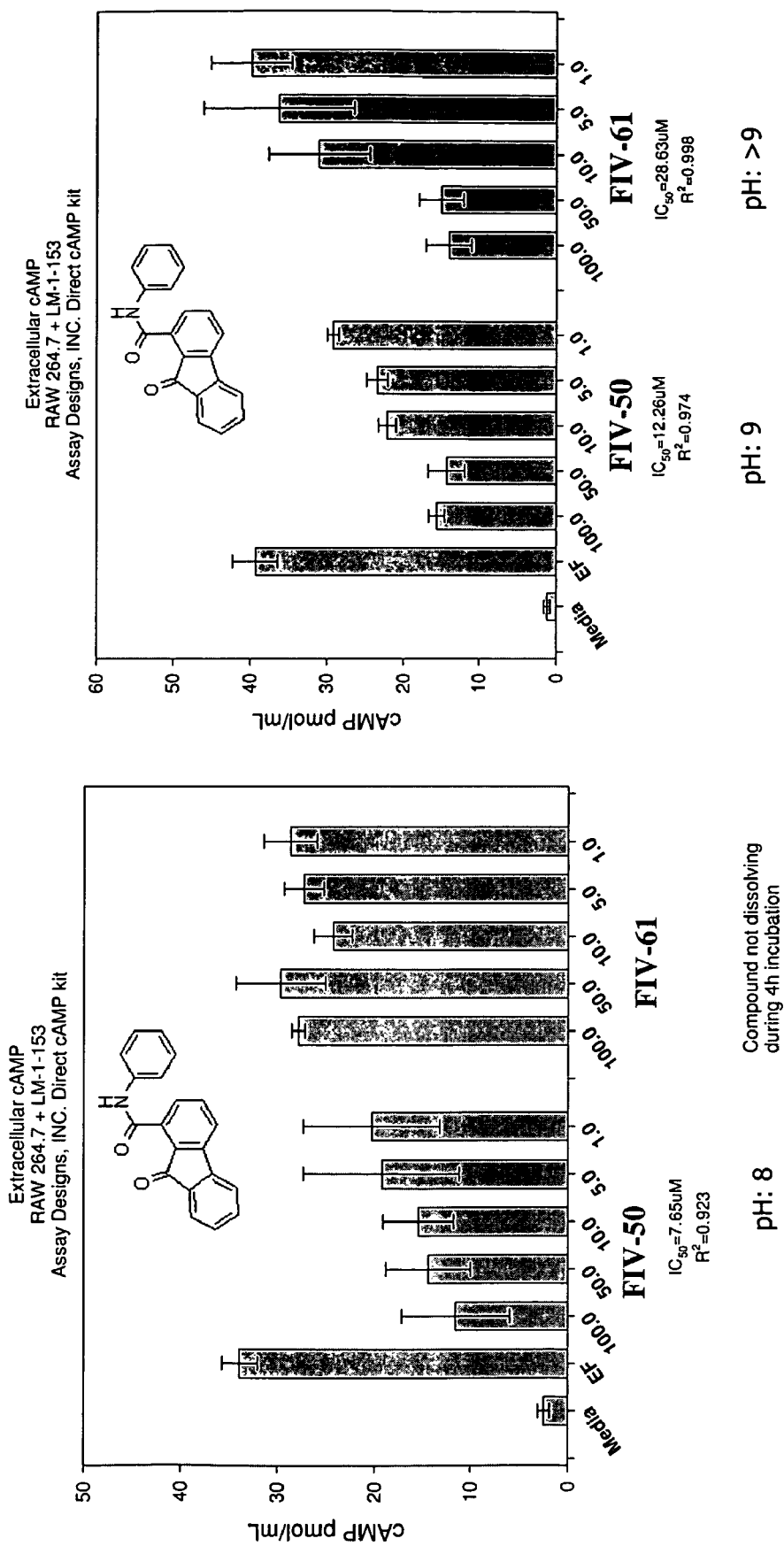
Figure 15B:
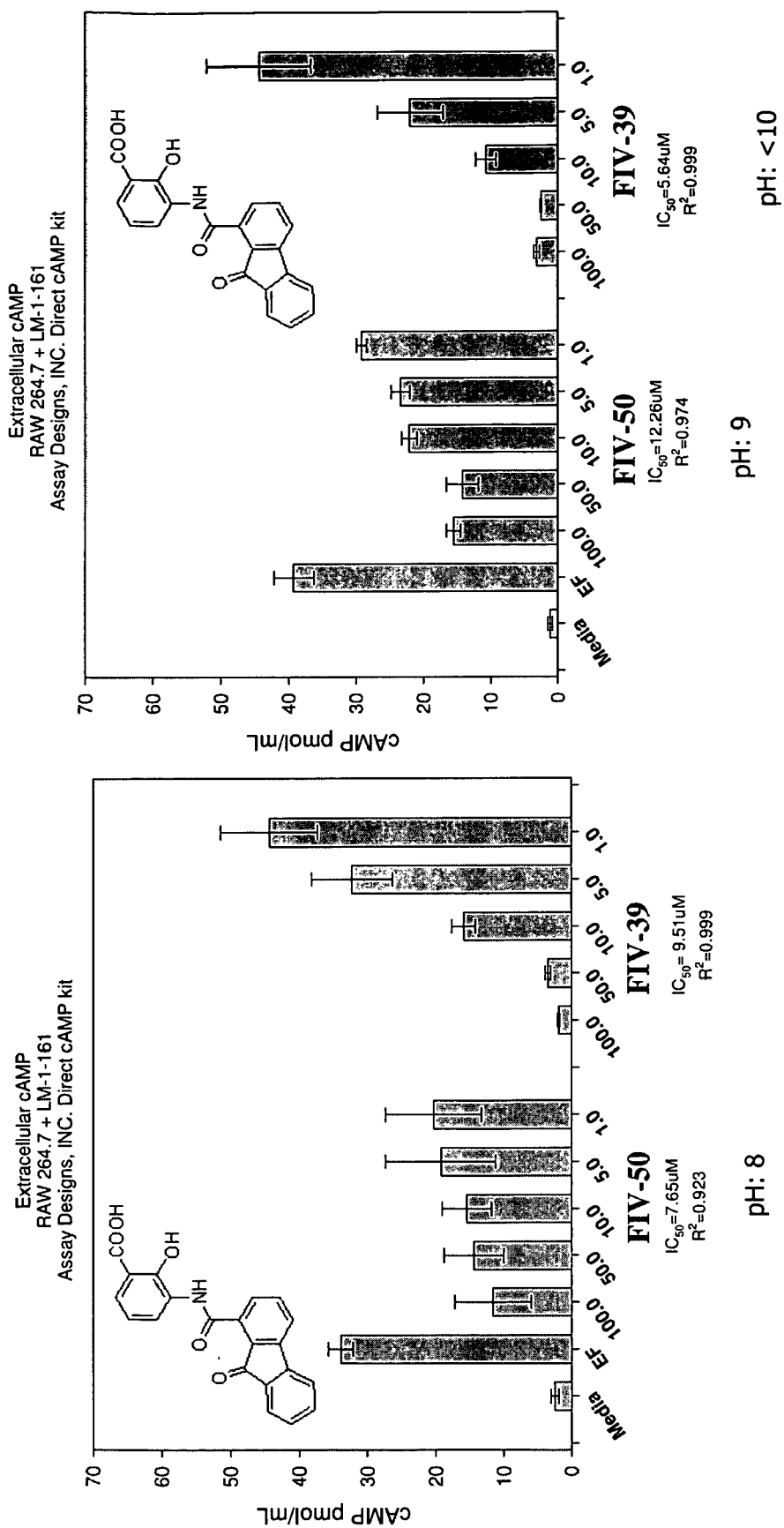
Figure 15C:
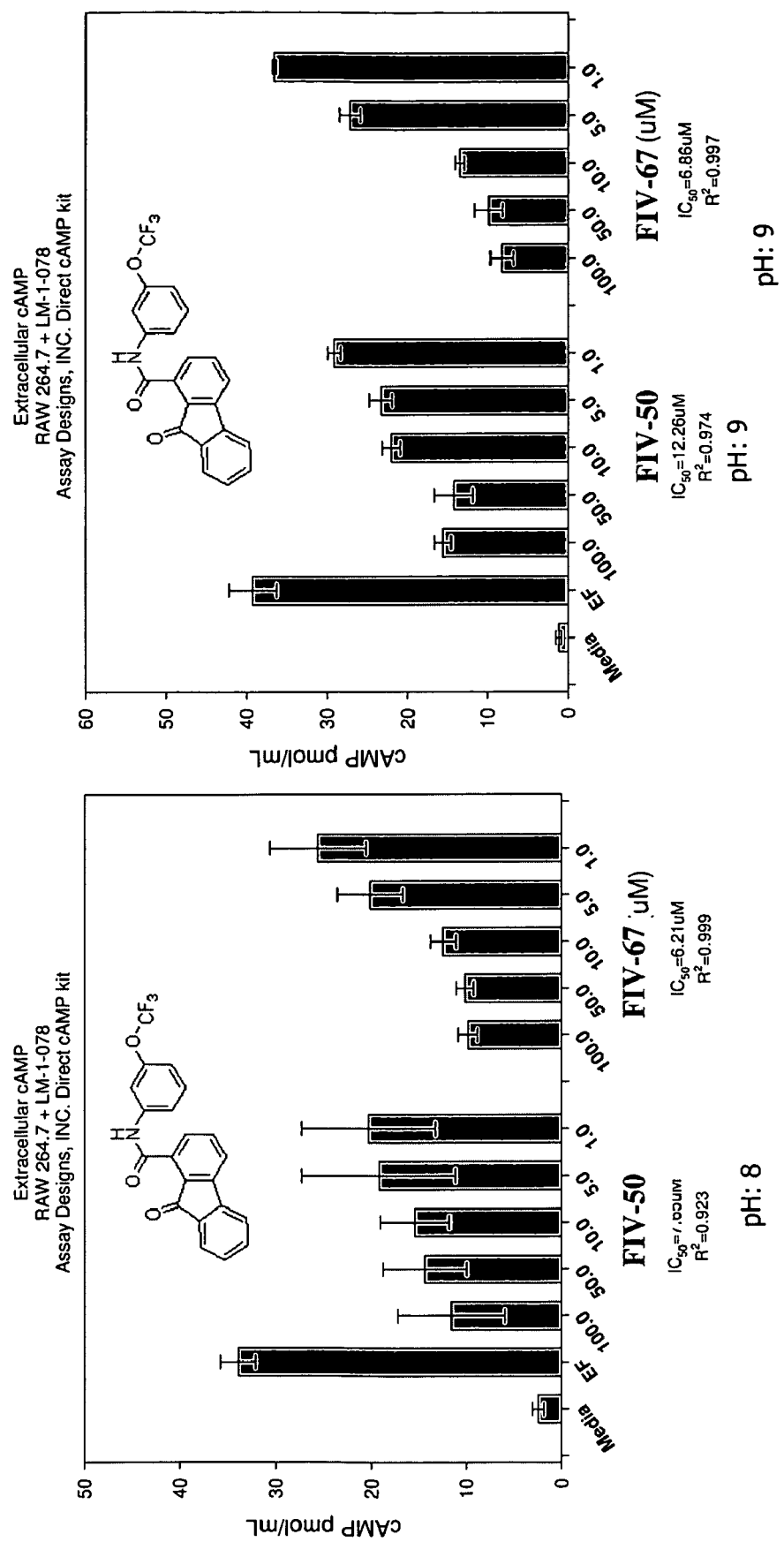
Figure 15D:
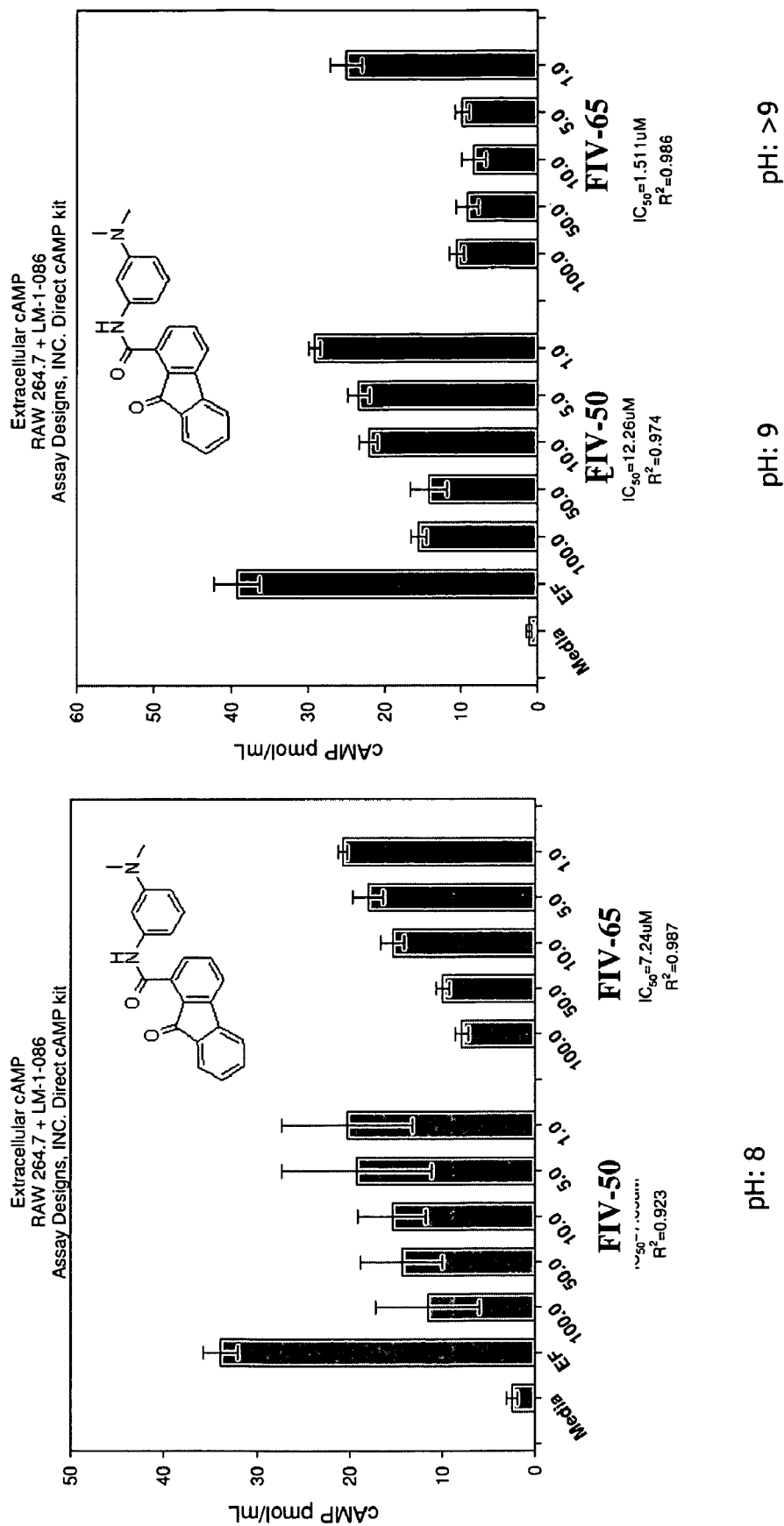
Figure 15E:
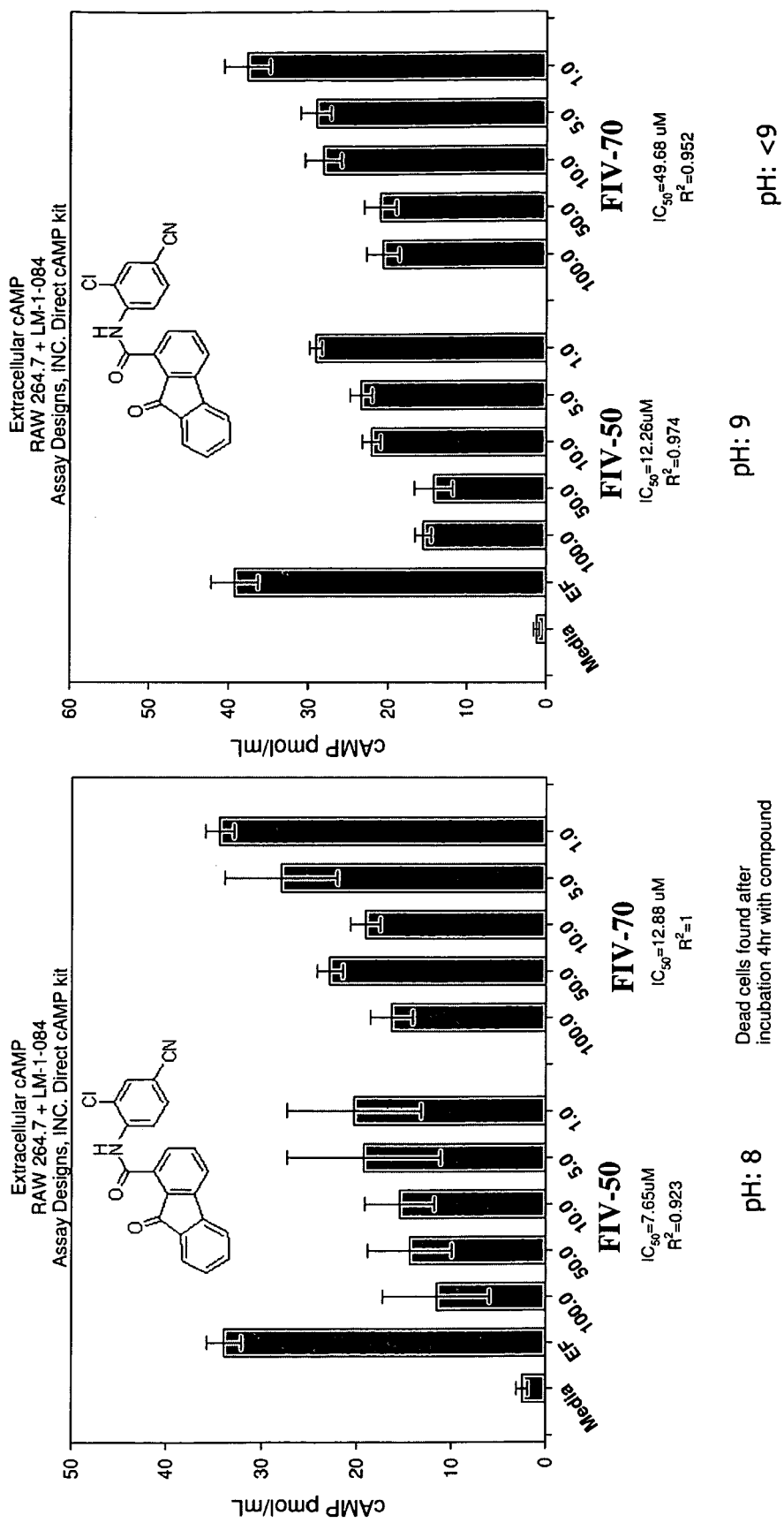
Figure 15F:
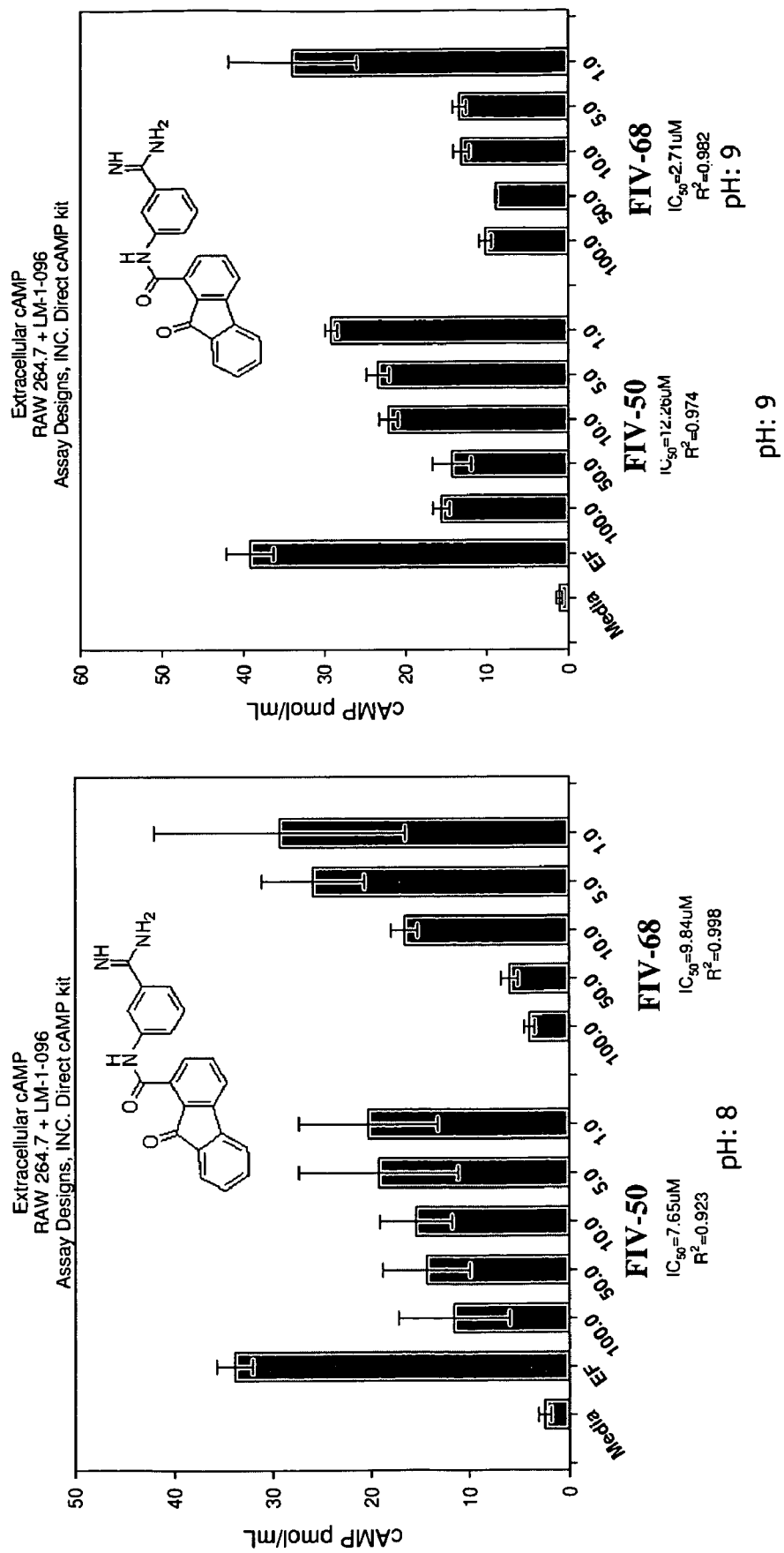
Figure 15G:
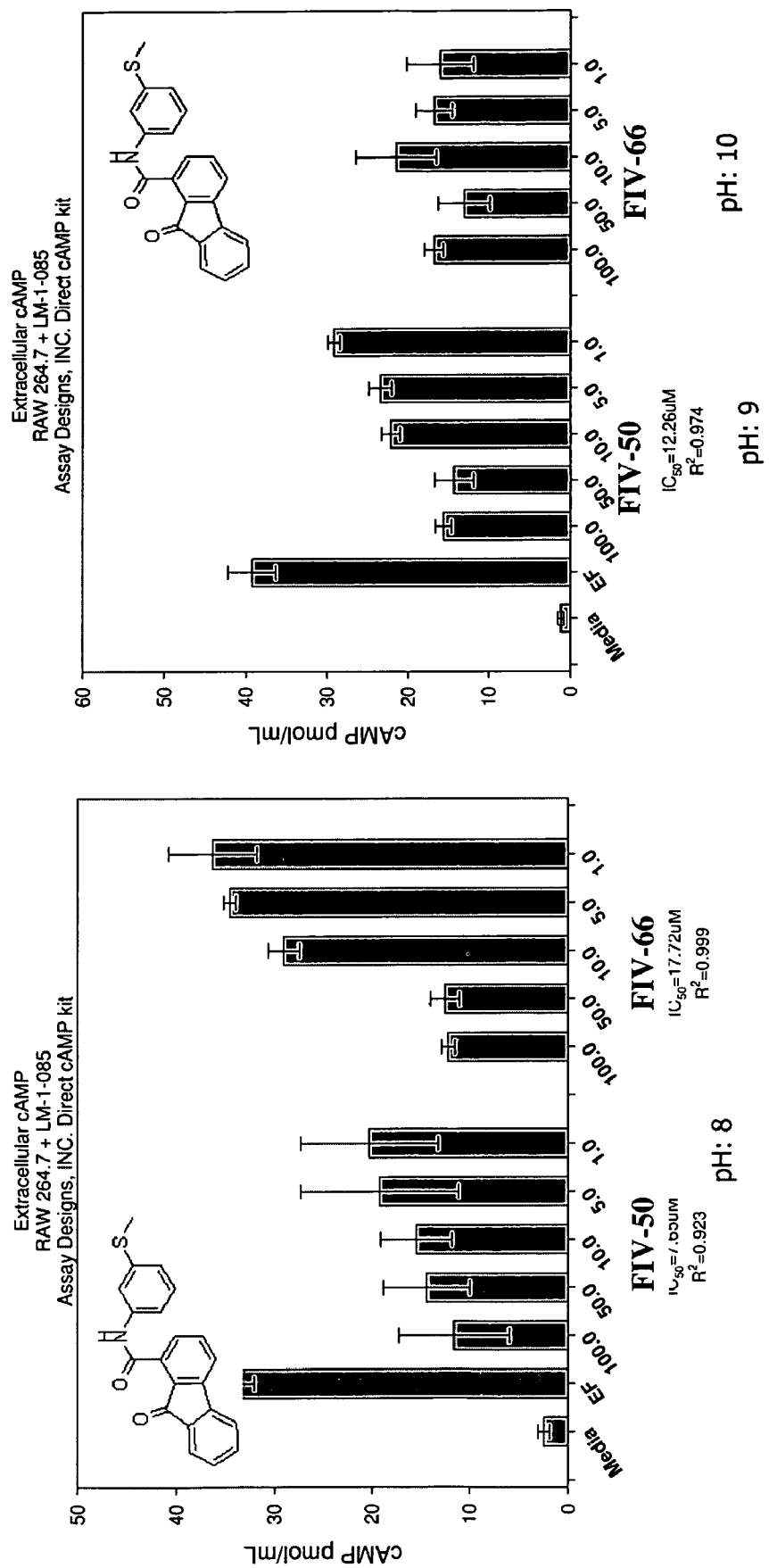
Figure 15H:
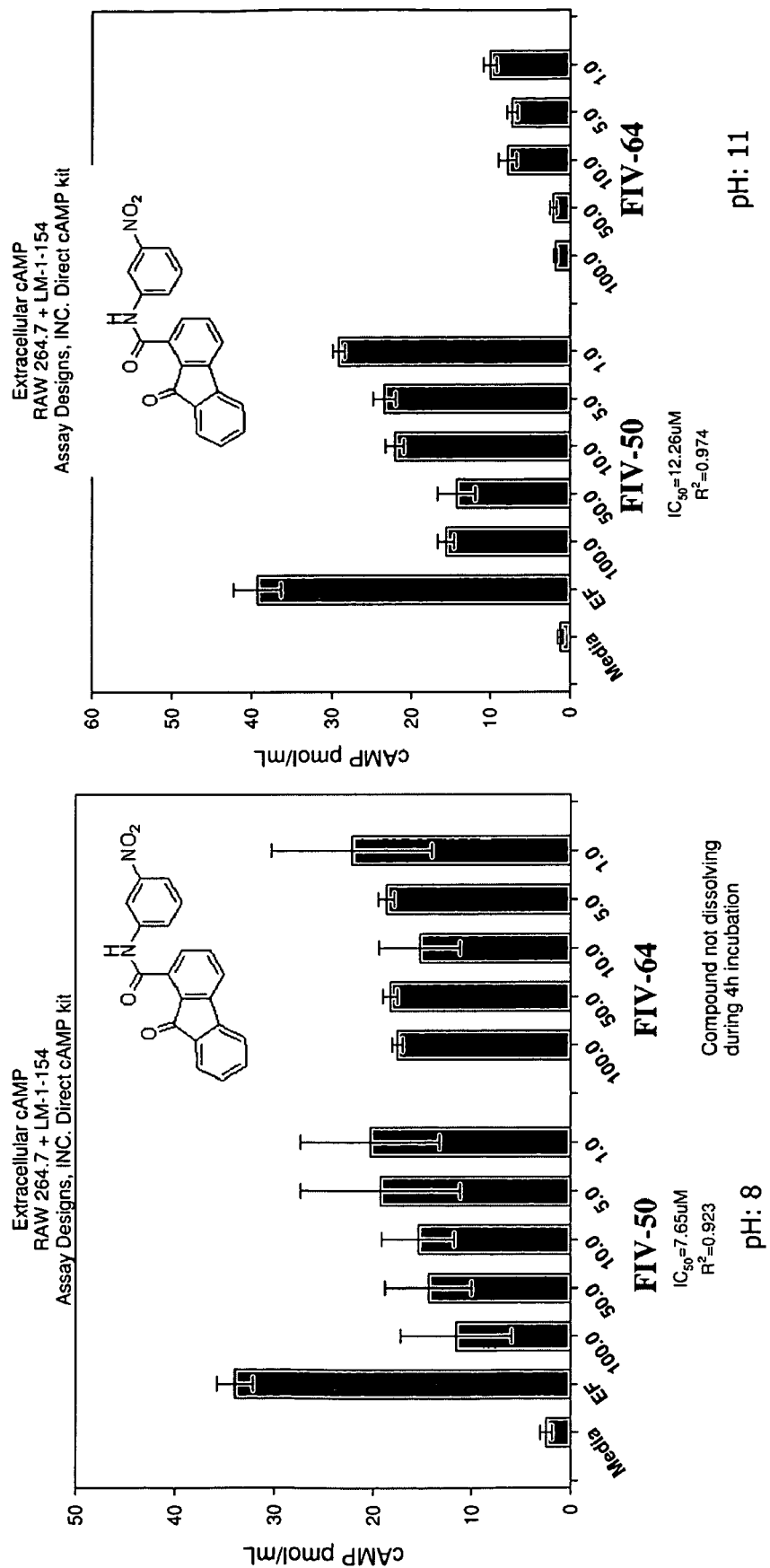
Figure 15J:
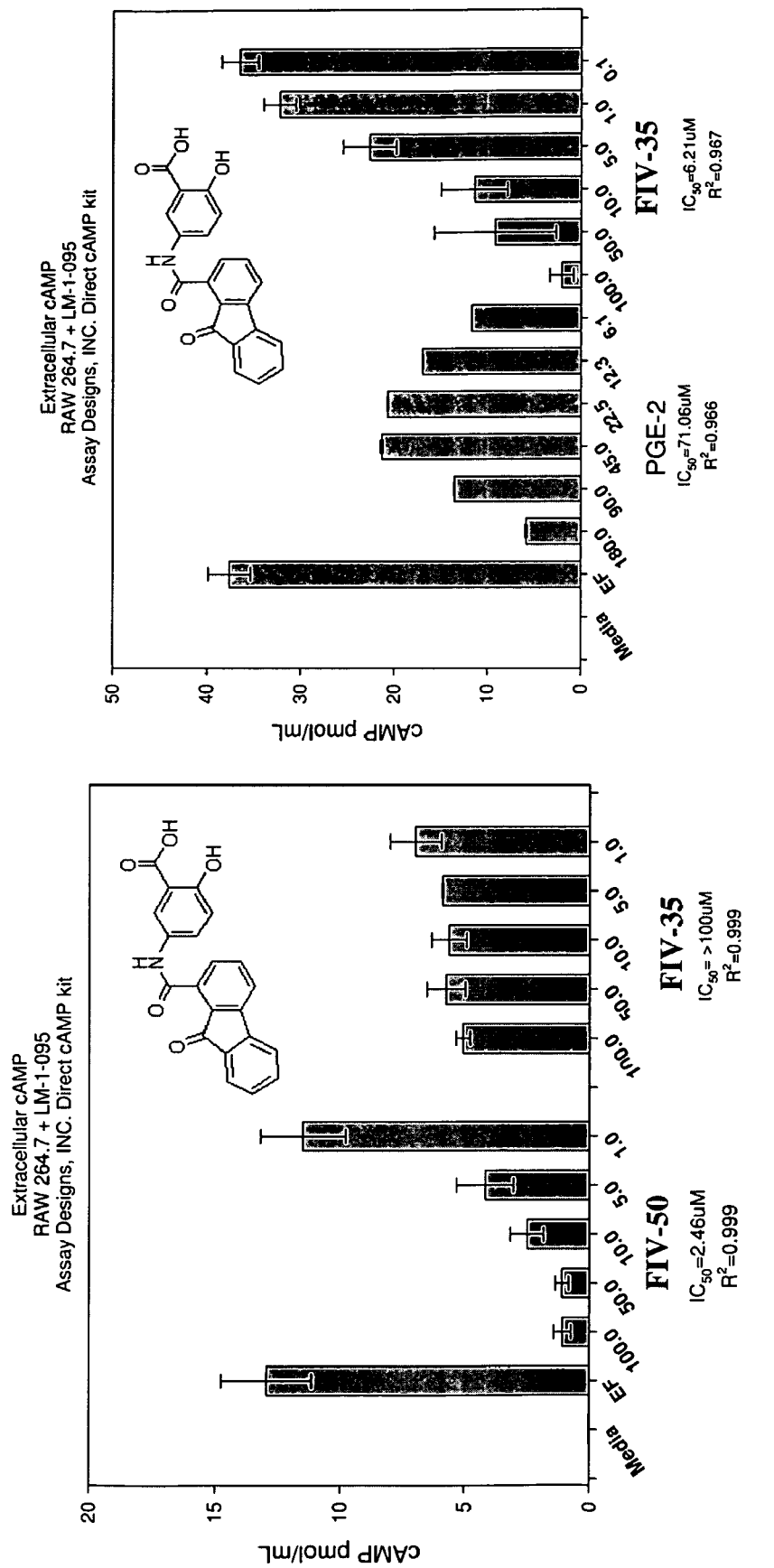
Figure 15K:
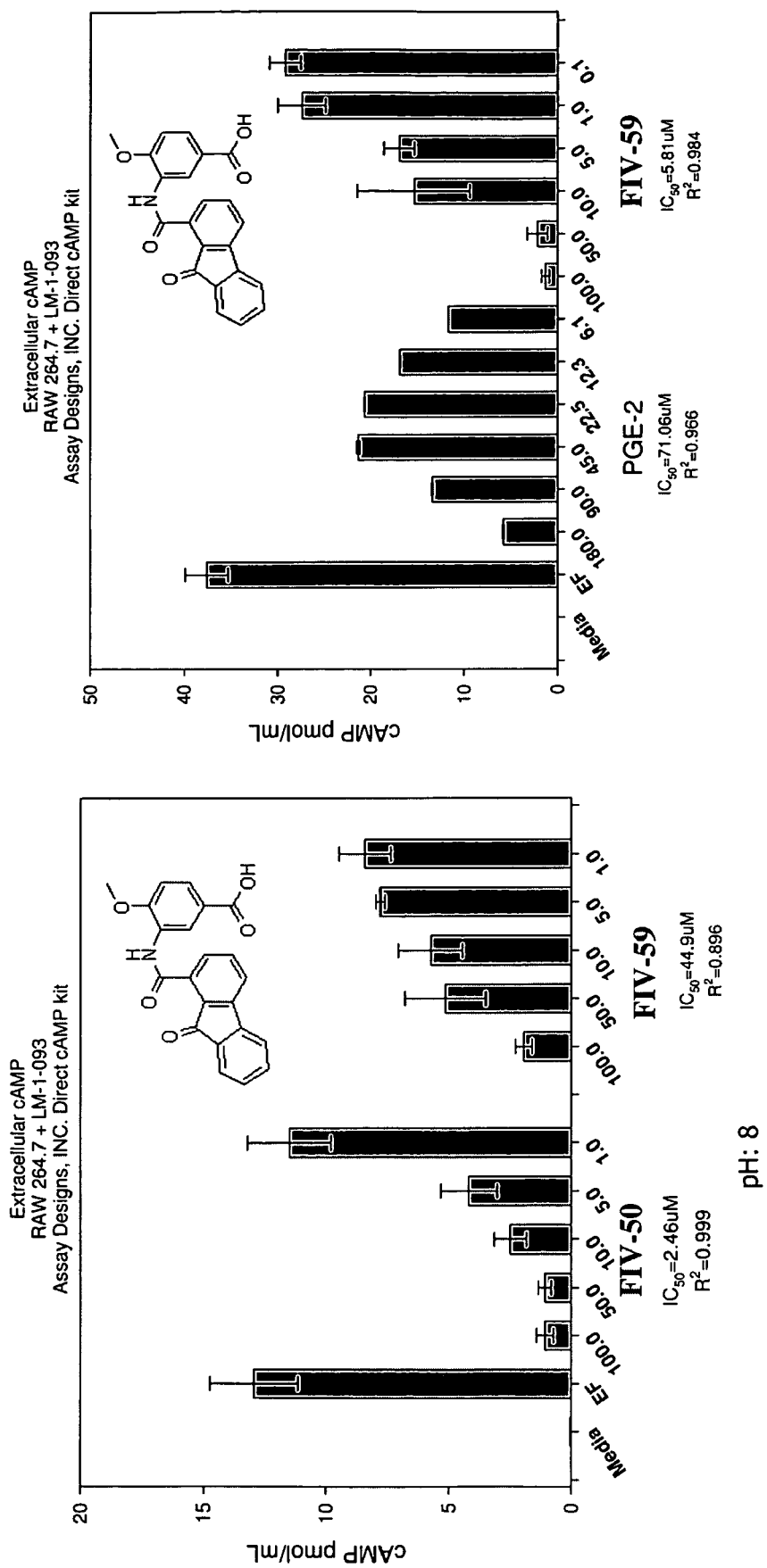
Figure 15L:
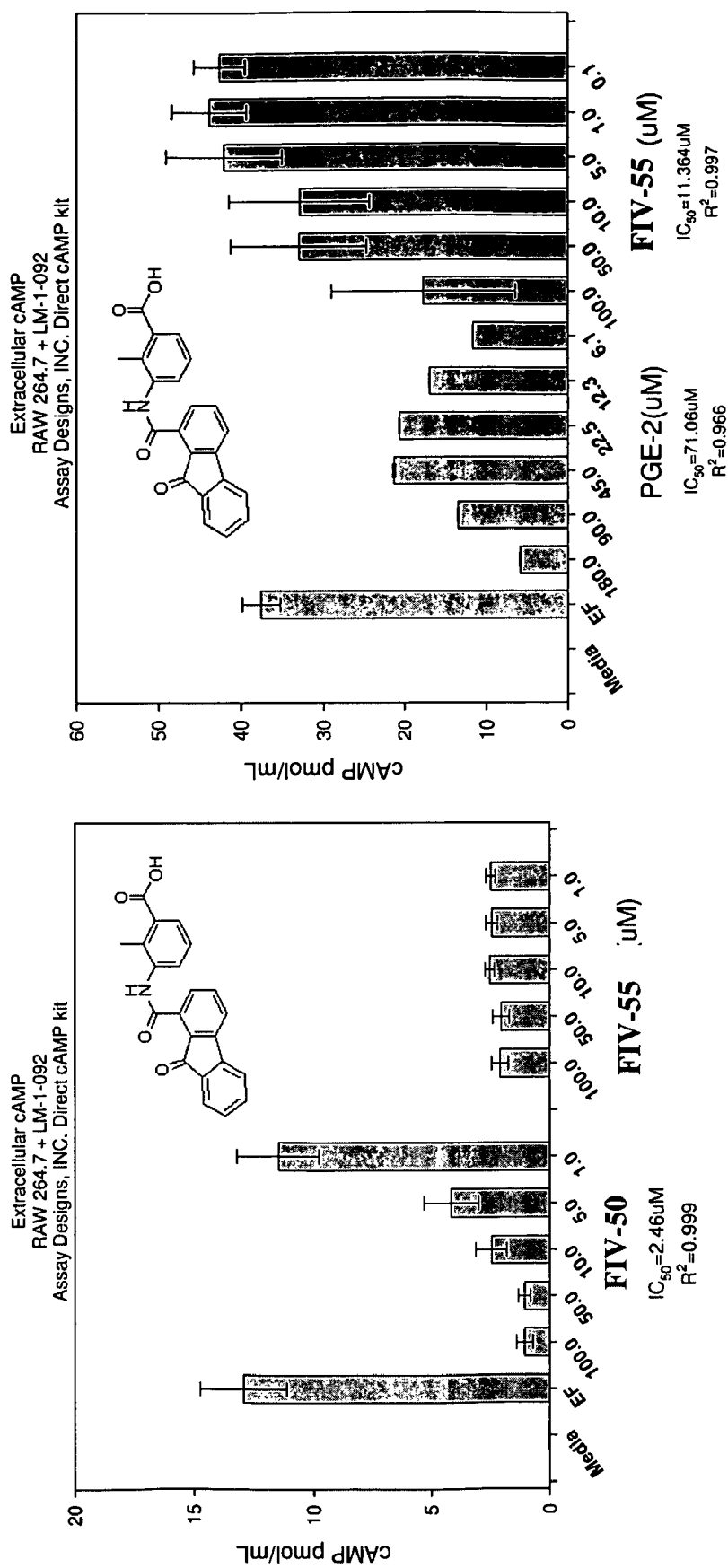
Figure 15N:
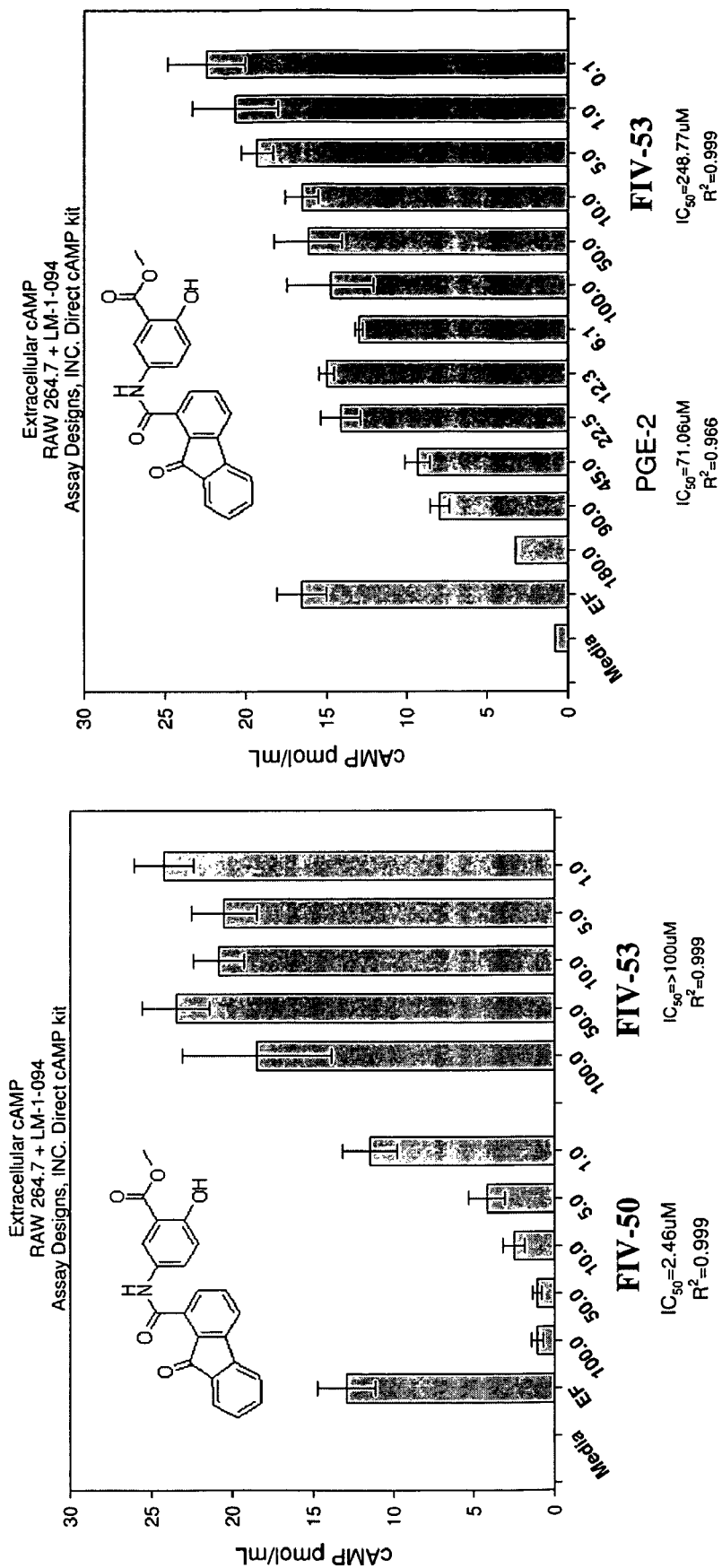
Figure 15O:
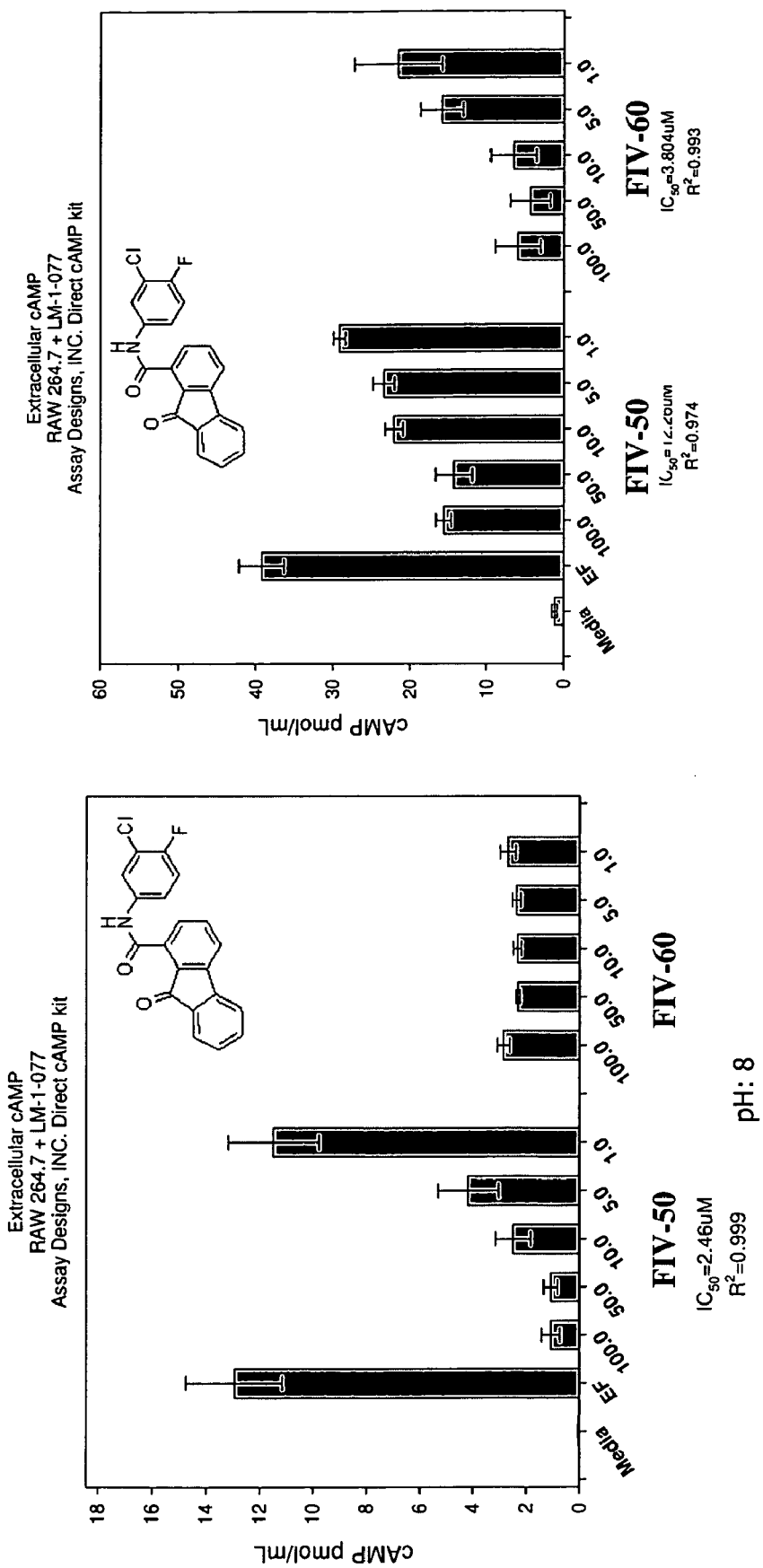
Figure 16B:
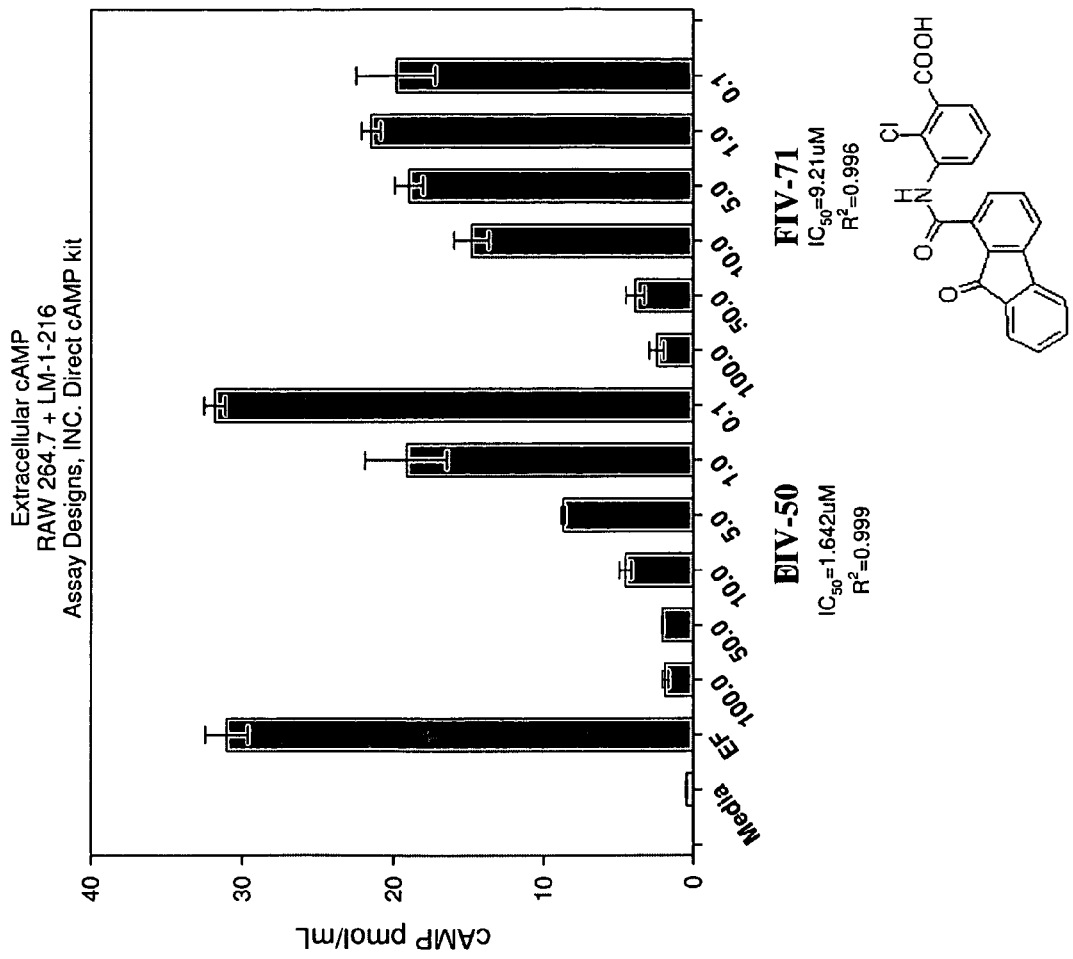
Figure 16C:
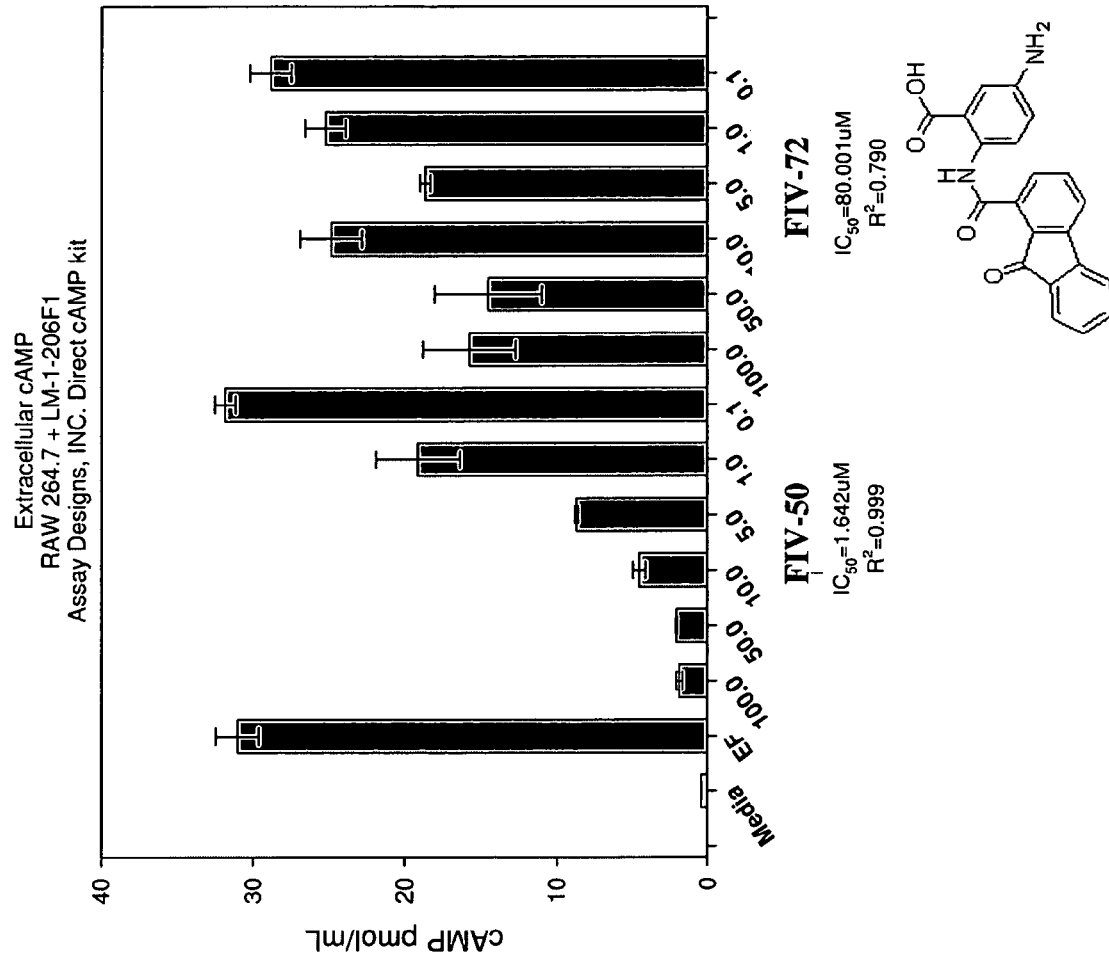
Figure 16D:
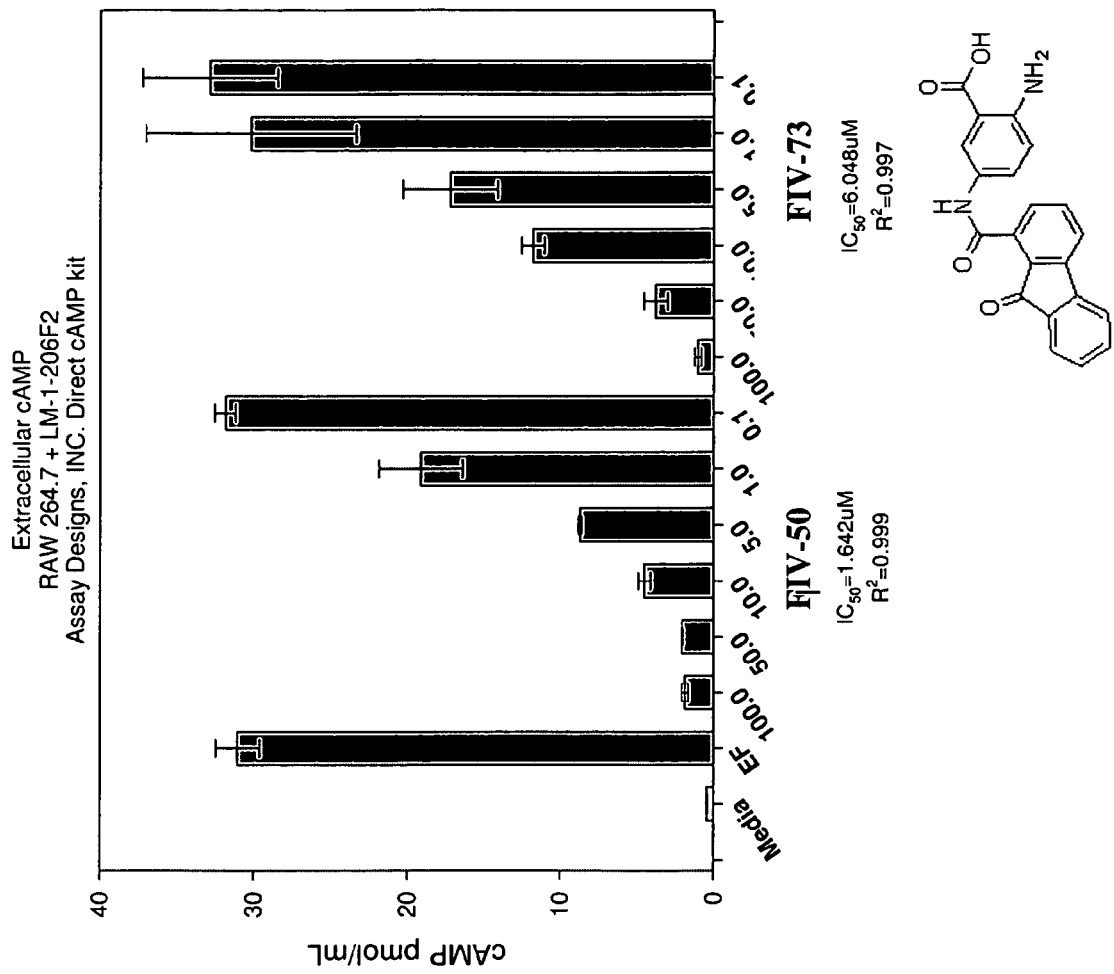
Figure 16E:
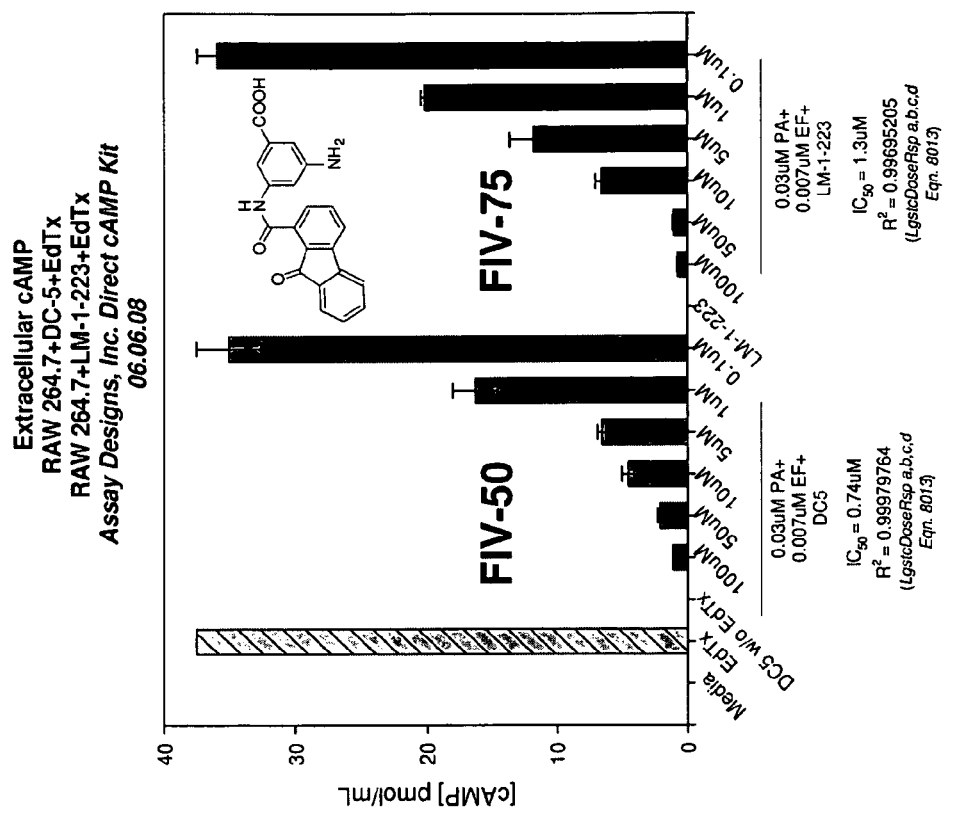
Figure 16F:
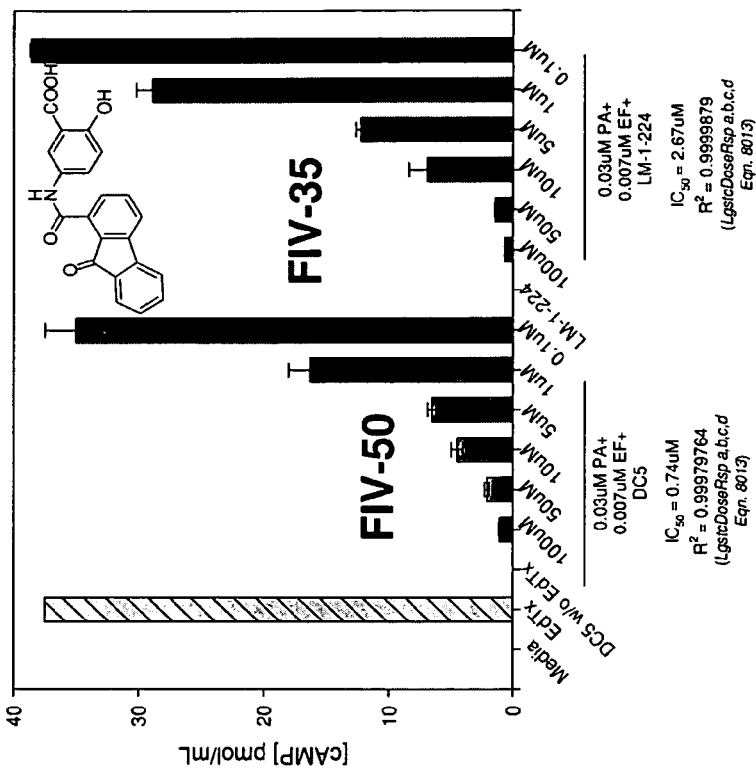

FIG. 14 shows a comparison of three selected compounds with $PGE_2$-imidazole for their ability to inhibit cAMP production induced by Edema Toxin (EdTx). RAW 264.7 cells were incubated with various concentrations of $PGE_2$-imidazole or the inhibitors and then treated with 30 nM PA and 7 nM EF for 4 hours. IBMX (50 μM, phosphodiesterase inhibitor) was added to each well. Each sample was done in triplicate. Note that all three compounds were more active than $PGE_2$-imidazole in this assay. The compounds are 1) FIII-1, 2) FII-1 and 3) FIV-50 in Table 1.

FIG. 15 shows a comparison of the cAMP levels from the ELISA assay with cells given edema factor between DC-5 treated cells and an additional compounds. Figures with two graphs show two independent assays at different pH. The additional compound in FIG. 15A is FIV-61; in FIG. 15B is FIV-39; in FIG. 15C is FIV-67; in FIG. 15D is FIV-65; in FIG. 15E is FIV-70; in FIG. 15F is FIV-68; in FIG. 15G is FIV-66; in FIG. 15H is FIV-64; in FIG. 15I is FIV-54; in 15J is FIV-35; in 15K is FIV-59; in FIG. 15L is FIV-55; in FIG. 15M is FIV-58; in FIG. 15N is FIV-53; in FIG. 15O is FIV-60.

FIG. 16 shows a comparison of the cAMP levels from the ELISA assay with cells given edema factor between DC-5 and an additional compound. All compounds pH was ~7-8 and the curve was fit against the Log Normal cumulative for all compounds. The additional compound in FIG. 16A is FIV-46; in FIG. 16B is FIV-71; in FIG. 16C is FIV-72; in FIG. 16D is FIV-73; in FIG. 16E is FIV-75; and in FIG. 16F is FIV-35.

Figure 17:
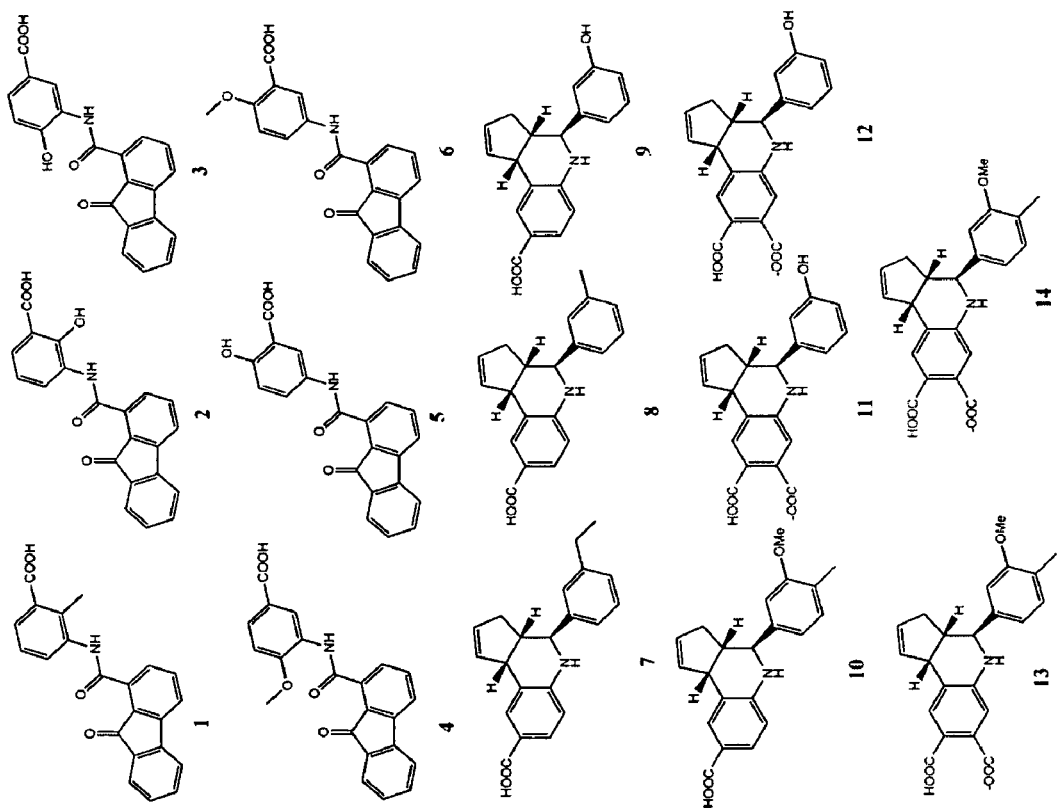

FIG. 17 shows the structures of exemplary compounds designed by modifying FIV-50 and FII-1 to modify activity.

Figure 18:
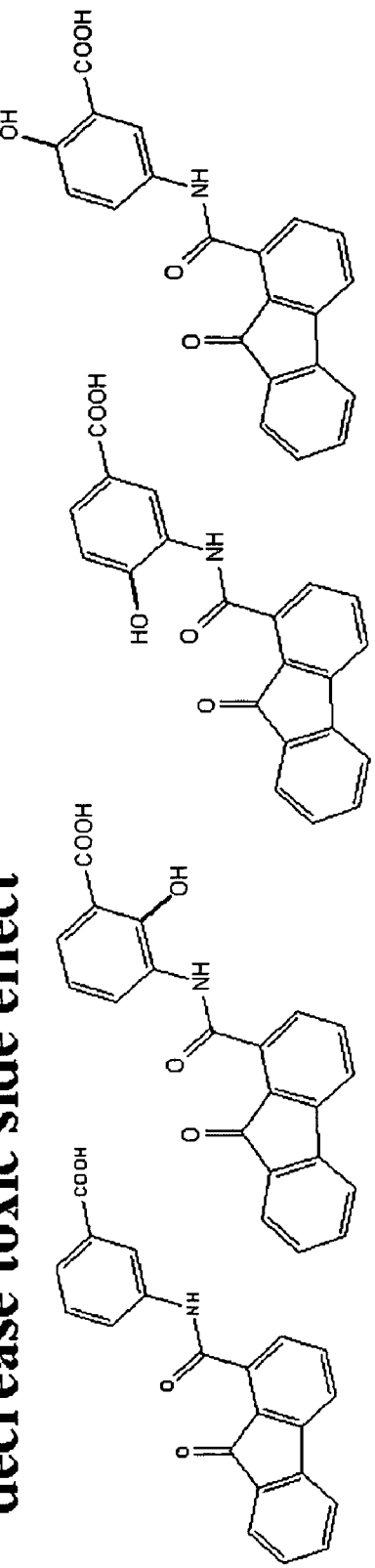

FIG. 18 shows exemplary compounds designed to be more soluble and less toxic and their corresponding computationally calculated mutagenicity.

Figure 19:
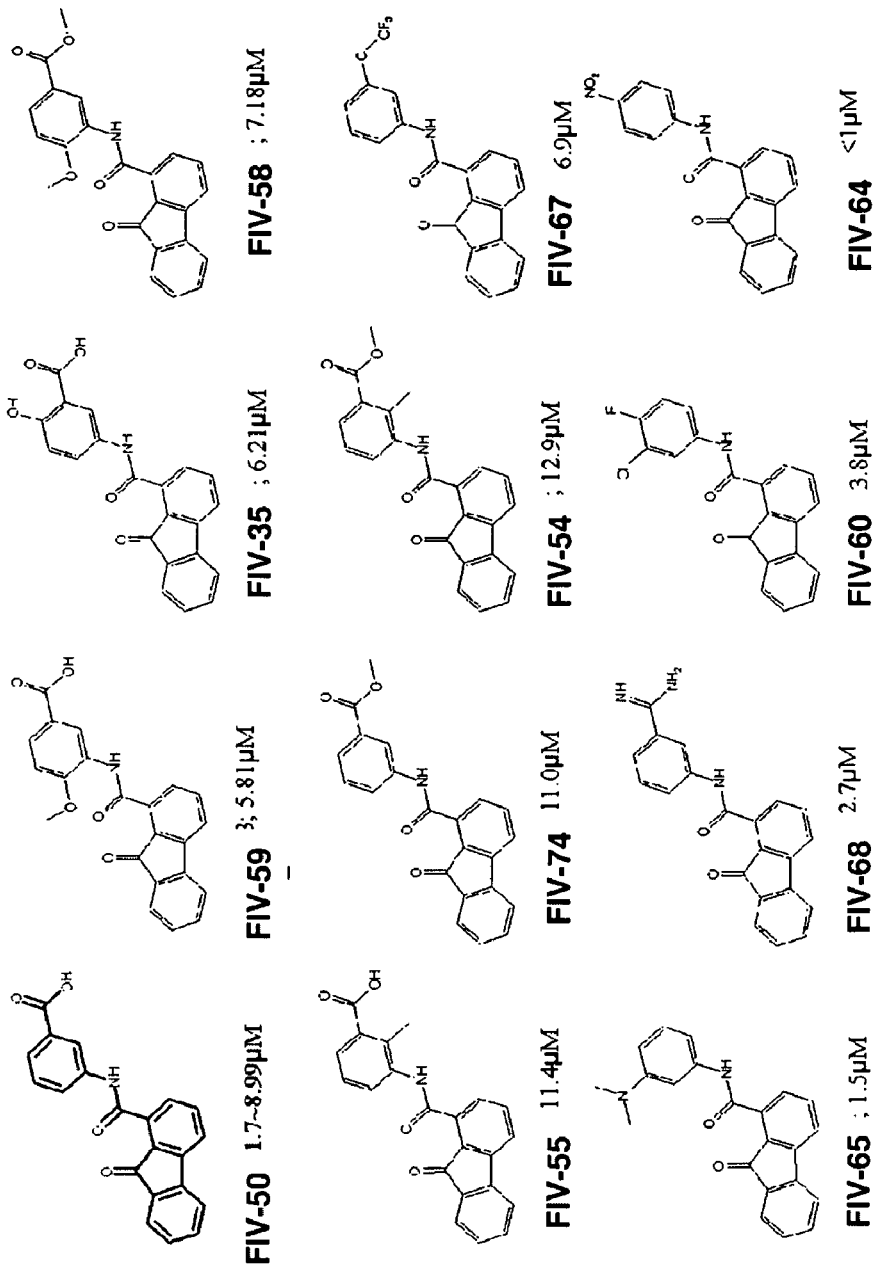

FIG. 19 shows exemplary FIV-50 derivatives with activities <20 μM.

Figure 20:
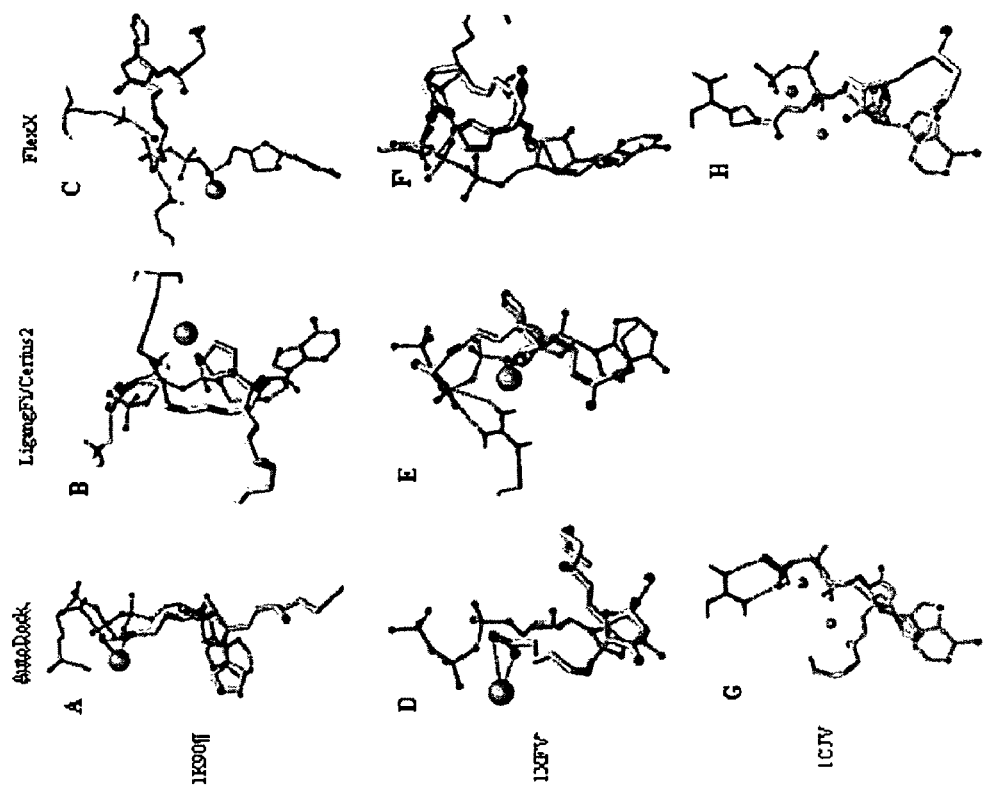

FIG. 20 demonstrates docking the inhibitor $PGE_2$-imidazole into 1K90 and 1XFV with three docking programs by comparing the best ranked pose with the experimental pose of 3'dATP. FIG. 20A is $PGE_2$-imidazole docked to 1K90 with AutoDock; FIG. 20B is $PGE_2$-imidazole docked to 1K90 with LigandFit/Cerius2; FIG. 20C is $PGE_2$-imidazole docked to 1K90 with FlexX; FIG. 20D is $PGE_2$-imidazole docked to 1XFV with AutoDock; FIG. 20E is $PGE_2$-imidazole docked to 1XFV with LigandFit/Cerius2; FIG. 20F is $PGE_2$-imidazole docked to 1XFV with FlexX.

Figure 21:
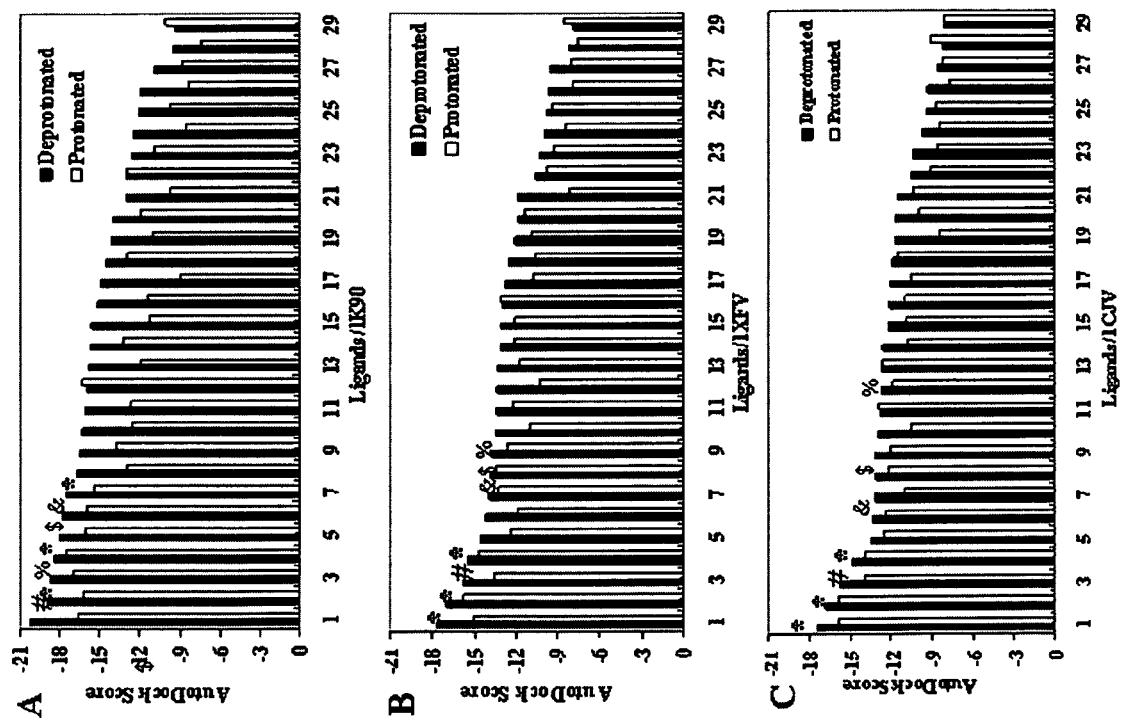

FIG. 21 compares the docking scores for the deprotonated states and protonated states of 25 compounds screened from NCI and ZINC databases and 4 ATP analogues, with the most active inhibitors of EF from the search marked by *. The docking scores for other known substrates and inhibitors of EF are indicated by symbols as follows: #: the CyaA inhibitor EMA. %: ATP; &: 3'dATP; $: 2'3'ddATP. FIG. 21A shows the compounds docked into 1K90 with AutoDock. FIG. 21B shows the compounds docked into 1XFV with AutoDock. FIG. 21C shows the compounds docked into 1CJV with AutoDock.

Figure 1:
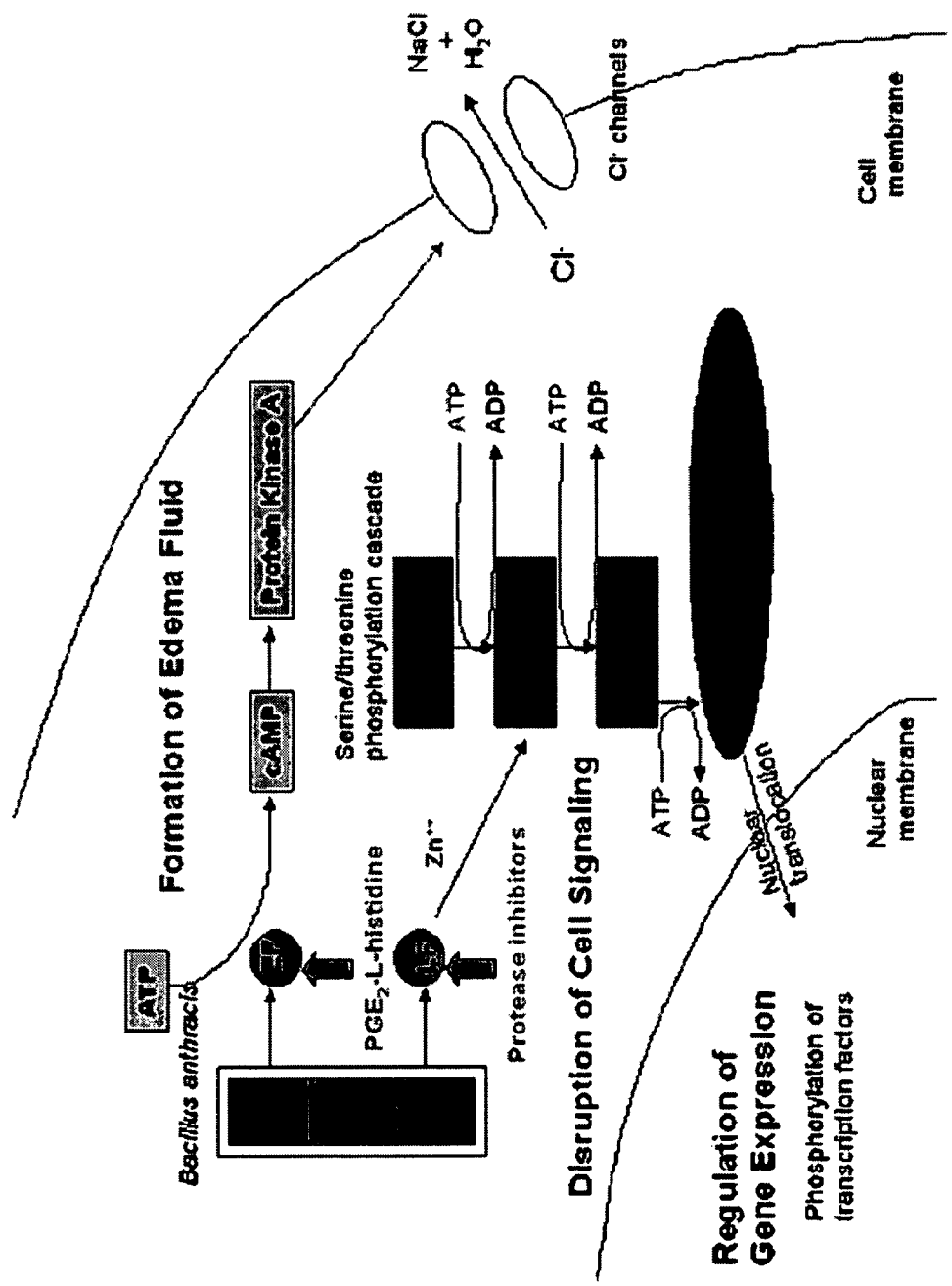
Figure 22:
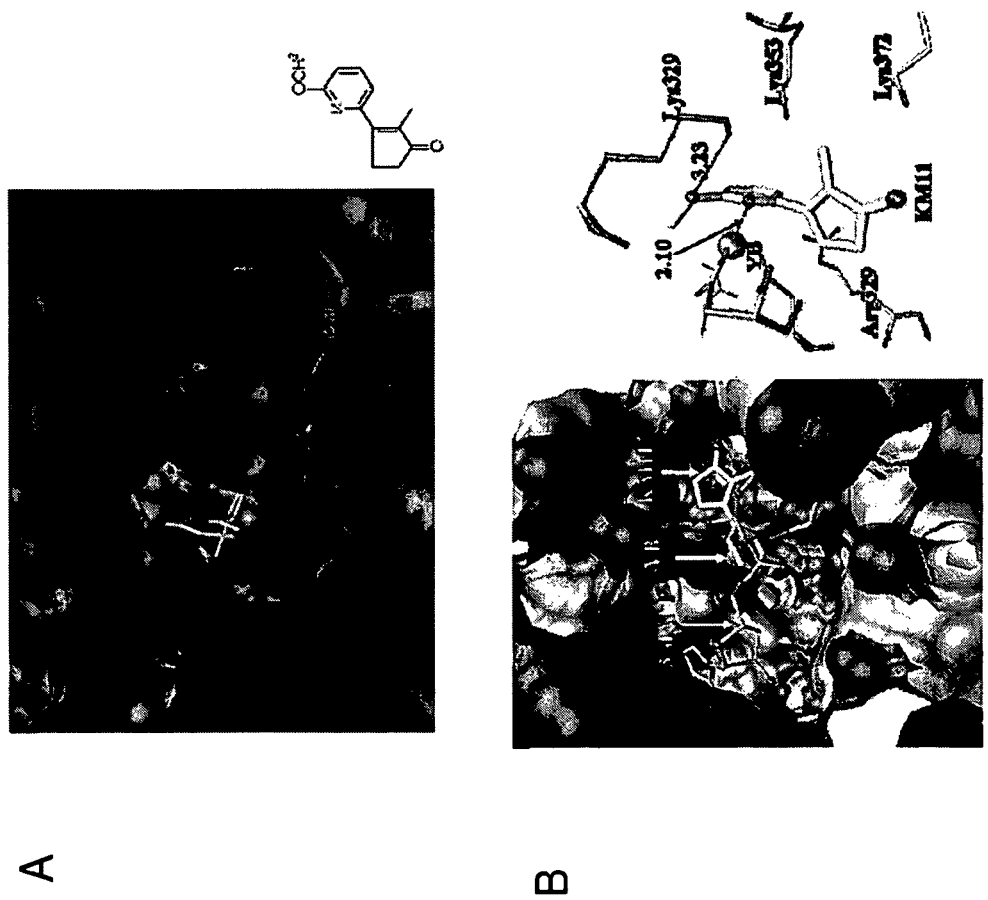

FIG. 22 is the lowest energy AutoDock conformation of the inhibitor KM011 in the EF active site. Note the methoxy group is close to the metal ion, and both rings are pointed toward the inner face of the active site. This is the only compound in the series that does this. FIG. 22B 1B shows the binding from the other side of the cleft, with an overlay of the ATP analogue position for clarity.

FIG. 23 shows an overlay of the docking positions of some exemplary compounds. Here, all of the compounds have a carbonyl that points toward the metal ion, but the additional rings face toward the front of the active site.

Figure 24:
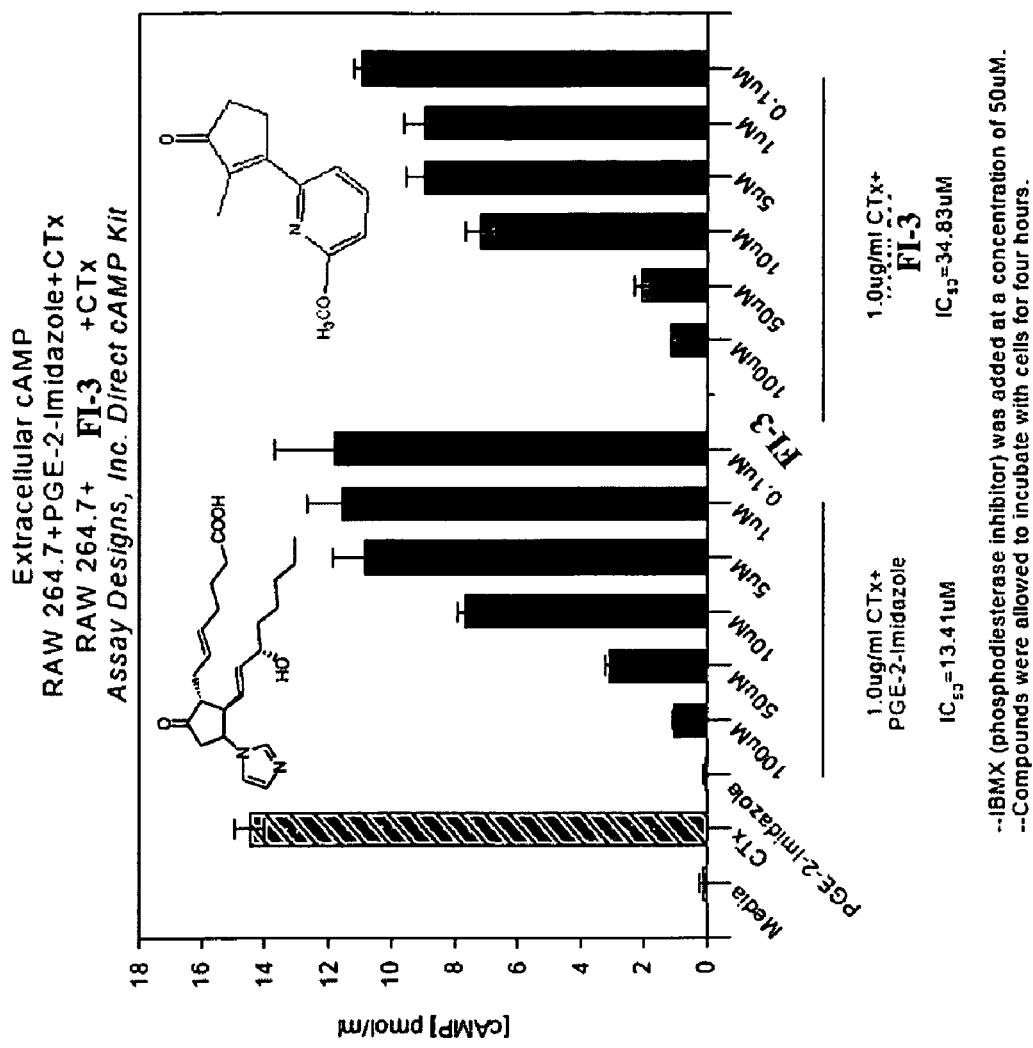

FIG. 24 is in vitro extracellular cAMP concentration assay with cholera toxin with compounds PEG-2-imidazole and FI-3.

Figure 25:
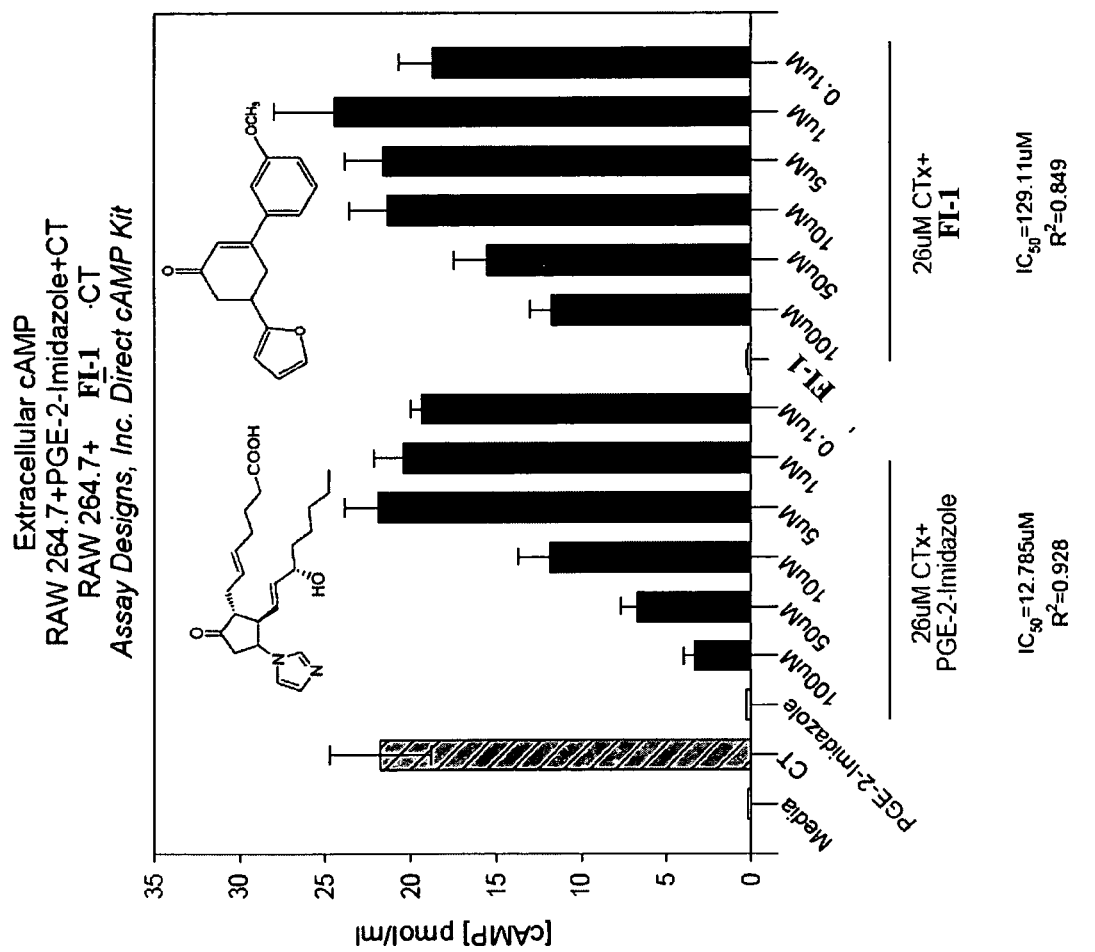

FIG. 25 is in vivo extracellular cAMP concentration assay with cholera toxin with compounds PEG-2-imidazole and FI-1.

Figure 26:
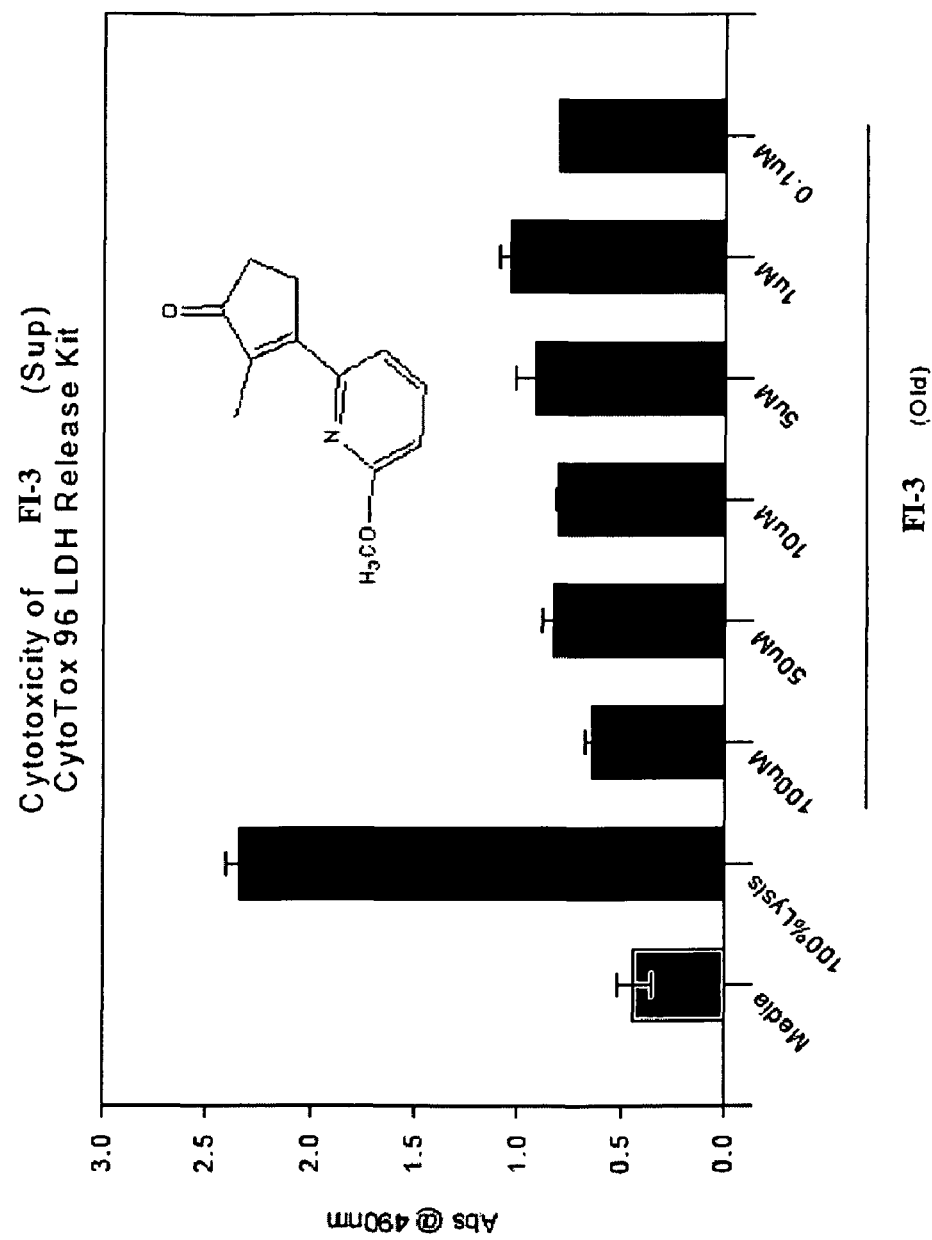

FIG. 26 is a LDH cytotoxicity assay for FI-3.

Figure 27:
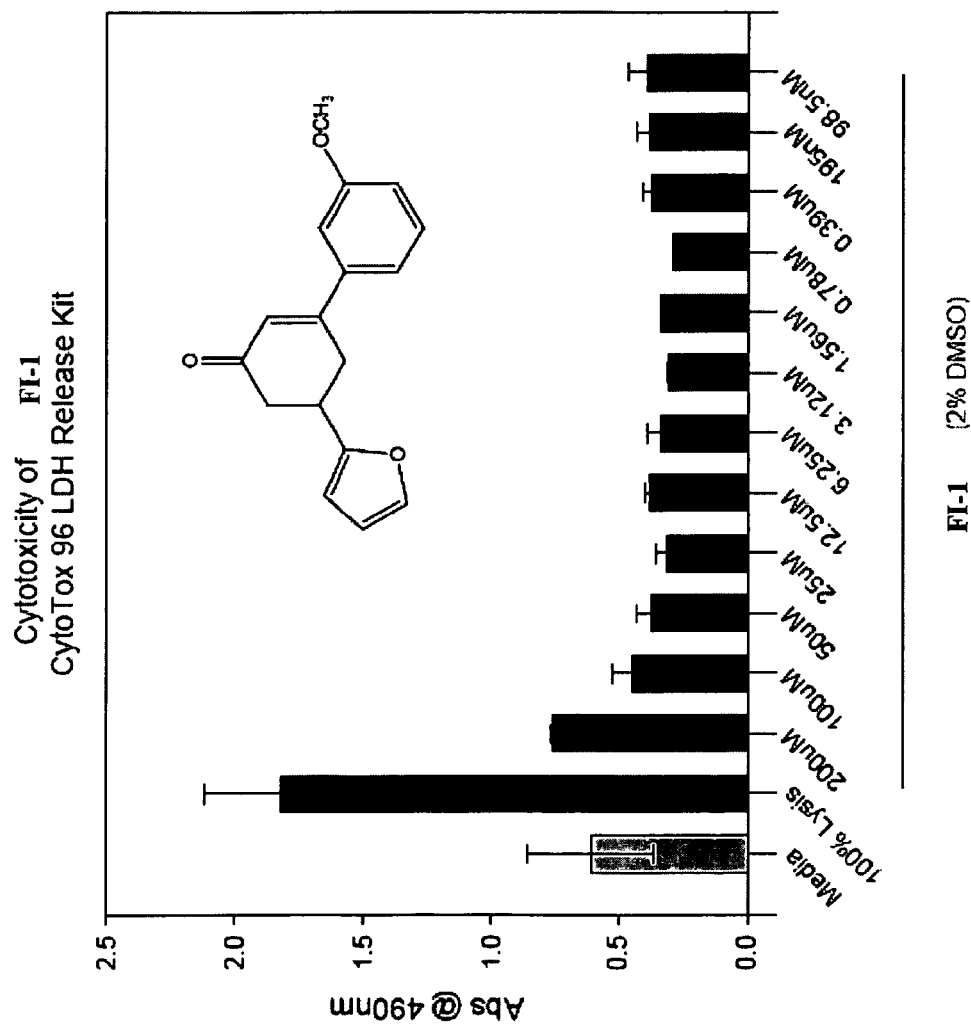

FIG. 27 is a LDH cytotoxicity assay for FI-1.

Figure 28:
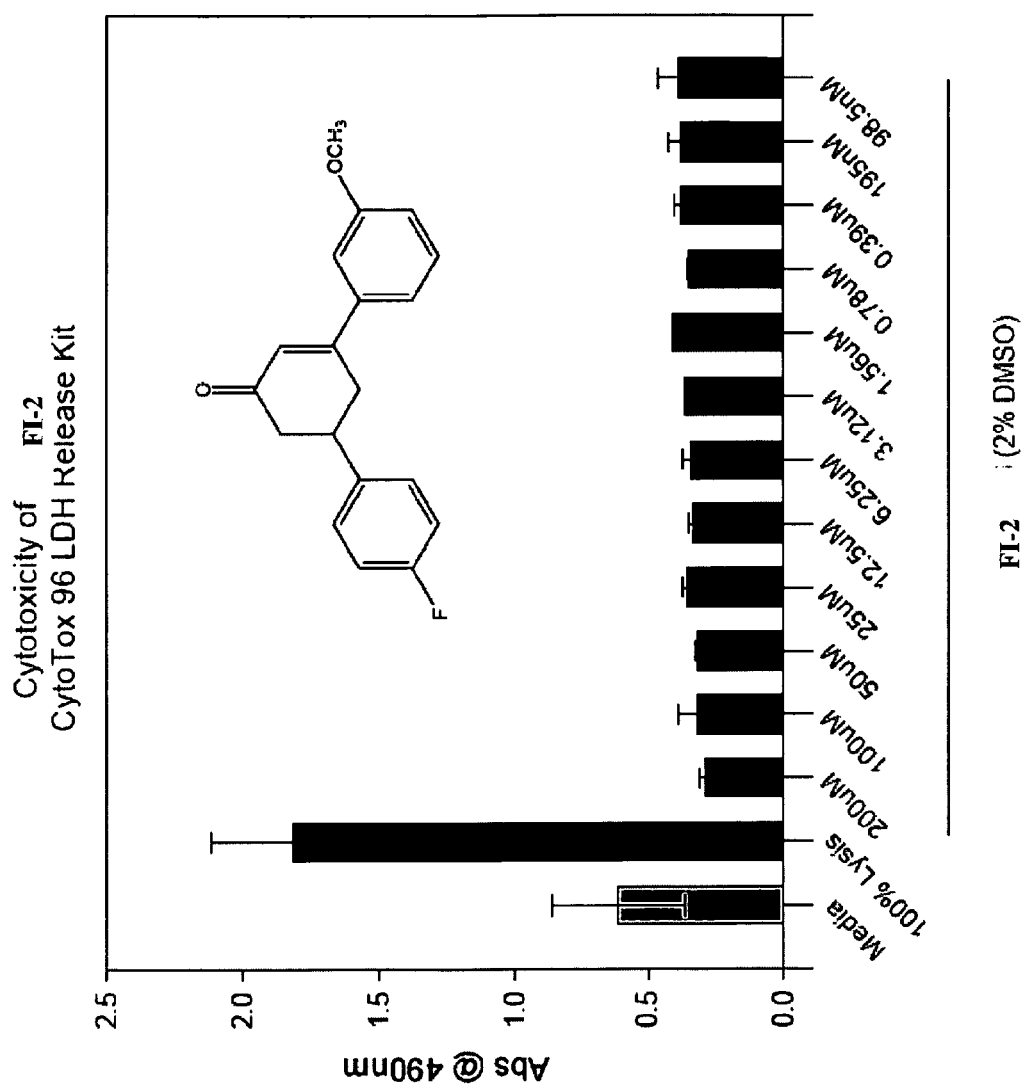

FIG. 28 is a LDH cytotoxicity assay for FI-2.

Figure 29:
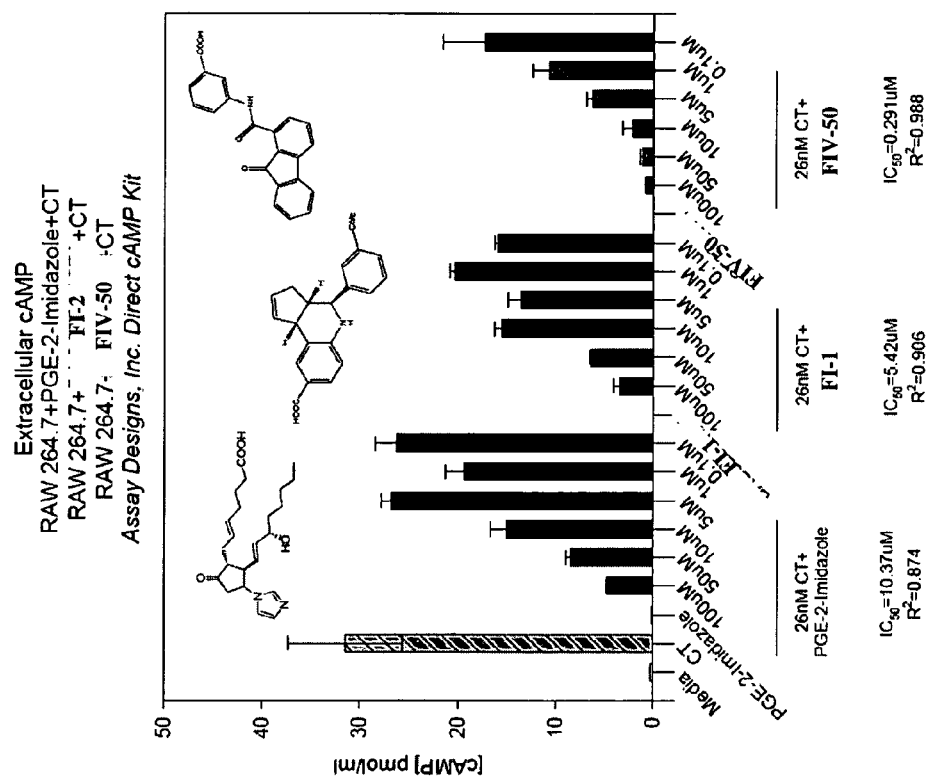

FIG. 29 is an extracellular cAMP assay with cholera toxin comparing the compounds PEG-2-imidazole, FII-1, and FIV-50.

Figure 30:
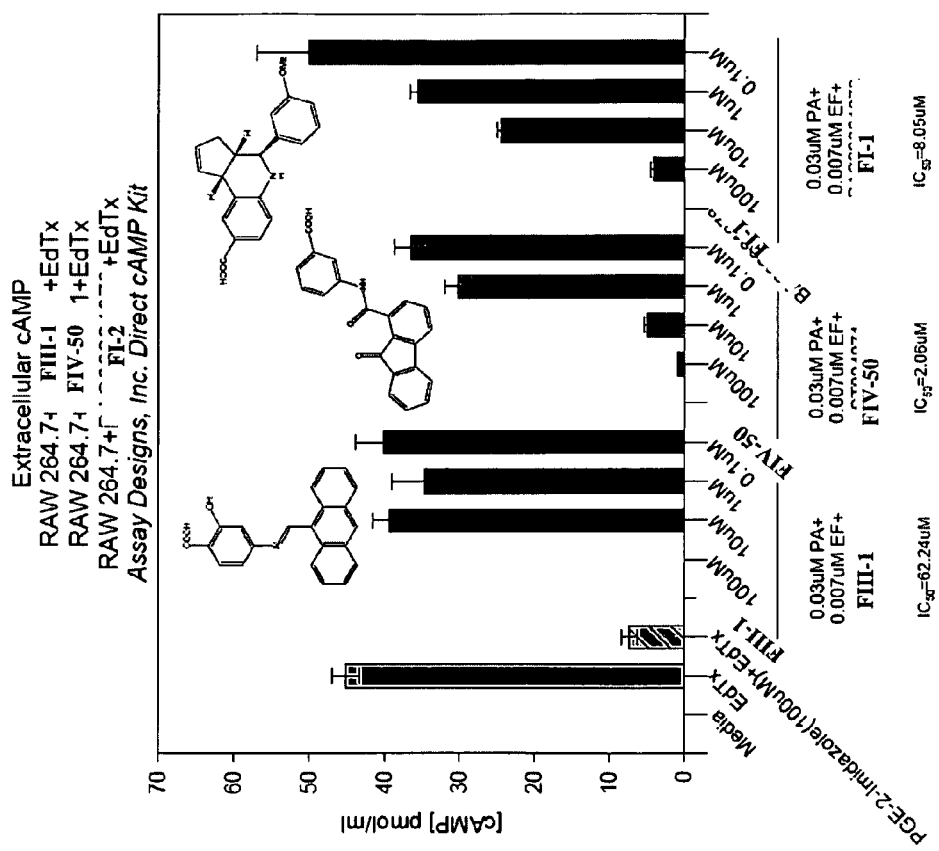

FIG. 30 is an extracellular cAMP assay with EF comparing FIII-1, FIV-50, and FII-1.

Figure 31:
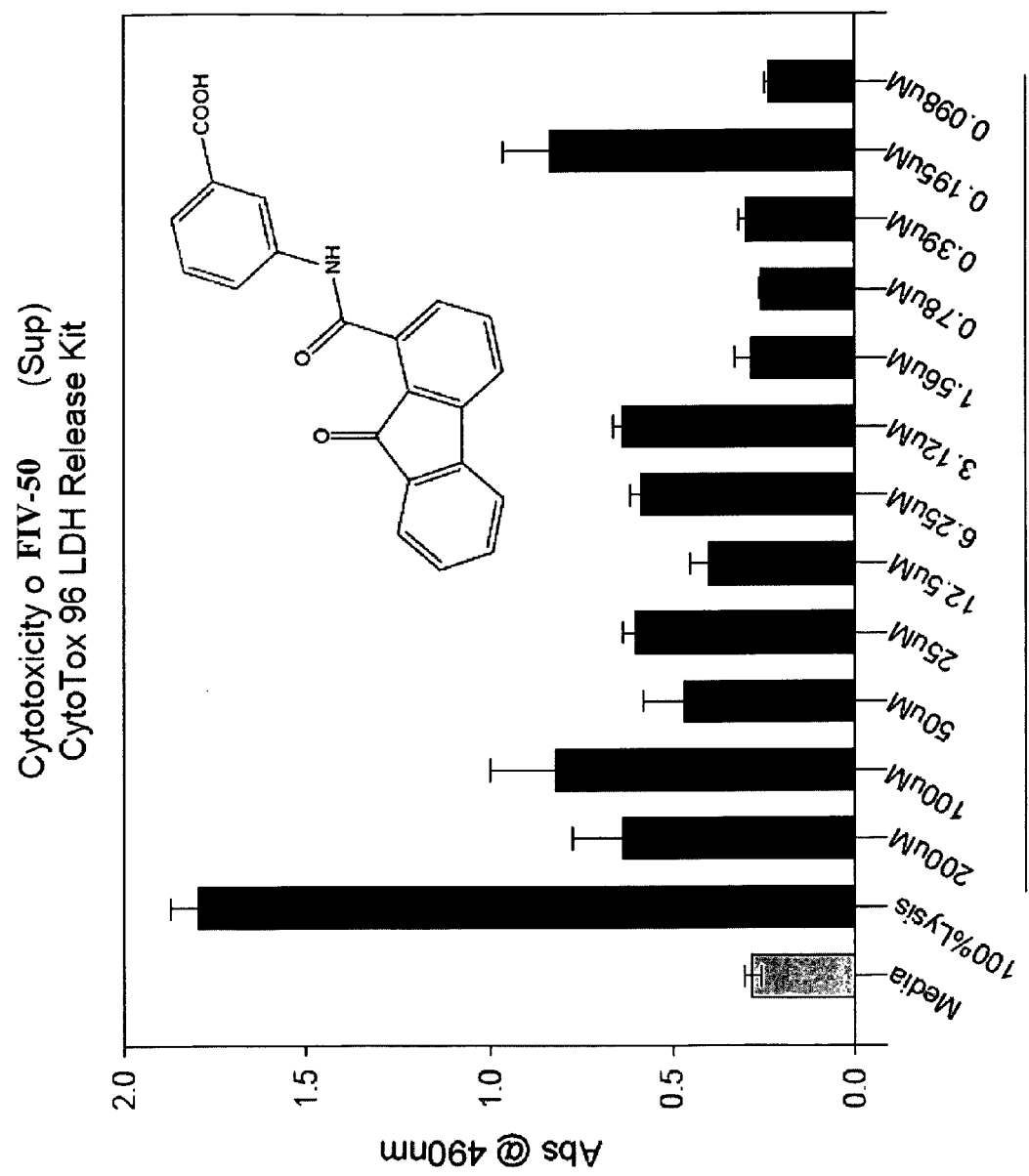

FIG. 31 is a LDH cytotoxicity assay for FIV-50.

Figure 32:
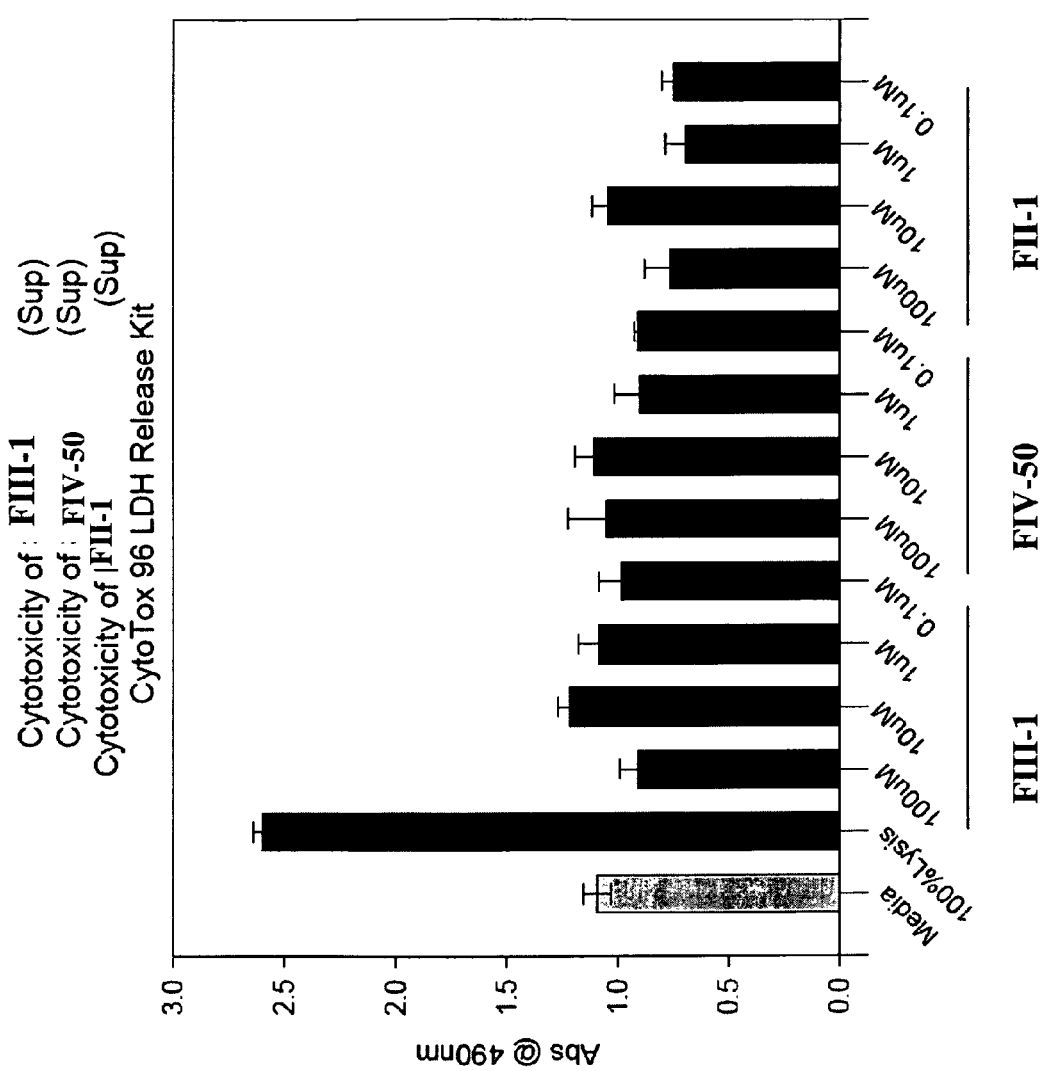

FIG. 32 is a LDH cytotoxicity assay for FIII-1, FIV-50, and FII-1.

Figure 33:
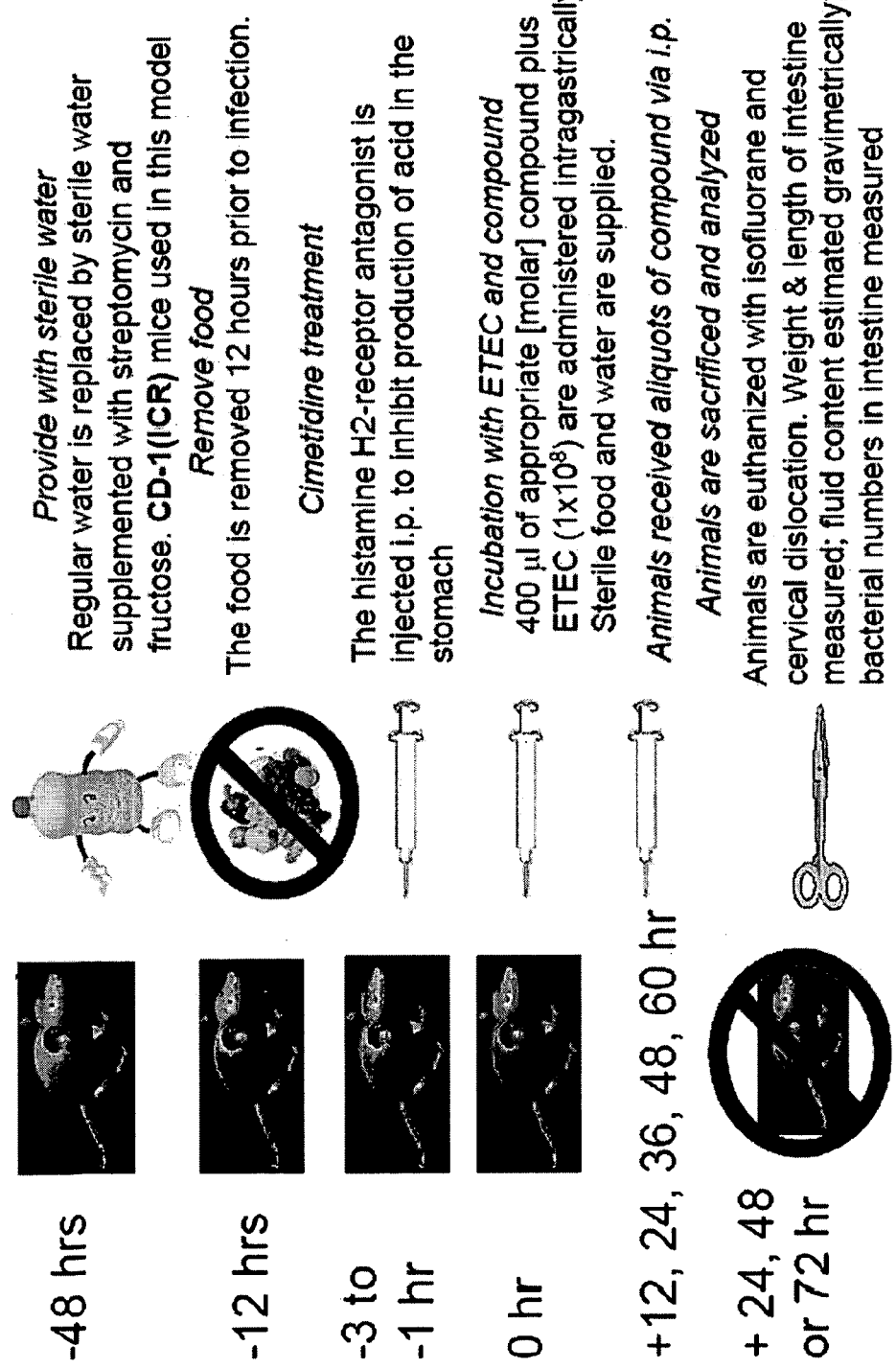

FIG. 33 is a schematic for the methods used in the mouse ETEC model experiments.

Figure 34:
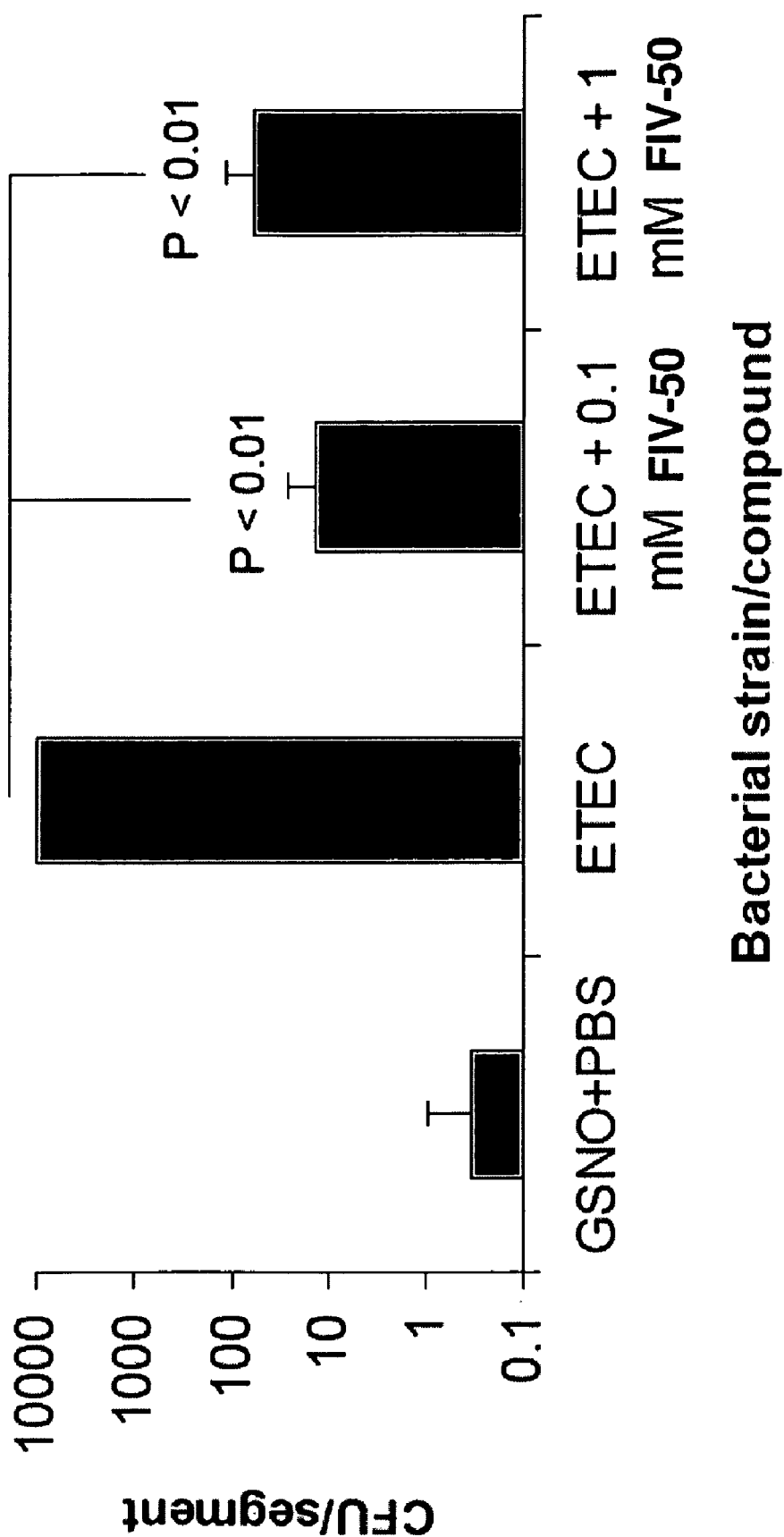

FIG. 34 shows CFU/segment given a specific dose of FIV-50 in the ETEC murine model.

Figure 35:
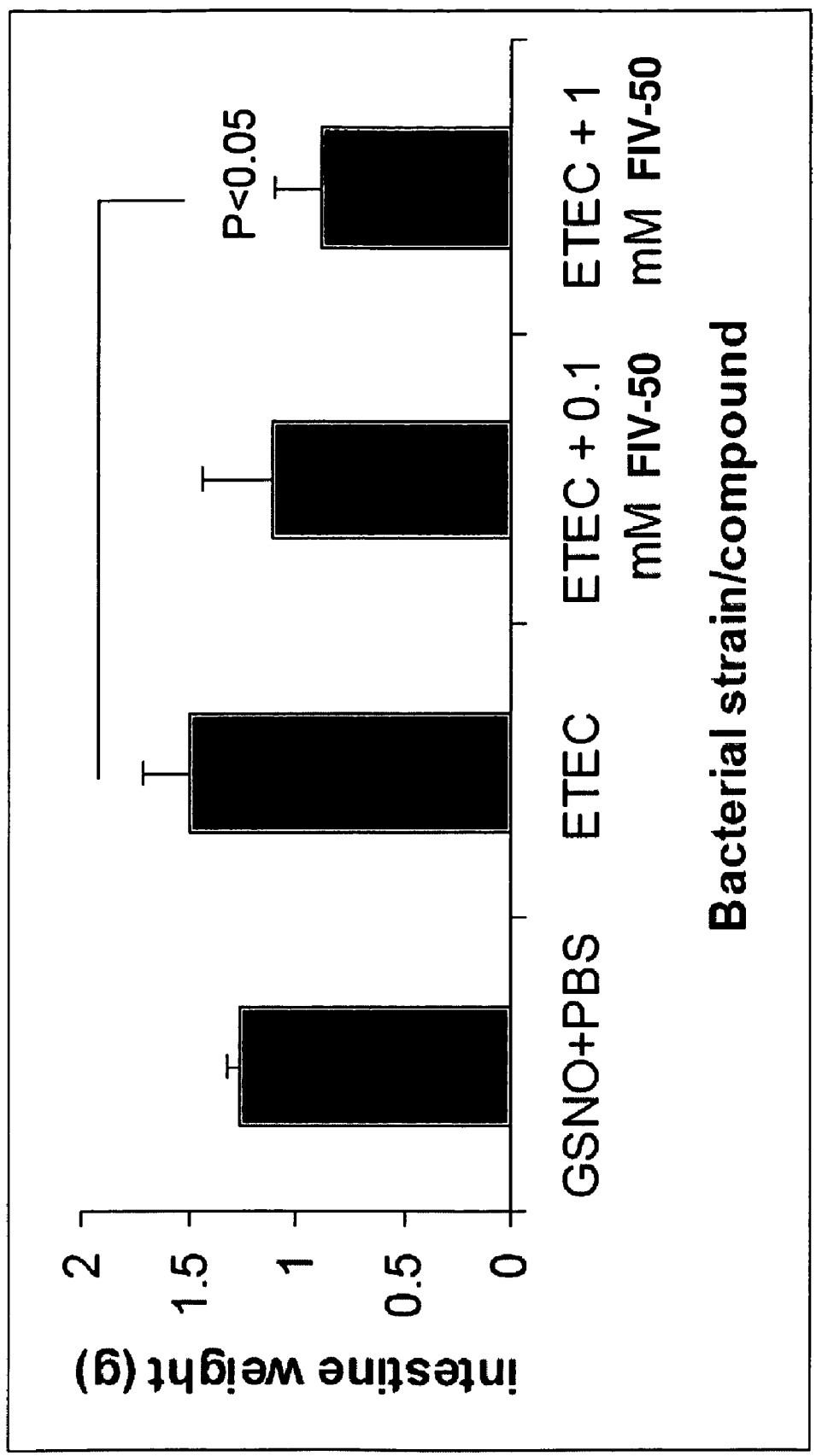

FIG. 35 demonstrates the intestinal weight given FIV-50 doses in the ETEC murine model.

Figure 36:
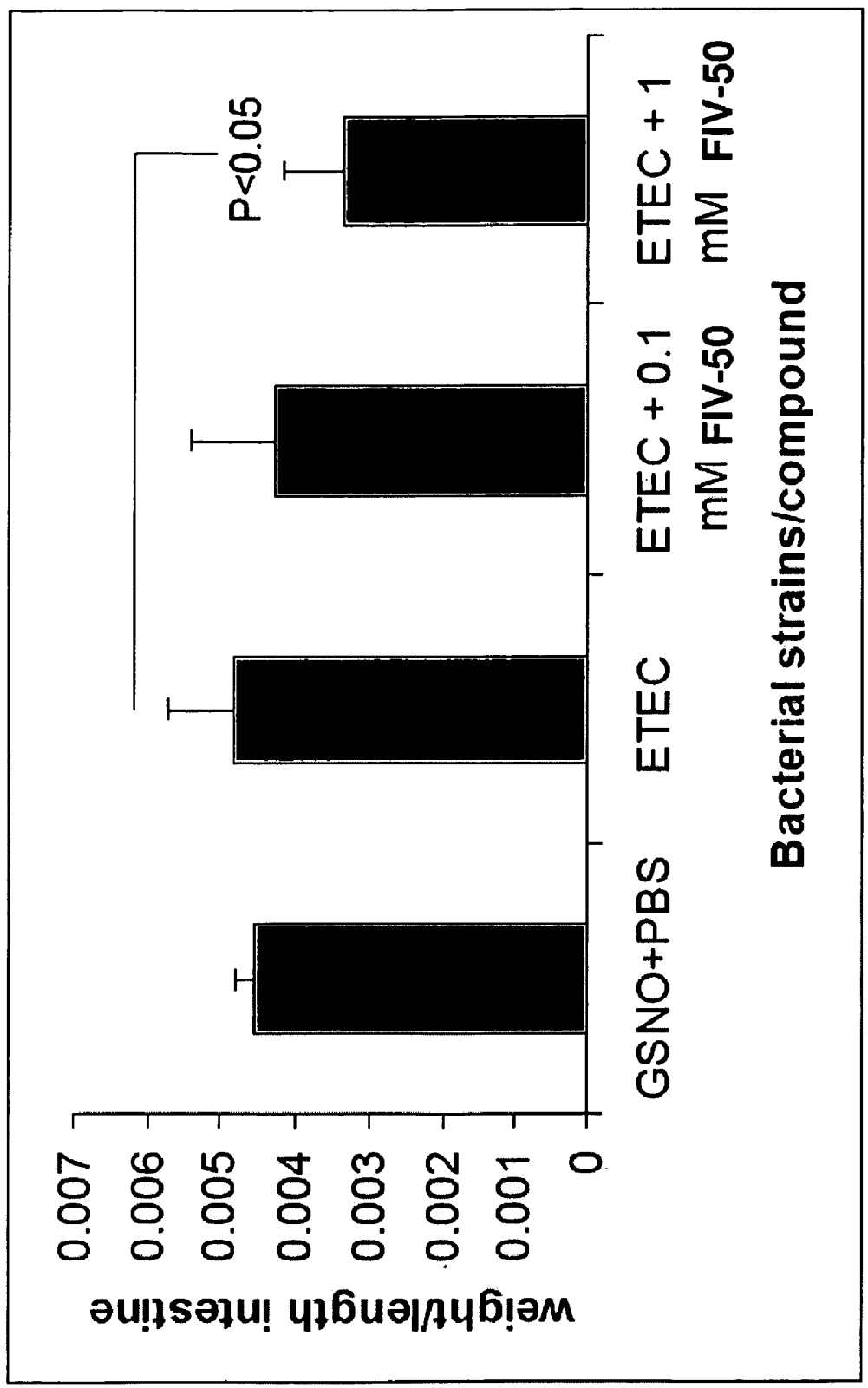

FIG. 36 shows the ratio of the weight and length given the FIV-50 dose in the ETEC murine model.

Figure 37:
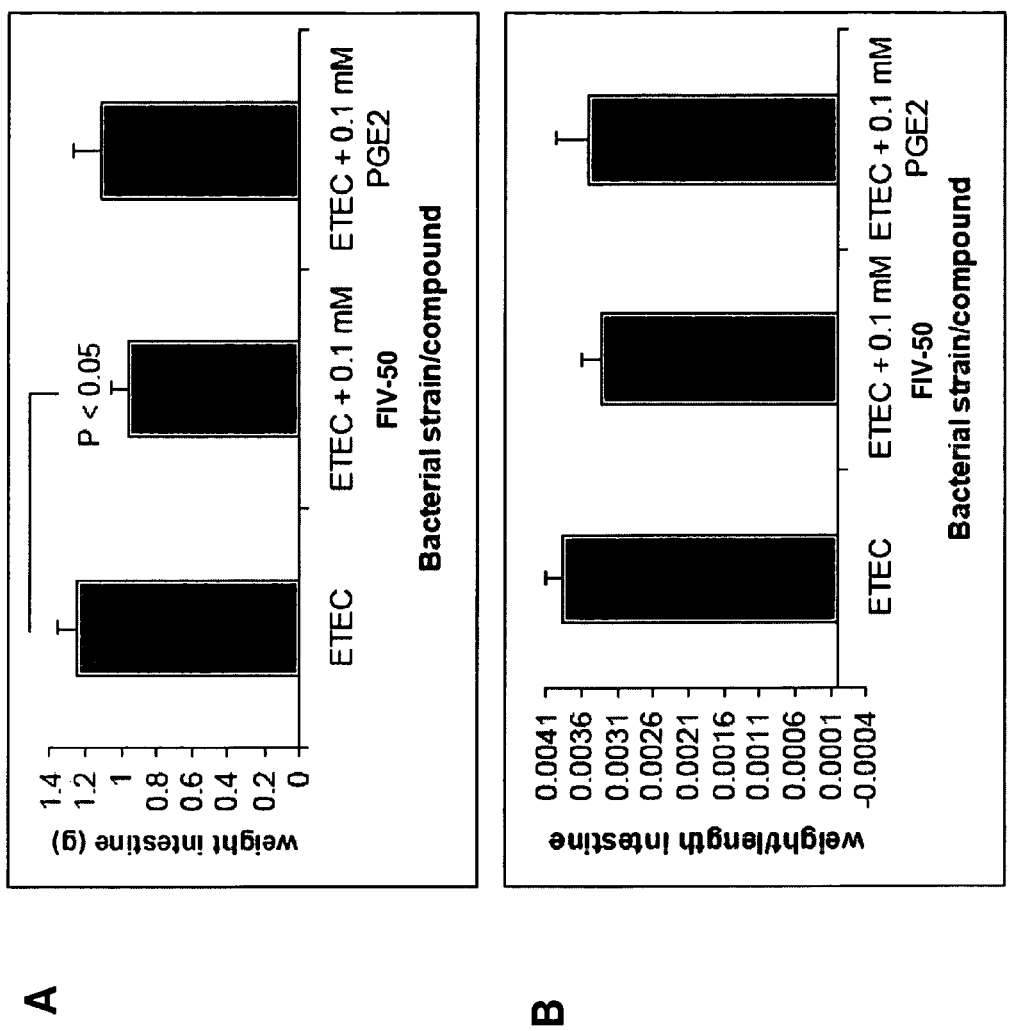

FIG. 37 compares treatment in the ETEC murine model of $PGE_2$-imidazole and FIV-50. FIG. 37A is the intestinal weight. FIG. 37B is the ratio of weight to length.

Figure 38:
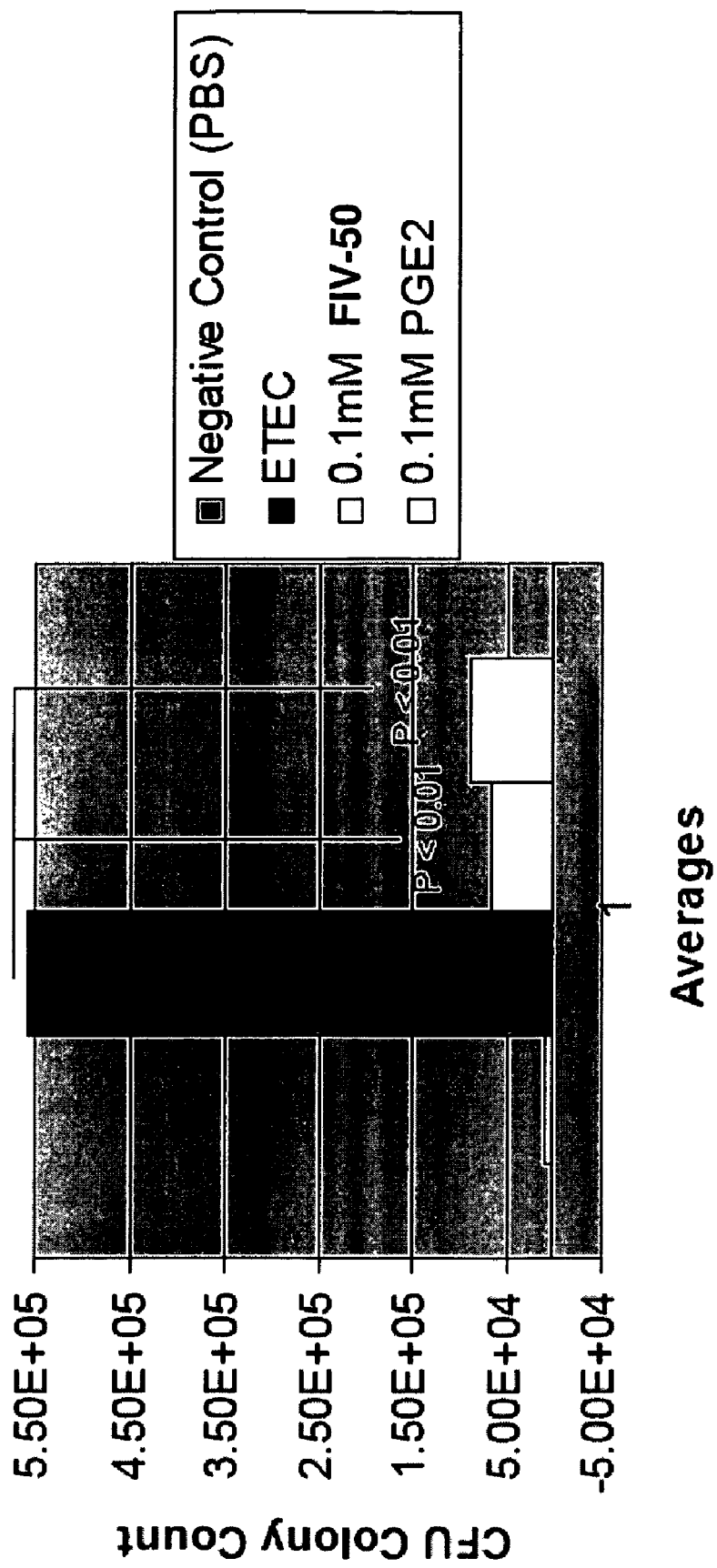

FIG. 38 shows the bacterial count in the ETEC murine model given different dosages of FIV-50.

Figure 39:
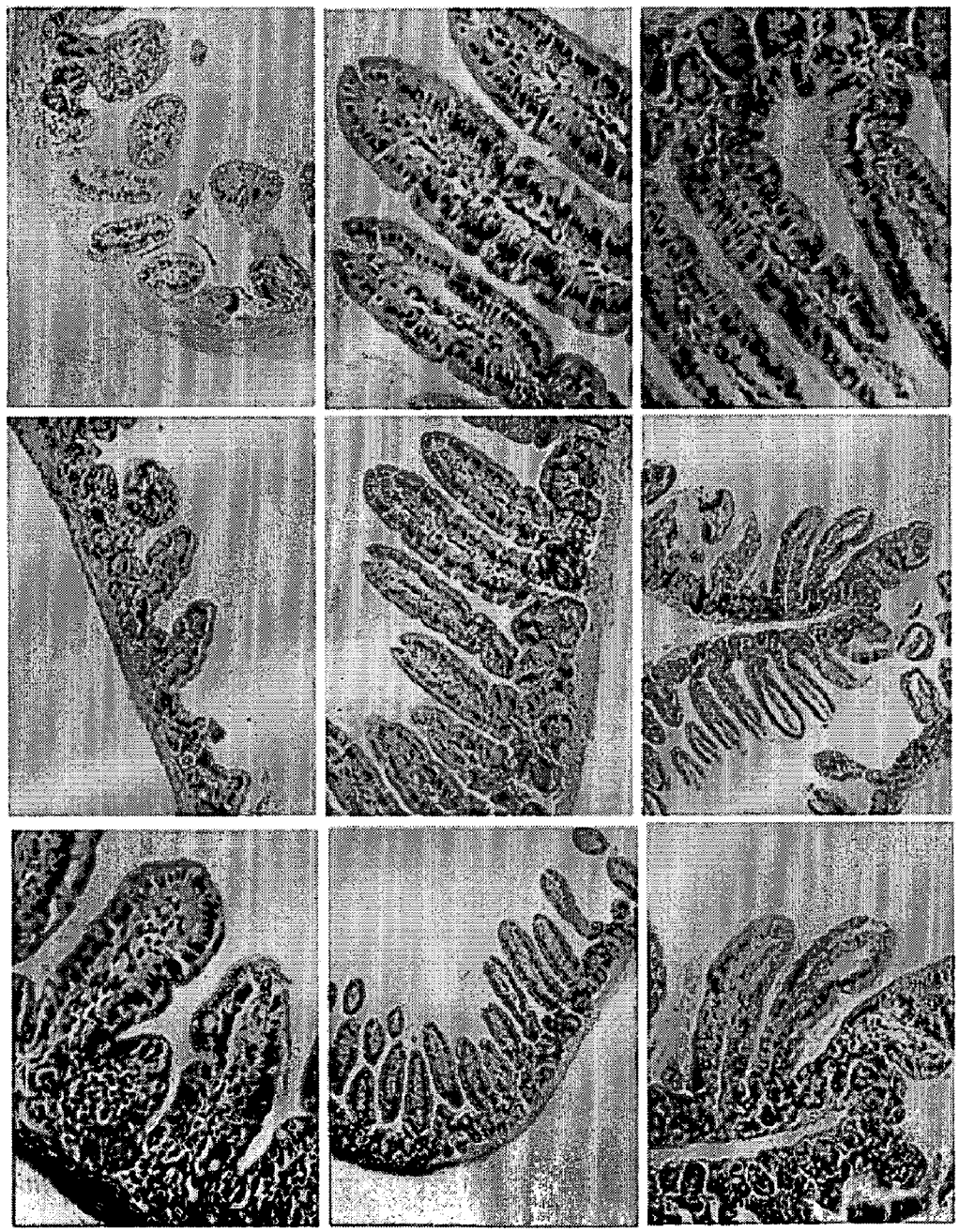

FIG. 39 shows the histology of the murine intestines given the ETEC model and treatment with FIV-50 or $PGE_2$-imidazole.

Figure 40:
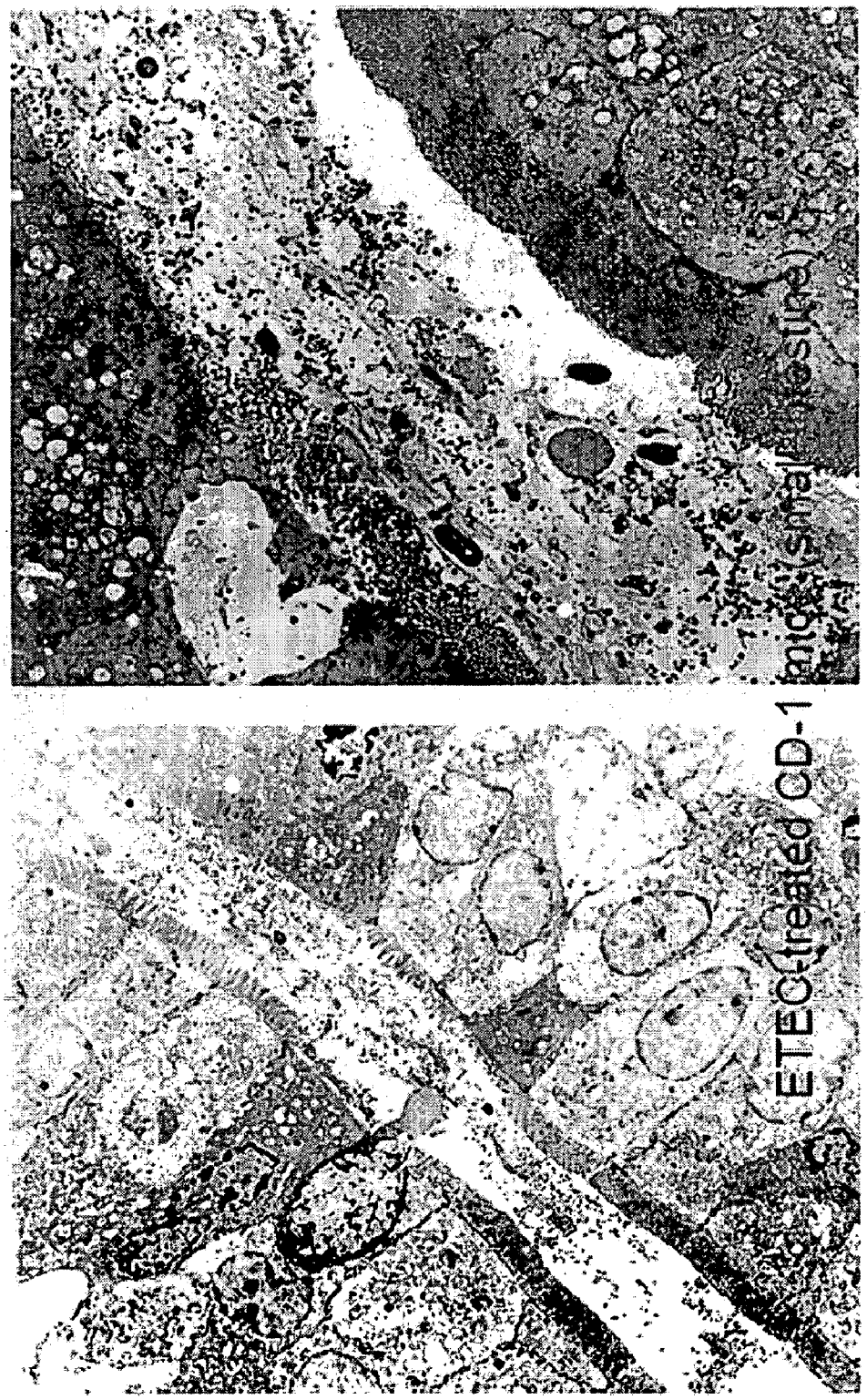

FIG. 40 shows electron microscopy of the CD-1 mouse intestine with $PGE_2$-imidazole treatment.

Figure 41:
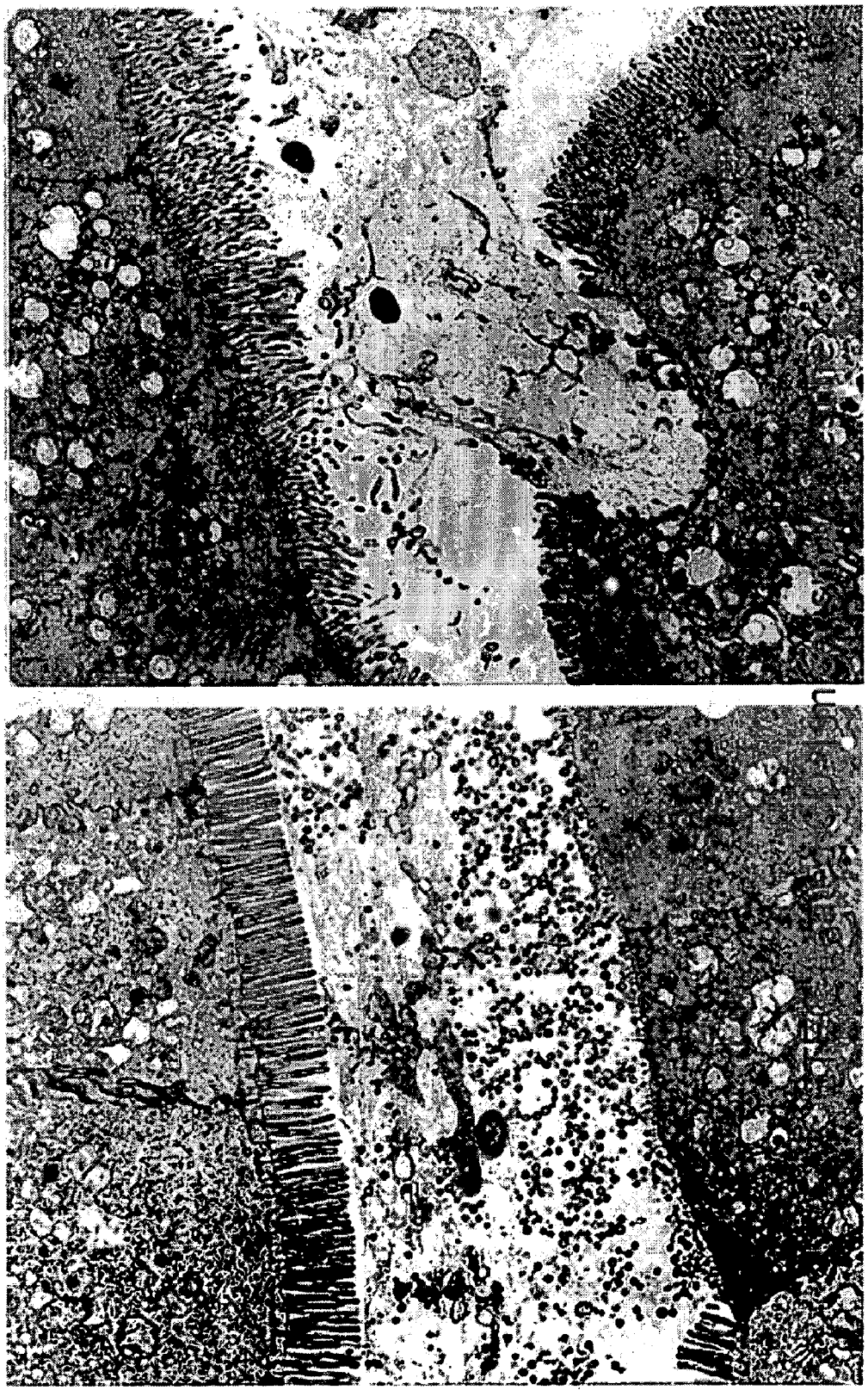

FIG. 41 shows 32,000× electron microscopy of the CD-1 mouse intestine with $PGE_2$-imidazole treatment.

Figure 42:
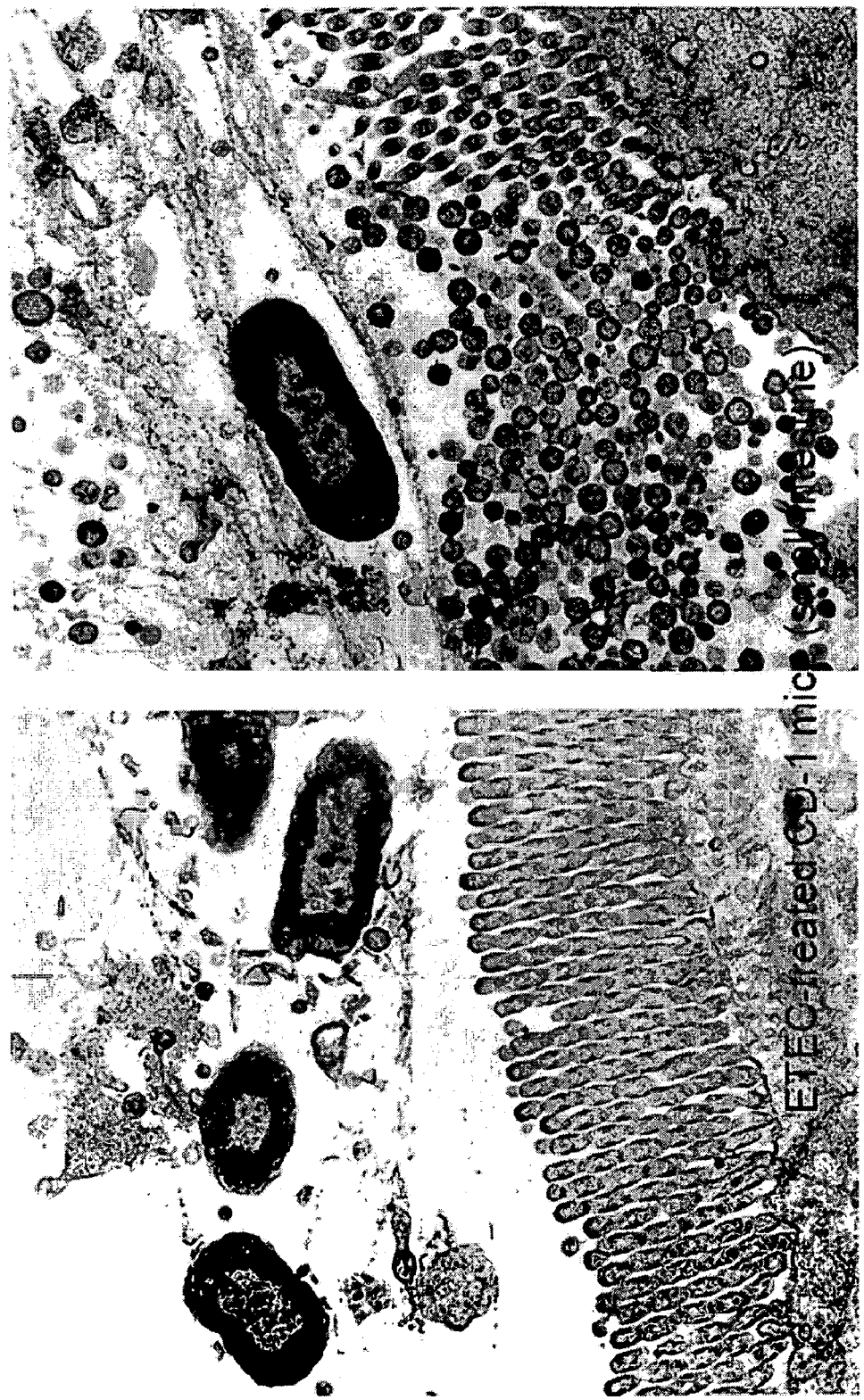

FIG. 42 shows 64,000× electron microscopy of the CD-1 mouse intestine with $PGE_2$-imidazole treatment.

Figure 43:

FIG. 43 shows electron microscopy of the CD-1 mouse intestine with $PGE_2$-imidazole treatment.

Figure 44:
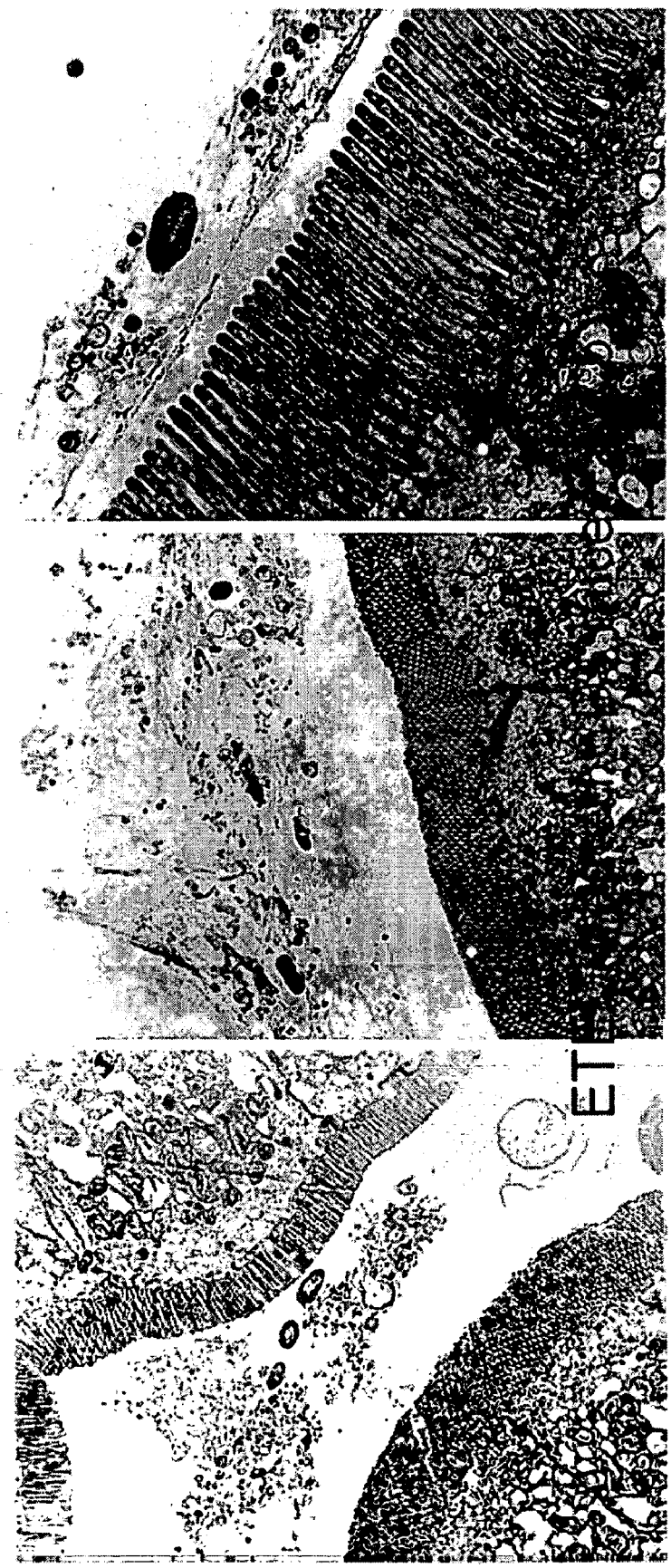

FIG. 44 shows electron microscopy of the CD-1 mouse intestine with FIV-50 treatment.

Figure 45:
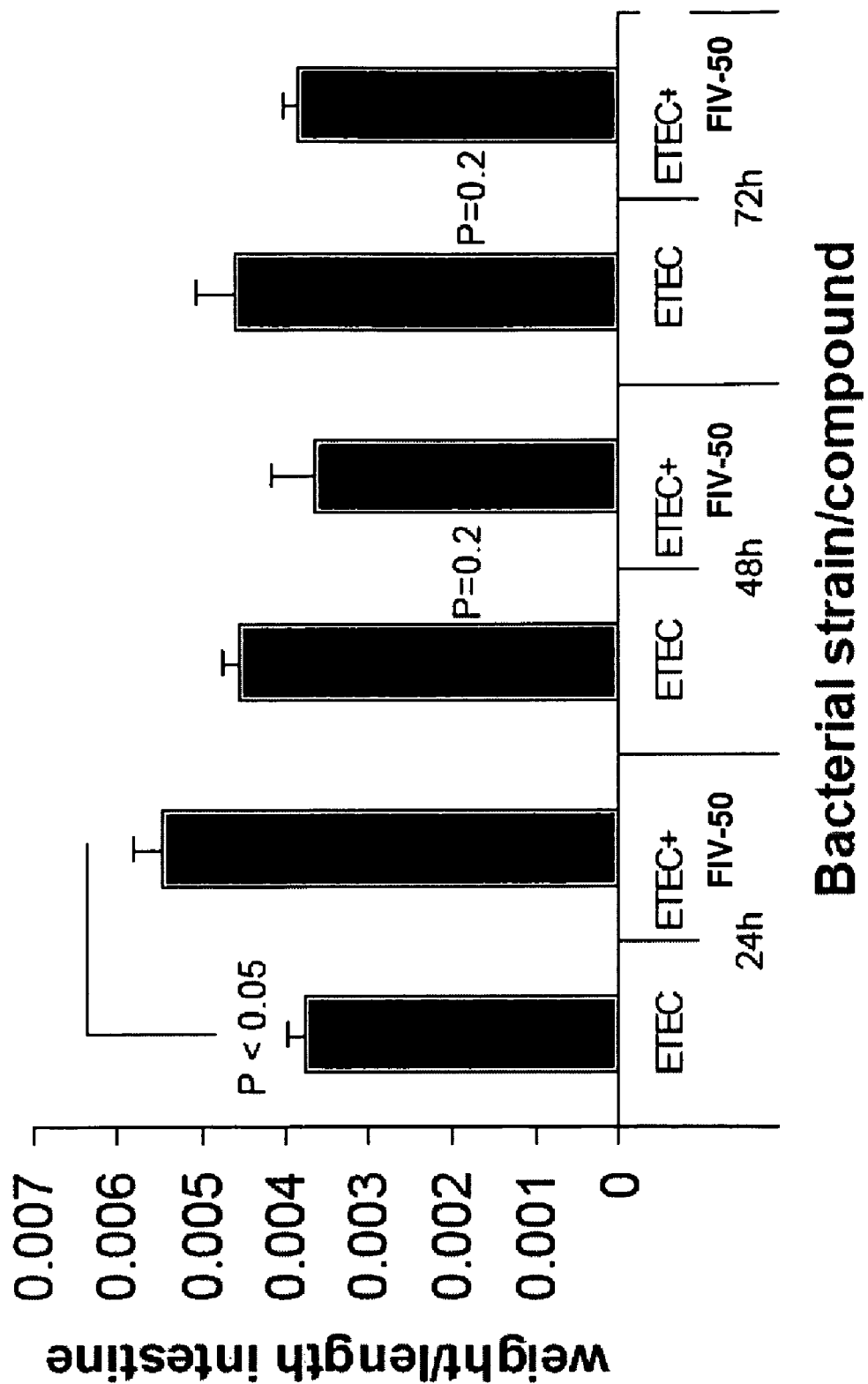

FIG. 45 shows weight/length in a time course of FIV-50 treated mice.

FIG. 46 demonstrates bacterial counts in the intestine of the treated mice.

Figure 47:
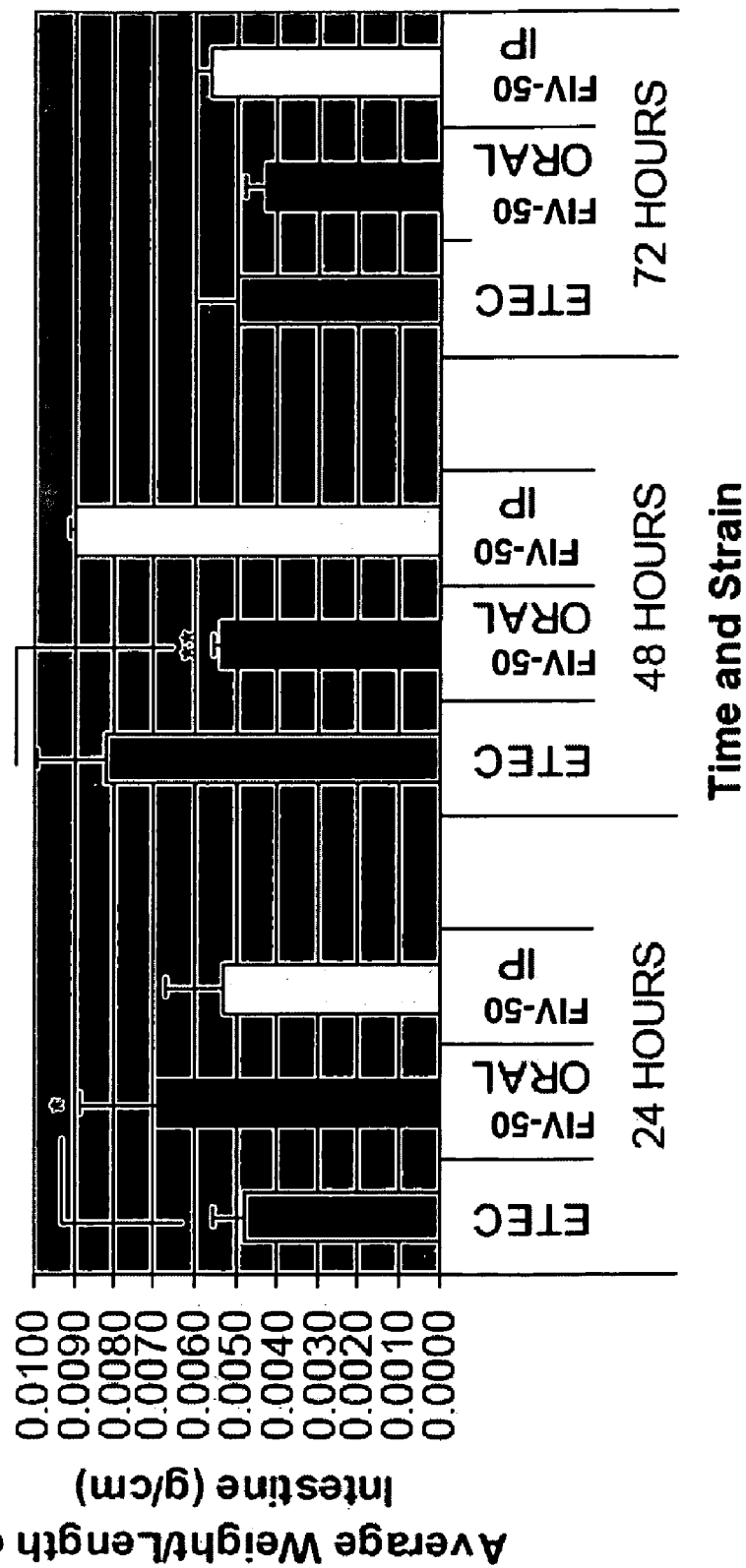

FIG. 47 is the average weight/length of the intestine of oral vs. i.p. FIV-50 initial dose treated mice.

Figure 48:
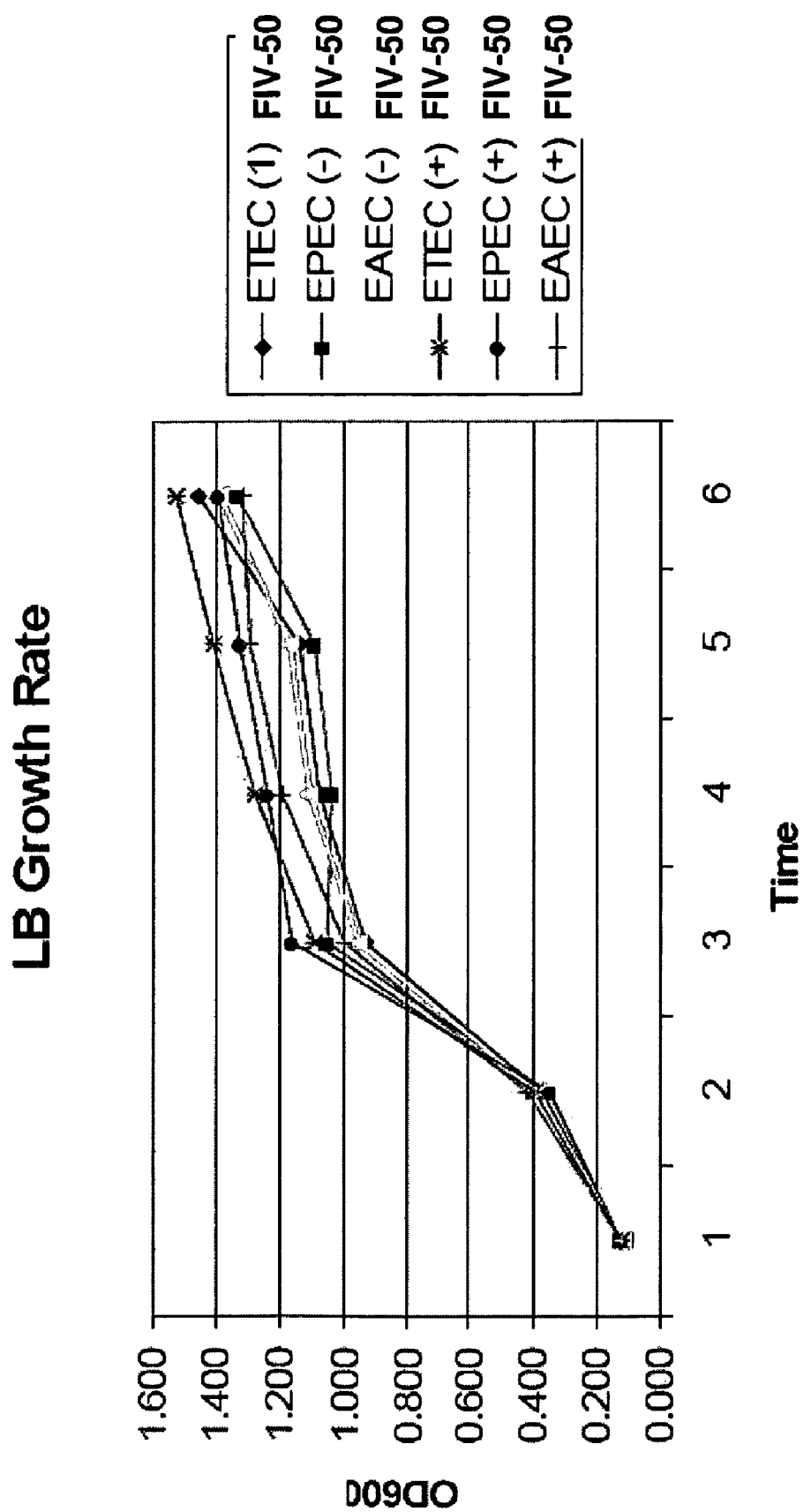

FIG. 48 shows the bacterial count in the mice intestine (ETEC: enterotoxigenic *E. coli*; EPEC: enteropathogenic *E. coli*; EAEC: enteroaggregative *E. coli*).

Figure 49:
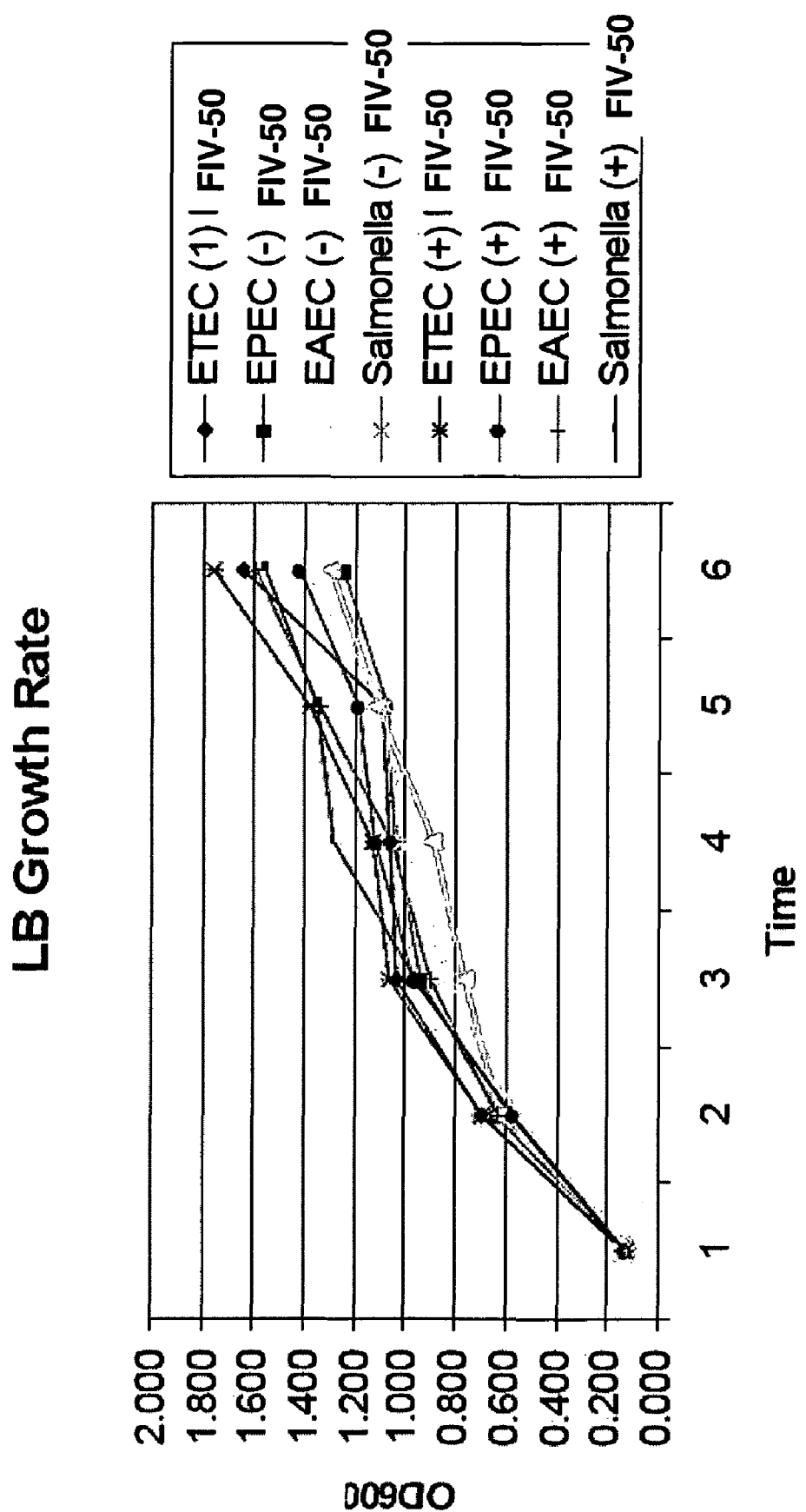

FIG. 49 demonstrates Bacterial growth rate in LB +/−FIV-50 (Additional strains).

Figure 50:
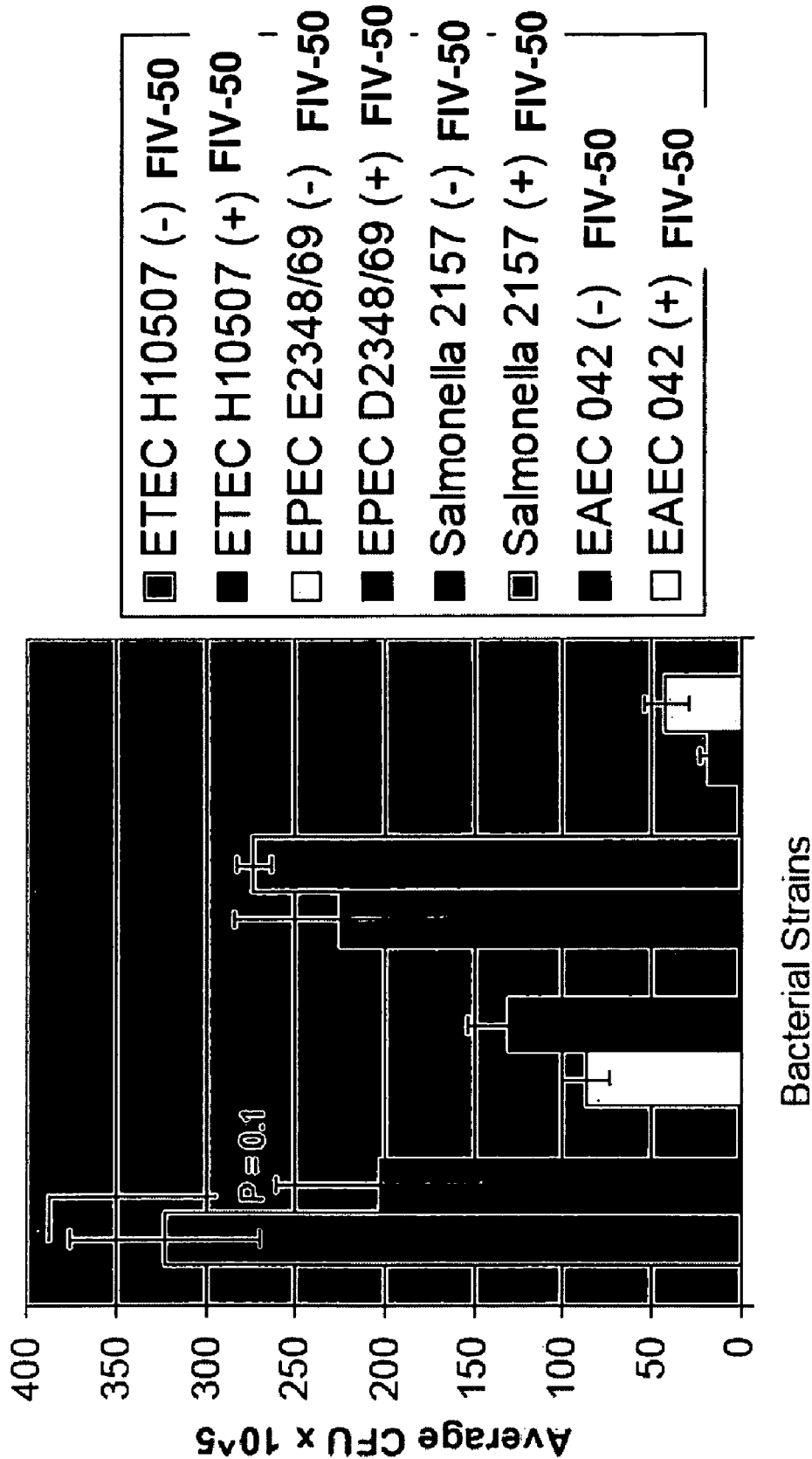

FIG. 50 shows the effect of FIV-50 on bacterial adhesion to HeLa cells (ETEC: enterotoxigenic *E. coli*; EPEC: enteropathogenic *E. coli*; EAEC: enteroaggregative *E. coli, S. typhimurium*).

Figure 51:
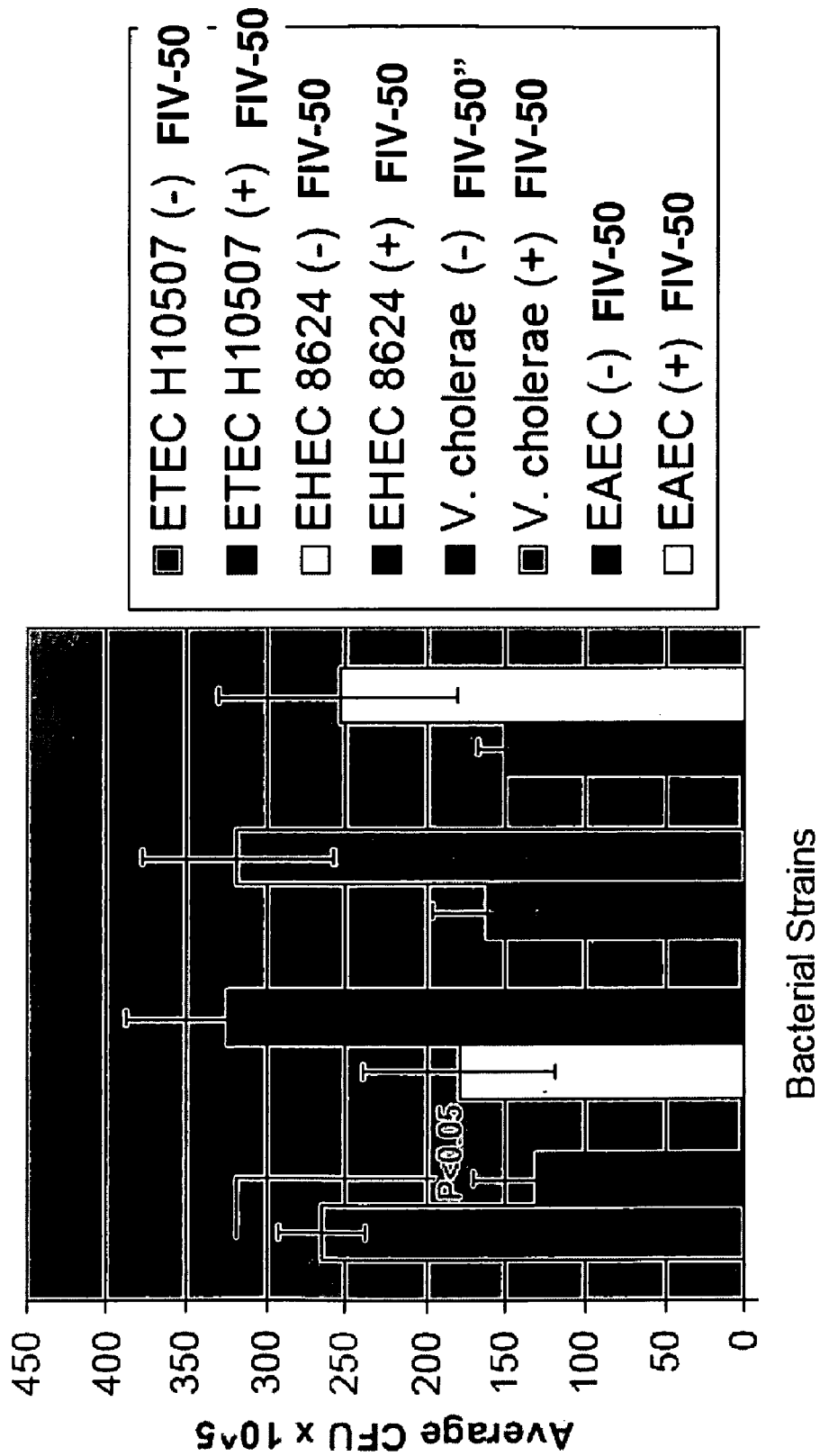

FIG. 51 shows the effect of FIV-50 on bacterial adhesion to HeLa cells (ETEC: enterotoxigenic *E. coli*; EHEC: enterohemorrhagic *E. coli*; EAEC: enteroaggregative *E. coli*, Vibriocholerae).

Figure 52:
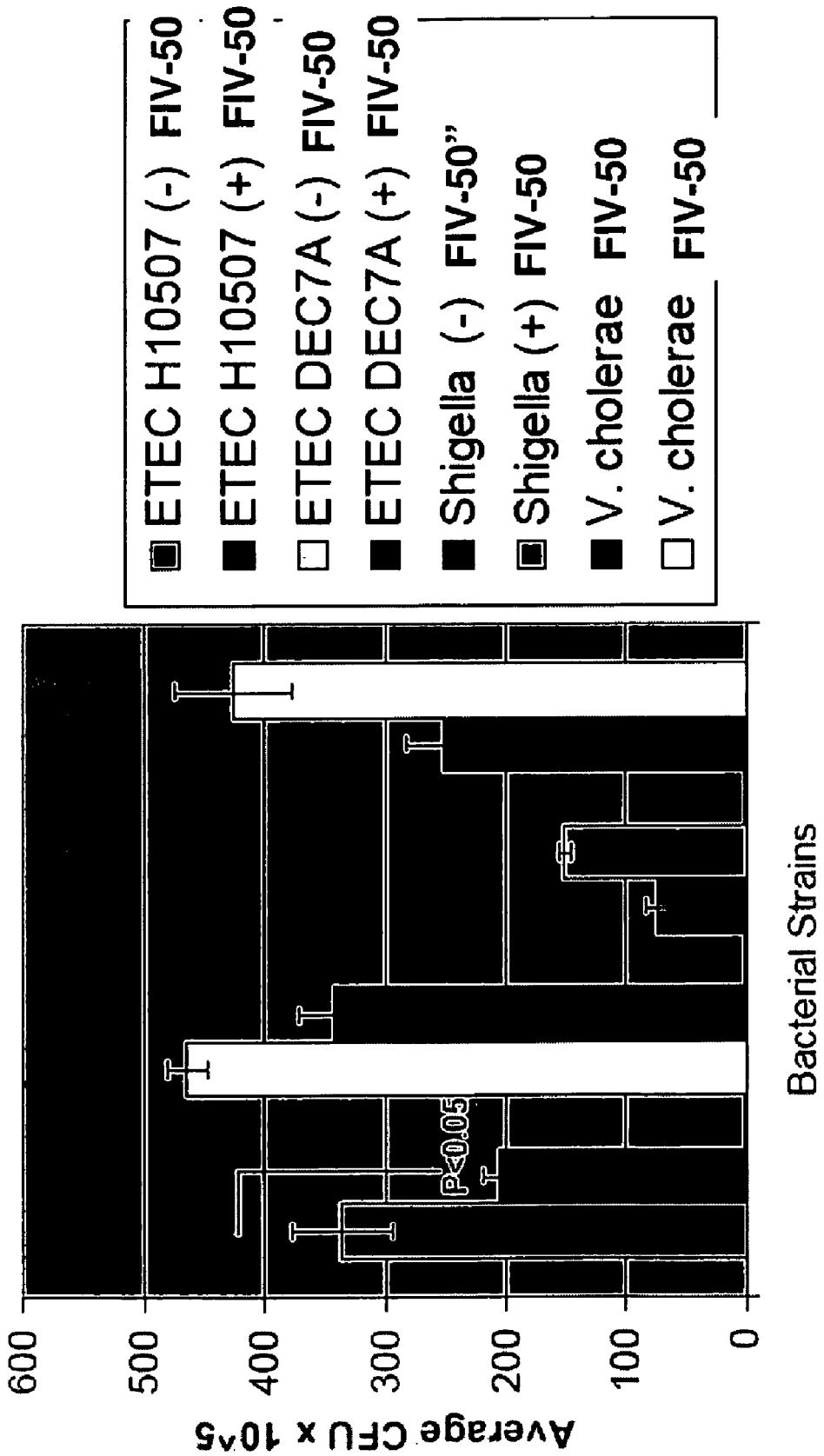

FIG. 52 shows the effect of FIV-50 on bacterial adhesion to HeLa cells (ETEC: enterotoxigenic *E. coli*; Vibriocholerae; *Shigella flexneri*).

Figure 53:
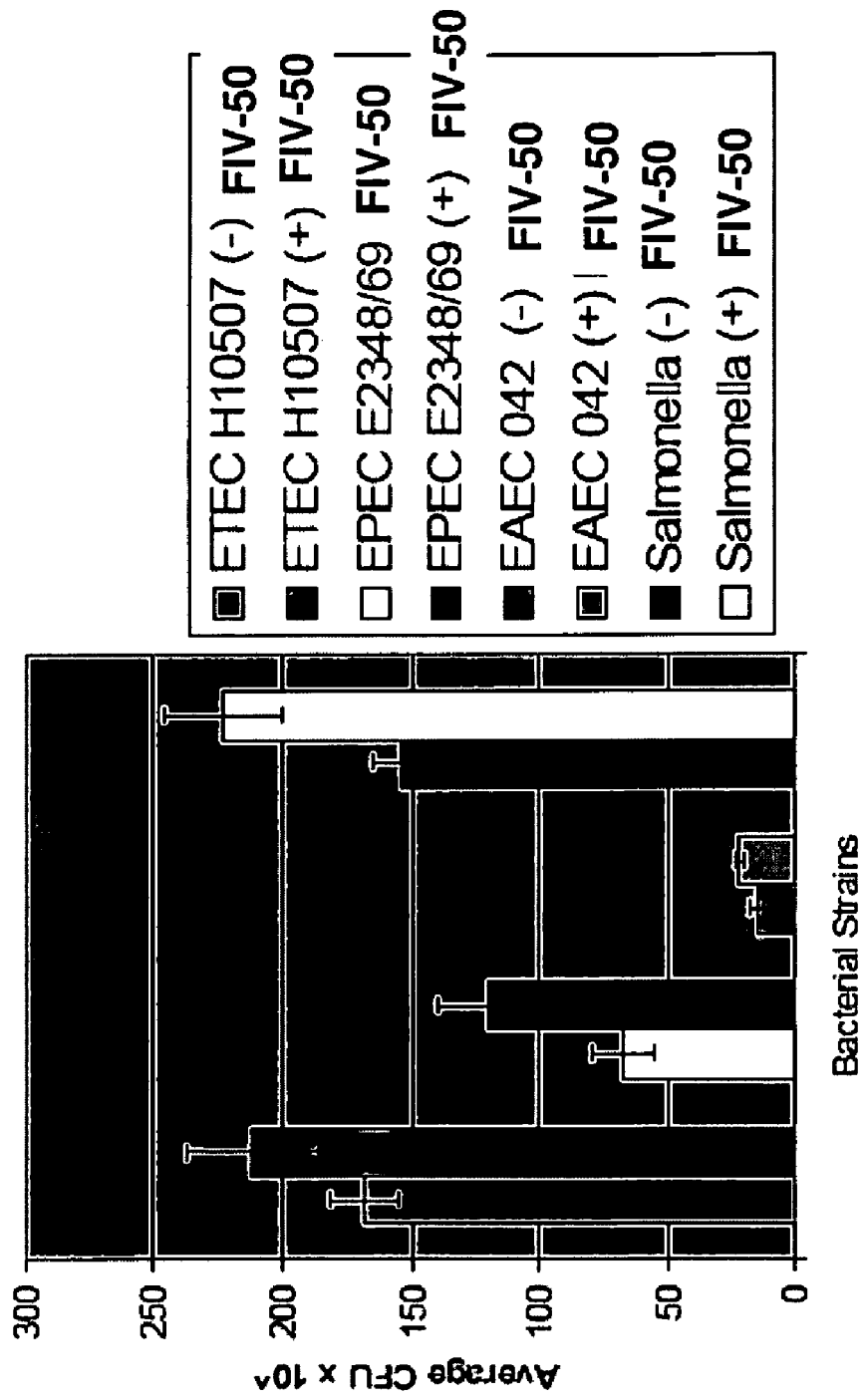

FIG. 53 demonstrates the effect of FIV-50 on bacterial adhesion to Caco-2 cells (ETEC: enterotoxigenic *E. coli*; EPEC: enteropathogenic *E. coli*; EAEC: enteroaggregative *E. coli, Salmonella typhimurium*).

Figure 54:
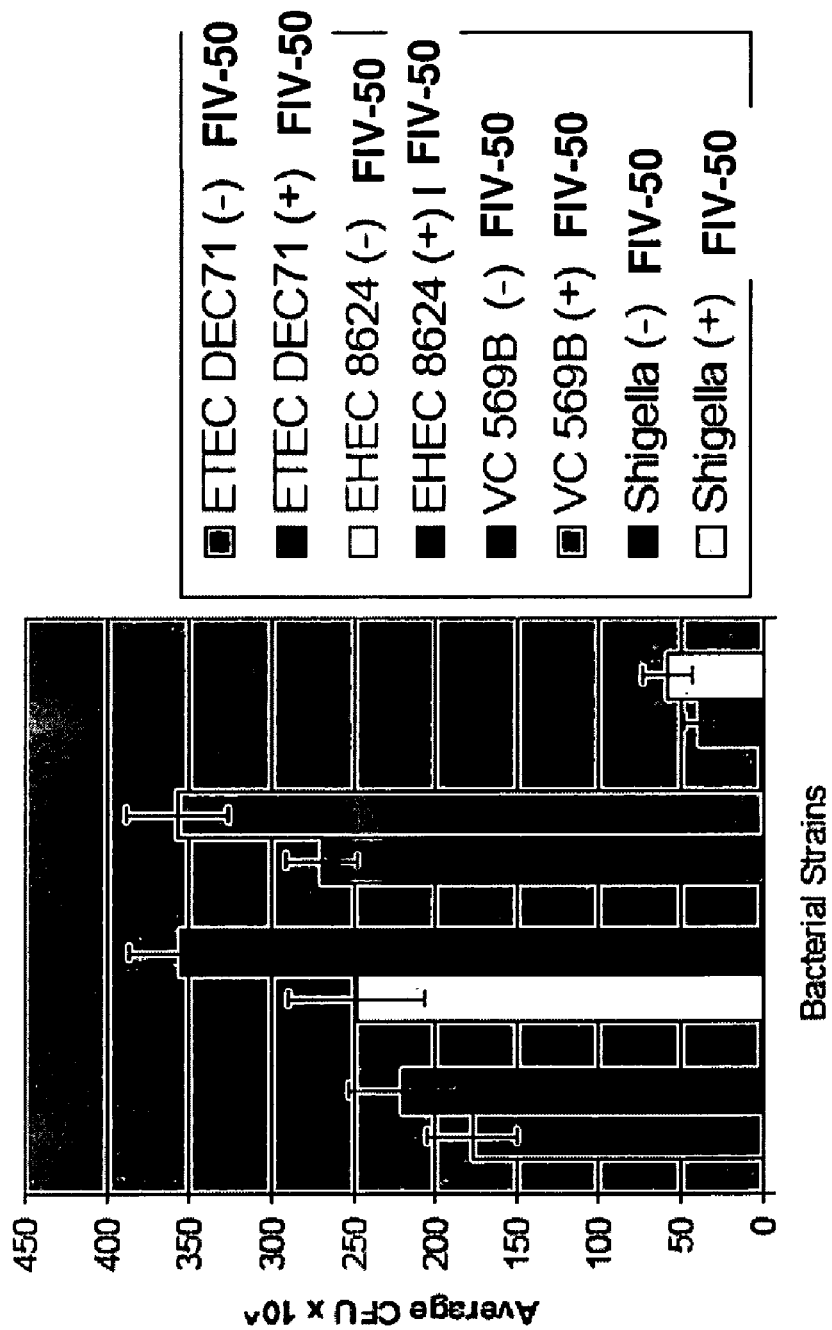

FIG. 54 shows the effect of FIV-50 on bacterial adhesion to Caco-2 cells (ETEC: enterotoxigenic *E. coli*; EHEC: enterohemorrhagic *E. coli*; Vibriocholerae, *Shigella flexneri*).

Figure 55:
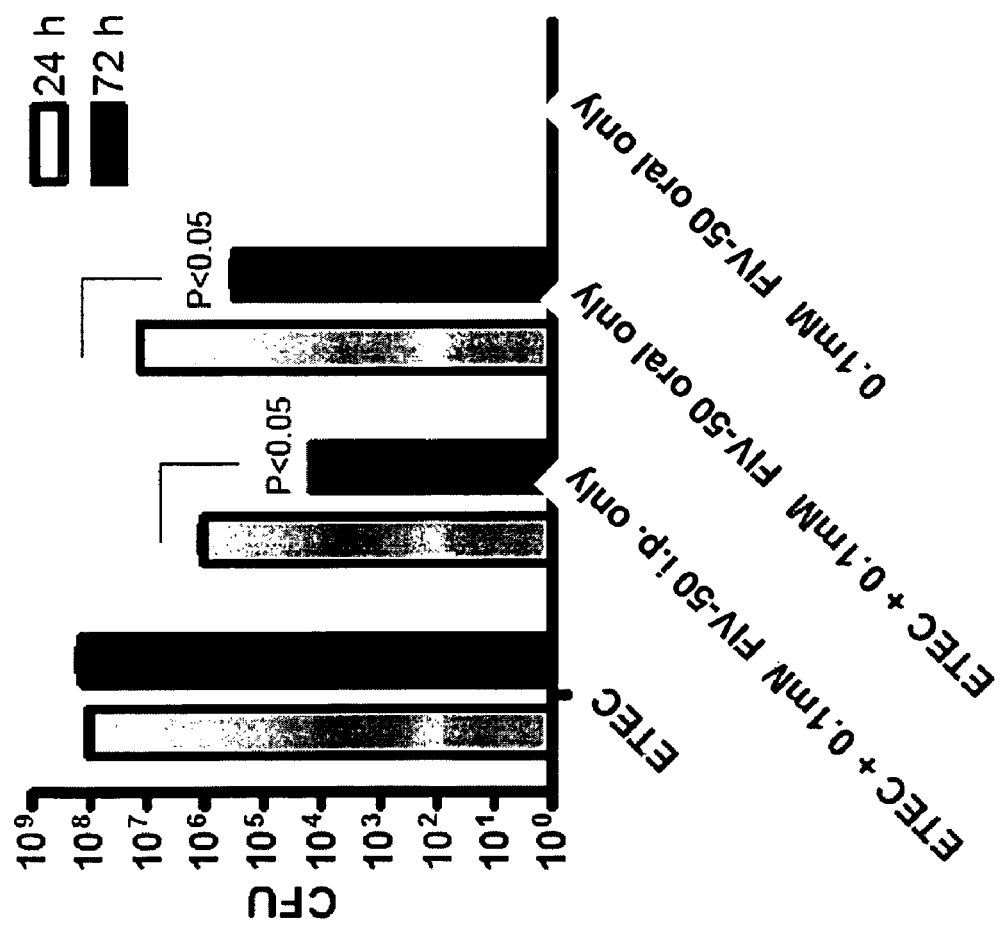

FIG. 55 shows bacterial counts in mice infected with ETEC.

Figure 56:
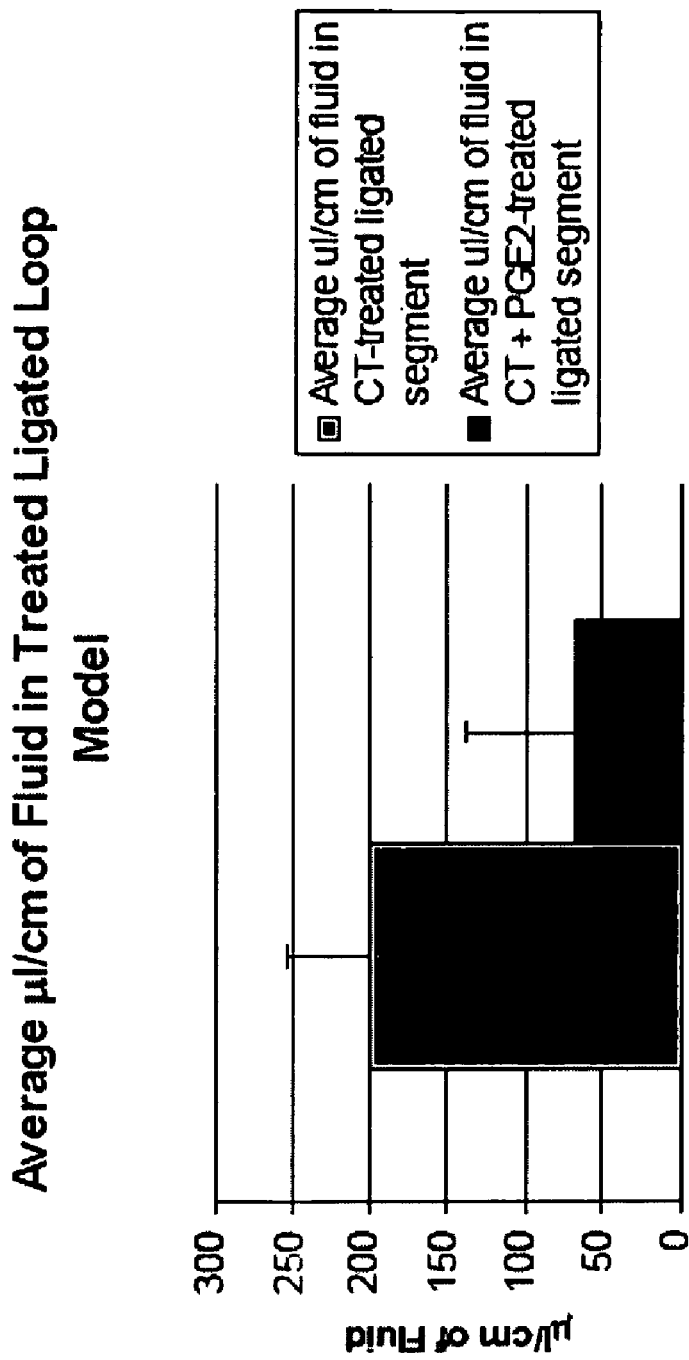

FIG. 56 demonstrates the effect of $PGE_2$-imidazole on mouse intestinal fluid loss during experimental infection with CT.

Figure 57:
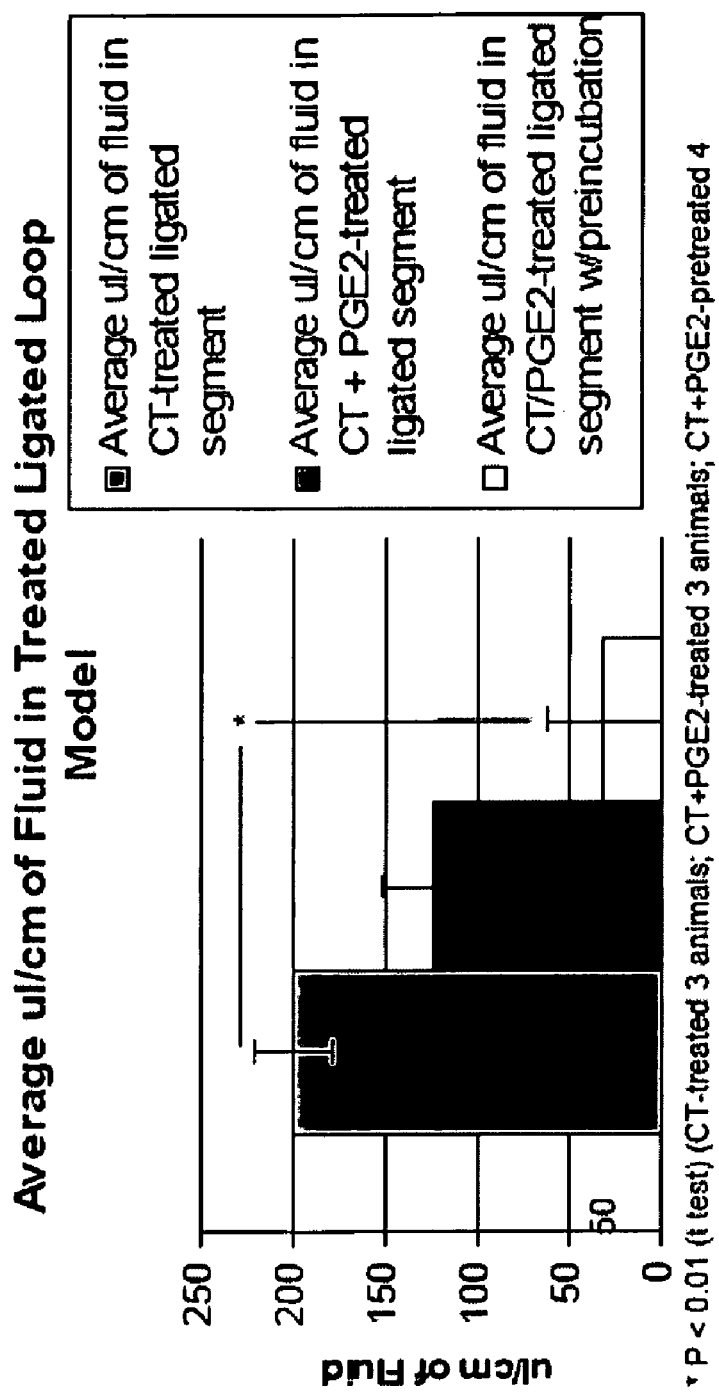

FIG. 57 shows the effect of pre-incubation with $PGE_2$-imidazole on mouse intestinal fluid loss during experimental infection with CT.

Figure 58:
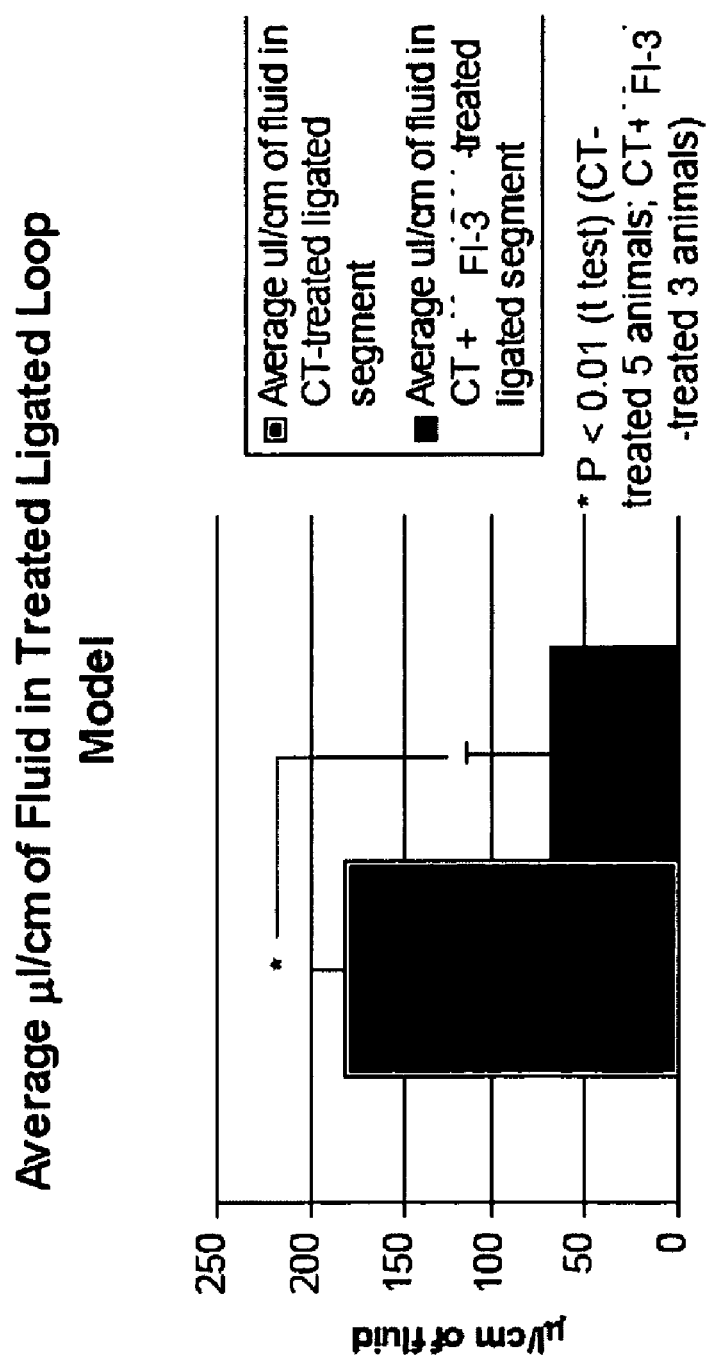

FIG. 58 demonstrates the effect of FI-3 on mouse intestinal fluid loss during experimental infection with CT.

Figure 59:
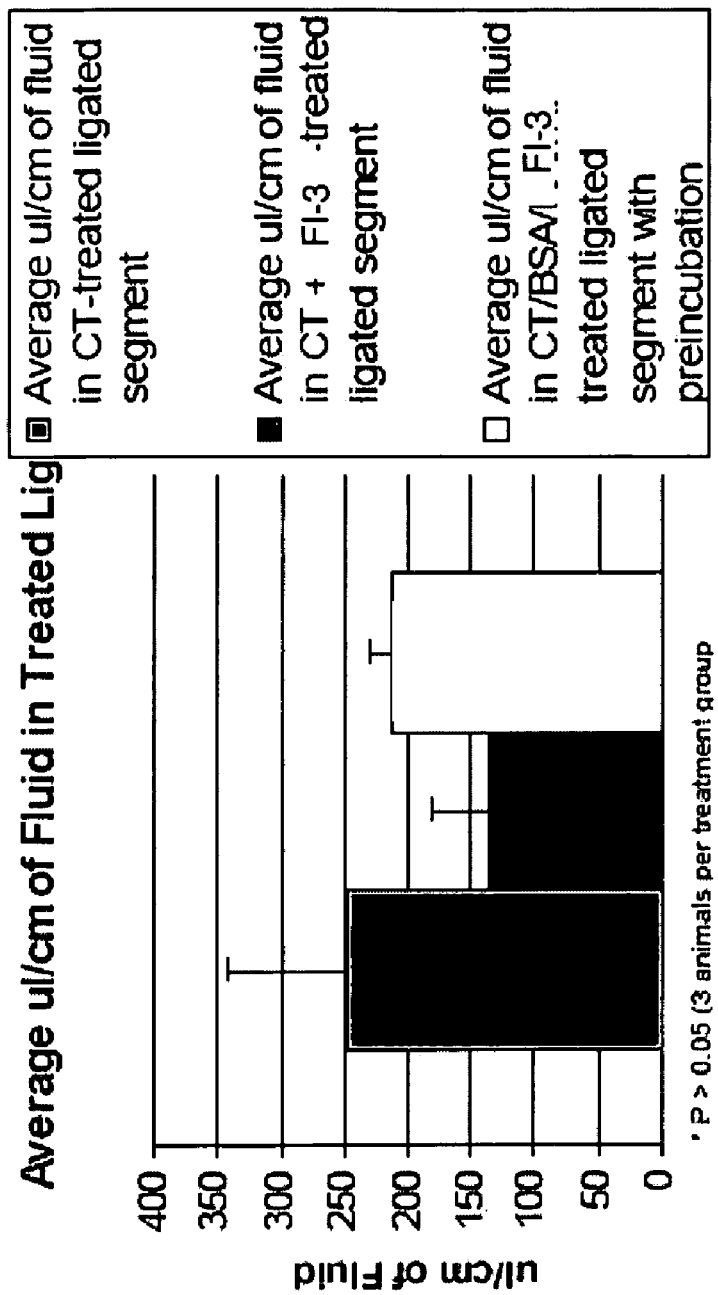

FIG. 59 demonstrates the effect of pre-incubation with FI-3 on mouse intestinal fluid loss during experimental infection with CT.

Figure 60:
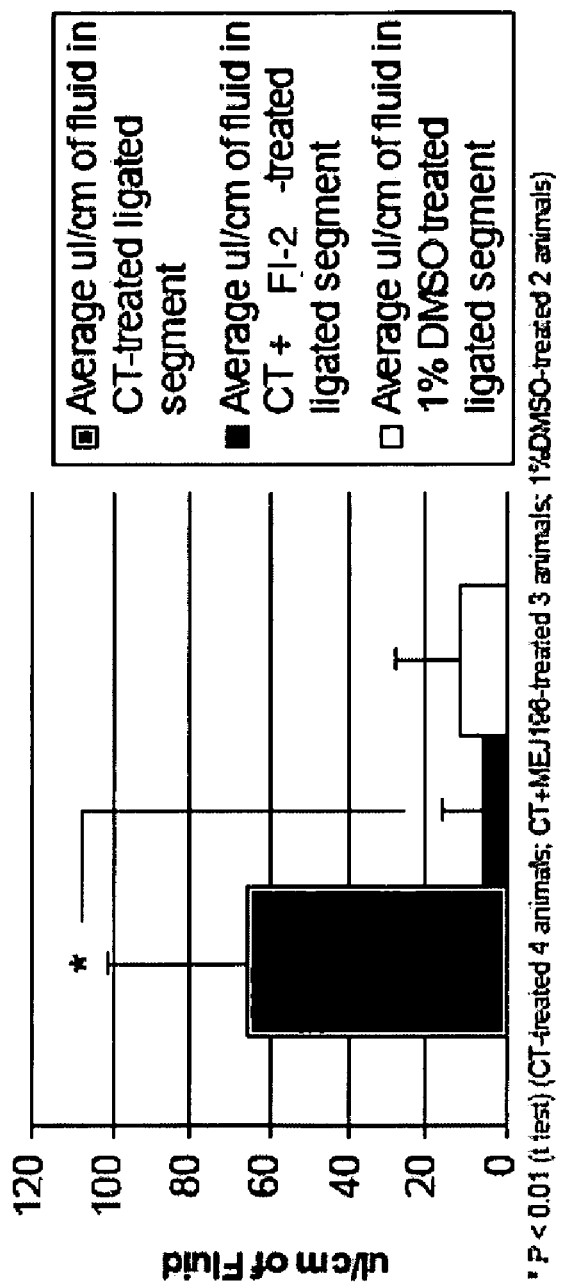

FIG. 60 demonstrates the effect of FI-2 on mouse intestinal fluid loss during experimental infection with CT.

Figure 61:
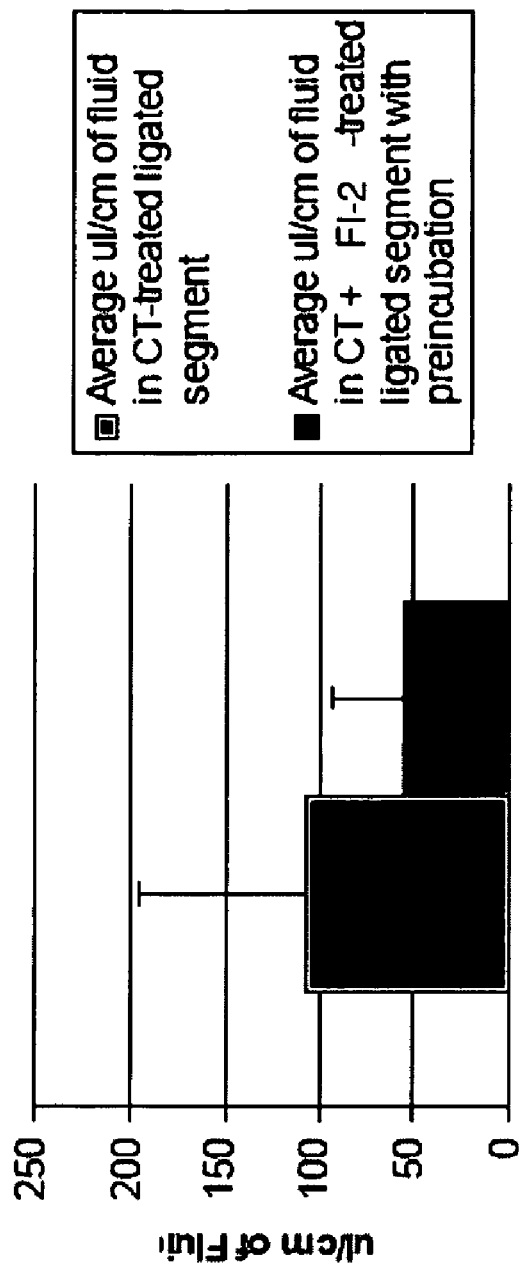

FIG. 61 shows the effect of pre-incubation with FI-2 on mouse intestinal fluid loss during experimental infection with CT.

Figure 62:
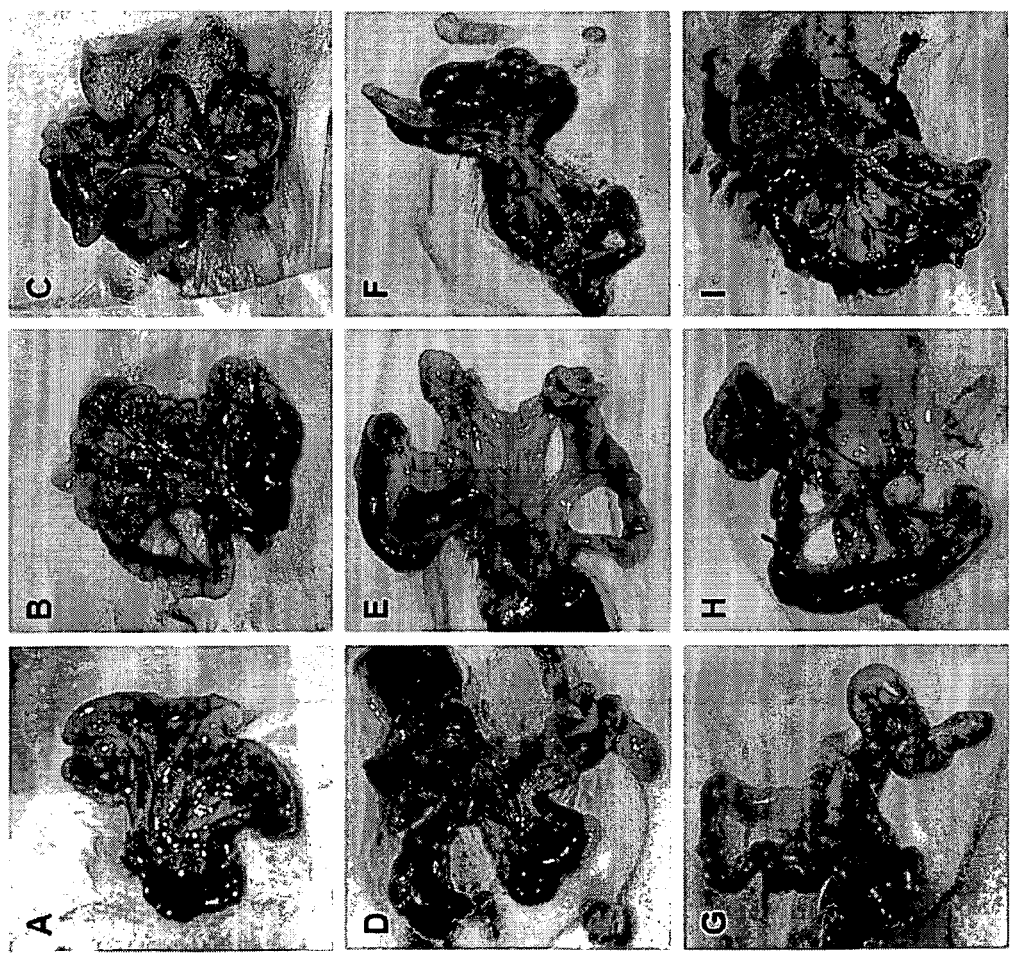

FIG. 62 is a visualization of the intestines of mice pre- and post-treated with FI-2. FIG. 62A is no treatment (prior to surgery); FIG. 62B is a mouse pre-treated with FI-2 i.p. for 4 h; FIG. 62C is FI-2-pre-treated mice post-ligation; FIG. 62D is the 1% DMSO-treated mouse control, 4 h; FIG. 62E is a 1% DMSO-treated mouse control, 7 h; FIG. 62F is a mouse pre-treated with FI-2 i.p. for 5.5 h; FIG. 62G is a mouse pre-treated with FI-2 i.p. for 7 h; FIG. 62H is a mouse loop ligation with CT-treatment; 3 h post-surgery; FIG. 62I is a mouse pre-treated with FI-2 i.p. for 4 h and then loop ligated with CT/FI-2; 3 h post-surgery.

Figure 63:
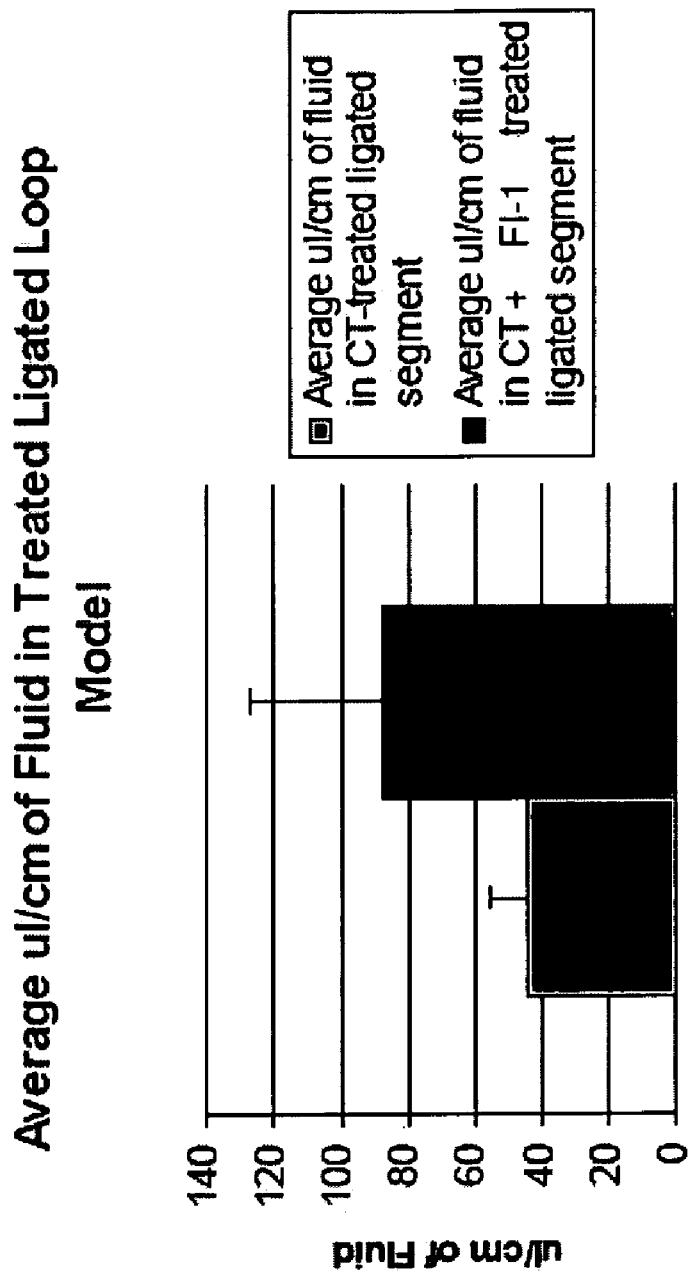

FIG. 63 demonstrates the effect of FI-1 on mouse intestinal fluid loss during experimental infection with CT.

Figure 64:
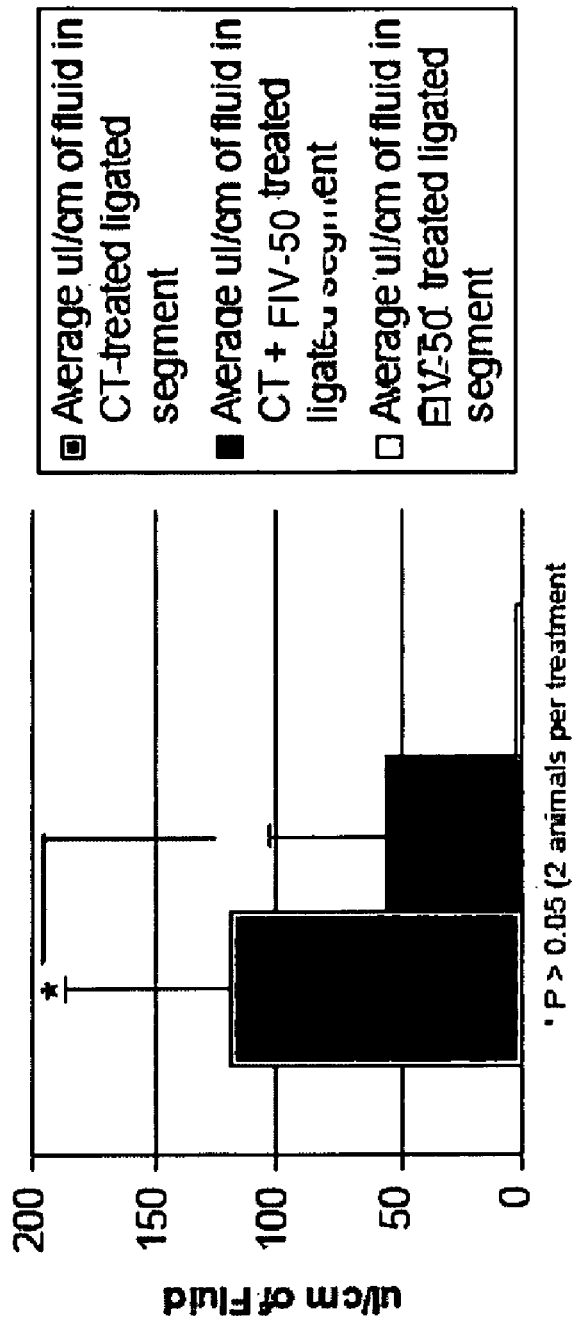

FIG. 64 shows the effect of FIV-50 on mouse intestinal fluid loss during experimental infection with CT.

Figure 65:
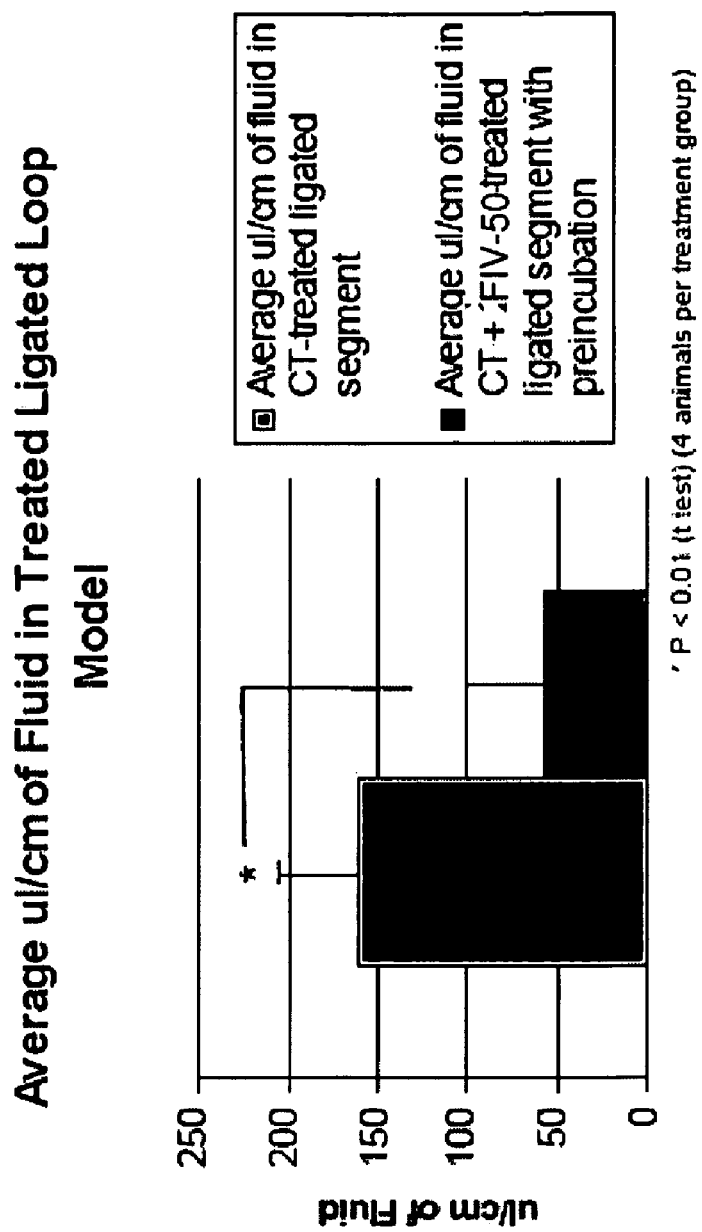

FIG. 65 demonstrates the effect of pre-incubation with FIV-50 on mouse intestinal fluid loss during experimental infection with CT.

Figure 66:
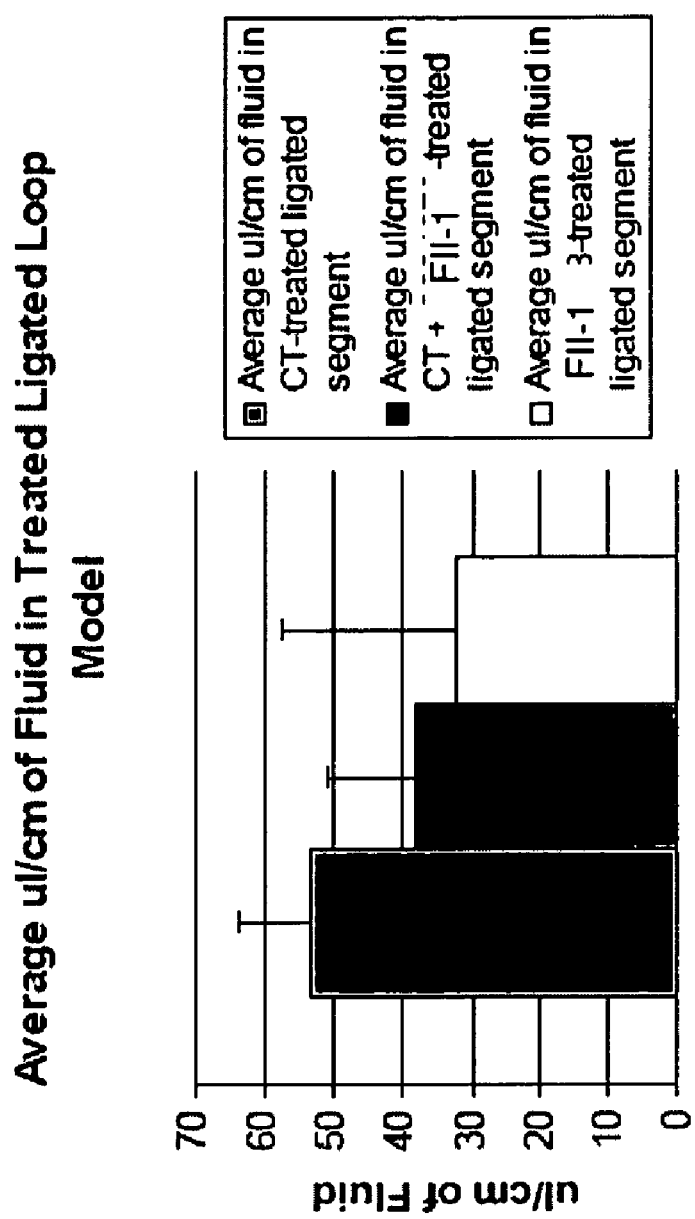

FIG. 66 shows the effect of pre-incubation with FII-1 on mouse intestinal fluid loss during experimental infection with CT.

Figure 67:
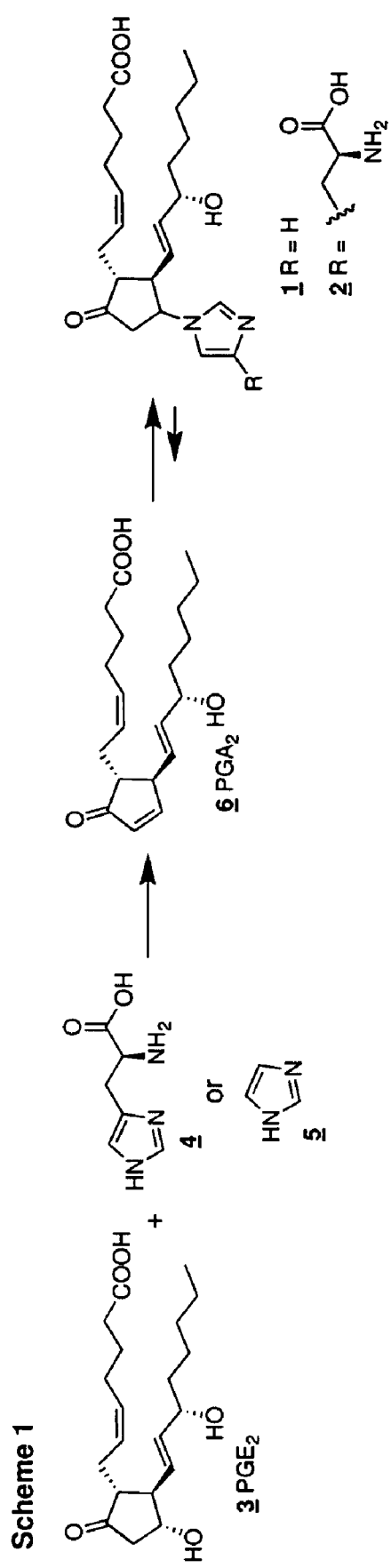

FIG. 67 shows a scheme with a covalent adduct formed as the intermediate.

Figure 68:
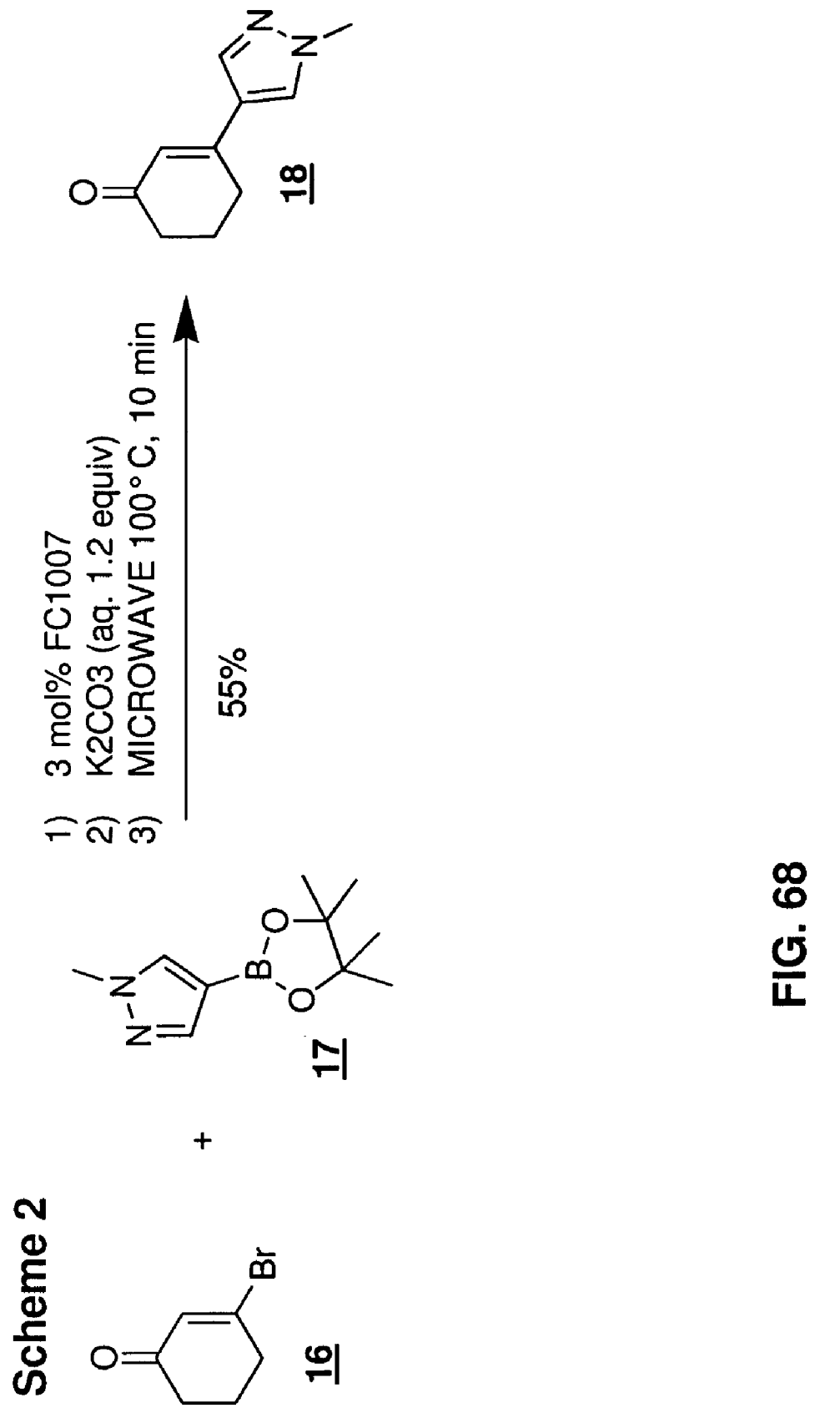

FIG. 68 is a scheme showing the use of the suzuki reaction to synthesis compounds.

Figure 2:
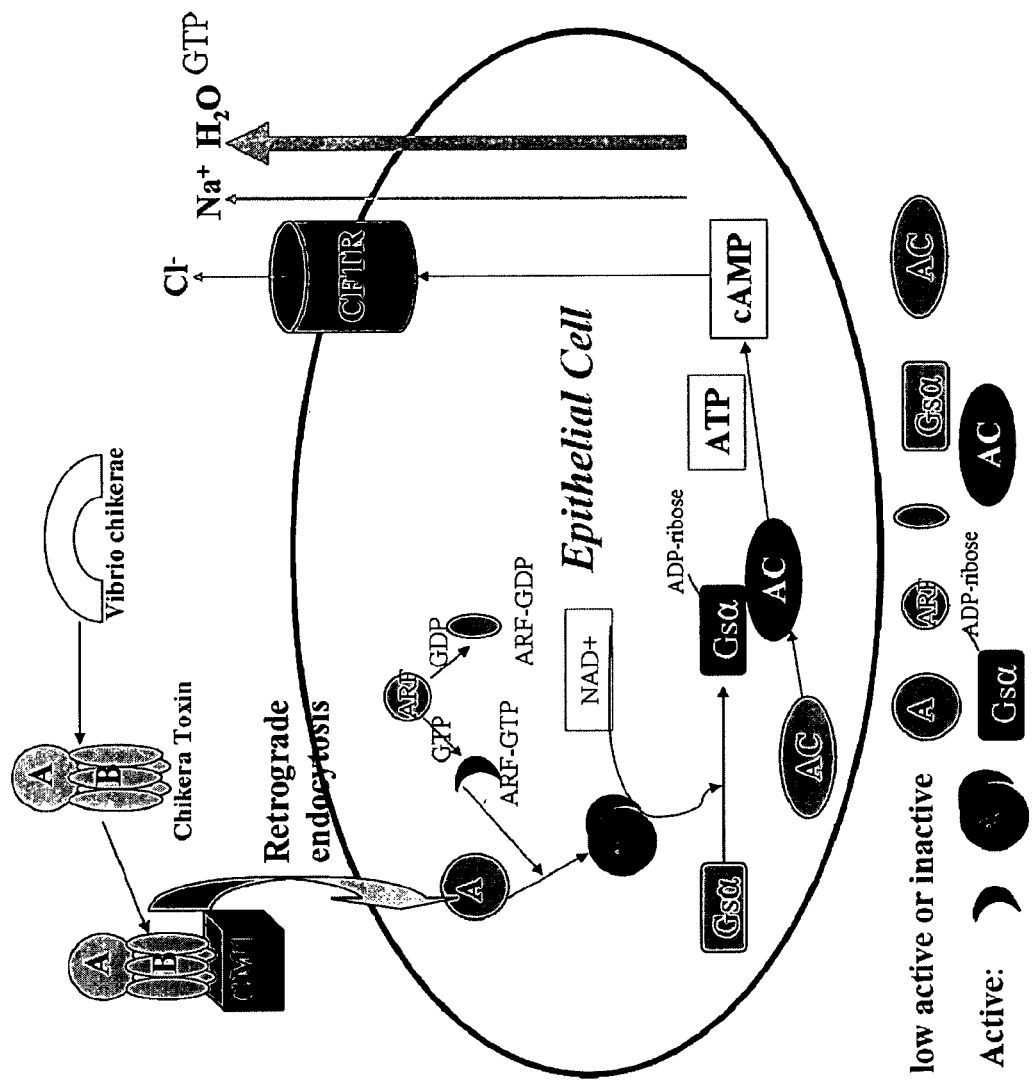
Figures 2, 69:
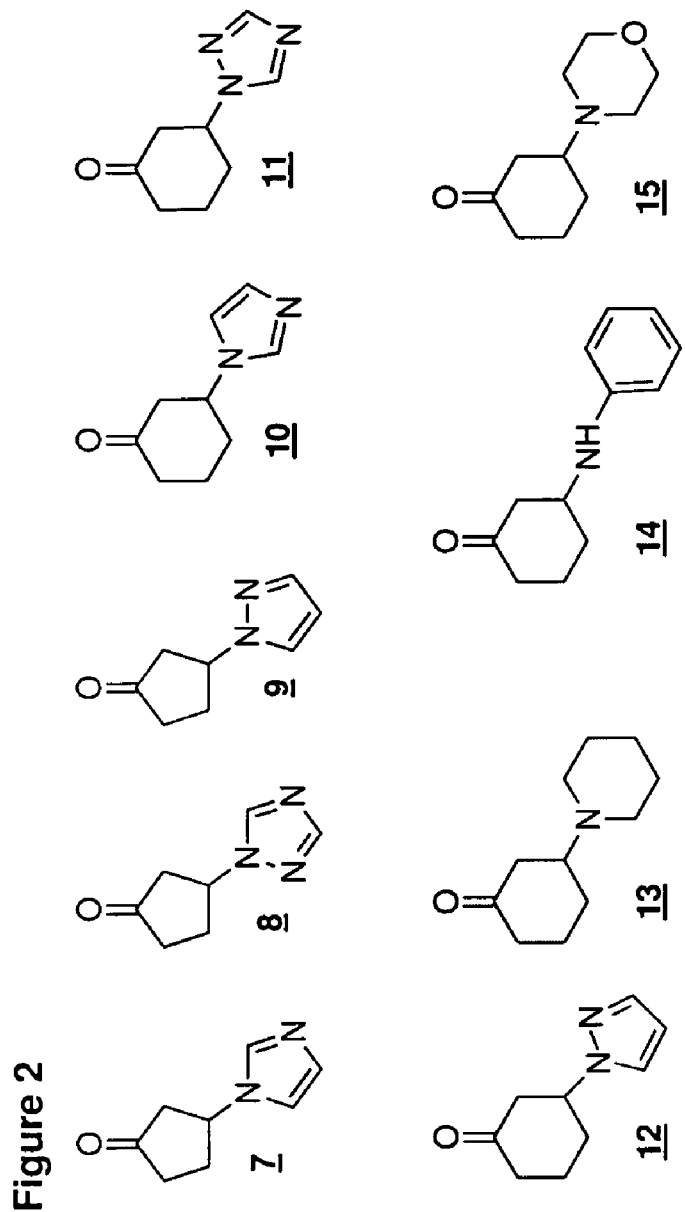

FIG. 69 shows a number of simple compounds that exhibit adenylyl cyclase inhibition activity.

FIG. 70 shows histidine and imidazole adducts of prostaglandin-$E_2$.

Figure 71:
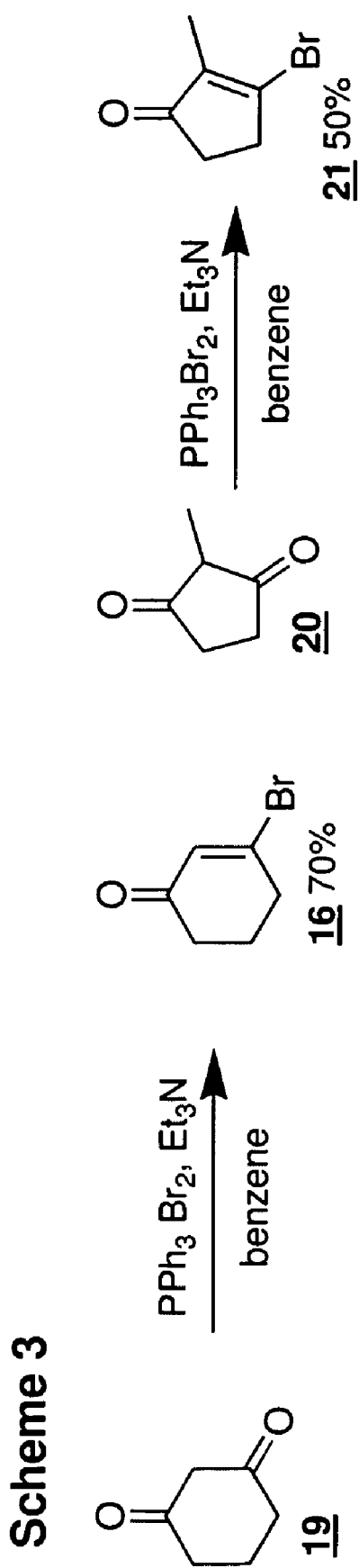

FIG. 71 is a scheme showing a single step reaction to make vinyl bromo enones.

Figure 72:
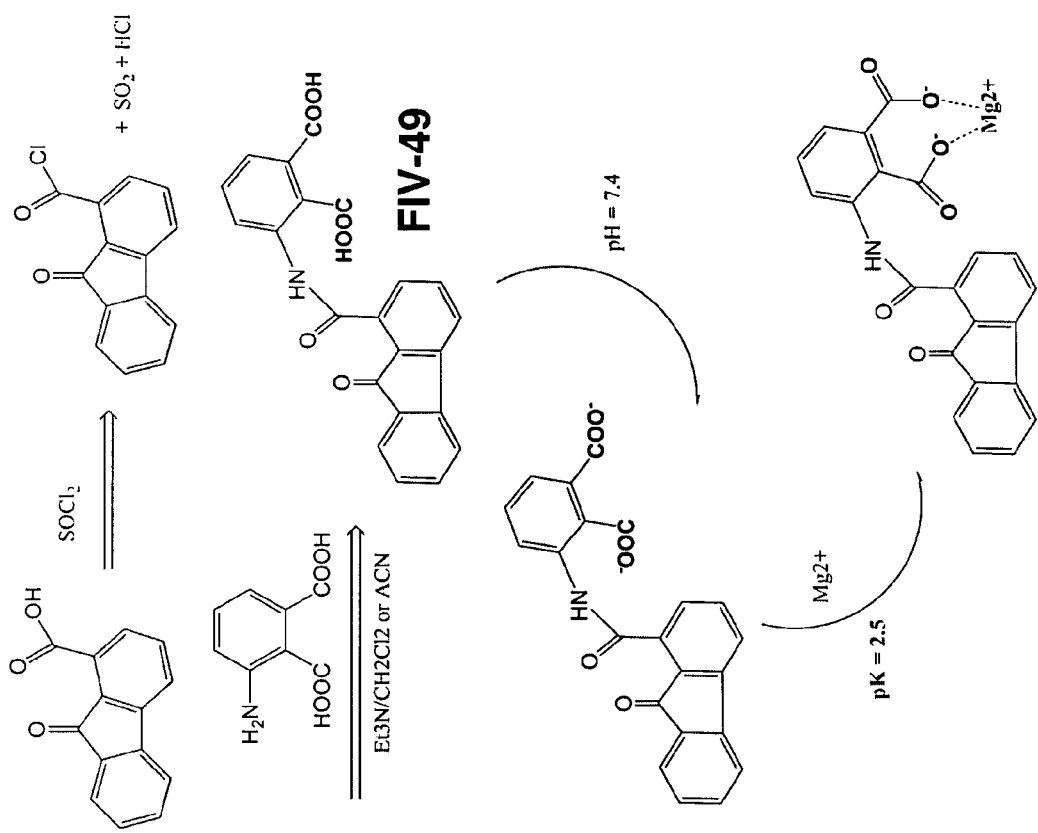

FIG. 72 is a depiction of a synthesis method to make the compound FIV-49.

DETAILED DESCRIPTION OF THE INVENTION

I. Exemplary Definitions

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The phrase "therapeutically effective amount" as used herein means that amount of a compound, material, or composition comprising a compound of the present invention that is effective for producing some desired therapeutic effect, e.g., treating (i.e., preventing and/or ameliorating) intestinal fluid loss, or a cAMP associated condition, at a reasonable benefit/risk ratio applicable to any medical treatment. In one embodiment, the therapeutically effective amount is enough to reduce or eliminate at least one symptom. One of skill in the art recognizes that an amount may be considered therapeutically effective even if the condition is not totally eradicated but improved partially. For example, the spread of the condition may be halted or reduced, a side effect from the condition may be partially reduced or completed eliminated, and so forth.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "binding affinity" refers to the strength of an interaction between two entities, such as a protein-protein interaction. Binding affinity is sometimes referred to as the $K_a$, or association constant, which describes the likelihood of the two separate entities to be in the bound state. Generally, the association constant is determined by a variety of methods in which two separate entities are mixed together, the unbound portion is separated from the bound portion, and concentrations of unbound and bound are measured. One of skill in the art realizes that there are a variety of methods for measuring association constants. For example, the unbound and bound portions may be separated from one another through adsorption, precipitation, gel filtration, dialysis, or centrifugation, for example. The measurement of the concentrations of bound and unbound portions may be accomplished, for example, by measuring radioactivity or fluorescence. Alternatively, binding affinity may be measured by docking or molecular dynamics simulations.

As used herein, a "subject" is an appropriate individual for the method of the present invention. A subject may be a mammal and in specific embodiments is any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, cows, mice, rats, and chimpanzees. Subjects may also be referred to as "patients" or "individuals".

The term "treatment" refers to any process, action, application, therapy, or the like, wherein a subject, including a human being, is subject to medical aid with the object of improving the subject's condition or one or more symptoms associated with a condition, directly or indirectly.

The term "cancer" as used herein is defined as a new growth of tissue comprising uncontrolled and progressive multiplication. In one embodiment of the invention, cancer leads to increased intestinal fluid loss. In another embodiment of the invention, cancer causes increased levels of cAMP.

As used herein, the term "reduces" refers to a decrease in intestinal fluid loss, inflammatory response, etc. as compared to no treatment with the compound of the present invention. Thus, one of skill in the art is able to determine the scope of the reduction of any of the symptoms and/or conditions associated with intestinal fluid loss or a cAMP related condition in which the subject has received the treatment of the present invention compared to no treatment and/or what would otherwise have occurred without intervention.

The term "preventing" as used herein refers to minimizing, reducing or suppressing the risk of developing a disease state or parameters relating to the disease state or progression or other abnormal or deleterious conditions.

As used herein, the term "inhibit" refers to the ability of the compound to block, partially block, interfere, decrease, reduce or deactivate a protein, for example, edema factor. Thus, one of skill in the art understands that the term inhibit encompasses a complete and/or partial loss of activity of a protein. Protein activity may be inhibited by a compound binding to the active site, or by other means, such as disabling a second protein that activates the inhibited first protein. For example, a complete and/or partial loss of activity of the Edema Factor may be indicated by a decrease in cAMP levels, decrease in bacterial growth or for example, adhesion, inhibition of quorum sensing, decrease in diarrhea or fluid flow into the intestine, decreased weight loss, temperature after infection, and/or mortality.

II. Exemplary Methods of Compound Design

One goal of rational drug design is to produce structural analogs of biologically active compounds or other effectors that would be expected to bind to a given site or biological surface, for example. By creating such analogs, it is possible to fashion drugs which are more active or stable than the natural molecules, which have different susceptibility to alteration or which may affect the function of various other molecules. In one approach, one would generate a three-dimensional structure for the protein or a fragment thereof. This could be accomplished by X-ray crystallography, computer modeling or by a combination of both approaches. In one approach lead compounds can be identified by similarity. An alternative approach, involves the random replacement of functional groups throughout the protein, and the resulting affect on function determined.

Thus, one may design drugs which have enhanced and improved biological activity, for example, anti-diarrheal relative to a starting structure of the invention. In addition, knowledge of the chemical characteristics of these compounds permits computer employed predictions of structure-function relationships.

III. Conditions Associated with Increased cAMP

General embodiments of the invention are the treatment and/or prevention of conditions associated with increased cAMP. One of skill in the art will know conditions that are associated with increased cAMP, however, exemplary conditions are listed below. In some embodiments of the invention, the cAMP condition is associated with the infection of a pathogen. In specific embodiments, the pathogen is *B. anthracis, V. cholerae, E. coli*, Pertussis, *Y. pestis*, or any combination thereof. In other embodiments of the invention, the increased levels of cAMP are associated with a cancer, or tumor. In other specific embodiments of the invention, increased cAMP levels are associated with certain drugs.

A. Adenylyl Cyclase and cAMP

Adenylyl cyclase converts ATP to cAMP, a crucial intracellular second messenger for a variety of cellular functions whose concentration is altered in response to a variety of environmental stimuli. Regulation of mammalian adenylyl cyclase is mediated by G proteins, which serve to link many surface receptors to effector proteins at the plasma membrane. Specific enzyme assays have been developed for several toxins that affect adenylyl cyclase activity directly, such as pertussis toxin and anthrax EF, and those that affect it indirectly, such as cholera toxin. Cholera toxin also has stimulatory effects on intestinal cellular adenylyl cyclase (Peterson et al., 1983; Peterson et al., 1988A; Peterson et al., 1988B, Peterson et al., 1989; Rabbani et al.).

Recently, a new in vitro cell-free and cell-based enzyme assays for the adenylyl cyclase activity of EF and have used them to detect inhibitors (e.g., FIV-50, $PGE_2$-L-histidine, and $PGE_2$-imidazole) that prevent increases in intracellular cAMP and edema fluid in the mediastium, the thoracic cavity, and other tissues has been developed. In the intestines and lungs, elevated levels of cAMP in epithelial cells stimulate $Cl^-$ secretion. The net transport of electrolytes out of the cells results in a transepithelial osmotic gradient that causes water to flow from the cells into the interstitial areas. Although it is clear that chloride channels can be regulated by cAMP-dependent protein kinases, past studies have not identified drugs that down regulate adenylyl cyclase nor has this potential been previously conceived as a strategy for controlling diseases such as anthrax. Although these mammalian adenylyl cyclase isoforms are uniformly regulated by G-proteins, the expression pattern and other regulatory properties of the nine principal AC isoforms vary widely, accounting for distinctive cell- and tissue specific patterns of AC responsiveness. Secreted bacterial adenylyl cyclases (e.g., *B. anthracis* EF and *B. pertussis* AC) are not regulated by G proteins and are not membrane bound. The genes of some mammalian AC isoforms, including AC4, AC7, and AC9, are expressed in a wide variety of tissues; however, other AC isoforms have a more restricted distribution in tissues (Simonds, 1999; Patel et al., 2001; Hanoune and Defer, 2001; Sunahara et al., 1998). For example, AC1 and AC8 are found only in neural tissue, while AC5 is expressed predominantly in heart and brain (Simonds, 1999).

B. Anthrax

The etiological agent of anthrax is *B. anthracis*, a large, gram-positive bacterial rod that forms spores during unfavorable environmental conditions (e.g., nutrient depletion). Infections with *B. anthracis* occur as cutaneous, intestinal, or inhalational anthrax. Most natural infections are of the cutaneous type, due to contact with *B. anthracis*-contaminated carcasses or products. The most severe form, and the most likely type of infection to result from aerosolized *B. anthracis* spores, is inhalational anthrax, which begins abruptly as an influenza-like syndrome, followed by high fever and chest pain, progressing rapidly to a systemic hemorrhagic disease with 80-100% mortality, unless treated promptly with antibiotics (Brachman, 1972). The traditional approach to control anthrax has been to prevent the infection through vaccination, when possible, or to prevent further bacterial growth by antibiotic administration post-infection. Friedlander et al. (Friedlander et al., 1993) reported that several antibiotic regimens (e.g., penicillin, ciprofloxacin, and doxycycline) administered from the day following exposure to a lethal dose of *B. anthracis* completely protected monkeys during 30 days of treatment. Each antibiotic provided significant long-term protection after discontinuation of the drugs (70-90%); whereas antibiotic-treated animals that were concomitantly vaccinated were 100% protected. However, antibiotic treatment is not sufficiently effective in treating inhalation forms of the disease after onset of symptoms. The disturbingly high mortality rate for the recent human victims, even when treated in a hospital setting, illustrated the need for better post-infection therapy. In addition to providing a possible cure for patients with advanced inhalation anthrax, inhibitory drugs that block the action of EF and LF may prove valuable in reducing the virulence of *B. anthracis* cells germinating from spores in the lungs after completion of antibiotic treatment.

The virulence of *B. anthracis* depends on the plasmids pXO1 and pXO2, which encode the genes (Leppla, 2000) for two types of extracellular products, the anthrax toxins and an anti-phagocytic poly-gamma-D-glutamic acid capsule (Brossier et al., 2000). The anthrax toxin components, encoded on noncontiguous genes within the pXO1 plasmid, are edema factor (EF, 89 kDa), lethal factor (LF, 90 kDa), and protective antigen (PA, 83 kDa). Antibodies to protective antigen (PA), which binds the toxin components to the cell receptors and facilitates toxin entry, protect animals from infection, indicating that anthrax is accurately classified as a toxin-mediated disease; however, bacteremia and sepsis are very important facets of these infections (Leppla, 2000). It was recently reported that human monoclonal anti-PA reduced the dissemination of *B. anthracis* from the lungs to the blood and other organs (Peterson et al., 2007). LF is a $Zn_{++}$-metalloprotease that can destroy the catalytic activity of several mitogen-activated protein kinase kinases, including MAPKK1, MAPKK2, MAPKK3b, MAPKK4, MAPKK6b, and MAPKK7b (Leppla, 2000; Vitale et al., 2000; Pellizzari et al., 1999; Vitale et al., 1998; Pellizzari et al., 2000), and two protease inhibitors (e.g., bestatin, captopril) are known to protect macrophages from lethal toxin (LeTx) in vitro (Inglesby, 1999). Importantly, Merck has developed a potent lfi inhibitor that may have therapeutic benefit in inhalation anthrax (Cummings et al., 2002; Shoop et al., 2005; Xiong et al., 2006). The PA component binds either the EF or LF components to cell membranes, and translocates the complexes into the eukaryotic cell. Thus, the PA component represents the binding domain for both EF and LF. In inhalation anthrax, the spores are inhaled deep into the lungs, where they germinate and give rise to the rapidly dividing vegetative cells. The antiphagocytic capsule protects anthrax bacilli from engulfment by macrophages and polymorphonuclear neutrophils. The pathogenic mechanism of EF and LF is illustrated in FIG. 1. EdTx and LeTx are crucial virulence factors in *B. anthracis* infections (Brossier et al., 2000; de Vos, 1994; Leppla, 2000). Erwin et al. (Erwin et al., 2001) observed that LeTx suppresses the production of proinflammatory cytokines (e.g., TNF<) by LPS-stimulated macrophages. This toxic effect on the macrophages' functional role in phagocytizing and killing of *B. anthracis* in the lungs and mediastinum during inhalation anthrax is thought to be very important in the pathogenesis of this disease. EF is a calmodulin dependent adenylyl cyclase (Leppla, 2000) that converts adenosine triphosphate (ATP) to 3',5'-adenosine monophosphate (cAMP). Despite the names of the lethal toxin and edema toxin, both of these protein toxins cause death in mice (Milne et al., 1995).

As mentioned above, anthrax toxin produced by *Bacillus anthracis*, the causative agent of anthrax, consists of three proteins; lethal factor (LF), protective antigen (PA) and edema factor (EF). Working in concert these proteins are responsible for the virulence associated with inhalation anthrax infections that if not promptly treated are often fatal (Brachman, 1972). Individually, the three proteins are not toxic, but the combination of PA and LF forms lethal toxin (LT), which causes death when injected into experimental animals (Brossier et al., 2000). The combination of PA and EF forms edema toxin (ET), which produces tissue edema at the site of infection. Edema and lethal toxins synergize their action against a host's innate immunity. It has been shown that the deletion of the EF or LF gene results in a reduction of virulence of anthrax bacteria (Brossier et al., 2000). Given that EF is an adenylyl cyclase, edema toxin's role in pathogenesis is thought to impair phagocyte function. For that reason small molecule inhibitors of EF may play a role in the treatment of inhalation anthrax infections, as well as other diseases that involve edema due to increased cyclic AMP production.

Edema Factor (EF), an extracellular $Ca^{2+}$/calmodulin-dependent (Drum et al., 2002; Shen et al., 2005) adenylyl cyclase toxin produced by *Bacillus anthracis*, catalyzes the intracellular production of cAMP from ATP (de Rooij et al., 1998; Lacy et al., 2002; Leppla et al., 1982). The tissue swelling caused by the increase in cAMP production contributes to the lethality of anthrax infections. High levels of cAMP perturb the water homeostasis of the cell, leading to abnormalities in the intracellular signaling pathways and chloride channel stimulation (Ajuja et al; 2004; Ascenzi et al., 2002; Peterson et al., 2001). While edema is difficult to observe directly in cells (Wu et al., 2003), cAMP generation from ATP can be easily assayed, when the protective Antigen (PA), another component of the Anthrax toxin cell (Guidi-Rontani et al., 2000), is supplied to transport EF into cells (Zmuda et al., 2005). Inhibiting the intracellular activity of EF is one way to treat late stage anthrax, and reduce the lethality of infections. Inhibitors of EF could be used to treat late stage infection with other bacteria, such as *Bordatella pertussis* (which causes whooping cough) and *Yersinia pestis* (plague), that produce toxins with similar areas (Hewlett et al., 1979; Hewlett et al., 1976; Munier et al., 1992).

Recent crystal structures of EF complexed with substrate analogues and small molecule inhibitors have identified the active site residues (Drum et al., 2000; Shen et al., 2005; Shen et al., 2004; Shen et al., 2004). There is some variation, however, in the absolute orientation of residues and the metal ion binding mode. While there is general agreement that there is only one metal bound to the EF protein (Drum et al., 2002), a second possibly catalytic metal ion has been visualized, bound to the phosphates of the ATP substrate (Shen et al., 2005). In contrast, mammalian adenyl cyclase has a typical 2-metal ion binding site, with both metals ligated by anionic groups on the protein and the substrate (Tesmer et al., 1999). All of these structures were done with larger metal ions. Another recent structure of a bacterial adenyl cyclase toxin, produced by *B. pertussis* (PT) (PDB file 1ZOT). shows 3 Mg ions in the active site, two of which have ligands to both protein and nucleotide, and one near the phosphate backbone. The metal ion(s) fix the position of ATP so that the 3' hydroxyl group on the ribose of ATP can be deprotonated during the production of cAMP. Several Lys and Arg residues in the active site are also near the phosphate oxygens of ATP. The active site of the mammalian enzyme is distinct, encouraging the search for inhibitors that are capable of binding specifically to the bacterial enzymes. For example, P-site inhibitors of mammalian Adenylyl Cyclase (AC), adenine nucleotides with a 3'-O phosphate or polyphosphate groups (Tesmer et al., 1999; Dessauer and Gilman, 19997; Gille et al., 2004; Johnson et al., 1997; Onda et al., 2001) have no effect on the catalytic activity of EF (Johnson et al., 1990). More selective inhibitors of EF have been identified by a combined computational and experimental approach, however, were found to be toxic (Soelaiman et al., 2003).

C. Cholera

Cholera, a potentially lethal disease is caused by the bacteria *Vibrio cholera*. The hallmark symptom of cholera is the production of watery diarrhea with varying degrees of dehydration ranging from none to severe and life-threatening. Onset of the disease is abrupt and characterized by the production of watery diarrhea without strain, tenesmus, or prominent abdominal pain, rapidly followed or sometimes preceded by vomiting. As the diarrhea continues, other symptoms of severe dehydration manifest, such as generalized cramps and oliguria. Physical examination will shown an alert patient most of the time despite the fact that the pulse is nonpalpable and blood pressure cannot be measured.

The "A" subunit of cholera toxin (CTA1) is an ADP-ribosyltransferase that activates adenylyl cyclase, which in turn elevates cAMP levels, which disturbs water homeostasis and leads to watery diarrhea. Cholera toxin is a AB5 enterotoxin that binds to GM1 gangliosides. Cholera toxin further increases cAMP levels and is the primary cause of massive fluid and electrolyte release associated with cholera. A mechanism for Cholera causing watery diarrhea is diagramed in FIG. 2.

D. Pertussis

Pertussis, also known as whooping cough, is caused by the bacterial *Bordetella pertussis*. Pertussis manifests after an incubation period ranging from less than 1 week up to 3 weeks, with symptoms such as mild conjunctival injection, malaise, and a low grade fever; after which a dry, nonproductive cough develops. A later phase is characterized by hematologic features, namely leukocytosis with lymphocyte predominance. The total white blood cell count, which may sometimes exceed 50,000 cells/mm$^3$ consists of a relative lymphocytosis with T and B cells and a less striking increase in neutrophils. Methods used in laboratory diagnosis include culturing of nasopharyngeal swabs on Bordet-Gengou medium, polymerase chain reaction (PCR), immunofluorescence (DFA), and serological methods.

*B. pertussis* produces a number of biologically active substances that play a role in the disease. These include the pertussis toxin and adenylyl cyclase toxin (ACT). ACT contains an adenylyl cyclase enzymatic domain that is able to enter mammalian cells, where it is activated by endogenous calmodulin to catalyze the production of cAMP from adenosine triphosphate. The resulting accumulation of cAMP to supraphysiologic levels results in impaired leukocyte functions. The toxin is a member of the RTX family of bacterial toxins (including *Escherichia coli* hemolysin and *Pasteurella haemolytica* leukotoxin) and is itself hemolytic, responsible for the zone of hemolysis associated with virulent *B. pertussis* on blood agar plates. Strains of *B. pertussis* that are defective in ACT production are avirulent in suckling mice, and antibodies against the toxin enhance bacterial uptake by phagocytes. More information can be found in Principles and Practice of Infectious Disease, 2000, incorporated here by reference in full.

E. Others

The present invention is also useful in the prevention, inhibition, or treatment of bacterial infections, including, but not limited to, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, Staphylococci, such as *Staphylococcus epidermidis, Staphylococcus aureus*, particularly in the nasopharynx, *Hemophilus influenzae*, pseudomonas species such as *Pseudomonas aeruginosa, Pseudomonas pseudomallei, Pseudomonas mallei*, brucellas such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, *Actinomycetes* species, *Treponema pallidum, Leptospirosa* species and related organisms. The invention may also be useful against gram negative bacteria such as *Klebsiella pneumoniae, Escherichia coli, Proteus, Serratia* species, *Acinetobacter, Yersinia pestis, Francisella tularensis, Enterobacter* species, *Bacteriodes* and *Legionella* species and the like. In addition, the invention may prove useful in controlling protozoan or macroscopic infections by organisms such as *Cryptosporidium, Isospora belli, Toxoplasma gondii, Trichomonas vaginalis, Cyclospora* species, for example, and for *Chlamydia trachomatis* and other *Chlamydia* infections such as *Chlamydia psittaci*, or *Chlamydia pneumoniae*, for example. In another embodiment of the invention is the treatment of waterborne diseases such as *Salmonella typhimurium, S. typhi*, Pathogenic *E. coli, Campylobacter jejuni, Proteus* sp. *Yersinia enterocolitica, Vibrio parahaemo-lyticus, Vibrio cholerae*, of course it is understood that the invention may be used on any pathogen which in anyway may affect the levels of cAMP in a subject. Many more strains of bacteria and viruses exist than have been described, and one of skill in the art will anticipate the compounds of the invention will inhibit some percentage of these unknowns.

A specific embodiment of the invention is drawn to treating infections with other pathogens that are waterborne and are associated with diarrheal disease. Exemplary pathogens include *Acinetobacter calcoaceticus, Aeromonas hydrophila, A. sobria, A. caviae, Campylobacter jejuni Enteritis, C. coli, Chromobacterium violaceum, Citrobacter* spp., *Clostridium perfringens*, type C, *Enterobacter* spp., *E. coli*, various serotypes, *Flavobacterium meninogsepticum, Francisella tularensis, Fusobacterium necrophorum, Klebsiella* spp., *Leptospira icterohaemorrahagia* and other *Leptospira* spp., *Legionella pneumophila* and other *Legionella* spp., *Morganella morganii, Mycobacterium tuberculosis, M. marinum* and other *Mycobacterium* spp., *Plesiomonas shigelloides, Pseudomonas pseudomallei, Pseudomanas* spp., *Salmonella enteritidis, S. montevideo* B, *S. typhimurium* and other *Salmonella serotypes, S. paratyphi* A and B, *S. typhi, Serratia marcesens, Shigella* spp., *Staphylococcus aureus, Vibrio cholerae, V. alginolyticus, V. fluvialis, V. mimicus, V. parahaemolyticus, V. vulnificus* and other *Vibrio* spp., *Yersinia enterocolitica*, (see for example, T. C. Hazen and G. A. Toranzos "Tropical Source Water" p. 33 in G. A. McFeters Drinking Water Microbiology [Springer Verlag New York 1990]).

In some embodiments of the invention, the composition is used in a subject infected with *E. coli, S. typimurium, A. hydrophila* and *V. parahemolyticus, K. pneumoniae, Y. enterocolitica* and *V. cholera*. Other diseases with clinical uses for these types of drugs include rotavirus, AIDs-related diarrhea, and Irritable Bowel Syndrome. Additional embodiments of the invention include treatment of patients over medicated with drugs like theophyline, an inhibitor of adenylyl cyclase. Another embodiment is the treatment of diarrhea in cancer patients.

IV. Intestinal Fluid Loss

A symptom of intestinal fluid loss is diarrhea, which refers to frequent loose or liquid bowel movement and leads to the loss of significant amounts of water and salts. Intestinal fluid loss may also be accompanied by abdominal cramps, fever, blood in the stool and bloating. loss of significant amounts of water and salts. Acute and severe diarrhea is a common cause of death in developing countries and a major cause of infant death worldwide.

In one embodiment enteric bacteria causes intestinal fluid loss symptoms such as diarrhea. Enteric bacterial pathogens exert multiple deleterious effects on the intestinal mucosa, including inflammation injury and enhancement of water and electrolyte transport from the intestinal epithelium. The basis for the increased transport of water and electrolytes from the intestine is hyperstimulation of ion transport, which is regulated by cyclic nucleotides, including cAMP. Many bacteria secrete protein enterotoxins that stimulate mucosal adenylyl cyclase, which upregulate cAMP levels in the epithelial cells. The cAMP binds to cellular protein kinase A, which, in turn, phosphorylates chloride channel proteins lining the epithelial cells. The chloride channels hypersecretes $Cl^-$ into the intestinal lumen, and $Na^+$ and $K^+$ and $HCO_3^-$ follow. In a specific embodiment of the invention, intestinal fluid loss is caused by the methods outlined above.

Several in vivo assays in a variety of laboratory animals can be used to document the effect of cAMP on intestinal fluid transport and in one embodiment is measured by ligating small intestinal loops which are constructed in mice under anesthesia using silk sutures. The enterotoxinogenic bacteria or the toxins they secrete (e.g., cholera toxin) are injected into the lumen of the intestinal loop. After 4-6 hours, the volume of fluid accumulating is measured and the length of the loop is measured in cm. In one embodiment, the results are expressed as ml/cm.

In another embodiment, an open intestinal assay is used and the mice are pre-treated with an antibiotic to reduce the population of resident bacteria in the mouse small intestine. No ligatures are constructed, and the bacteria or enterotoxins are administered via a blunt gastric feeding needle by mouth. After a period of time (12-24 hours), the volume of fluid accumulating in the entire intestinal tract is estimated by dissecting out the intestinal tract and weighing it, along with the weight if the remaining animal carcass. In one embodiment, the results are expressed as a ratio of intestinal weight to carcass weight.

In another embodiment of the invention, inhibitors of adenylyl cyclase reduce the amount of cAMP and hence reduce the amount of intestinal fluid in the intestinal loops or intestine.

In one embodiment, the invention is concerned with the treatment or prevention of intestinal fluid loss. In general embodiments, the intestinal fluid loss is the result of infection with a pathogen. In specific embodiments, the pathogen is *B. anthracis, V. cholerae, E. coli, Pertussis, Y. pestis*, or any combination thereof. In other embodiments, the intestinal fluid loss is the result of an increase in cAMP levels. In another embodiment, the intestinal fluid loss is the result of cancer.

V. Compositions of the Invention

The term "derivative" as used herein is a compound that is formed from a similar compound or a compound that can be considered to arise from another compound, if one atom is replaced with another atom or group of atoms. Derivative can also refer to compounds that at least theoretically can be formed from the precursor compound.

The term "functionally active derivative" or "functional derivative" is a derivative as previously defined that retains the function of the compound from which it is derived.

An embodiment of the invention is the composition comprising a therapeutically effective amount of a compound or a pharmaceutically acceptable salt thereof wherein the general formula of the compound is selected from the group consisting of:

Formula I

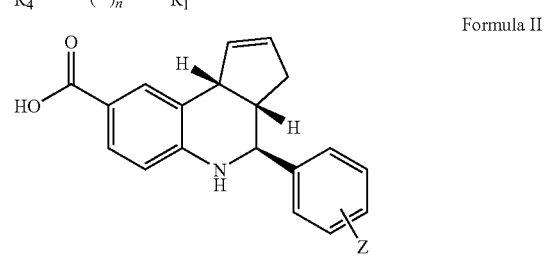

Formula II

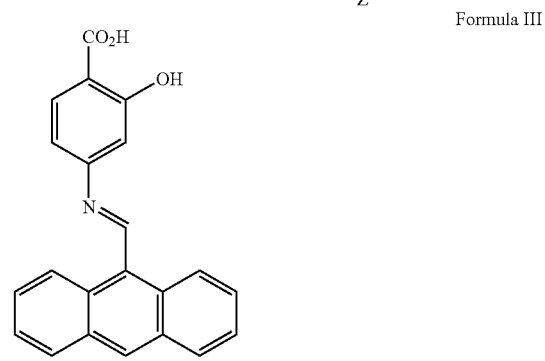

Formula III

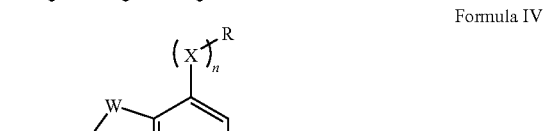

Formula IV

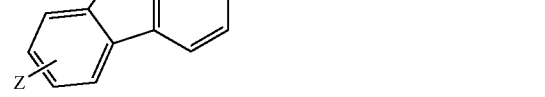

Formula V

-continued

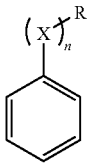
Formula VI

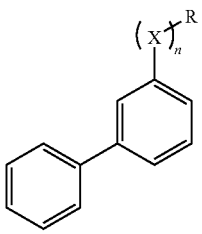
Formula VII

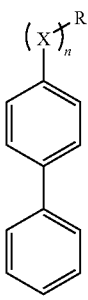
Formula VIII

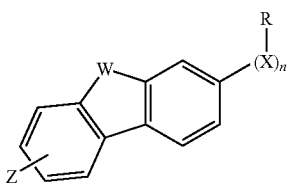
Formula and combinations thereof wherein, 1) R is cyclic or bicyclic ring structure; 2) $R_1$ is a cyclic or bicyclic ring structure; 3) $R_4$ is a hydrogen, cyclic or bicyclic ring structure; 4) Z is selected from the group consisting of hydrogen, alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate; 5) W is selected from the group consisting of CO, NH, methylene, sulfur atom, oxygen atom and thionyl; and, 6) m and n are the same or different and are 0 or 1.

In general embodiments of the invention, R is a substituted or unsubstituted and selected from the group consisting of: phenyl, pyranonyl, pyridyl, imidazolyl, 1,8-naphthyridinyl, and N-oxide pyridyl; $R_1$ is substituted or unsubstituted and selected from the group consisting of phenyl, pyridyl, and furanyl; $R_4$ is a cyclic or bicyclic ring structure, substituted or unsubstituted and selected from the group consisting of phenyl, pyridyl, and furanyl;

In specific embodiments of the invention, R is mono, di, tri, tetra, or appropriately penta substituted with a functional group selected form the group consisting of: hydrogen, alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. In other specific embodiments of the invention $R_1$ is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof. In another specific embodiment of the invention, $R_4$ is mono, di, tri, tetra, or appropriately penta substituted with a functional group selected form the group consisting of alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, unsubstantiated or substituted branched or unbranched alkyl, (C1-C3) alkenyl, unsubstantiated or substituted branched or unbranched aryl, unsubstantiated or substituted branched or unbranched alkylaryl, unsubstantiated or substituted branched or unbranched carbohydrate and any combination thereof.

In specific embodiments of the invention, the composition comprises one or more of the group consisting of FIV-50, FIV-1, FIV-29, FIV-31, FIV-34, FIV-35, FIV-39, FIV-40, FIV-46, FIII-1, FII-1, FI-3, FI-1, FI-2, FIV-54, FIV-58, FIV-55, FIV-53, FIV-67, FIV-70, FIV-65, FIV-68, FIV-66, FIV-61, FIV-60, FIV-64, FIV-71, FIV-46, FIV-72, FIV-73, FIV-49, FIV-75, and any combination thereof.

A. Chemical Structures and Groups

As used herein, the terminology "biological activity" is meant to include enzymatic activity and binding to other molecules including inhibitors and substrates.

The term "analog" as used herein, is understood as being a substance which does not comprise the same basic carbon skeleton and carbon functionality in its structure as a "given compound", but which can mimic the given compound by incorporating one or more appropriate substitutions such as for example substituting carbon for heteroatoms.

The term "alkyl" as used herein, is understood as being straight or branched chains having up to seven carbon atoms. The term "lower alkyl" as used herein, is understood as being straight or branched chains having up to four carbon atoms and is a sub-grouping for the term "alkyl".

The term "substituted alkyl" as used herein, is understood as being such straight or branched chain chains having up to 7 carbon atoms wherein one or more, and one, two, or three hydrogen atoms may be replaced by a substituent selected from the group consisting of hydroxy, amino, cyano, halogen, trifluoromethyl, —NH(lower alkyl), —N(lower alkyl)$_2$, lower alkoxy, lower alkylthio, and carboxy, aryl and heteroaryl.

The terms "lower alkoxy" and "lower alkylthio" as used herein, are understood as being such lower alkyl groups as defined above attached to an oxygen or sulfur atom.

The term "cycloalkyl" as used herein, is understood as being saturated rings of 3 to 7 carbon atoms.

The term "alkenyl" as used herein, is understood as being straight or branched chains of 3 to 7 carbon atoms having one or two double bonds. Some embodiments of "alkenyl" groups are straight chains of 3 to 5 carbon atoms and having one double bond.

The term "substituted alkenyl" as used herein, is understood as being such straight or branched chains of 3 to 7 carbon atoms having one or two double bonds and wherein a hydrogen atom has been replaced by a substituent selected from the group consisting of hydroxy, amino, halo, trifluoromethyl, cyano, —NH(lower alkyl), —N(lower alkyl)$_2$, lower alkoxy, lower alkylthio, and carboxy.

The term "alkylene" as used herein, is understood as being divalent straight or branched chains having up to seven carbon atoms (i.e. —CH$_2$—, —(CH$_2$)$_2$—, —(CH$_2$)$_3$—, —(CH$_2$)$_4$—, —CH$_2$—CH(CH$_3$)—, etc.).

The term "aryl" as used herein, is understood as being phenyl, 1-naphthyl, and 2-naphthyl. The term "substituted aryl" as used herein, is understood as being phenyl, 1-naphthyl and 2-naphthyl having a substituent selected from the group consisting of phenyl, heteroaryl, lower alkyl, lower alkoxy, lower alkylthio, halo, hydroxy, trifluoromethyl, amino, —NH(lower alkyl), and —N(lower alkyl)$_2$, as well as being mono-, di- and tri-substituted phenyl, 1-naphthyl, and 2-naphthyl comprising substituents selected from the group consisting of methyl, methoxy, methylthio, halo, hydroxy, and amino.

The term triphenylmethyl is herein abbreviated as Trt (trityl).

The term "heteroaryl" as used herein, is understood as being unsaturated rings of five or six atoms containing one or two O— and/or S-atoms and/or one to four N-atoms, provided that the total number of hetero-atoms in the ring is 4 or less. The heteroaryl ring is attached by way of an available carbon or nitrogen atom. Exemplary heteroaryl groups include 2-, 3-, or 4-pyridyl, 4-imidazolyl, 4-thiazolyl, 2- and 3-thienyl, and 2- and 3-furyl. The term "heteroaryl" as used herein, is understood as also including bicyclic rings wherein the five or six membered ring containing O, S and N-atoms as defined above is fused to a benzene or pyridyl ring. Exemplary bicyclic rings include but are not limited to 2- and 3-indolyl as well as 4- and 5-quinolinyl. The mono or bicyclic heteroaryl ring can also be additionally substituted at an available carbon atom by a substituent selected from the group consisting of lower alkyl, halo, hydroxy, benzyl and cyclohexylmethyl. Additionally, if the mono or bicyclic ring has an available N-atom, then such an atom can also be substituted by one of the N-protecting groups such as N-carbamates, N-phenylsulfenyl, N-phenylsulfonyl, N-2,4-dinitrophenyl, N-lower alkyl, N-benzyl, or N-benzhydryl or any other applicable group known in the art (T. W. Greene, P. G. M. Wuts: Protective Groups in Organic Synthesis, 2$^{nd}$ Edition, John Wiley & Sons, NY, 1991, incorporated herein by reference).

The terms "halogen" or "halo" as used herein, is understood as being chlorine, bromine, fluorine and iodine.

The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. It is also understood that the compositions of the invention may additionally exist as anions or cations. Nontoxic, pharmaceutically acceptable salts may be used, although other salts may be useful, as for example in isolation or purification steps.

A "pharmaceutically acceptable salt" of a compound recited herein is an acid or base salt that is suitable for use in contact with the tissues of human beings or animals without excessive toxicity or carcinogenicity, and may be without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH$_2$)$_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences,* 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is embodied.

Examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Examples of basic salts include but are not limited to ammonium salts; alkali metal salts such as sodium, lithium, and potassium salts; alkaline earth metal salts such as calcium and magnesium salts; salts comprising organic bases such as amines (e.g., dicyclohexylamine, alkylamines such as t-butylamine and t-amylamine, substituted alkylamines, aryl-alkylamines such as benzylamine, dialkylamines, substituted dialkylamines such as N-methyl glucamine (especially N-methyl D-glucamine), trialkylamines, and substituted trialkylamines); and salts comprising amino acids such as arginine, lysine and so forth. The basic nitrogen-containing groups may be quaternized with agents such as lower alkyl halides (e.g. methyl, ethyl. propyl, and butyl chlorides, bromides and iodides), dialkyl sulfates (e.g. dimethyl, diethyl, dibutyl, and diamyl sulfates), long chain halides (e.g. decyl, lauryl, myrtistyl and stearyl chlorides, bromides and iodides), arylalkyl halides (e.g. benzyl and phenethyl bromides), and others known in the art.

Prodrugs and solvates of the present invention are also contemplated herein. The term "prodrug" as used herein, is understood as being a compound which, upon administration to a subject, undergoes chemical conversion by metabolic or chemical processes to yield a compound of the present invention, or a salt and/or solvate thereof. Solvates of the compounds of the invention may also be hydrates.

All possible stereoisomers of the present invention are contemplated as being within the scope of the present invention. Individual stereoisomers of the compounds of the present invention may, for example, be substantially free of other stereoisomers, or may be admixed, for example, as racemates or admixed with other selected or all other stereoisomers. The chiral centers of the present invention can have the S— or the R-configuration, as defined by the IUPAC 1974 Recommendations.

When a particular group with its bonding structure is denoted as being bonded to two partners, e.g. —OCH$_2$—, then it is understood that either of the two partners may be bound to the particular group at one end, and the other partner is necessarily bound to the other end of the particular group.

Methods for the preparation and/or separation and isolation of single stereoisomers from racemic mixtures or non-racemic mixtures of stereoisomers are well known in the art. For example, optically active (R)— and (S)— isomers may be prepared using chiral synthons or chiral reagents, or resolved using conventional techniques. When desired, the R- and S-isomers may be resolved by methods known to those skilled in the art, for example by: formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts or solvents, or by converting an enantiomer to the other by asymmetric transformation. For a mixture of enantiomers, enriched in a particular enantiomer, the major component enantiomer may be further enriched (with concomitant loss in yield) by recrystallization.

The symbol "-" means a single bond, "=" means a double bond, and "≡" means triple bond. When a group is depicted removed from its parent formula, the " ⌇ " symbol will be used at the end of the bond which was theoretically cleaved in order to separate the group from its parent structural formula.

When a group "R" is depicted as existing on a ring system, for example in the formula

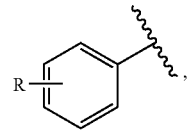

then a substituent "R" may reside on any atom of the ring system, assuming replacement of the depicted, implied, or expressly defined hydrogen from one of the ring atoms, so long as a stable structure is formed.

When a group "R" is depicted as existing on a fused ring system, as for example in the formula

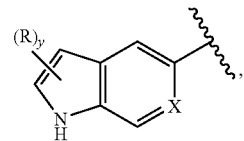

then a substituent "R" may reside on any atom of the fused ring system, assuming replacement of the depicted (e.g. the —NH— in the formula above), implied (e.g. as in the formula above, where the hydrogens are not shown but understood to be present), or expressly defined hydrogen (e.g. where in the formula above, "X" equals —CH—) from one of the ring atoms, so long as a stable structure is formed. In the example depicted, the "R" group may reside on either the 5-membered or the 6-membered ring of the fused ring system. In the formula depicted above, when y is 2 for example, then the two "R" may reside on any two atoms of the ring system, again assuming each replaces a depicted, implied, or expressly defined hydrogen on the ring. When there are more than one such depicted "floating" groups, as for example in the formula

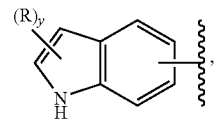

where there are two groups, namely, the "R" and the bond indicating attachment to a parent structure. In such cases, the "floating" groups may reside on any atoms for the ring system, again assuming each replaces a depicted, implied, or expressly defined hydrogen on the ring.

When a group "R" is depicted as existing on a saturated ring system, as for example in the formula

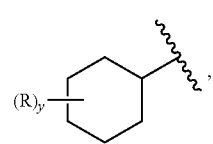

where "y" can be more than one, assuming each replaces a currently depicted, implied, or expressly defined hydrogen on the ring, then where the resulting structure is stable, two "R's" may reside on the same carbon. A simple example is when R is a methyl group, then in this instance there would exist a geminal dimethyl on a carbon of the depicted ring. In another example, two R's on the same carbon, including that carbon, may form a ring, thus creating a spirocyclic ring structure with the depicted ring.

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to eight carbon atoms. Examples of lower alkyl groups include methyl, ethyl, propyl, isopropyl, butyl, s-butyl, t-butyl, isobutyl, pentyl, cyclopentyl, hexyl, cyclohexy, and the like. Higher alkyl refers to alkyl groups containing more that 6 carbon atoms. Exemplary alkyl groups are those of $C_{20}$ or below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus either "butyl" or "$C_4$alkyl" is meant to include n-butyl, sec-butyl, isobutyl, t-butyl, isobutenyl and but-2-ynes, for example; "propyl" or "$C_3$alkyl" each include n-propyl, propenyl, and isopropyl, for example. Alkyls with variable numbers of carbons may be named by using number ranges as subscripts, as for example, lower alkyl is equivalent to $C_{1-8}$alkyl.

"Alkylene" refers to divalent straight or branched chain consisting solely of carbon and hydrogen atoms, containing no unsaturation and having from one to ten carbon atoms, e.g., methylene, ethylene, propylene, n-butylene and the like. Alkylene is a subset of alkyl, referring to the same residues as alkyl, but having two points of attachment and specifically fully saturated. Examples of alkylene include ethylene (—$CH_2CH_2$—), propylene (—$CH_2CH_2CH_2$—), 2-dimethylpropylene (—$CH_2C(CH_3)_2CH_2$—), and, 2-cyclohexylpropylene, (—$CH_2CH(C_6H_{13})CH_2$—).

"Alkylidene" refers to a straight or branched unsaturated divalent chain consisting solely of carbon and hydrogen atoms, having from two to ten carbon atoms, e.g., ethylidene, propylidene, n-butylidene, and the like. Alkylidene is a subset of alkyl, referring to the same residues as alkyl, but having two points of attachment and specifically double bond unsaturation. The unsaturation present includes at least one double bond and a double bond can exist between the first carbon of the chain and a carbon atom of the rest of the molecule to which it is attached.

"Alkylidyne" refers to a straight or branched unsaturated divalent chain consisting solely of carbon and hydrogen atoms having from two to ten carbon atoms, e.g., propylid-2-ynyl, n-butylid-1-ynyl, and the like. Alkylidyne is a subset of alkyl, referring to the same residues as alkyl, but having two points of attachment and specifically triple bond unsaturation. The unsaturation present includes at least one triple bond and a triple bond can exist between the first carbon of the chain and a carbon atom of the rest of the molecule to which it is attached.

Any of the above functional groups, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl with a vinyl substituent at the 2-position of said group.

"Alkoxy" or "alkoxyl" refers to the group —O-alkyl, for example including from 1 to 8 carbon-atoms of a straight, branched, cyclic configuration, unsaturated chains, and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O—(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of between about 2 and about 20, in another example, between about 2 and about 10, and in a further example between about 2 and about 5. Another exemplary substituted alkoxy group is hydroxyalkoxy or —$OCH_2(CH_2)_yOH$, where y is for example an integer of between about 1 and about 10, in another example y is an integer of between about 1 and about 4. Thus, where a group is defined as —OR, where "R" is optionally substituted alkyl, then such a group would include, but not be limited to, hydroxyalkoxy, polyalkoxy, and the like.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine; isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparaghe, proline and hydroxyproline. A "side chain of an α-amino acid" refers to the group found on the α-carbon of an α-amino acid as defined above, for example, hydrogen (for glycine), methyl (for alanine), benzyl (for phenylalanine), and the like.

"Amino" refers to the group —$NH_2$. "Substituted amino," refers to the group —NHR or —NRR where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, e.g., diethylamino, methylsulfonylamino, furanyl-oxy-sulfonamino.

"Aryl" refers to aromatic 6- to 14-membered carbocyclic rings include, e.g., benzene, naphthalene, indane, tetralin, fluorene and the like.

"Arylalkyl" refers to a residue in which an aryl moiety is attached to a parent structure via one of an alkylene, alkylidene, or alkylidyne. Examples include benzyl, phenethyl, phenylvinyl, phenylallyl and the like. The aryl, alkylene, alkylidene, or alkylidyne portion of an arylalkyl group may be optionally substituted. "Lower arylalkyl" refers to an arylalkyl where the "alkyl" portion of the group has one to eight carbons.

"Halogen" or "halo" refers to fluorine, chlorine, bromine or iodine. Dihaloaryl, dihaloalky); trihaloaryl etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" refers to a stable 3- to 15-membered ring that consists of carbon atoms and from one to five heteroatoms selected from the group consisting of nitrogen, phosphorus, oxygen and sulfur. For purposes of this invention, the heterocyclyl ring may be a monocyclic, bicyclic or tricyclic ring system, which may include fused or bridged ring systems, either aromatic, saturated, or combinations thereof; and the nitrogen, phosphorus, carbon or sulfur atoms in the hetemycyl ring may be optionally oxidized to various oxidation states, for example for the purposes of this invention and to negate undo repetition in the description the corresponding N-oxide of pyridine derivatives, and the like, are understood to be included as compounds of the invention. In addition, the nitrogen atom may be optionally quaternized; and the ring may be partially or fully saturated or aromatic. Examples of such heterocyclyl rings include, but are not limited to, azetidinyl, acridinyl, benzodioxolyl, benzodioxanyl, benzofuranyl, carbazoyl, cinnolinyl, dioxoianyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, indanyl, isoxazolyl, isoxazqlidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydmfuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl ring system.

"Heteroaryl" refers specifically to an aromatic heterocyclyl ring system.

"Heterocyclylalkyl" refers to a residue in which a heterocyclyl ring is attached to a parent structure via one of an alkylene, alkylidene, or alkylidyne. Examples include (4-methylpiperazin-1-yl)methyl, (morpholin-4-yl)methyl, 2-(oxazolin-2-yl)ethyl, 4(4-methylpiperazin-1-yl)-2-butenyl, and the like. The heterocyclyl, alkylene, alkylidene, or alkylidyne portion of an arylalkyl group may be optionally substituted. "Lower heterocyclylalkyl" refers to an arylalkyl where the "alkyl" portion of the group has one to eight carbons.

The term "imino" refers to a substitution on a carbon atom, more specifically to a doubly bonded nitrogen. For example, an imine, an amidine, and an oxime, all contain the "imino" group.

"Optional" or "optionally" means that the subsequently described event or circumstance may or may not occur, and that the description includes instances where said event or circumstance occurs and instances in which it does not. It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. "Optionally substituted" refers to all subsequent modifiers in a term, for example in the term "optionally substituted $C_{1-8}$alkylaryl," optional substitution may occur on both the "$C_{1-8}$alkyl" portion and the "aryl" portion of the molecule; and for example, optionally substituted alkyl includes optionally substituted cycloalkyl groups, which in turn are defined as including optionally substituted alkyl groups, potentially ad infinitum. If a heterocyclic ring is "optionally substituted," then both the carbon and any heteroatoms in the ring may be substituted thereon. Examples of optional substitution include, but are not limited to alkyl, halogen, alkoxy, hydroxy, oxo, carbamyl, acylamino, sulfonamido, carboxy, alkoxycarbonyl, acyl, alkylthio, alkylsulfonyl, nitro, cyano, amino, alkylamino, cycloalkyl and the like. Thus, for example, if a group "—C(O)R" is described, where "R" is optionally substituted alkyl, then, "R" would include, but not be limited to, —$CH_2$Ph, —$CH_2CH_2$OPh, —CH=$CHPhCH_3$, —$C_3H_4CH_2$N(H)Ph, and the like.

The term "ortho" is normally used in reference to relative position of two substituents on a benzene ring; however, in this application the term "ortho" is meant to apply to other aromatic ring systems where two substituents reside on adjacent carbons. "For example, 3-bromo-4-fluoro-thiophene possesses a bromo group and a fluoro group which have an ortho, or 1,2-positional relationship, to each other.

The term "oxo" refers to a substitution on a carbon atom, more specifically to a doubly bonded oxygen. For example, an oxo-morpholine, a cyclohexanone, and an acyl group, all contain the "oxo" functionality.

"Substituted" alkyl, aryl, and heterocyclyl, refer respectively to alkyl, aryl, and heterocyclyl, wherein one or more (for example up to about 5, in another example, up to about 3) hydrogen atoms are replaced by a substituent independently selected from the group: optionally substituted alkyl (e.g., fluoroalkyl), optionally substituted alkoxy, alkylenedioxy (e.g. methylenedioxy), optionally substituted, amino (e.g., alkylamino and dialkylamino), optionally substituted amidino, optionally substituted aryl (e.g., phenyl), optionally substituted arylalkyl (e.g., benzyl), optionally substituted aryloxy (e.g., phenoxy), optionally substituted arylalkyloxy (e.g., benzyloxy), carboxy (—COOH), carboalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heterocyclylalkyl, optionally substituted heterocyclyl, nitro, sulfanyl, sulfinyl, sulfonyl, and thio.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S($O_2$)—H, —S($O_2$)-(optionally substituted alkyl), —S($O_2$)-optionally substituted aryl), —S($O_2$)-(optionally substituted heterocyclyl), —S($O_2$)-(optionally substituted alkoxy), —S($O_2$)-optionally substituted aryloxy), and —S($O_2$) -(optionally substituted heterocyclyloxy).

The term "thiono" refers to a substitution on a carbon atom, more specifically to a doubly bonded sulfur. For example, a thioketone and a thioamide both contain the "thiono" functionality:

"Yield" for each of the reactions described herein is expressed as a percentage of the theoretical yield.

In some embodiments, as will be appreciated by those in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) may contain two substitution groups.

Some of the compounds of the invention may have imino, amino, oxo or hydroxy substituents off aromatic heterocyclyl ring systems. For purposes of this disclosure, it is understood that such imino, amino, oxo or hydroxy substituents may exist in their corresponding tautomeric form, i.e., amino, imino, hydroxy or oxo, respectively.

Compounds of the invention are generally named using ACD/Name (available from Advanced Chemistry Development, Inc. of Toronto, Canada). This software derives names from chemical structures according to systematic application of the nomenclature rules agreed upon by the International Union of Pure and Applied Chemistry (IUPAC), International Union of Biochemistry and Molecular Biology (IUBMB), and the Chemical Abstracts Service (CAS). Exemplary Compounds of the invention The following are provided as exemplary compounds only. One of skill in the art will know given the embodiments above other compounds provided for by the current invention. Compounds may also be referred to by their IUPAC names shown in Table 1.

TABLE 1

| Compound | IUPAC Nomenclature | Structure |
| --- | --- | --- |
| FIV-1 | 4-Methoxy-3-[(9-oxo-9H-fluorene-1-carbonyl)-amino]-benzoic acid | 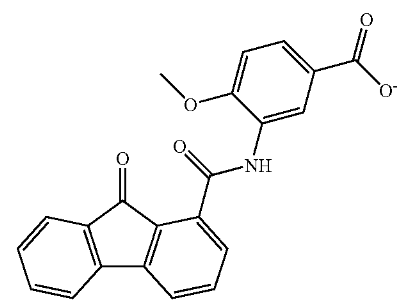 |
| FIV-2 | 2-Methoxy-5-[(9-oxo-9H-fluorene-1-carbonyl)-amino]-benzoic acid | 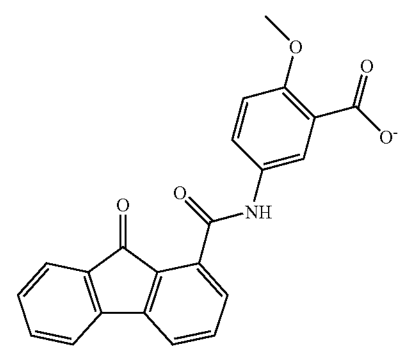 |
| FIV-3 | 3-Methoxy-5-[(9-oxo-9H-fluorene-1-carbonyl)-amino]-benzoic acid | 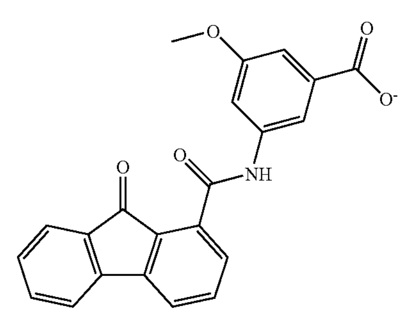 |

TABLE 1-continued

| Compound | IUPAC Nomenclature | Structure |
|---|---|---|
| FIV-4 | 4-Methyl-3-[(9-oxo-9H-fluorene-1-carbonyl)-amino]-benzoic acid | 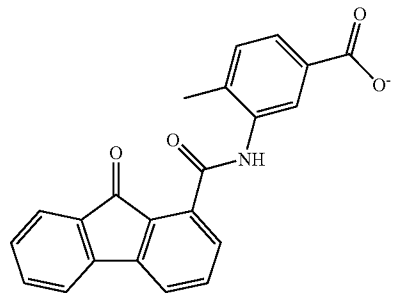 |
| FIV-5 | 2-Methyl-5-[(9-oxo-9H-fluorene-1-carbonyl)-amino]-benzoic acid | 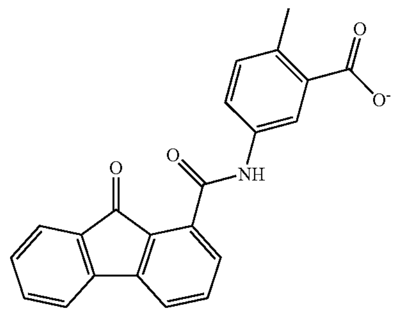 |
| FIV-6 | 2-Fluoro-5-[(9-oxo-9H-fluorene-1-carbonyl)-amino]-benzoic acid | 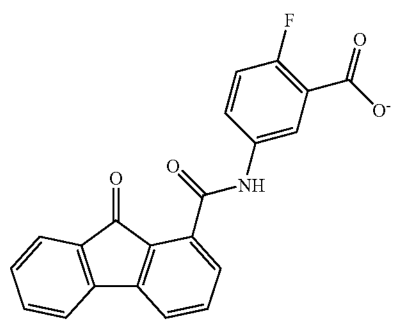 |
| FIV-7 | 4-Fluoro-3-[(9-oxo-9H-fluorene-1-carbonyl)-amino]-benzoic acid | 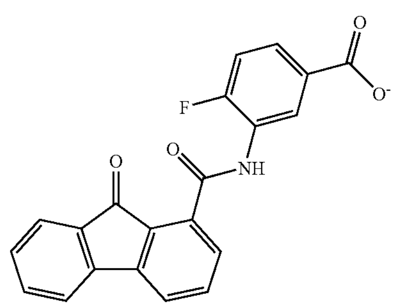 |
| FIV-8 | 9-Oxo-9H-fluorene-1-carboxylic acid [1,8]naphthyridin-4-ylamide | 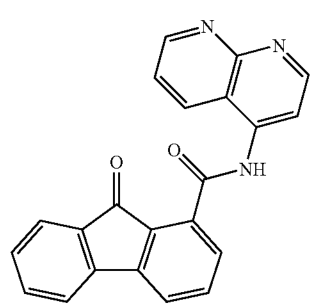 |

TABLE 1-continued

| Compound | IUPAC Nomenclature | Structure |
|---|---|---|
| FIV-9 | 3-[(9H-Fluorene-1-carbonyl)-amino]-benzoic acid | 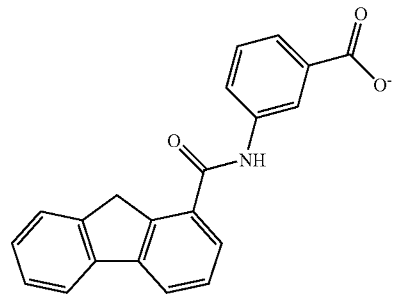 |
| FIV-10 | 3-[(Dibenzofuran-4-carbonyl)-amino]-benzoic acid | 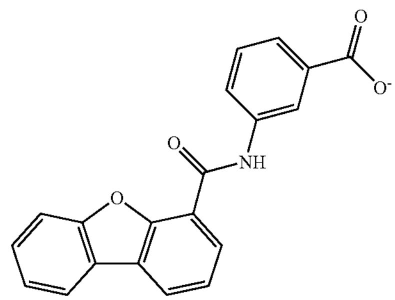 |
| FIV-11 | 3-[(9H-Carbazole-1-carbonyl)-amino]-benzoic acid | 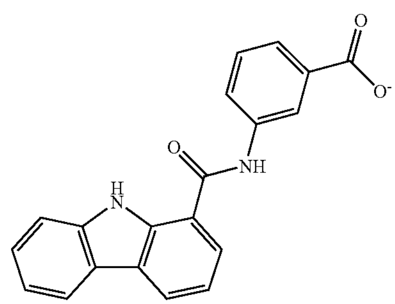 |
| FIV-12 | 3-[(9-Thioxo-9H-fluorene-1-carbonyl)-amino]-benzoic acid | 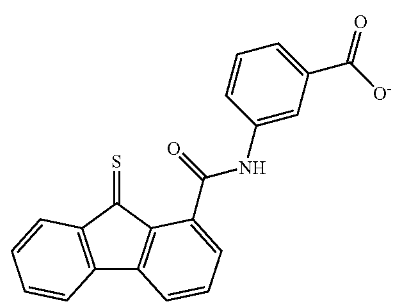 |
| FIV-13 | 3-[(Dibenzothiophene-4-carbonyl)-amino]-benzoic acid | 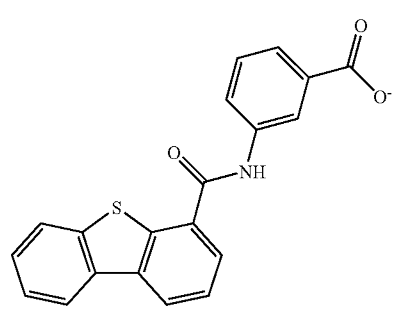 |

TABLE 1-continued

| Compound | IUPAC Nomenclature | Structure |
|---|---|---|
| FIV-14 | 7-[(9-Oxo-9H-fluorene-1-carbonyl)-amino]-benzo[1,3]dioxole-5-carboxylic acid | 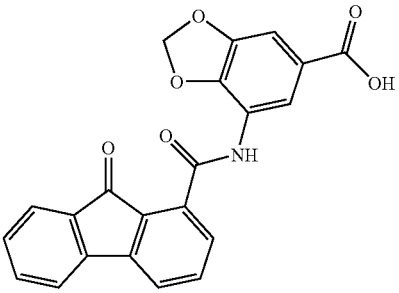 |
| FIV-15 | 6-[(9-Oxo-9H-fluorene-1-carbonyl)-amino]-benzo[1,3]dioxole-4-carboxylic acid | 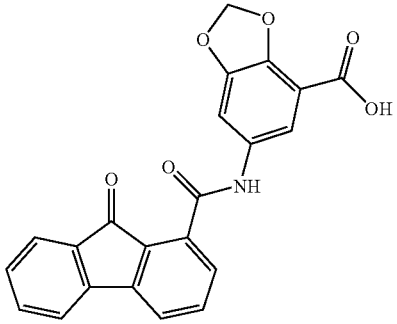 |
| FIV-16 | 4-Hydroxy-3-[(9-oxo-9H-fluorene-1-carbonyl)-amino]-benzoic acid | 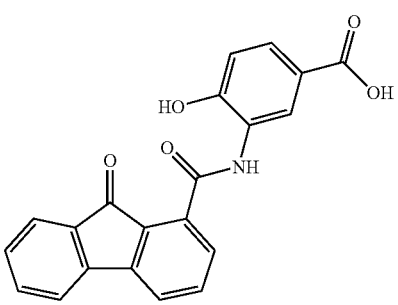 |
| FIV-17 | 1-Methyl-2-oxo-5-[(9-oxo-9H-fluorene-1-carbonyl)-amino]-1,2-dihydro-pyridine-3-carboxylic acid | 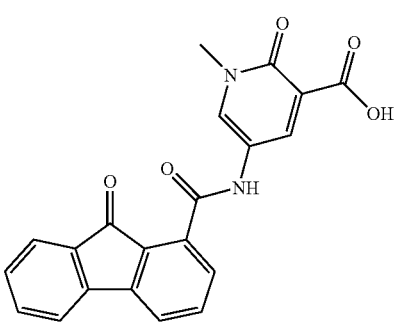 |
| FIV-18 | 4-Oxo-1-[2-oxo-2-(9-oxo-9H-fluoren-1-yl)-ethyl]-1,4-dihydro-pyridine-3-carboxylic acid | 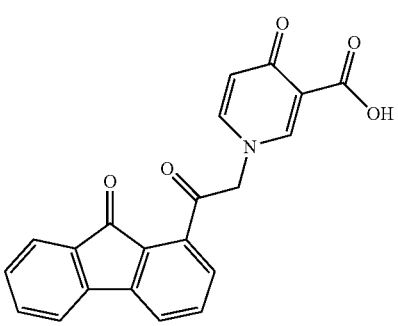 |

TABLE 1-continued

| Compound | IUPAC Nomenclature | Structure |
|---|---|---|
| FIV-19 | 4-Oxo-1-{[(9-oxo-9H-fluorene-1-carbonyl)-amino]-methyl}-1,4-dihydro-pyridine-3-carboxylic acid | 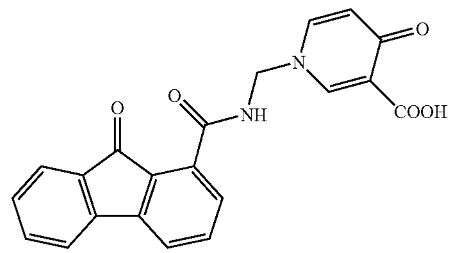 |
| FIV-20 | 2-Oxo-1-{[(9-oxo-9H-fluorene-1-carbonyl)-amino]-methyl}-1,2-dihydro-pyridine-3-carboxylic acid | 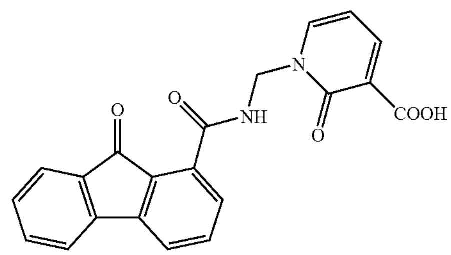 |
| FIV-21 | 1-{[(9-Oxo-9H-fluorene-1-carbonyl)-amino]-methyl}-1H-imidazole-4-carboxylic acid | 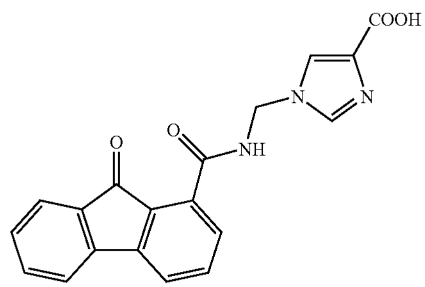 |
| FIV-22 | 9-Oxo-9H-fluorene-1-carboxylic acid (5-hydroxy-4-oxo-4H-pyran-2-ylmethyl)-amide | 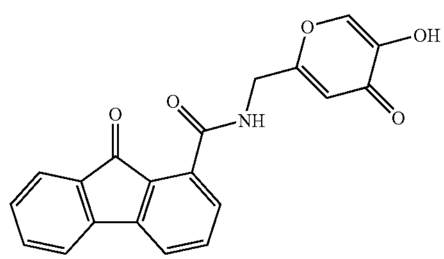 |
| FIV-23 | 9-Oxo-9H-fluorene-1-carboxylic acid (3,5-dihydroxy-4-oxo-4H-pyran-2-ylmethyl)-amide | 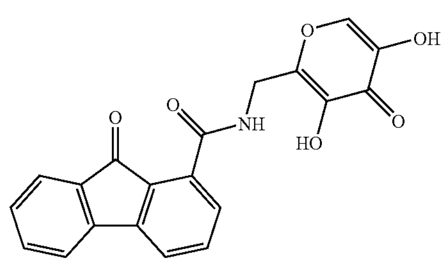 |
| FIV-24 | 9-Oxo-9H-fluorene-1-carboxylic acid (5-hydroxy-1-methyl-4-oxo-1,4-dihydro-pyridin-2-ylmethyl)-amide | 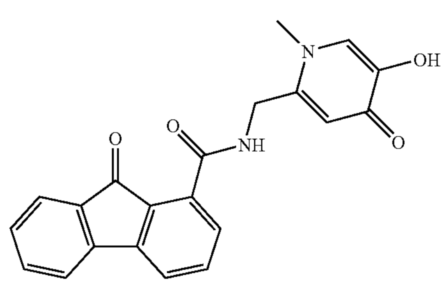 |

TABLE 1-continued

| Compound | IUPAC Nomenclature | Structure |
|---|---|---|
| FIV-25 | 9-Oxo-9H-fluorene-1-carboxylic acid (5-hydroxy-4-oxo-1,4-dihydro-pyridin-2-ylmethyl)-amide | 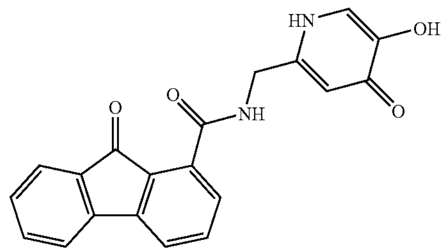 |
| FIV-26 | 9-Oxo-9H-fluorene-1-carboxylic acid (3,5-dihydroxy-4-oxo-1,4-dihydro-pyridin-2-ylmethyl)-amide | 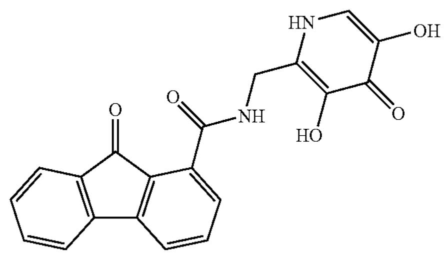 |
| FIV-27 | 3-Hydroxy-5-[(9-oxo-9H-fluorene-1-carbonyl)-amino]-benzoic acid | 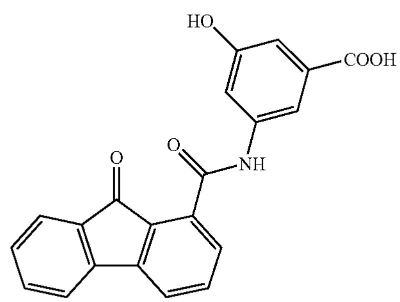 |
| FIV-28 | 3,4-Dihydroxy-5-[(9-oxo-9H-fluorene-1-carbonyl)-amino]-benzoic acid | 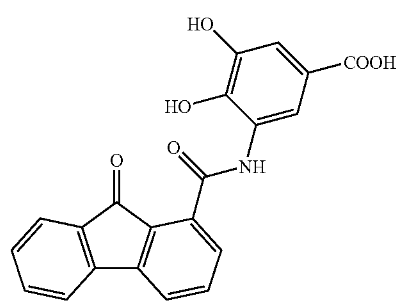 |
| FIV-29 | (S)-Amino-{3-[(9-oxo-9H-fluorene-1-carbonyl)-amino]-phenyl}-acetic acid | 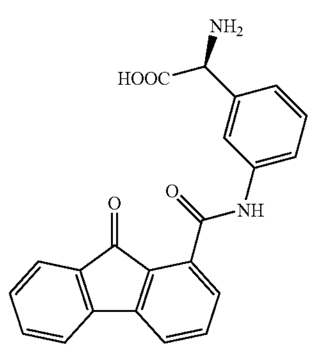 |

TABLE 1-continued

| Compound | IUPAC Nomenclature | Structure |
| --- | --- | --- |
| FIV-30 | (R)-Amino-{3-[(9-oxo-9H-fluorene-1-carbonyl)-amino]-phenyl}-acetic acid | 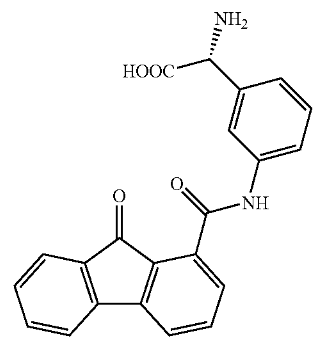 |
| FIV-31 | (S)-Hydroxy-{3-[(9-oxo-9H-fluorene-1-carbonyl)-amino]-phenyl}-acetic acid | 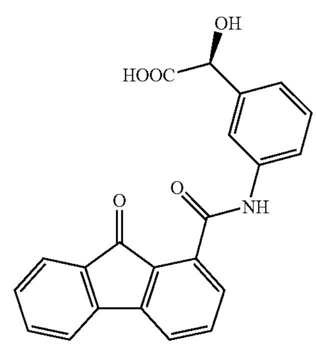 |
| FIV-32 | (R)-Hydroxy-{3-[(9-oxo-9H-fluorene-1-carbonyl)-amino]-phenyl}-acetic acid | 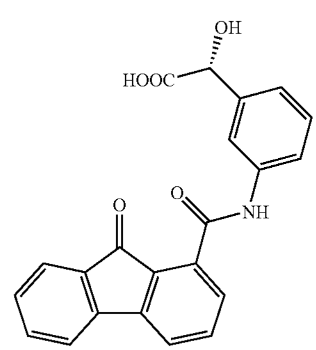 |
| FIV-33 | 2,3-Dihydroxy-5-[(9-oxo-9H-fluorene-1-carbonyl)-amino]-benzoic acid | 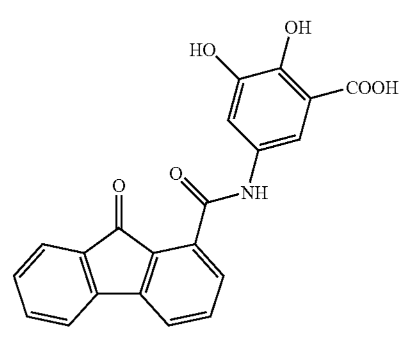 |

TABLE 1-continued

| Compound | IUPAC Nomenclature | Structure |
| --- | --- | --- |
| FIV-34 | 2-Amino-5-[(9-oxo-9H-fluorene-1-carbonyl)-amino]-benzoic acid | 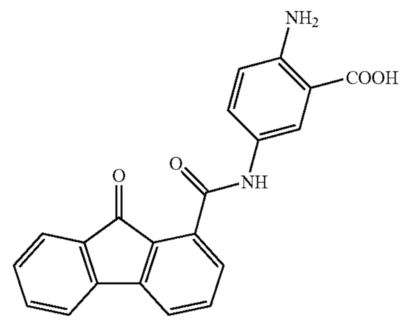 |
| FIV-35 | 2-Hydroxy-5-[(9-oxo-9H-fluorene-1-carbonyl)-amino]-benzoic acid | 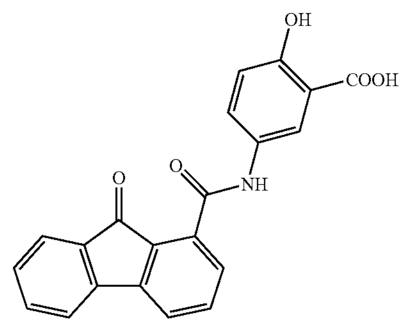 |
| FIV-36 | 2,4-Dihydroxy-5-[(9-oxo-9H-fluorene-1-carbonyl)-amino]-benzoic acid | 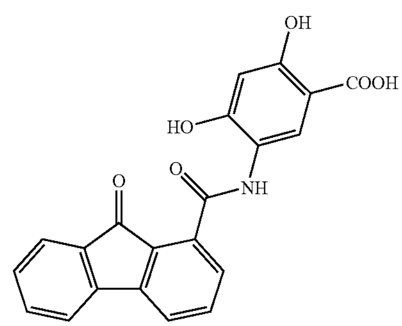 |
| FIV-37 | 4-Amino-3-[(9-oxo-9H-fluorene-1-carbonyl)-amino]-benzoic acid | 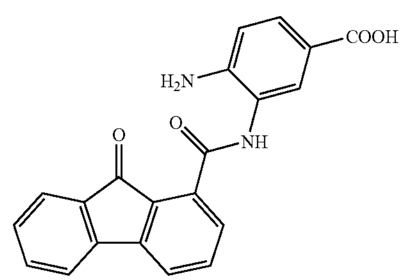 |
| FIV-38 | 9-Oxo-9H-fluorene-1-carboxylic acid (4,6-dihydroxy-5-oxo-5H-benzocyclohepten-1-yl)-amide | 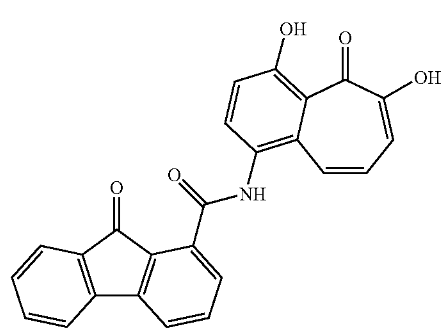 |

TABLE 1-continued

| Compound | IUPAC Nomenclature | Structure |
|---|---|---|
| FIV-39 | 2-Hydroxy-3-[(9-oxo-9H-fluorene-1-carbonyl)-amino]-benzoic acid | 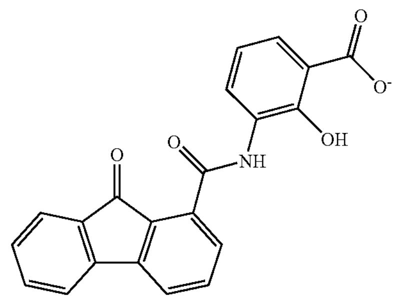 |
| FIV-40 | 2-Amino-3-[(9-oxo-9H-fluorene-1-carbonyl)-amino]-benzoic acid | 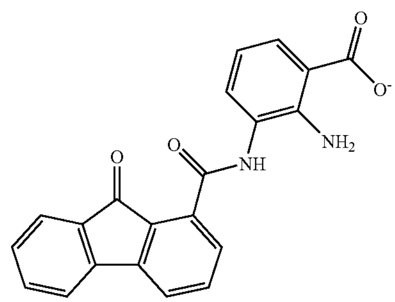 |
| FIV-41 | Dibenzothiophene-4-carboxylic acid (3-formyl-4-hydroxy-phenyl)-amide | 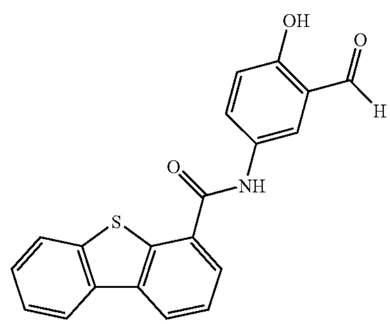 |
| FIV-42 | Dibenzothiophene-4-carboxylic acid (3-formyl-2-hydroxy-phenyl)-amide | 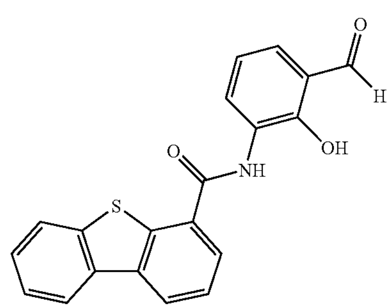 |
| FIV-43 | 2-Hydroxy-3-[(9-oxo-9H-fluorene-1-carbonyl)-amino]-benzoic acid | 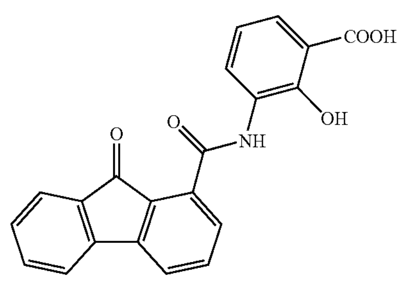 |

TABLE 1-continued

| Compound | IUPAC Nomenclature | Structure |
| --- | --- | --- |
| FIV-46 | 9-Oxo-9H-fluorene-1-carboxylic acid (3-hydroxycarbamoyl-phenyl)-amide | 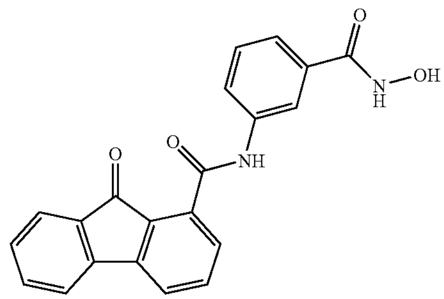 |
| FIV-47 | 2-hydroxy-6-((9-oxo-9H-fluorene-1-carboxamido)methyl)pyridine 1-oxide | 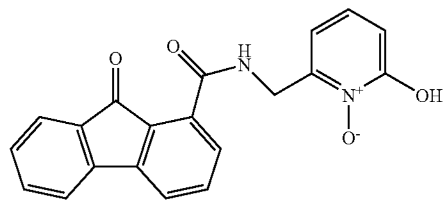 |
| FIV-48 | 2-mercapto-6-((9-oxo-9H-fluorene-1-carboxamido)methyl)pyridine 1-oxide | 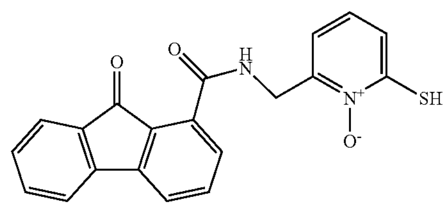 |
| FIV-49 | 3-[(9-Oxo-9H-fluorene-1-carbonyl)-amino]-phthalic acid | 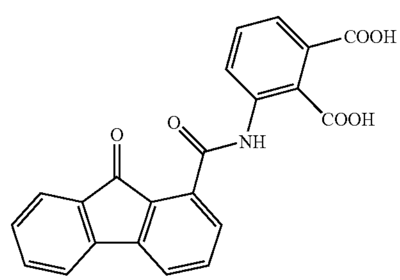 |
| FIV-50 | 3-[(9-Oxo-9H-fluorene-1-carbonyl)-amino]-benzoic acid | 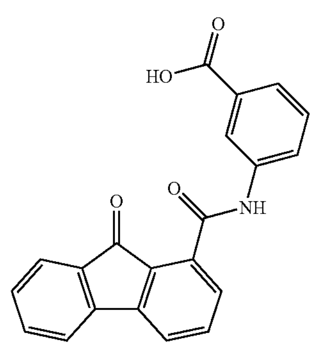 |
| FIV-51 | 3-[(9-Oxo-9H-fluorene-1-carbonyl)-amino]-benzoic acid methyl ester | 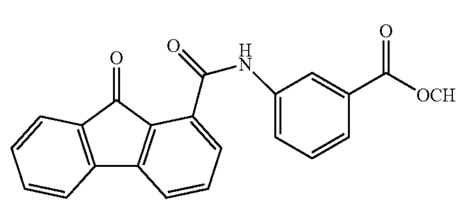 |

TABLE 1-continued

| Compound | IUPAC Nomenclature | Structure |
|---|---|---|
| FIV-53 | 2-Hydroxy-5-[(9-oxo-9H-fluorene-1-carbonyl)-amino]-benzoic acid methyl ester | 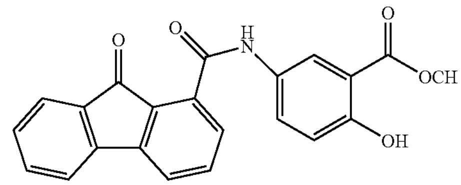 |
| FIV-54 | 2-Methyl-3-[(9-oxo-9H-fluorene-1-carbonyl)-amino]-benzoic acid methyl ester | 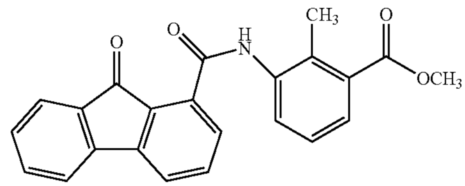 |
| FIV-55 | 2-Methyl-3-[(9-oxo-9H-fluorene-1-carbonyl)-amino]-benzoic acid | 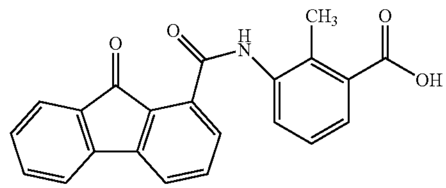 |
| FIV-56 | 9-Oxo-9H-fluorene-1-carboxylic acid (3-cyano-phenyl)-amide | 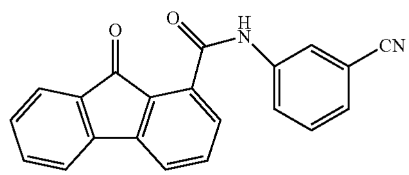 |
| FIV-57 | 9-Oxo-9H-fluorene-1-carboxylic acid (3-sulfamoyl-phenyl)-amide | 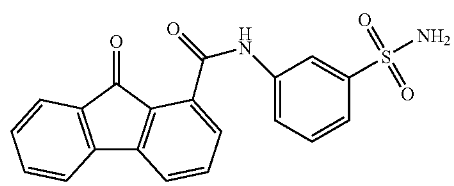 |
| FIV-58 | 4-Methoxy-3-[(9-oxo-9H-fluorene-1-carbonyl)-amino]-benzoic acid methyl ester | 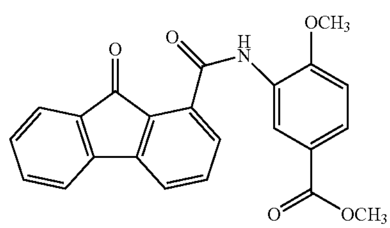 |
| FIV-59 | 4-Methoxy-3-[(9-oxo-9H-fluorene-1-carbonyl)-amino]-benzoic acid | 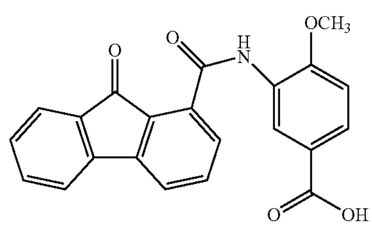 |
| FIV-60 | 9-Oxo-9H-fluorene-1-carboxylic acid (3-chloro-4-fluoro-phenyl)-amide | 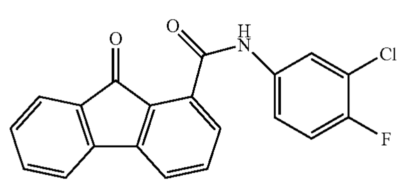 |

| Compound | IUPAC Nomenclature | Structure |
|---|---|---|
| FIV-61 | 9-Oxo-9H-fluorene-1-carboxylic acid phenylamide | 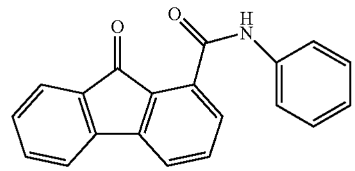 |
| FIV-62 | 9-Oxo-9H-fluorene-1-carboxylic acid (3-carbamoyl-phenyl)-amide | 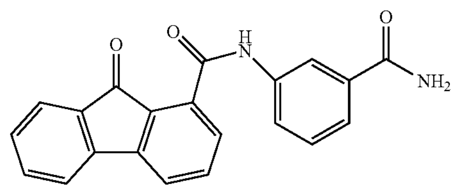 |
| FIV-63 | 9-Oxo-9H-fluorene-1-carboxylic acid (3-methylcarbamoyl-phenyl)-amide | 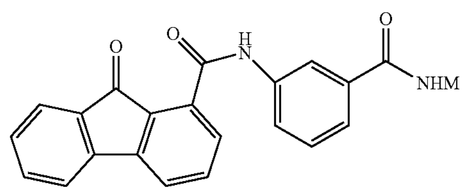 |
| FIV-64 | 9-Oxo-9H-fluorene-1-carboxylic acid (4-nitro-phenyl)-amide | 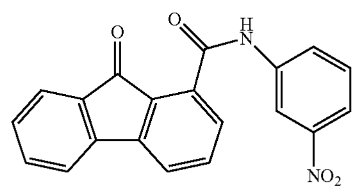 |
| FIV-65 | 9-Oxo-9H-fluorene-1-carboxylic acid (3-dimethylamino-phenyl)-amide | 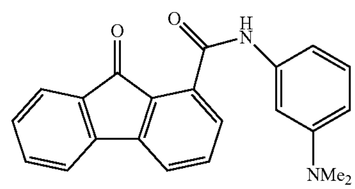 |
| FIV-66 | 9-Oxo-9H-fluorene-1-carboxylic acid (3-methylsulfanyl-phenyl)-amide | 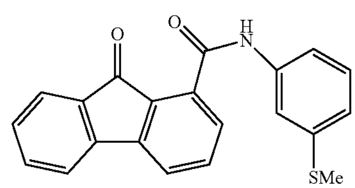 |
| FIV-67 | 9-Oxo-9H-fluorene-1-carboxylic acid (3-trifluoromethoxy-phenyl)-amide | 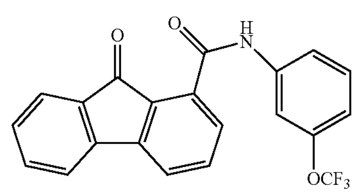 |
| FIV-68 | 9-Oxo-9H-fluorene-1-carboxylic acid (3-carbamimidoyl-phenyl)-amide | 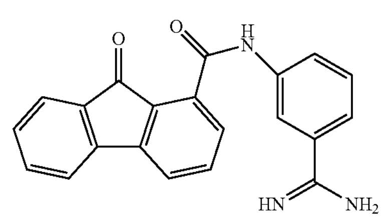 |

TABLE 1-continued

| Compound | IUPAC Nomenclature | Structure |
| --- | --- | --- |
| FIV-70 | 9-Oxo-9H-fluorene-1-carboxylic acid (2-chloro-4-cyano-phenyl)-amide | 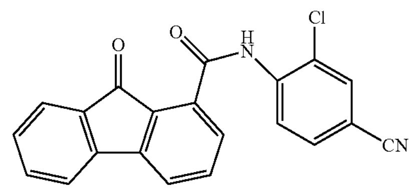 |
| FIV-74 | | 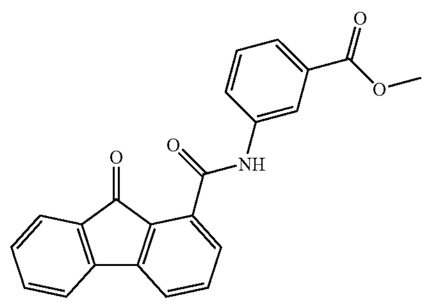 |
| FIV-75 | | 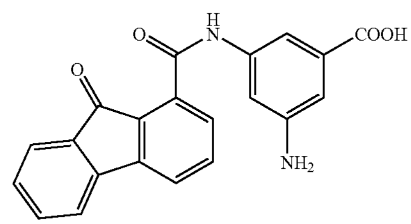 |
| FI-1 | 5-Furan-2-yl-3-(3-methoxy-phenyl)-cyclohex-2-enone | 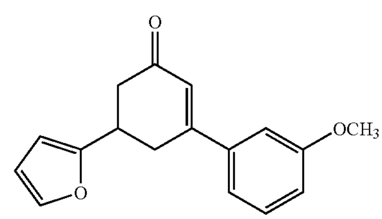 |
| FI-2 | 5-(4-Fluoro-phenyl)-3-(3-methoxy-phenyl)-cyclohex-2-enone | 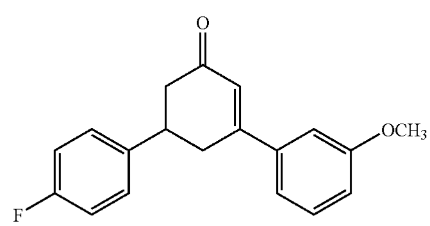 |
| FI-3 | 3-(6-Methoxy-pyridin-2-yl)-2-methyl-cyclopent-2-enone | 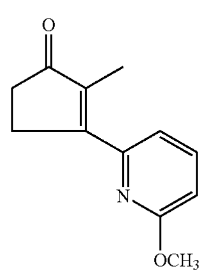 |

TABLE 1-continued

| Compound | IUPAC Nomenclature | Structure |
|---|---|---|
| FVII-1 | 3-[(Biphenyl-3-carbonyl)-amino]-benzoic acid | 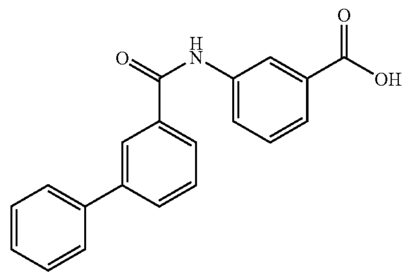 |
| FVI-1 | 3-Benzoylamino-benzoic acid | 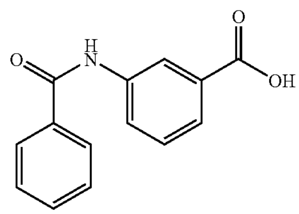 |
| FVI-2 | 3-Benzoylamino-benzoic acid methyl ester | 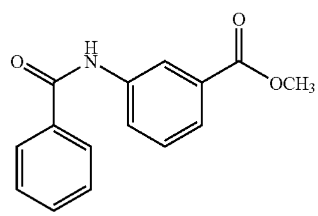 |
| FVIII-1 | 3-[(Biphenyl-4-carbonyl)-amino]-benzoic acid methyl ester | 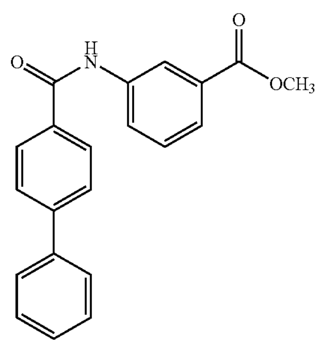 |
| FV-1 | 3-[(1H-Indole-7-carbonyl)-amino]-benzoic acid methyl ester | 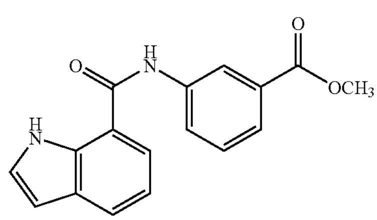 |
| FV-2 | 3-[(1H-Indole-7-carbonyl)-amino]-benzoic acid | 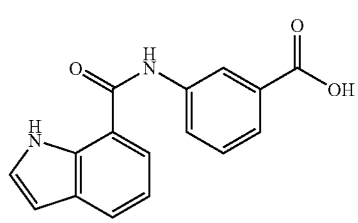 |

TABLE 1-continued

| Compound | IUPAC Nomenclature | Structure |
|---|---|---|
| FII-1 | | 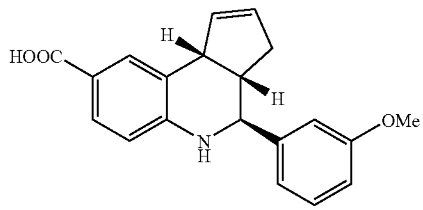 |
| FII-2 | 4-(3-Methoxy-phenyl)-3a,4,5,9b-tetrahydro-3H-cyclopenta[c]quinoline-7-carboxylic acid | 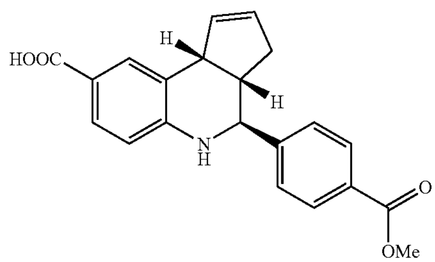 |
| FIII-1 | 4-[(Anthracen-9-ylmethylene)-amino]-2-hydroxy-benzoic acid | 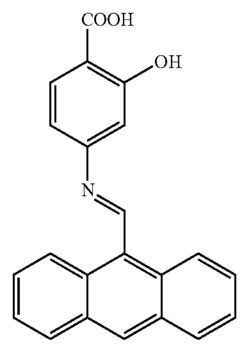 |
| FIV-71 | 2-Chloro-3-[(9-oxo-9H-fluorene-1-carbonyl)-amino]-benzoic acid | 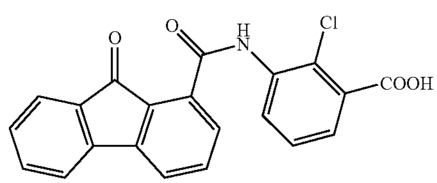 |
| FIV-72 | 5-Amino-2-[(9-oxo-9H-fluorene-1-carbonyl)-amino]-benzoic acid | 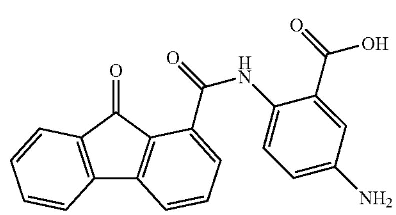 |
| FIV-73 | 2-Amino-5-[(9-oxo-9H-fluorene-1-carbonyl)-amino]-benzoic acid | 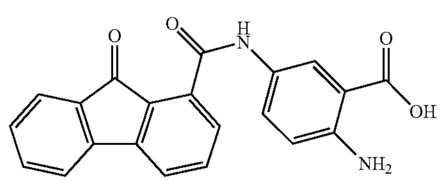 |

TABLE 1-continued
| Compound | IUPAC Nomenclature | Structure |
|---|---|---|
| FI-4 | 3-Phenylcyclohex-2-enone | 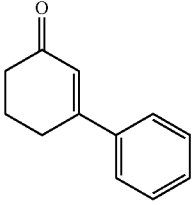 |
| FI-5 | 3-Pyridin-3-yl-cyclohex-2-enone | 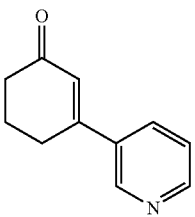 |
| FI-6 | 3-Dibenzofuran-4-yl-cyclohex-2-enone | 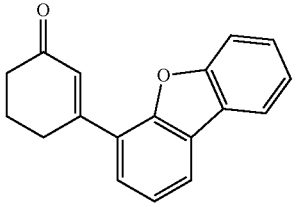 |
| FI-7 | 3-Benzo[b]thiophen-2-yl-cyclohex-2-enone | 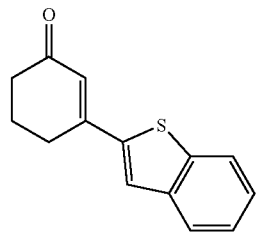 |
| FI-8 | 3-(1-Methyl-1H-pyrazol-4-yl)-cyclohex-2-enone | 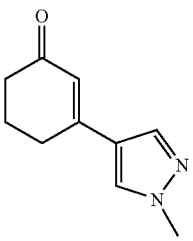 |
| FI-9 | 3-(6-Methoxy-pyridin-2-yl)-cyclohex-2-enone | 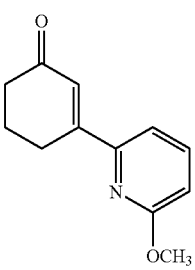 |

TABLE 1-continued

| Compound | IUPAC Nomenclature | Structure |
|---|---|---|
| FI-10 | 3-Thiazol-2-yl-cyclohex-2-enone | 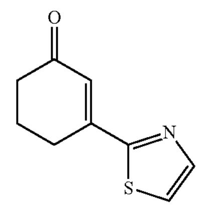 |
| FI-11 | 3-Thiophen-3-yl-cyclohex-2-enone | 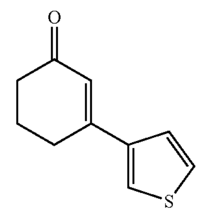 |
| FI-12 | 3-Thiophen-2-yl-cyclohex-2-enone | 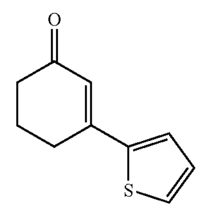 |
| FI-13 | 3-Furan-3-yl-cyclohex-2-enone | 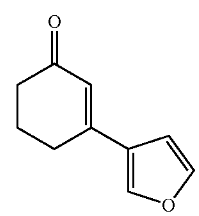 |
| FI-14 | 3-(6-Methoxy-pyridin-3-yl)-2-methyl-cyclopent-2-enone | 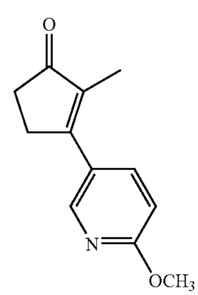 |
| FI-15 | 3-(3-Methoxy-phenyl)-cyclohex-2-enone | 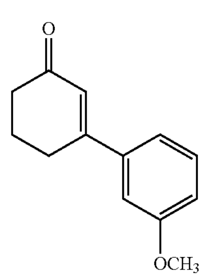 |

TABLE 1-continued
| Compound | IUPAC Nomenclature | Structure |
|---|---|---|
| FI-16 | 3-Quinolin-6-yl-cyclohex-2-enone | 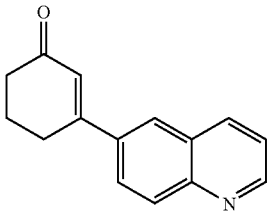 |
| FI-17 | 3-(1H-Indol-5-yl)-cyclohex-2-enone | 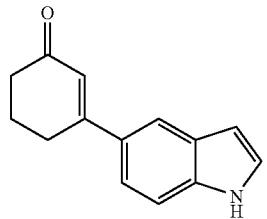 |
| FI-18 | 3-Benzo[1,3]dioxol-5-yl-cyclohex-2-enone | 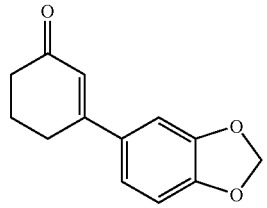 |
| FI-19 | 3-(3-Hydroxy-phenyl)-cyclohex-2-enone | 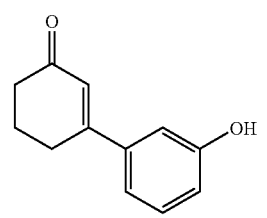 |
| FI-20 | 3-(1H-Indol-5-yl)-5,5-dimethyl-cyclohex-2-enone | 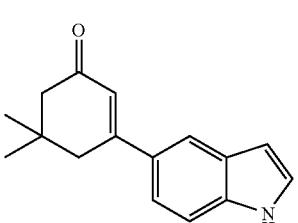 |
| FI-21 | 3-(6-Methoxy-pyridin-2-yl)-2-methyl-cyclopent-2-enone | 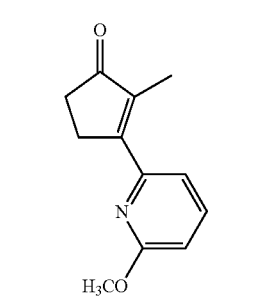 |

| Compound | IUPAC Nomenclature | Structure |
| --- | --- | --- |
| FI-22 | 2-Methyl-3-quinolin-6-yl-cyclopent-2-enone | 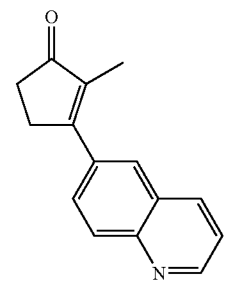 |
| FI-23 | 2-Methyl-3-(1-methyl-1H-pyrazol-4-yl)-cyclopent-2-enone | 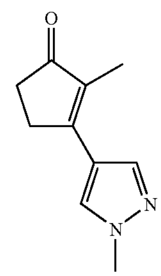 |
| FI-24 | 2-Methyl-3-pyridin-3-yl-cyclopent-2-enone | 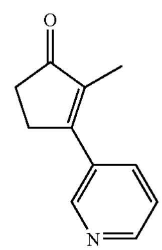 |
| FI-25 | 3-(1H-Indol-5-yl)-2-methyl-cyclopent-2-enone | 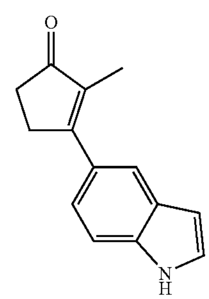 |
| FI-26 | 3-Dibenzofuran-4-yl-5,5-dimethyl-cyclohex-2-enone | 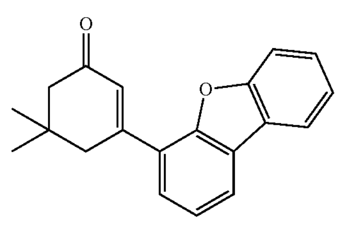 |
| FI-27 | 3-(2-Methoxy-phenyl)-cyclohex-2-enone | 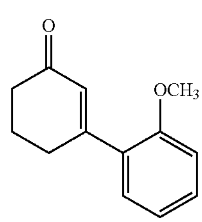 |

B. Exemplary Synthesis Methods

Below are exemplary methods to synthesize fluorenone type compounds. The following reactions are known to one of skill in the art and are included as examples but are not limited to the following methods. As one of skilled in the art will appreciate that there are alternatives to the following synthetic methods.

Lab Scale Chemistry:

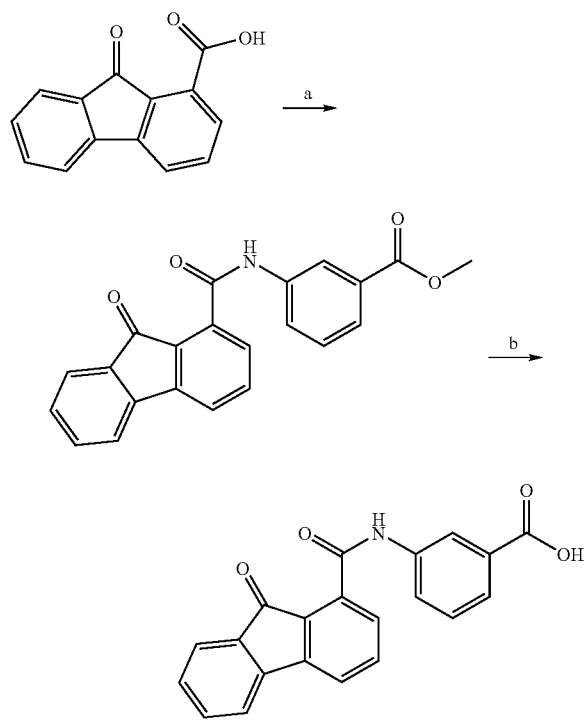

Step a: Amide Coupling

In a 100 ml round bottom flask was added 9-fluoroenone-1-carboxylic acid (1.02 g, 4.55 mmol, 1 equiv), (Benzotriazol-1-yloxy)-tris-(dimethylamino)phosphonium hexafluorophosphate (BOP) (2.21 g, 5 mmol, 1.1 equiv.) and $CH_3CN$ (50 mL). Then diisopropyl ethyl amine (DIPEA) (13.6 mmol, 2.38 mL, 3.0 equiv.) was added and the reaction mixture became homogeneous. After 5 min. stirring at room temperature methyl 3-aminobenzoate (5 mmol, 0.76 g, 1.1 equiv.) were added. The reaction was monitored by TLC and LCMS. Upon reaction completion, the product precipitated out. The precipitates were filtered and washed with $CH_2Cl_2$, $H_2O$, affording the desired product in 91% yield.

Step b: Methyl Ester Cleavage:

To a 500 ml round bottom reaction flask was added Methyl 3-(9-oxo-9H-fluorene-1-carboxamido)benzoate (1.61 g, 4.5 mmol, 1 equiv), $LiOH \cdot H_2O$ (0.57 g, 13.5 mmol, 3 equiv) and $THF:H_2O$ (100 mL:100 mL). The mixture was refluxed overnight. Upon reaction completion monitored by TLC, the solvent was evaporated; the mixture was diluted in $CH_2Cl_2$ and acidified with 0.5 M HCl until pH=6. The precipitated solid was then filtered and washed with $CH_2Cl_2$ and $H_2O$, affording the desired product in 98% yields.

Process Chemistry:

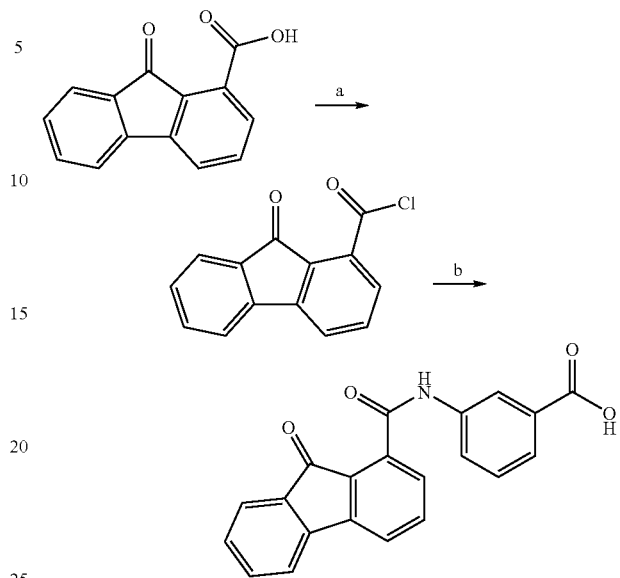

Step a: Acid Chloride Formation

To a dried and tared 500 ml round bottom reaction flask equipped with a stirring bar was added 3-[(9-oxo-9H-fluorene-1-carbonyl)-amino]-benzoic acid (88.7 mmol, 19.9 g) and thionyl chloride (200 ml). The mixture was refluxed 3 hrs. Upon reaction completion monitored by TLC, the thionyl chloride was distilled off. The resulted solid was dried under vacuum overnight to remove traces amount of thionyl chloride, affording the crude acid chloride in 97% yield.

Step b: Amide Bond Formation Via Acid Chloride

To a stirred solution of 3-aminobenzoic acid (13.4 g, 97.6 mmol, 1.1 equiv) and triethylamine (44.9 ml, 322 mmol, 3.3 equiv) dissolved in 120 mL dry $CH_2Cl_2$ at 0° C. was added dropwise a solution of 9-oxo-9H-fluorene-1-carbonyl chloride (88.7 mmol, 1 equiv) in 120 mL dry $CH_2Cl_2$. Stirring was continued at 0° C. for 1 h and at room temperature for 3 h. Upon complete, the reaction mixture was diluted with 100 mol $CH_2Cl_2$, and acidified by 2N HCl until pH=3. The precipitate was filtered, washed with $H_2O$, $CH_2Cl_2$, and dried to give the desired product in 94% yield.

While the above are exemplary methods, the compositions of the present invention and any functionally active derivatives thereof may be obtained by any suitable means. In specific embodiments, the derivatives are synthesized. The chemical synthesis of the derivatives may employ well known techniques from readily available starting materials. Such synthetic transformations may include, but are not limited to protection, de-protection, oxidation, reduction, metal catalyzed C—C cross coupling, Heck coupling or Suzuki coupling steps (see for example, March's Advanced Organic Chemistry: Reactions, Mechanisms, and Structures, 5th Edition John Wiley and Sons by Michael B. Smith and Jerry March, incorporated here in full by reference.)

VI. Combination Treatments

In one embodiment, the compounds of the invention may be used in combination with other treatments. Exemplary combinations treatments are listed below; however, one of skill in the art would know of other treatments that could be made in combination with the current invention to provide additional treatment to the subject.

A. Antibacterials

Antibacterials are generally used to reduce or prevent infection. Non-limiting examples of antibacterials include antibiotic antibacterials, synthetic antibacterials, leprostatic antibacterials rickettsia antibacterials, tuberculostatic antibacterial or a combination thereof. Antibiotics are well known in the art and one of skill in the art would know which antibiotics to use depending on various known factors such as type of pathogen or infection locations, for example. Antibiotic treatment of diarrheal disease may also be counter indicated, as this can lead to subsequent infections, e.g. with *Clostridiam difficile* or other multidrug resistant bacteria, yeast or fungi. A skilled artisan will know the correct treatment. The following are exemplary antibacterials.

a) Antibiotic Antibacterials

Non-limiting examples of antibiotic antibacterials include an aminoglycoside (e.g., amikacin, apramycin, arbekacin, a bambermycin, butirosin, dibekacin, dihydrostreptomycin, a fortimicin, gentamicin, isepamicin, kanamycin, micronomicin, neomycin undecylenate, netilmicin, paromomycin, ribostamycin, sisomicin, spectinomycin, streptomycin, streptonicozid, tobramycin), an amphenol (e.g., azidamfenicol, chloramphenicol, chloramphenilcol palmitate, chloramphenicol pantothenate, florfenicol, thiamphenicol), an ansamycin (e.g., rifamide, rifampin, rifamycin, rifaximin), a β-lactam (e.g., a carbapenem, a cephalosphorin, a cephamycin, a monobactam, an oxacephem, a penicillin), a lincosamide (e.g., clindamycin, lincomycin), a macrolide (e.g., azithromycin, carbomycin, clarithromycin, erythromycin acistrate, erythromycin estolate, erthromycin glucoheptonate, erythromycin lactobionate, erythromycin lactobionate, erythromycin propionate, erythromycin stearate, josamycin, leucomycin, midecamycin, miokamycin, oleandomycin primycin, primycin, rokitamycin, rosaramicin, roxithromycin, spiramycin, troleandomycin), polypeptides (e.g., amphomycin, bacitracin, capreomycin, colistin, enduracidin, enviomycin, fusagungine, a gramicidin, a gramicidin S, mikamycin, polymyxin, polymyxin B-Methanesulfonic acid, pristinamycin, ristoceitin, teicoplanin, thiostrepton, tuberactinomycin, tyrocidine, tyrothricin, vancomycin, viomycin, viomycin pantothenate, virginiamycin, zinc bacitracin), tetracycline (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin, tetracycline) or a miscellaneous antibiotic antibacterial (e.g., cycloserin, mupirocin, tuberin).

Non-limiting examples of a carbapenem β-lactam include imipenem. Non-limiting examples of a cephalosporin β-lactam include cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime proxetil, cefroxadine, cefsulodin, ceftazidime, cefteram, cftezole, ceftibuten, ceftizoxime, ceftriaxone, cefuroxime, cefuzonam, cephacetrile sodium, cephalexin, cephaloglycin, cephaloridine, cephalosporin C, cephalothin, cephapirin sodium, cephradine and pivcefalexin. Non-limiting examples of a cephamycin β-lactam include cefbuperazone, cefmetazole, cefminox, cefotetan and cefoxitin. Non-limiting examples of a monobactam β-lactam include aztreonam, carumonam and tigemonam. Non-limiting examples of a oxacephem β-lactam include flomoxef and moxolactam. Non-limiting examples of a penicillin β-lactam include amidinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carfecillin sodium, carindacillin, clometocillin, cloxacillin, cyclacillin, dicloxacillin diphenicillin sodium, epicillin, fenbenicillin, floxacillin, hetacillin, lenampicillin, metampicillin, methicillin sodium, mezlocillin, nafcillin sodium, mezlocillin, nafcillin sodium, oxacillin, penamecillin, penethamate hydridide, penicillin G benethiamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hhdrabamine, penimepicycline, phenethicillin potassium, piperacillin, pivampicillin, propicillin, quinacillin, sulbenicillin, talampicillin, temocillin and ticarcillin.

b) Synthetic Antibacterials

Non-limiting examples of synthetic antibacterials include 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifuprazine, nifurtoinol, nitrofurantion), quinolones and quinone analogs (e.g., amifoxacin, cinoxacin, ciprofloxacin, levofloxin, difloxacin, enoxacin, fleroxacin, flumequine, lomefloxacin, miloxacin, nalidixic acid, norfloxacin, ofloxacin, oxolinic acid, pefloxacin, pipemidic acid, piromidic acid, rosoxacin, temafloxacin, tosulfoxacin), sulfonamides (e.g., acetyl sulfamethoxypraxine, acetyl sulfisoxazole, azosulfamide, benzylsulfamide, chloramine-B, chloramine-T, dichloramine T, formosulfathiazole, $N^2$-formylsulfisomidine, $N^4$-β-D-glucosylsulfanilamide, mafenide, 4'-(methylsulfanoyl)sulfanilamide, ρ-nitrosulfathiazole, phthalysulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicylic acid, $N^4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole), sulfones (acedapsone, acediasulfone, acetosulfone sodium, dapsone, diathymosulfone, glucosulfone sodium, solasulfone, succisulfone, sulfanilic acid, p-sulfanilylbenzylamine, p,p'-sulfonyldianiline-N,N'diagalactoside, sulfoxone sodium, thiazolsulfone), and miscellaneous synthetic antibacterials (e.g., clofoctol, hexedine, methenamine, methenamine anhydromethylene-citrate, methenamine hippurate, methenamine mandelate, methenamine sulfosalicylate, nitroxoline, xibornol).

c) Liprostatic Antibacterials

Non-limiting examples of leprostatic antibacterials include acedapsone, acetosulfone sodium, clofazimine, dapsone, diathymosulfone, glucosulfone sodium, hydnocarpic acid, solasulfone, succisulfone and sulfoxone sodium.

d) *Rickettsia* Antibacterials

Non-limiting examples of *rickettsia* antibacterials, also known as antirickettsials, include p-aminobenzoic acid, chloramphenicol, chloramphenicol palmitate, chloramphenicol pantothenate and tetracycline.

e) Tuberculostatic Antibacterials

Non-limiting examples of tuberculostatic antibacterials include p-aminosalicylic acid, p-aminosalicylic acid hydrazine, benzoylpas, 5-bromosalicylhydroxamic acid, capreomycin, clofazimine, cyacetacide, cycloserine, dihydrostrptomycin, enviomycin, ethambutol, ethionamide, 4'-formylsuccinanilic acid thiosemicarbazone, furonazide, glyconiazide, isobutol, isoniazide, isoniazid methanesulfonate, morphazinamide, opiniazide, parsiniazide, phenyl aminosalicylate, protionamide, pyrazinamide, rifampin, salinazide, streptomycin, subathizone, sulfoniazide, thiacetazone, tiocarlide, tuberactinomycin, tubercidin, tuberin verazide, viomycin and vicmycin pantothenate.

B. Anti-Inflammatory

Anti-inflammatory agents are agents that decrease the signs and symptoms of inflammation. A wide variety of anti-inflammatory agents are known to one of skill in the art. Most commonly used are the nonsteroidal anti-inflammatory agents (NSAIDs) which work by inhibiting the production of prostaglandins. Non-limiting examples include, ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, and magnesium salicylate. Another group of anti-inflammatory agents comprise steroid based potent anti-inflammatory agents, for example, the corticosteroids which are exemplified by dexamethason, hydrocortisone, methylprednisolone, prednisone, and triamcinolone as non-limiting examples. Several of these anti-inflammatory agents are available under well known brand names, for example, the NSAIDs comprising ibuprofen include Advil, Motrin IB, Nuprin; NSAIDs comprising acetaminophens include Tylenol; NSAIDs comprising naproxen include Aleve.

C. Anti-Diarrheal Drugs

Any anti-diarrheal drug may be used in combination with the current invention. Exemplary anti-diarrheal drugs include loperamide, bismuth subnitrate, bismuth subcarbonate or berberine chloride, bisacodyl, magnesium hydroxide, loperamide, diphenoxylate, and dioctyl sodium sulfosuccinate.

D. Others

One of skill in the art would know of specific treatments and additional drugs that can be used in combination with the current invention. In one embodiment, the invention additionally comprises LT inhibitory drugs. In a specific embodiment the LT inhibitory drug is selected from the group consisting of bestatin, captopril, adefovir, and any combination thereof.

VII. Pharmaceutical Preparations

Pharmaceutical compositions of the present invention comprise an effective amount of one or more of the inventive compound claimed or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one of the inventive compounds or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The inventive compound may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The inventive composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a the inventive compound and/or composition, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the inventive compound may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In certain embodiments of the present invention, the inventive compounds are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and in certain embodiments about 1% to about 2%.

B. Parenteral Compositions and Formulations

In further embodiments, the inventive compound may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, isotonic agents may be used, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, two exemplary methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other embodiments of the invention, the inventive active compound may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethey-lene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VIII. Kits

Any of the compositions described herein may be comprised in a kit. In a non-limiting example, the composition of the invention, lipid, and/or additional agent, may be comprised in a kit. The kits will thus comprise, in suitable container means, the composition of the invention and a lipid, and/or an additional agent of the present invention.

The kits may comprise a suitably aliquoted composition, lipid and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and suitably aliquoted. Where there are more than one component in the kit, the kit also will generally contain a second, third or other additional container into which the additional components may be separately placed. However, various combinations of components may be comprised in a vial. The kits of the present invention also will typically include a means for containing a compound of the invention, lipid, additional agent, and any other reagent containers in close confinement for commercial sale. Such containers may include injection or blow-molded plastic containers into which the desired vials are retained.

Therapeutic kits of the present invention are kits comprising a chemical compound of the invention or pharmaceutically acceptable salts thereof, protein, polypeptide, peptide, inhibitor, gene, vector and/or other effectors. Such kits will generally contain, in suitable container means, a pharmaceutically acceptable formulation of a chemical compound of the invention or a pharmaceutically acceptable salt thereof, in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution also being used. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which a chemical compound of the invention in a formulation are placed and suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate chemical compound of the invention within the body of an animal. Such an instrument may be a syringe, pipette, forceps, and/or any such medically approved delivery vehicle.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Protein Database Structures Used and Active Site Regions 1) 1K90 (Drum et al., 2002): the crystal structure of the adenylyl cyclase domain of anthrax edema factor (EF) in complex with both calmodulin and a non-cyclizable nucleotide analogue, 3'-deoxy-ATP (3'dATP) with resolution 2.75 Å and R-Value 0.225. The non-cyclizable 3'dATP lies at the substrate-binding pocket, which is shown in FIGS. 3(A and E). In 1K90, the metal is $Yb^{3+}$, a crystallization additive, rather than $Mg^{2+}$, the presumed physiological metal ion. The one $Yb^{3+}$ coordinates with 2 negatively charged carboxyl groups from residues Asp491 (Yb—O distance: 2.14 Å, 2.56 Å), Asp493 (2.16 Å, 2.23 Å) and His577 (Yb—N, 2.78 Å) and coordinates with a negative charged oxygen atom from the α-phosphate group of 3'-dATP(Yb—O: 2.38 Å). Besides forming coordinate bonds with $Yb^{3+}$, the most notable phosphate interactions are made by Lys 346 (which contacts oxygen atoms from all three phosphates, the hydrogen bond distance between Lys346 and α-, β-, and γ-phosphate are about 2.66 Å, 2.47 Å and 1.80 Å respectively) and Arg 329 (which interacts with the β-phosphate with hydrogen bond length 2.19) and Lys 372 and Ser 354, which interact with the γ-phosphate with hydrogen bond 1.6 Å and 2.5 Å respectively.

2) 1XFV (Shen et al., 2005), the crystal structure of anthrax edema factor in complex with calmodulin and a non-cyclizable nucleotide analogue, 3'dATP with resolution 3.35 Å and R-Value 0.263. Two magnesium ions, which are about 4.32 Å away from each other, are located at the catalytic site of EF and ATP. Like 1K90, the non-cyclizable 3'-dATP lies at the substrate-binding pocket, which is shown in FIGS. 3(B and F). Of the two metal ions, one coordinates with residues Asp491, Asp493, His577 and negatively charged oxygen atoms form the phosphate group of 3'dATP. The other one coordinates only with the negative charged oxygen atoms of 3'dATP and does not have any direct interactions with the protein. So, when docking $PGE_2$-imidazole to 1XFV, the metal ion which does not have ligands to the protein was removed. Residues Lys346, Arg329, Lys372 hydrogen bond with the negatively charged oxygen atoms of 3'dATP.

3) 1CJV (Tesmer et al., 1999): The crystal structure of the complex of Gs-α with the catalytic domains of mammalian adenylyl cyclase and complex with β-L-2',3'-dideoxyatp (2'3'-ddATP) with resolution 3.00 Å and R-Value 0.203. The active site is shown in FIGS. 3(C and G). In the active site of mammalian adenylate cyclase (from 1CJV), there are two metal ions (Zn and Mg), which are 3.68 apart. Residues Asp396 and Asp440 provide bridging carbonyl and lie between the metals to chelate the two metals. Besides forming coordinate bonds with the residues, the Mg ion also forms coordinate bonds with the oxygen atoms from the three phosphate of 2'3'-ddATP, while the Zn ion forms coordinate bind only with the an oxygen atom from the α-phosphate group.

4): 1ZOT: Crystal Structure of Adenylyl Cyclase Toxin Of *Bordetella pertussis* in complex with adenine-9-yl-ethoxymthyl-hydroxyphosphinyl-diphosphate (EMA) with resolution 2.20 Å and R-Value 0.252. Three magnesium ions (Mg901, Mg902 and Mg903) are found in the active site. In addition to coordinating with 2 negative charged carboxyl groups from residues Asp190 and Asp188, Mg901 also coordinates with one oxygen atom of the α-phosphate. Mg903 coordinates with the other oxygen atom of the α-phosphate. Around the phosphate groups, there are four positive charge residues: Arg41, Lys58, Lys65 and Lys84. Only Lys65 has strong interaction with the γ-phosphate group. FIG. 3 shows the active site of the four proteins.

Figure 4:
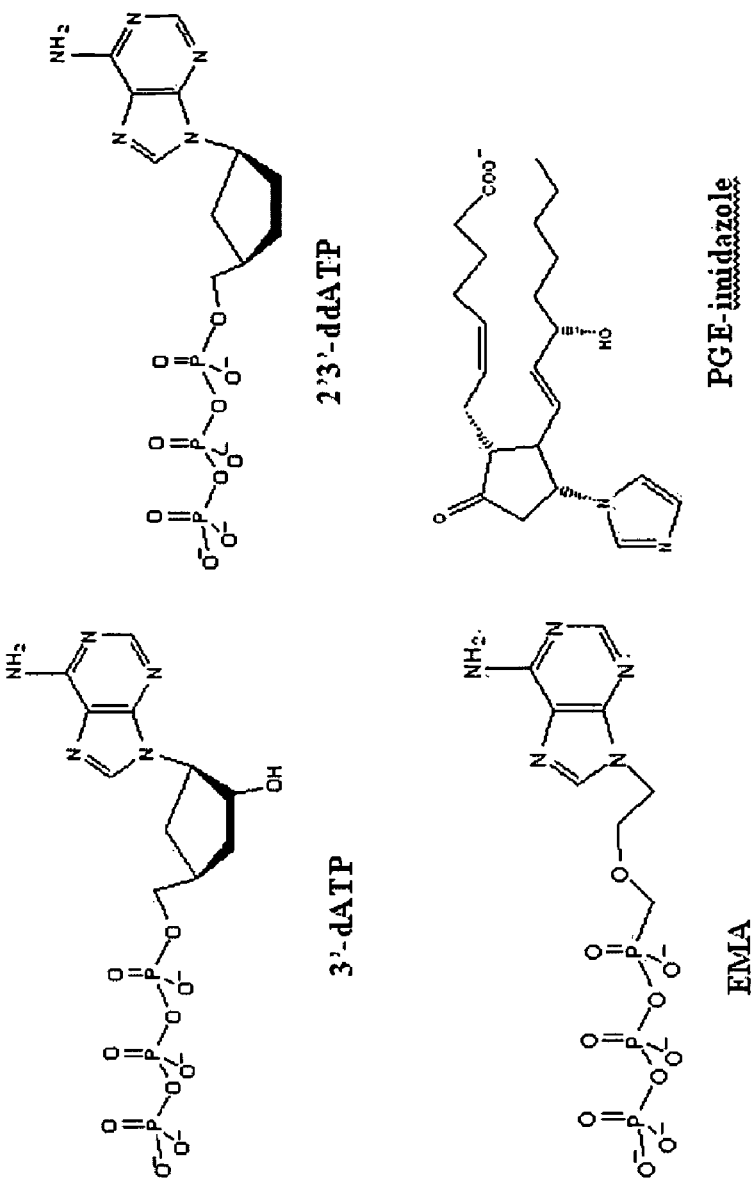

Control Ligands (FIG. 4): 3d'ATP, 2'3'ddATP and EMA are non-cyclizable nucleotide analogues of ATP. $PGE_2$-imidazole is a known inhibitor for Edema Factor. All carboxyl groups and phosphate groups were deprotonated. For all the dockings of 1K90, $Yb^{3+}$ was replaced with $Mg^{2+}$. Tests done with Autodock and different metal ions and charges indicated that there was relatively little difference in the scoring or ranking of ligands. $PGE_2$-imidazole was synthesized as previously described and stored frozen.

Mammalian adenylyl cyclase (FIG. 3D, FIG. 3H) has a true 2 metal ion active site. The bound $Zn^{2+}$ and $Mg^{2+}$ both have ligands to the protein and the substrate. The $Mg^{2+}$ ion chelates the α, β, γ phosphates of 2'3'-ddATP, Asp396 and Asp440. The $Zn^{2+}$ ion chelates the α-phosphates of 2'3'-ddATP, Asp396 and Asp440.

Example 2

Docking Programs and Methods

1) AutoDock (version 3.0.5) (Brisson et al., 2004; Morris et al., 1996): To set search parameters, the Lamarckian Genetic Algorithm (LGA) was used and the number of GA runs was 200 and population size was 100. The active site was defined using AutoGrid. The grid size was set to 90×90×90 points with grid spacing of 0.375 Å. The center of the ligand from the corresponding crystal structure was set to be the grid box center. The ligand and solvent were removed from the crystal structure and the remaining protein model was used in docking procedure. The best ranked conformation is selected from the conformation with the lowest binding energy. For the Zn ion in 1CJV, its parameters are set to radius, 0.87 Å; well depth, 0.35 kcal/mol and charge: +0.95e.

2) LigandFit/Cerius2(version 4.10) (Venkatachalam et al., 2003): Procedures are as implemented in Cerius2 (version 4.10). The poses are evaluated by DockScore. There are two types of DockScore, one is based on forcefield, and the other one is based on Piecewise Linear Potential (PLP). The best ranked pose from PLP DockScore was selected. The protein models were generated after the ligand and solvent were removed. The definitions of the active sites were based on the ligand in the crystal structure. The 'Max number of poses Saved' was set to 100. The 'Setup energy grid using' was set to PLP v.1.

3) FlexX (Rarey et al., 1996; Bohm, 1992; Bohm, 1994; Bohm, 1996; Bohm, 1998), as implemented in sybyl7.0: exceCyaA the number of conformations is set to 100, other default settings were used for the docking. For FlexX docking, the best ranked pose was selected from the FlexX Score. Formal charges of the ligands are assigned by the SYBYL program.

FlexX. FlexX (Rarey et al., 1996; Bohm, 1992; Bohm, 1994; Bohm, 1996; Bohm, 1998; Jones et al., 1997) was used to dock with EF the compounds obtained from UNITY search of the NCI database. As included in SYBYL, FlexX uses an incremental construction algorithm, where the ligand is decomposed at rotatable bonds into discrete fragments. Then a base fragment is chosen and placed in the active site by using a technique called pose clustering (Rarey et al., 1996). The other parts of the ligand are then added in such a way as to maximize interactions with the protein. Default docking settings were used, except that the number of conformations was set to 100. Formal charges of the metals were assigned by the SYBYL program.

AutoDock. The compounds obtained from the ZINC database screening were docked with EF using AutoDock version 3.0.5 (which proved more accurate (Chen et al., 2007) and was easier to implement in parallel for multiple dockings than FlexX) AutoDock (Morris et al., 1998; Morris et al., 1996) provides three different algorithms for docking: simulated annealing (SA), genetic algorithm (GA) and "Lamarckian" genetic algorithm (LGA), which was used in these studies. Docked conformations are rated by a scoring function that includes terms for van der Waals, hydrogen bond, and electrostatic interactions, plus internal energy of the ligand. For initial screening, default parameters (10 iterations) were used. This was increased to 60 iterations and the results compared. For final scoring, the number of iterations was set to 200 and population size to 100. The ligand and solvent molecules were removed from the crystal structure to obtain the docking grid and the active site was defined using AutoGrid. The grid size was set to 90×90×90 points with grid spacing of 0.375 Å. The grid box was centered on the center of the ligand from the corresponding crystal structure complexes. For the $Zn^{2+}$ ion in PDB 1CJV, the parameters were set as described by Hu et al. (Hu et al., 2003; Hu et al., 2004): radius=0.87 Å, well depth=0.35 kcal/mol, and charge=+0.95. The $Mg^{2+}$ ions used Amber force field potentials as defined in the AutoDock program. The absolute, but not the relative docking energies, were altered by the charge assigned to the magnesium. A partial charge of +0.8 was assigned since if the formal charge was set to +1.2, the interaction of the ligand and the carboxyl group of the ligand was overestimated and led to very short O—Mg distances. The conformation with the lowest binding energy was used to analyze ligand placement in the active site.

Docking scores for different active sites: Docking/binding values are relative, dependent on the active site, and cannot be directly related to Km values for enzymes. However, a compound with a higher binding/docking energy to a given active site than that for known ligands (such as ATP and its analogues and the EF inhibitor, $PGE_2$imidazole) is more likely to function as an inhibitor than those with lower values. Binding energies of the latter are used as a cutoff value for docking energies when selecting compounds for longer docking.

Example 3

Pharmacophore Design Methods

Fragment database. The fragment database consisted of 3-D structures (MOL2 files built in SYBYL) of about 60 small molecules, containing hydrogen bond donor/acceptor or hydrophobic moieties, with at most one rotatable bond. These were either common ionizable molecules, or were selected from the SYBYL fragment database.

HINT score: The Hydropathic INTeractions, or HINT, program (Fornabaio et al., 2003; Fornabaio et al., 2004; Cozzini et al., 2002) utilizes experimental solvent partitioning data as a basis for an empirical molecular interaction model that calculates free energy scores that were shown to accurately reproduce experimental measurements of binding (Fornabaio et al., 2003; Fornabaio et al., 2004; Cozzini et al., 2002). "Hydropathic" interactions are non-covalent interactions such as hydrogen-bonding, acid-base, Coulombic, and hydrophobic interactions. The HINT calculation is the summation of hydropathic interactions between all atom pairs:

$B = \Sigma\Sigma b_{ij}$ $b_{ij} = S_i a_i S_j a_j R_{ij} T_{ij} + r_{ij}$ where $b_{ij}$ is the interaction score between atoms i and j, S is the solvent accessible surface area, a is the hydrophobic atom constant, $R_{ij}$ and $r_{ij}$ are the functions of distance between i and j, and $T_{ij}$ is a logic function with value of 1 and −1, depending on the character of interacting polar atoms. In practice, a HINT score difference of 500 corresponds to an energy difference of about 1 kcal/mol.

Ab intio pharmacophore design: The goal of the pharmacophore design was to find a scaffold of fragments with flexible distance constraints that would optimally fill the active site. The optimal binding position of each molecule in the fragment database in the active site of EF (PDB 1K90) was obtained by translating and rotating the fragment, using an algorithm reported previously (Kellogg and Chen, 2004), so that the best HINT score for the interaction of the fragment and active site was achieved. The coordinates of the small molecules that had the best HINT score with the receptor were saved. The molecule with the best interaction energy was incorporated into the receptor so as to block that area in the active site. Then the fragments were redocked into this compound receptor to find secondary optimal binding locations that did not sterically conflict with previously bound fragments. The five fragments with the most favorable HINT scores surround the position of 3'dATP in the crystal structure of EF, but also indicate additional possible strong interaction sites peripheral to this. Different combinations of these five fragments at the indicated relative positions were used to identify several pharmacophores such that a given pharmacophore included three or four fragments.

Example 4

Database Screening Methods

A UNITY (in SYBYL from Tripos) search was conducted using the pharmacophores obtained as above. All hydrogen atoms in the fragments were removed and distance constraints (i.e., the distances between the heavy atoms of the bound fragments in the configuration shown in FIG. 5 were automatically extracted from a PDB file used to start the 3D UNITY searches. For example, one constraint would be the distance, in angstroms (Å), in the pharmacophore of FIG. 5, between the center of the phenyl ring (a hydrophobic site) and the midpoint of the two oxygens of the carboxyl group (a hydrogen bond acceptor). The 3D-pharmacophore search was done in the NCI-2000 database, containing ~250,000 structures, as integrated in SYBYL. All compounds in the database were stored as 3-D structures converted from their 2-D forms by SYBYL's CONCORD module. Although only one conformation is stored for each entry, UNITY uses a conformationally flexible 3D searching algorithm for ligands such that molecules with matching conformations can be identified regardless of the conformation stored.

Figure 6:
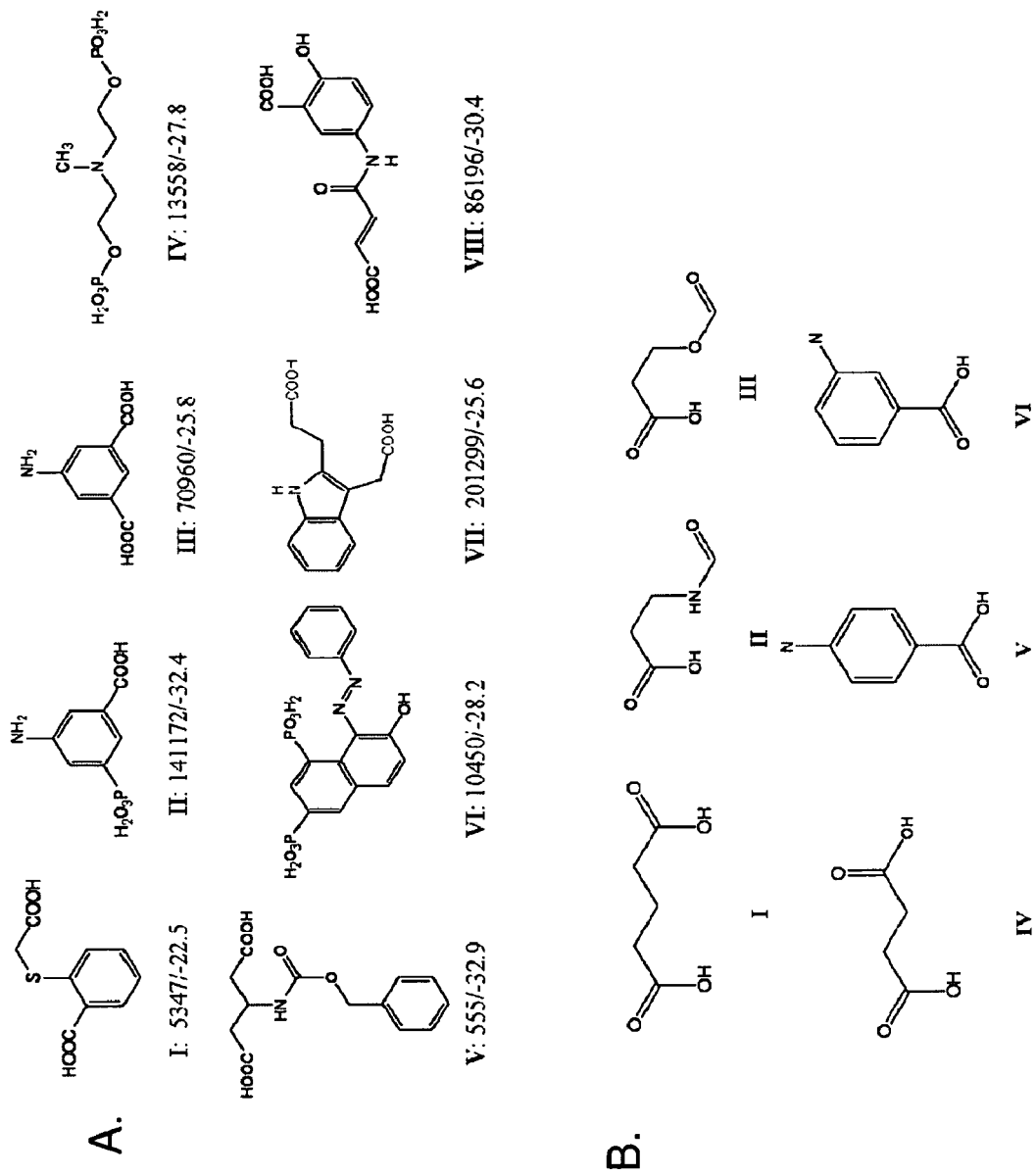

Compounds similar to the pharmacophore were then selected based on docking energies. The compounds were docked into the EF active site using FlexX and those with the lowest ChemScores were selected (FIG. 6A). These compounds were then further decomposed into 2-D fragments (FIG. 6B), selected based on major interactions with the metal and the active site, such as hydrogen bonding, hydrophobic, and metal coordination interactions and were used for searching the ZINC database. A 2D search of the ZINC database was used at this point for convenience.

ZINC (Irwin et al., 2005) is a web database of over 2.7 million commercially available compounds for virtual screening. The 2-D fragments of the compounds identified computationally with FlexX from the NCI database were input into the ZINC database search by drawing the structures in the molecular editor provided. Compounds were sorted based on AutoDock and FlexX scores for binding to target enzymes.

Example 5

Overview Of Computational Design Process

Figure 7:
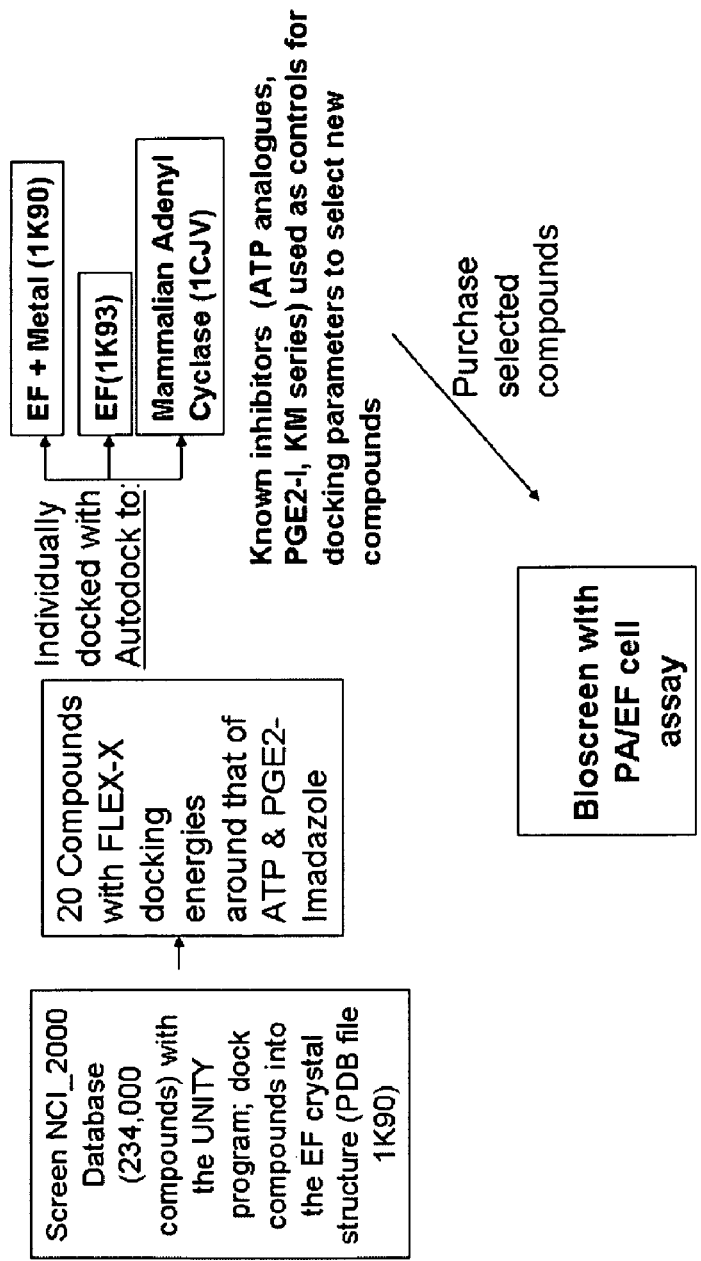
Figure 8:

Crystal structures of anthrax EF, complexed with substrate analogues and small molecule inhibitors, were used to identify the active site residues (Drum et al., 2002; Shen et al., 2005; Shen et al., 2004; Shen et al., 2002; Shen et al., 2004). Since the active site of the mammalian AC is distinct from that of the toxin, inhibitors were designed to bind specifically to anthrax EF. Previous studies have identified nucleotide-like inhibitors of adenylyl cyclases, starting from ATP (Tesmer et al., 1999; Johnson et al., 1997; Wang et al., 2007; Gottle et al., 2007) or by molecular docking of large libraries (Soelaiman et al., 2003). To expand the types of molecules considered, and choose more specific inhibitors, a fragment based de novo approach was used based on crystal structures of anthrax EF (drum et al., 2002; Shen et al., 2005; Guo et al., 2004) to determine a framework molecule (3D-pharmacophore) that would bind best to the active site. This was used to screen ~250,000 compounds in the NCI database. Compounds selected from the NCI database, with FlexX docking scores better than those for nucleotide analogue inhibitors and $PGE_2$-imidazole, an effective inhibitor of toxin induced edema (Peterson et al., 2001), were selected. Two-dimensional (2-D) fragments from these compounds were selected and used to search the ZINC database (Irwin and Shoichet, 2005). From an initial list of about 10,000 compounds, AutoDock was used to select about 100 compounds that had good molecular docking/binding scores to EF. These were further selected based on low molecular weight and log P values, and 19 were purchased and assayed for their ability to inhibit the EF-induced production of cAMP in mammalian cells. The basic steps of the procedure are summarized in FIG. 7. This same process was used for CTA1 to design and dock ligands (FIG. 8 and FIG. 9).

Example 6

Preparation of Edema Factor Pharmacophore Screening

A structure-based, de novo method that required no knowledge of the natural substrate was used to identify non-nucleotide inhibitors of EF. A library of small molecule fragments was docked to the EF-active site in existing crystal structures and those with highest HINT scores assembled into a 3D-pharmacophore. The distance constraints were based on those extracted from the interfragment distance in the active site (+/−a given tolerance), for use with the UNITY program.

Figure 10:
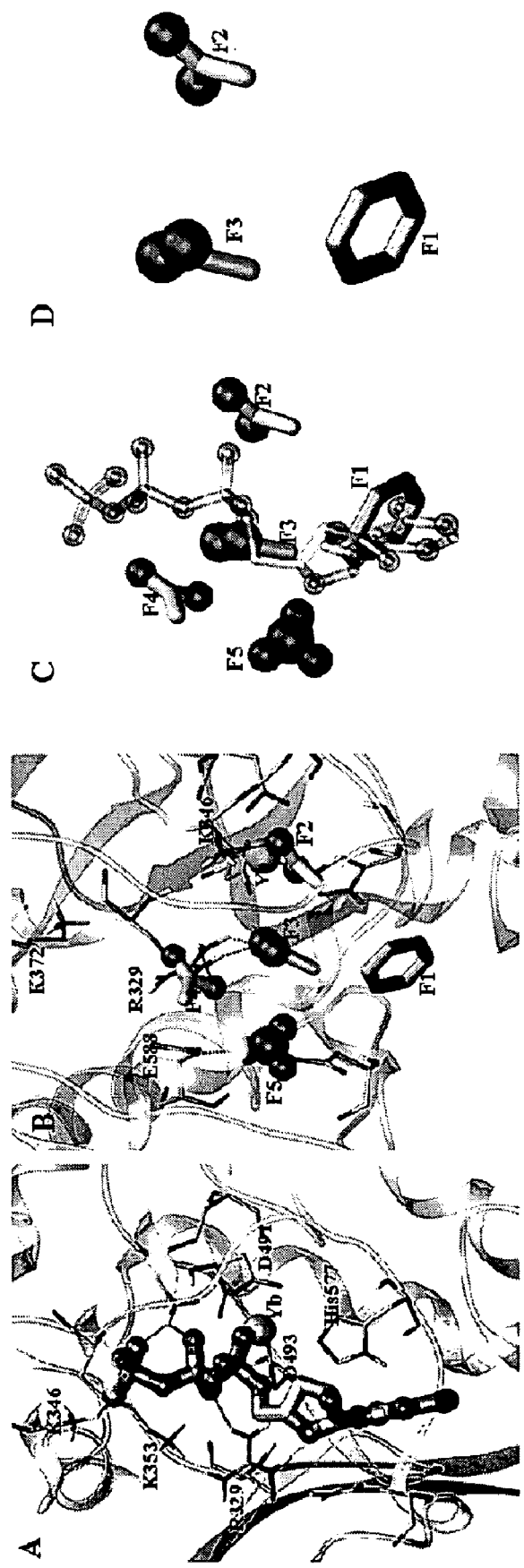

The goal of the pharmacophore design was to find a scaffold of fragments with flexible distance constraints that would optimally fill the active site. The optimal binding position of each molecule in the fragment database in the active site of EF (PDB 1K90) was obtained by translating and rotating the fragment so that the best HINT score for the interaction of the fragment and active site was achieved. The coordinates of the small molecules that had the best HINT score with the receptor were saved. The molecule with the best interaction energy was incorporated into the receptor so as to block that area in the active site. Then the fragments were redocked into this compound receptor to find secondary optimal binding locations that did not sterically conflict with previously bound fragments. The five fragments with the most favorable HINT scores (FIG. 10b) overlaid the position of 3'dATP in the crystal structure (FIG. 10c). Different combinations of these five fragments at the indicated relative positions were used to identify several pharmacophores such that a given pharmacophore included three or four fragments (FIG. 10d).

Figure 5:
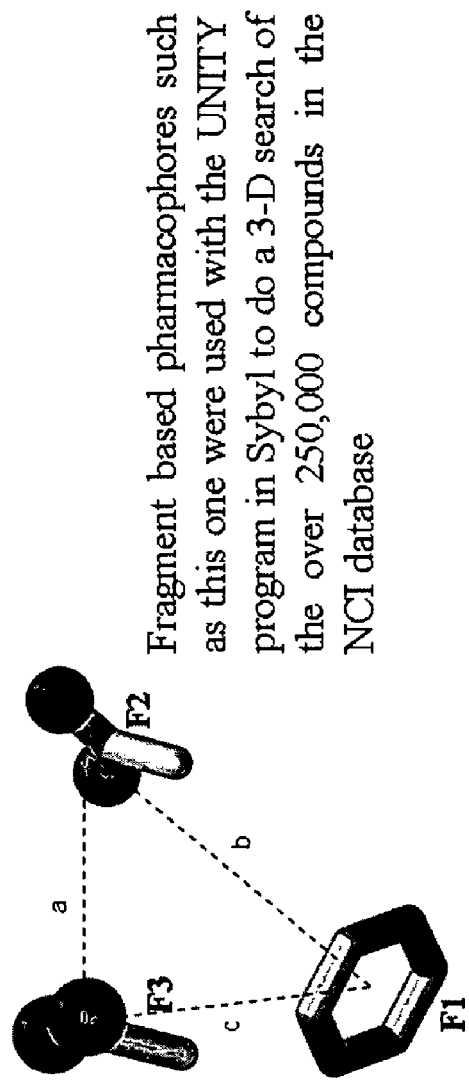

The fragment library search and docking were conducted and 5 fragments with HINT scores greater than 700 for the indicated positions and no interfragment steric hindrance were used to define pharmacophores for UNITY searches of the NCI database (FIG. 5). The fragments to some extent overlay the position of the substrate analogue, 3'dATP, in the active site (FIG. 4); the strongest binding fragment, F1, is a phenyl ring that is located exactly over the center of the purine ring, while fragments F2, F3, and F4 are carboxyl groups near that lie near the phosphate groups. Fragment F2 is within hydrogen bond distance of the metal ion and Lys346 in the EF active site, while F3 and F4 interact with Arg329. Fragment F5 contains an ammonium group which interacts with Glu588.

NCI database search with UNITY (in SYBYL from Tripos) was conducted using the pharmacophores described above. The compounds most similar to the pharmacophore were then selected based on docking energies. A total of 82 compounds that matched the pharmacophores within the constraint distance tolerance were obtained from the NCI database screening. The compounds were docked into the EF active site using FlexX and those with the lowest ChemScores were selected (FIG. 6A). Analysis of the docking results further outlined fragments/groups that had strong interactions with EF. These compounds were then further decomposed into 2-D fragments (FIG. 6B) to obtain substructures to search the ZINC database. The substructures were selected based on major interactions with the metal and the active site, such as hydrogen bonding, hydrophobic, and metal coordination interactions and were used for searching the ZINC database.

For example, docking results showed that discrete areas of compound V in FIG. 6A, form strong, ionic enhanced hydrogen bonds between the carboxyl/carbonyl groups and the bound metal ion or the positively charged residues of EF, Arg329, Lys346, Lys353. The para and meta-amino benzoic acids V and VI (FIG. 6B), substructures of these compounds that also had high HINT energies when docked into the active site, were thus selected for use in 2D screening of the ZINC library.

To search a wider range of chemical space than is available in the NCI Database, the substructures obtained from the original pharmacophore screening were used to obtain a list of compounds from the much larger ZINC database. Searches with the substructures of FIG. 6B were contained within approximately 10,000 compounds in the ZINC database, using the search tools provided at that website. The compounds were saved in MOL2 format files, using the ZINC tools. The original pharmacophores and the fragments of FIG. 6B were used to search for related compounds in the ZINC database. These searches resulted in about 10,000 compounds, which were ranked according to their ability to bind to the EF active site in silico. AutoDock was used to rank the compounds, as it performed very well in docking substrates with anthrax EF (PDB 1K90 and PDB 1XFV) and mammalian AC (PDB 1CJV).

Example 7

Selection of FIII-1, FIV-50, And FII-1 for Further Study

Figure 11:
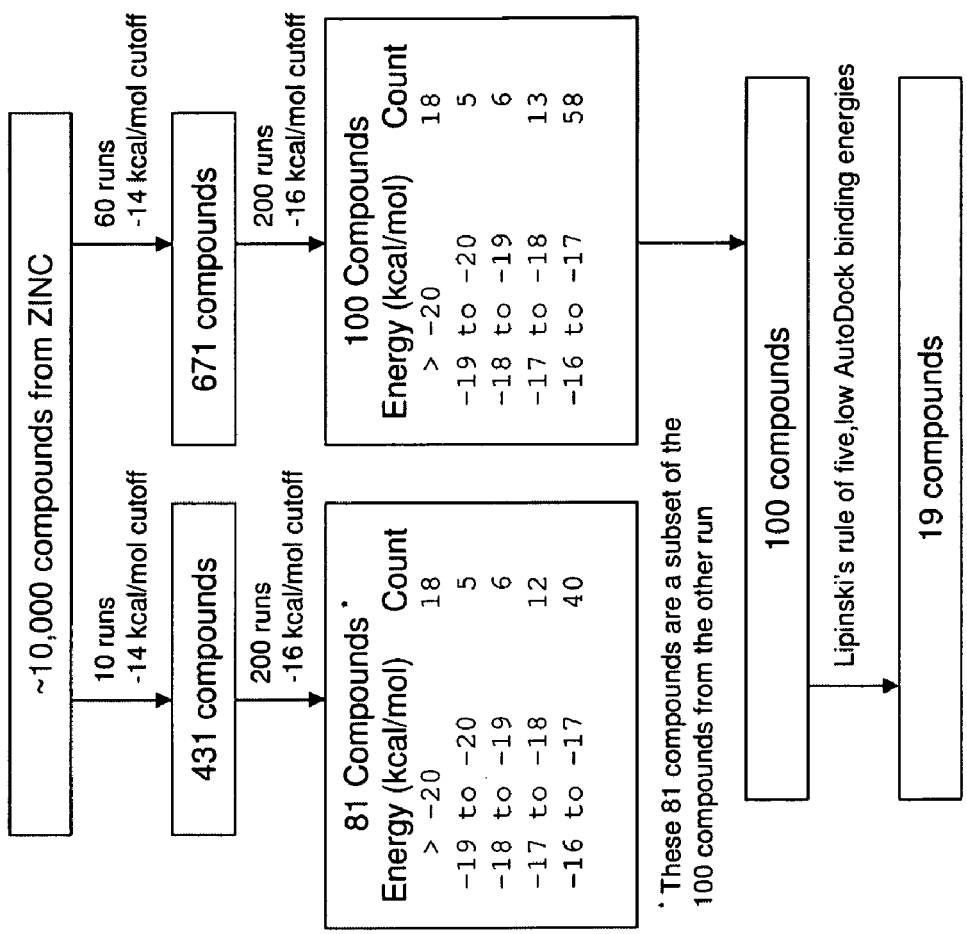
FIG. 11 shows a flowchart illustrating the scheme used to select the final set of 19 compounds from approximately 10,000 initial hits from the ZINC database.

Some studies indicated that the default conditions of AutoDock did not give usable results with the known inhibitors. Thus, a series of control experiments was performed using a subset of the compounds to test the effect of the charge on the metal ion (Chen et al., 2007, incorporated by reference here in full) and the number of iterations on how compounds were sorted according to their docking scores. These results indicated that 60 iterations were adequate to select the compounds with the lowest binding scores from the variety of compounds, but that to obtain the lowest energies and most accurate positioning, one needed to use considerably longer docking times. Minimum energies were consistently found in about 200 iterations. A multistep strategy (FIG. 11) was used to speed up the calculations. All 10,000 compounds were docked for either 10 (default) or 60 genetic algorithm (GA) iterations. A binding energy cutoff of −14 kcal/mol (the lowest binding energy when docking 3'dATP with EF) was used to discriminate between inactive compounds and those with reasonable binding to the active site. More compounds were below the threshold energy if when the dockings ran longer (431 hits for the first procedure with 10 GA runs vs 671 hits for the second procedure with 60 GA runs). All of these compounds were then redocked, with the number of GA runs raised to 200 for greater accuracy and the binding energy cutoff was changed to −16 kcal/mol to obtain more active compounds. This step produced 81 and 100 hits respectively from the two initial lists. These results indicated that although more low energy compounds using higher initial docking times was obtained, the difference in the end was only with respect to compounds that had relatively higher energy values.

The properties and structures of the 100 compounds with the most favorable AutoDock scores (i.e., those with binding energy less than or equal to −16 kcal/mol) were compared. FIG. 12 shows the AutoDock scores for 19 compounds, as well as controls for previously selected inhibitors, ATP and analogues thereof.

About 10,000 compounds, from over 2.7 million compounds in the ZINC database, had a similar molecular framework. These were ranked according to their docking scores, using methodology that was shown to achieve maximum accuracy (i.e, how well the docked position matched the experimentally determined site for ATP analogues in crystal structures of the complex).

Example 8

In Vitro Assay of Inhibition Edema Factor Camp Production

Figure 13:
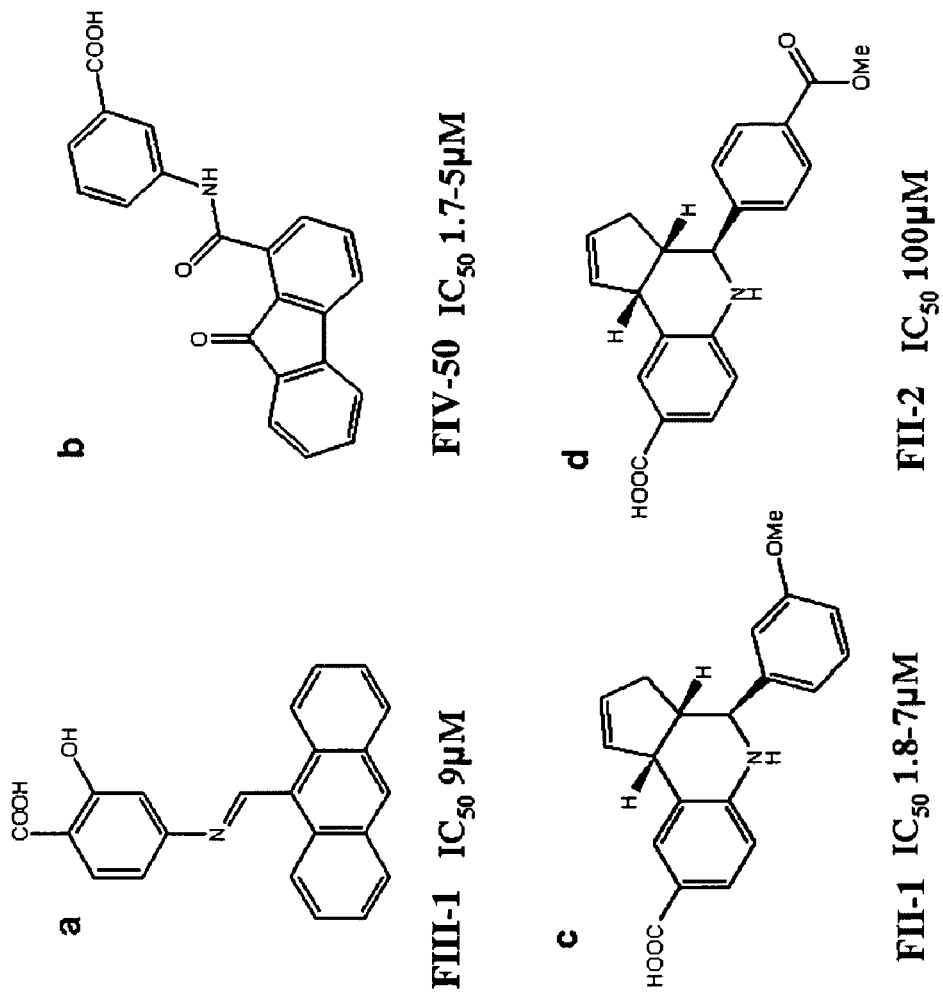
FIG. 13 shows four compounds with their corresponding IC50 values.

Three of the compounds from Example 7 had better activity than the $PGE_2$-imidazole control, and multiple compounds derived from the original three also have improved activity. The inhibitory activities of the compounds were compared to that of a previously known inhibitor, $PGE_2$-imidazole (Peterson et al., 2001), which inhibits the EF-induced production of cAMP in cells in the range of 100 µM (FIG. 13). These three compounds from the above list, with quite different molecular structures, had $IC_{50}$ values in the low µmolar range (FIG. 13): 3-[(9-oxo-9H-fluorene-1-carbonyl)-amino]-benzoic acid (FIV-50 in Table 1; ZINC #75209; 1.7-5 µM), 4-(3-methoxy-phenyl)-3a,4,5,9b-tetrahydro-3H-cyclopenta[c]quinoline-8-carboxylic acid (FII-1; ZINC #75022; 1.8-7 µM), and 4-[(anthracen-9-ylmethylene)-amino]-2-hydroxy-benzoic acid (FIII-1; ZINC #132715; 9 µM). Despite their diverse structures, none of which resemble ATP, all 3 of these compounds overlaid well with the initial pharmacophore and docked to positions close to that of ATP in crystal structures of EF complexes. Common substructures in all three compounds were a planar aromatic structure, which docks near the position of the (planar) purine of ATP (and centers on the phenyl fragment F1 position), and a carboxyl group (that corresponds approximately to the carboxyl fragment F2) that interacts in the docking with the metal ion and positively charged side chains in EF. IC50 values of FIV-50 range from 0.291 to 12.26 with a mean of 4.74, and a standard deviation of 4.37. None of the three initial compounds resembled any known drug or metabolite. However, FII-1 has some similarity to a phosphatase inhibitor family identified experimentally by assaying a diversity library of 10,000 compounds (Brisson et al., 2004).

FIG. 3E, 3F, and FIG. 14 illustrate how well the lowest energy docking conformation of the three active compounds corresponds to both the initial pharmacophore and that of the ATP analogue in the crystal structure of EF. Further design of these compounds to enhance pharmaceutical properties was done, and the assays of activity for these derivatives are found in FIG. 15A-O and FIG. 16A-D.

Example 9

Redesign of FIV-50

Three methods for redesigning the compound have been explored, based on 1) reselecting compounds from ZINC that are close in structure to FIV-50, or that contain building blocks with good organic synthesis possibilities; 2) adding fragments at specific positions using the program Leapfrog or by hand based on the initial pharmacophore; and 3) having a chemist draw compounds that would be logical next generation and easy to synthesize. In each of these cases, compounds have been chosen by their AutoDock, and Gold scores for binding.

1954 diphenyl ZINC compounds were docked with GOLD (Chemscore) and AutoDock. More than 60 compounds have better ChemScore than the initial compound (FIV-50). However, only one compound had a better AutoDock score than the initial compound. The data shows that there is no linear relationship between the AutoDock Score and the GOLD ChemScore. The diphenyl compounds which have good AutoDock scores also have good GOLD ChemScore. But some compounds having good ChemScores but not good AutoDock scores.

Larger compounds selected from ZINC specifically to fit the pharmacophore were also docked. The UNITY program implemented in SYBYL was used to search the ZINC database, which contains about 4.6 million compounds, for the compounds (hits) that matched the fragment based pharmacophores. All compounds in the ZINC database were downloaded in mol2 format and then converted to the format used by the UNITY program. Distance constraints were added the fragments and the UNITY program was run to search the compounds in the ZINC database for the compounds with match the pharmacophore. In all, about 20,000 hits were obtained, which were then docked to the prepared CTA active site using three different programs.

The hits obtained by screening the ZINC database with UNITY were docked with AutoDock3, 4 and GOLD. To get accurate AutoDock results, the number of runs should be 200, which would take 0.5~1 hour per compound. Thus, the first 20,000 hits with the number of runs set to 10 was docked. Then about 2,000 compounds (~10%) were selected for accurate docking by setting the number of runs to 200. More than 100 compounds that have the AutoDock4 scores better than the substrate NAD+ and more than 100 compounds that have the AutoDock3 scores better than NAD+ were obtained. The scores from AutoDock3, AutoDock4 and GOLD do not correlate well with each other. No compound was ranked in top 10 based on all three scoring functions.

Shown below in Table 2 are various computationally determined values for exemplary compounds of the invention. Also shown are experimentally produced IC50 values determined by the cAMP-specific ELISA (Assay Designs, Ann Arbor, Mich.).

TABLE 2

|  | Auto-Dock4 | BE (AD3) | DE (AD3) | GOLD | cLogP | MW | IC50 |
|---|---|---|---|---|---|---|---|
| FIV-50 | −11.8 | −14.3 | −14.49 | 31.97 | 4.29 | 343 | 1.7-9.0 |
| FIV-1 | −11.45 | −14.54 | −14.87 | 29.4 | 4.19 | 373 | 5.8 |
| FIV-29 | −11.18 | −15.22 | −14.68 | 37.09 | 2.72 | 372 | ND |
| FIV-31 | −12.75 | −15.13 | −14.86 | 33.48 | 3.26 | 373 | ND |
| FIV-34 | −11.74 | −14.83 | −14.45 | 34.66 | 3.57 | 358 | ND |
| FIV-35 | −11.33 | −14.53 | −14.58 | 34.69 | 3.99 | 359 | 6.2 |
| FIV-39 | −12.09 | −14.4 | −14.67 | 32.58 | 3.99 | 359 | 5.6 |
| FIV-40 | −11.43 | −14.84 | −15.03 | 33.02 | 3.57 | 358 | ND |
| FIV-46 | −8.87 | −15.33 | −14.93 | 32.77 | 3.56 | 358 | ND |
| FI-3 | −5.8 | −8.31 | −8.28 | 27.43 | 2.22 | 203.2 | 30 |
| FI-1 | −7.33 | −10.5 | −5.16 | 26.09 | 3.14 | 268.3 | 20 |
| FI-2 | −7.81 | −11.5 | −6.11 | 27.92 | 4.2 | 296.3 | 28 |
| FII-1 | −11.58 | −16.76 | −16.03 | 34.16 | 4.52 | 340.4 | 44 |
| FIII-1 | −10.59 | −14.02 | −14.02 | 33.15 | 3.36 | 320.67 | 20 |
| FIV-54 | −8.32 | −7.04 | −7.04 | 27.16 | 5.06 | 371.4 | 12.9 |
| FIV-58 | −8.06 | −16.99 | −17.21 | 26.29 | 4.64 | 387.4 | 7.2 |
| FIV-55 | −11.99 | −18.91 | −17.96 | 33.67 | 4.61 | 356.4 | 11.4 |
| FIV-53 | −8.61 | −16.98 | −17.06 | 32.06 | 4.45 | 373.4 | ND |
| FIV-67 | −7.86 | −16.01 | −15.34 | 26.35 | 5.6 | 383.3 | 6.9 |
| FIV-70 | −7.92 | −12.57 | −11.1 | 28.97 | 4.47 | 358.8 | 50 |

Example 10

Exemplary Methods to Modify Compounds to Increase Solubility and Reduce Toxic Side-Effects

Compounds were submitted to an organic chemistry toxicity analysis website that predicts the likelihood a compound drawn by the user will have toxic (mutagenic, tumorigenic, irritant and reproductive) effects. The algorithm is based on comparing known toxic compounds to drugs generally recognized as safe (GRAS) and illustrates the fragments of the user-specified molecule that are considered suspect.

The prediction process locates possible problem centers from a precomputed set of structural fragments that give rise to toxicity alerts in the structure drawn in by the user. The toxic fragment lists were assembled from fragmenting compounds of the RTECS database that had known toxicity (e.g. mutagenicity). Each molecule was first cut at every rotatable bond, leading to a set of core fragments. These in turn were used to reconstruct all possible bigger fragments that were a substructure of the original molecules. The frequencies of the toxic structures in the list of 3000 traded drugs considered largely free of toxic effects was also determined. A fragment was considered a risk factor if found often as a substructure of harmful compounds but never or rarely in traded drugs. The site indicates their process recognized about 80% of known mutagenic, irritant or tumorigenic compounds as such, and only identified about 10% of the GRAS compounds as having toxic potential.

Table 3 lists the results for FIV-50 and FII-1. The areas of FIV-50 and FII-1 that might cause mutagenicity and irritating side effects, according to this analysis, were actually on the side chains, specifically on the benzene ring itself and not the oxyfluorene or cyclopentylquinolone rings. Table 3 shows the estimated side effects, docking scores and calculated log P of FIV-50 and FII-1

TABLE 3

| Compound | Mutagenicity | Tumorigenicity | Irritating Effects | Reproductive Effects | ADk4 | AD3 (BE) | AD3 (DE) | cLogP |
|---|---|---|---|---|---|---|---|---|
| FIV-50 | High Risk | Low Risk | Medium Risk | Low Risk | −11.93 | −18.95 | −19.4 | 4.29 |
| FII-1 | Low Risk | Low Risk | Low Risk | High Risk | −11.64 | −17.8 | −17.02 | 3.59 |

TABLE 2-continued

|  | Auto-Dock4 | BE (AD3) | DE (AD3) | GOLD | cLogP | MW | IC50 |
|---|---|---|---|---|---|---|---|
| FIV-65 | −7.51 | −16 | −15.91 | 32.17 | 4.77 | 342.4 | 1.5 |
| FIV-68 | −9.68 | −17.52 | −17.7 | 32.56 | 3.15 | 341.4 | 2.71 |
| FIV-66 | −7.81 | −15.65 | −13.93 | 29.82 | 5.27 | 345.4 | ND |
| FIV-61 | −7.06 | −11.7 | −11.3 | 30.84 | 4.77 | 299.3 | 28.6 |
| FIV-60 | −7.59 | −12.18 | −12.09 | 31.03 | 5.45 | 351.8 | 3.8 |
| FIV-64 | −12.65 | −15.72 | −15.49 | 35.55 | 4.7 | 344.3 | ND |

The structures of FIV-50 and FII-1 were then altered by introducing changes to minimize the side effects and to reduce the log P values to increase the solubility without reducing the binding affinities. FIG. 17 lists the structures of compounds obtained by modifying FIV-50 and FII-1, to convert them so that their estimated mutagenicity, tumorigenicity, irritating and reproductive effects would be low risk. Additional FIV-50 derivatives are listed in FIG. 18.

The docking pictures of FII-1 indicated that the carboxyl group on the cycloopentylquinolone ring was near the metal ion, and that activity could be enhanced by adding yet another carboxyl here. The side effects, including mutagenicity and irritating effects, of 14 of the redesigned compounds are expected to be low, and their solubilities (calculated log P), except for compound 1, are better than that of FIV-50. The docking scores are, for the most part, unaffected by the additions.

Other compounds were designed with modifications on the benzoic acid moiety of FIV-50, to optimize metal ion binding. Here, an approach based on testing various substituents that would affect the ionization potential (or pKa) of the carboxylic acid was used. From the modifications made and tested so far (FIG. 19), there is little clear indication that the most active compounds are indeed better metal chelators.

Table 4 shows the results of the calculations done for various mutagenicity determinants.

TABLE 4

|  | Mutagenicity | Tumorigen | Irritant | Reproductive. |
|---|---|---|---|---|
| FIV-50 | high | low | mid | low |
| FIV-1 | mid | low | low | low |
| FIV-29 | low | low | low | low |
| FIV-31 | low | low | low | low |
| FIV-34 | high | high | mid | low |
| FIV-35 | low | low | low | low |
| FIV-39 | low | low | low | low |
| FIV-40 | mid | low | low | low |
| FIV-46 | mid | low | low | low |
| FI-3 | low | low | low | low |
| FI-1 | low | low | low | high |
| FI-2 | low | low | low | high |
| FIII-1 | high | low | low | low |
| FII-1 | low | low | low | high |
| FIV-54 | low | low | low | low |
| FIV-58 | low | low | low | low |
| FIV-55 | low | low | low | low |
| FIV-53 | low | low | low | low |
| FIV-67 | low | low | low | low |
| FIV-70 | low | low | low | low |
| FIV-65 | high | low | high | low |
| FIV-68 | low | low | low | low |
| FIV-66 | low | low | low | low |
| FIV-61 | low | low | low | low |
| FIV-60 | low | low | low | low |
| FIV-64 | * | * | * | * |

Example 11

Comparison of Docking Programs

The AutoDock, LigandFit/Cerius2, and FlexX docking programs were compared using three tests of their ability to correctly determine interactions of substrates and inhibitors of the edema factor (EF) of *Bacillus anthracis*. In the first test, the RMSD between the lowest energy positions of a substrate analogue (3'-dATP or 2',3'-ddATP), as determined by the three programs, and that in two different co-crystal structures of EF were determined. The lowest energy AUTODOCK cluster was also the closest to the crystal structure position. While the overall correlation was relatively weak, the Autodock program was most consistent with the experimental results.

While these programs have all been shown to be useful for various projects, it is not clear which approach is best suited to docking proteins with metal ions in their active sites, such as EF and PT. A comparison of the performance of AutoDock, LigandFit/Cerius2 and FlexX, in docking known substrates and inhibitors of EF to the four protein active sites is shown in FIG. 20. The docking accuracy was assessed by comparing the docked positions of ATP analogues (3'dATP or 2',3'-ddATP) in the active sites of EF and CYAA with those determined experimentally by X-ray crystallography. Also compared was how the programs docked a known inhibitor of both of these bacterial AC toxins, $PGE_2$-imidazole (Peterson et al., 2001). As a final control, ATP analogues and $PGE_2$-imidazole were docked into the active site of mammalian adenyl cyclase, which has a completely different active site. It was determined 1) which docking program is more accurate in predicting the substrate interaction mode; 2) the differences between the programs in determining protein-ligand and metal ion-ligand interactions. Results indicated that the AutoDock program was adequate for screening compound libraries to select inhibitors of bacterial adenyl cyclase toxins. Additionally, it was found that the three best compounds according to their docking scores were all active in a bioassay.

Example 12

Docking of Formula 1 Type Structures

The FI-3 compound has most consistently been active in the in vitro cAMP assays of EF and in Cholera toxin. As Table 5 below shows, this compound has mediocre scores regardless of the scoring program or if docked into the active site of either of two crystal structures of Anthrax edema factor (PDB file names 1 K90 and 1XFV). The relatively unfavorable energy values (the lower the energy, the tighter the anticipated binding to the target) are due to the relatively small size of the KM11. It is noted that perhaps because of the small size, both rings of the compound in the docked position (FIG. 22) bind deeply into the active site pocket, and especially close to the metal ion. The more recent active compounds from MEJ (FIG. 23) have a more extended conformation. Selected assay results (IC50) are shown in Table 5.

TABLE 5

| | | | | | |
|---|---|---|---|---|---|
| FI-1 | 20.4 μM | >100 | | | |
| FI-2 | 21.4 μM | 27.3 uM | | | |
| FI-3 | 38.8 μM | 64.1 uM | 29.85 | 11.1 | 29.44 |

Example 13

Bioassay Exemplary Materials and Methods $PGE_2$-imidazole, used as the positive control in the biological assays, was synthesized as previously described (Peterson et al., 2001) and stored frozen. $PGE_2$-imidazole was first identified as an inhibitor of cholera toxin activity, (Peterson et al., 2001) but has also been shown to be an effective inhibitor of anthrax EF in the μM range. Other compounds were obtained from the National Cancer Institute (NCI) or purchased from Asinex, Ryan Scientific, Sigma-Aldrich, TimTec, or synthesized as discussed. Compounds were dissolved in cell culture medium or DMSO, and where necessary the pH was set to neutrality with small amounts of NaOH or HCl.

Solution conditions for FIV-50: in neat DMSO, pharmaceutical grade, the compound was taken up with minimal water content. Here it is soluble to at least 100 mM. To dilute into buffer or water, 1-2 milliequivalents of NaOH (so for every μl of the 100 mM solution in DMSO, use 1-2 μl of 0.1 N NaOH) for every mM of FIV-50 was used.

Cell culture. Murine monocyte/macrophage cells (RAW 264.7) were propagated in T75 flasks containing Dulbecco's Modified Eagle's Medium (DMEM) (Mediatech, Inc., Herndon, Va.) at 37° C. with 5% $CO_2$. The culture media contained 10% fetal bovine serum (FBS), 100 μg/ml penicillin/streptomycin and L-glutamine.

Cell Assay for EF: Cells were plated 1×10⁶ cells per well in DMEM containing 10% FBS, 100 µg/ml penicillin/streptomycin and L-glutamine with isobutylmethylxanthine (IBMX) (50 µM) IBMX in 48 well tissue culture plates and allowed to adhere overnight at 37° C. in 5% $CO_2$. $PGE_2$-imidazole, PA (2.5 µg/ml) and EF (0.625 µg/ml) were diluted with assay media containing DMEM (without phenol red) with 100 µg/ml penicillin/streptomycin and L-glutamine. Media was aspirated from the cells and replaced with the varying concentrations of $PGE_2$-imidazole or a compound of interest along with PA and EF or other cAMP producing protein. The plates were then incubated for 4 hours at 37° C. in 5% $CO_2$. Following incubation, the culture supernatants were removed (extracellular cAMP) and transferred to a new 48 well plate for cAMP determination.

cAMP determination. The extracellular cAMP concentration in the culture supernatants was measured with a cAMP-specific ELISA from Assay Designs, Inc. (Ann Arbor, Mich.) per manufacturer directions. Previous assays of the toxin effects have shown that the extracellular levels were more reliable than the intracellular levels of cAMP. A recent report describing the ribonucleotide efflux mechanism further supports the use of this assay (Lin et al., 2008).

Estimation of cytotoxic effects. All compounds were tested for cytotoxicity, and any that elicited a cytotoxic response within the concentration range tested (up to 100 µM) discarded. Cytotoxicity was measured by visual observation of the control cells (compound without PA/EF added) and quantitatively by lactate dehydrogenase (LDH) enzyme release from a murine monocyte-macrophage cell line (RAW 264.7; American Type Culture Collection, Manassas, Va.) (Peterson et al., 2006) or the MTT assay, which is a colorimetric test based on the uptake of 3-(4,5-dimethylthiazolyl-2)-2,5-diphenyltetrazolium bromide (MTT) by proliferating cells (cytotoxic compounds reduce the MTT taken by cells as the drug concentration is increased) (Peterson et al., 2007). For the LDH assay, the RAW 264.7 cells were propagated in Dulbecco's modified essential medium supplemented with 10% fetal bovine serum, 100 µg/ml penicillin-streptomycin, and 2 mM L-glutamine (Mediatech, Inc., Herndon, Va.) at 37° C. with 5% $CO_2$ using tissue culture flasks. Subsequently, the cells were plated in 96-well flat-bottom tissue culture plates (Corning) at a density of 1×10⁶ cells/ml and incubated overnight at 37° C. in 5% $CO_2$. The monolayers were washed twice with Dulbecco's modified essential medium devoid of serum or phenol red. Cytotoxicity was measured as a function of the amount of LDH enzyme released from the macrophages into the cell culture supernatants. Various dilutions of compounds were incubated for 4 h at 37° C. in 5% $CO_2$. LDH release into the culture supernatant of the macrophage cells was measured using the CytoTox 96 nonradioactive cytotoxicity assay kit (Promega, Madison, Wis.) and quantitated by measuring wavelength absorbance at 490 nm. An increase in color of the culture medioium was an indication of cytotoxicity.

For the MTT assay, a kit purchased from the American Type Culture Collection (Manassas, Va.) was used. J774A.1 murine monocyte/macrophage-like cells (ATCC) were plated at 5×10⁵ cells/ml and grown to 60 to 80% confluence at 37° C. overnight in 5% $CO_2$. Twofold dilutions of each compound were added to the cells and incubated for 4 h. After incubation, 10 µl/well of yellow tetrazolium MTT salt was added to the cells and left for 2 h. The salt was reduced by metabolically active cells. The resulting intracellular purple formazan was solubilized overnight in detergent reagent (ATCC catalog no. 30-1010K) provided in the MTT assay kit. The reaction product was measured at 570 nm and quantified. Reduction in color was an indication of cytotoxicity.

Example 14

Inhibition of cAMP Production In Vitro with Cholera Toxin

Because the in vivo assay uses cholera toxin (AB5 enterotoxin) to induce fluid and electrolyte secretion by increasing cAMP and because it does so via a different pathway than *B. anthracis* edema factor, studies were initiated to determine if these compounds could also inhibit cholera toxin in in vitro assays. For these studies, RAW264.7 cells were utilized. They were propagated as described above.

Plating Cells for Assay. Cells were counted using a hemacytometer and 1×10⁶ cells were plated per well in a 48 well tissue culture plate. Cells were allowed to adhere to the plastic overnight at 37° C. in 5% $CO_2$.

Cell Assay. In a new 48 well plate, experimental conditions were made to be transferred to 48 well plate containing cells. Toxin and inhibitor concentrations were calculated and volumes were distilled into the 48 well plate. Experimental conditions were then transferred to the 48 well plate containing cells and plates were allowed to incubate for 4 hours at 37° C. in 5% $CO_2$. At the end of 4 hour incubation period, the culture supernatants were removed (extracellular cAMP) and transferred to a new 48 well plate. Assay Designs' Correlate-EIA Direct cyclic AMP kit was used to quantitatively determine amounts of extracellular cAMP from supernatants in duplicate.

FIGS. 24 and 25 are data from FI-3 and FI-1. In this assay, FI-3 inhibits cholera toxin induced cAMP, but not quite as well as $PGE_2$-imidazole. Further shown is that, FI-1 did not inhibit cAMP induced by Cholera toxin (FIG. 25).

Example 15

Toxicity Studies of Compounds with LDH

Studies were initiated to determine if exemplary compounds were cytotoxic to cells in vitro (LDH assays) before using them in the mouse ileal loop model.

LDH assays. Briefly, murine monocyte/macrophage cells (RAW 264.7) were plated in a 96-well plate tissue culture plate at 5×10⁵ cells/ml in each well. Cells were allowed to adhere to the plate overnight at 37° C./5% $CO_2$. The next day, cells were rinsed with clear DMEM, (200 ul). Dilutions of test articles were made in separate tubes and added to the cells. Lysis Buffer was added to wells labeled "100% Lysis" and the cells were allowed to incubate at 37° C./5% $CO_2$ for 3 hours. The plate was centrifuged at 200×g for 5 minutes and 50 µl of supernatant was added to another sterile 96 well tissue culture plate. Substrate Mix was added to each well and allowed to incubate at room temperature with no light for at least 30 minutes. Stop Solution was added to each well and the plate is read at 490 nm.

It should be noted that none of the compounds treated were cytotoxic in vitro in the LDH assay used (FIG. 26, FIG. 27, FIG. 28). Although FI-1 did not inhibit in vitro accumulation of cAMP in either assay, it was tested in the in vivo assay. None of the compounds were cytotoxic in LDH assays.

Data generated from both EdTx and CT assays are shown in FIG. 29 and FIG. 30. Note that the inhibition of cAMP release is either equal to or better than that of $PGE_2$-imidazole. Neither of these compounds was cytotoxic in in vitro LDH assays (FIG. 31 and FIG. 32).

Example 16

Enterotoxic E. coli Mouse In Vitro Studies of FIV-50

The experimental design for this example is demonstrated in FIG. 33. Briefly, at −48 hrs mice were provided with sterile water supplemented with streptomycin and fructose. Food was removed 12 hrs prior to infection. At −3 to −1 hrs a histamine H2-receptor antagonist was injected i.p. to inhibit production of acid in the stomach. At 0 hrs the mice were incubated 400 µM of the compound to be tested and with Enterotoxigenic E. coli (ETEC) ($1\times100^8$) were administered intragastrically. At 12, 24, 36, and 60 hrs from initial incubation the animals received aliquots of the test compound via i.p. at 24, 48, or 72 hrs the animals were euthanized with isofluorane and cervical dislocation. Weight and length of the intestine was measured, fluid content estimated gravimetrically, and bacterial numbers in the intestine were counted.

Different dosages of FIV-50: The DC-4 treatment had an inhibitory effect on the amount of bacteria (ETEC) recovered from the intestinal fluid at 72 hrs even at concentrations of 0.1 mM (FIG. 34). An increase in fluid (estimated by weight of the intestine) was reduced in the presence of FIV-50 when measured at 72 h post infection (FIG. 35). Although difference between groups using the weight/length ratio are not as drastic as just weight, it is more common in the scientific literature to relate fluid loss to intestinal length. Due to the intestinal distention in mice treated with ETEC, the ratio is representing a true reduction in fluid based on the weight and length (FIG. 36).

The effect of FIV-50 in comparison to $PGE_2$-imidazole was measured. Eight animals were used per group with 4 groups: (1) negative control CD-1 mice group+GSNO+PBS; (2) CD-1+ETEC bacteria; (3) CD-1+ETEC bacteria+0.1 mM FIV-50; (4) CD-I+ETEC bacteria+1 mM$PGE_2$-imidazole. Animals received ETEC ($1\times10^8$)+/−FIV-50 (0.1 mM) or $PGE_2$-imidazole (0.1 mM) at time 0 h. FIV-50 or $PGE_2$-imidazole i.p. boosters were administered at 12, 24, 36, 48 and 60 h prior to euthanize at 72 h. Data was obtained at 72 h post infection. Intestine weight, weight/length intestinal ratio, and colony forming units (CFU) in the intestinal fluid were analyzed by a two-tailed Student's t-test for independent samples.

Reduction in the weight of the intestine (indicative of fluid accumulation) was observed in FIV-50- and $PGE_2$-imidazole-treated mice (FIG. 37A). A larger reduction in weight was observed in ETEC+FIV-50-treated animals. The effect was more pronounced in FIV-50-treated than $PGE_2$-imidazole treatment. Although differences calculating ratio weight/length were not statistically different, the effect on total fluid accumulation in FIV-50-treated animals was still evident (FIG. 37A).

Both compounds had an effect on bacterial recovery from the intestinal fluid at 72 hrs post infection (FIG. 38). These results suggest that the ability of the ETEC bacteria to colonize and persist in the intestine is diminished in presence of $PGE_2$-imidazole or FIV-50. If bacteria are unable to colonize, they will be flushed out from the intestine.

Initial examination of the tissues indicated that the integrity of the surface in the small intestine was altered in ETEC only-treated animals, as demonstrated by shortening of the microvilli length and necrotic tissue (FIG. 39, top pictures). In contrast, the integrity of the intestine was intact in FIV-50- as well as $PGE_2$-imidazole-treated animals (also infected with ETEC) (FIG. 39, middle and bottom pictures).

Ultrastructural studies of the small intestine of mice infected with ETEC only, demonstrated destruction of the microvilli and cell death (FIG. 40). Control tissue (non infected) was used for comparison. FIGS. 41 and 42 demonstrates more examples of tissue destruction due to bacterial toxicity (higher magnification, 32,000× and 64,000× respectively). Integrity of the intestinal epithelia barrier was maintained when the animals infected with ETEC were also treated with $PGE_2$-imidazole (FIG. 43). As observed in the EM images, the microvilli of the cells looks fairly intact (small areas of microvilli destruction), but no evidence of cell killing was found. Integrity of the intestinal epithelia barrier was fully maintained in CD1 mice infected with ETEC and receiving FIV-50 (FIG. 44). As observed in the EM images, the microvilli of the cells was intact (no signs of microvilli destruction), and no evidence of cell killing was also evident. Microscopically, FIV-50 was more effective than $PGE_2$-imidazole in preventing tissue from ETEC damage.

Destruction of the small intestinal microvilli was observed in the ETEC-infected animals. Reduction of the damage was evident in the $PGE_2$-imidazole, but the protection was more evident in the FIV-50-treated animals. No evidence of toxicity was observed in animals treated with $PGE_2$-imidazole or FIV-50 (no bleeding, integrity of the intestinal epithelia was maintained, no cell death was evident).

Time course after FIV-50 treatment: 32 animals were used: (1) 4 CD-1 mice per group at 24 h, (n=8); (2) 4 mice per group at 48 h (n=8); (3) 8 mice per group at 72 h (n=~16). Animals received ETEC ($1\times10^8$)+/−FIV-50 (0.1 mM) at time 0 h. FIV-50 boosters were administered at 12, 24, 36, 48 and 60 h. Groups of animals were euthanized at 24, 48 and 72 h. Data was obtained at 24 h (4 mice per group), 48 h (4 mice per group) and 72 h (8 mice per group) post infection. Intestine weight, weight/length intestinal ratio, and colony forming units (CFU) in the intestinal fluid were analyzed by a two-tailed Student's t-test for independent samples.

A transient increase in fluid accumulation was observed at 24 h in animals treated with FIV-50 (FIG. 45). This fluid accumulation progressively decreases significantly over time (24-72 hr.) No statistical significance was observed between ETEC+FIV-50 at 72 h. Note: it was observed that a more significant effect is obtained when the FIV-50 is freshly prepared.

Bacteria were enumerated in the intestinal fluid, raw data is included from selected animals to demonstrate significant differences between ETEC-treated (ETEC) vs. ETEC-treated+FIV-50 animals (FIV-50) at different 24, 48 and 72 h post infection. Data presented here is only at 72 h (P<0.01 in animals treated with FIV-50 vs. ETEC) (FIG. 46). 3-logs differences in the number of bacteria recovered was observed.

Comparison of FIV-50 treatment—oral vs. i.p. treatment: To evaluate whether the initial peak in fluid at 24 h was due to the administration of FIV-50 via the oral route, these animals were compared with ETEC-infected animals only receiving FIV-50 by the i.p. route. 72 animals were used, (1) 24 CD-1 mice receiving ETEC (n=8 at 24, 8 at 48 h and 8 at 72 h); (2) 24 CD-1 mice receiving ETEC+FIV-50 oral and i.p. (n=8 at 24, 8 at 48 h and 8 at 72 h); (3) 24 CD-1 mice receiving ETEC+FIV-50 only i.p. (n=8 at 24, 8 at 48 h and 8 at 72 h); Animals received ETEC ($1\times10^8$)+/−FIV-50 (0.1 mM) at time 0h (oral). One group only started receiving FIV-50 after 12 h i.p. FIV-50 i.p. boosters were administered at 12, 24, 36, 48 and 60 h. Animals were euthanized at 24, 48 and 72 h. Data was obtained at 24 h (4 mice per group), 48 h (4 mice per group) and 72 h (8 mice per group) post infection. Weight/ length intestinal ratio was analyzed by a two-tailed. Student's t-test for independent samples.

An increase in fluid accumulation was observed at 24 h (*P<0.05) in ETEC-treated+FIV-50-oral animals (FIV-50 oral) (FIG. 47). Elimination of the initial oral inoculation reduced the fluid accumulation. Maximum effect of FIV-50 was observed at 48 h (P<0.01) in this experiment. However, at 72 h post infection, fluid accumulation in the FIV-50 oral treated animals was less than control (ETEC).

Bacterial growth kinetics in presence or absence of FIV-50: To determine whether the differences in intestinal colonization were attributed to killing of the organisms by FIV-50, a series of in vitro studies to establish antibacterial effect of FIV-50 was performed. Cultures of ETEC H10507 or other enteric bacteria (isolates of pathogenic *E. coli* and *Salmonella*) were grown in Luria-Bertani (LB) broth in presence or absence of 0.1 mMFIV-50. Growth of strains was monitored by measuring absorbance at 600 nm at one hour increments for 6 h as well as quantification by serial diluting and plating at 0 and 6 h to evaluate growth rates. The optical density of the cultures directly corresponds to the colony forming units/ml of bacteria: 1 OD600=$8\times10^8$ bacteria.

The data showed that FIV-50 have no effect on growth because no differences in grow rate were observed in absence or in presence of FIV-50 (FIG. 48). Therefore, the effects observed in the intestinal colonization were not due to killing of the organism by FIV-50. FIG. 49 is similar to previous slide, no differences in growth were observed in bacteria incubated with or without FIV-50.

Bacterial adhesion to cultured epithelial cells: To further determine whether FIV-50 was having an effect on bacterial adhesion, an experiment was designed to evaluate in vitro adherence on tissue culture cells. Bacteria were grown statically in LB broth overnight at 37° C. and inoculated at a multiplicity of infection of approximately 10:1 onto semiconfluent cultured epithelial cells monolayers (HeLa cells in exp 6 and Caco-2 cells in exp 7) grown on 24-well microtiter plates. Before use, the cells were washed with sterile phosphate-buffered saline (PBS, pH 7.4) and replenished with DMEM (Dulbecco's minimal essential medium, tissue culture media). Bacteria and cells were incubated for 3 h at 37° C. and 5% $CO_2$, and then cells were washed five times with 1 ml of PBS. To quantify *E. coli* adherence, the bacteria were recovered with 200 µl of 0.1% Triton X-100 in PBS buffer and plated on Luria agar plates containing the proper antibiotic. Data are expressed as CFU/mL of adherent bacteria recovered from triplicate wells and represent at least two separate experiments performed in triplicate.

Reduction in adherence was only observed in ETEC (no statistical significant) (FIG. 50). Therefore, the results suggest that FIV-50 is not interfering with binding of bacteria to cells in vitro and supports the importance of in vivo studies were inhibitory effect on adhesion is probably due to adenylyl cyclase inhibition $1\times10^6$ HeLa cells were infected with $1\times10^7$ bacteria +/−FIV-50 and adhesion quantified after 3 h. (HeLa cells are a standard cell line used in bacterial adhesion assays). FIG. 51 is similar to previous slide, reduction in adherence was only observed in ETEC. Slight increase in adherence in the other strains was not statistically significant. FIV-50 is not interfering with binding of bacteria to cells or preventing bacterial growth. $1\times10^6$ HeLa cells were infected with $1\times10^7$ bacteria +/−FIV-50 and adhesion quantified after 3 h. FIG. 52 is similar to the two previous slides, the reduction in adherence was observed in ETEC, but in this case adherence of two different ETEC strains was reduced and the same effect was not observed in other pathogens (no producing LT toxin). $1\times10^6$ HeLa cells were infected with $1\times10^7$ bacteria +/−FIV-50 and adhesion quantified after 3 h. Also tested was the effect of FIV-50 on bacterial adhesion to Caco-2 cells FIV-50. In this case, no reduction in adherence was observed in bacterial samples incubated with FIV-50, instead, a slight increase in adherence was observed in FIV-50-treated cells (no statistical significant) (FIG. 53). The effect maybe due to the type of cells used or the lack of the proper receptors on the cells. $1\times10^6$ Caco-2 cells were infected with $1\times10^7$ bacteria +/−FIV-50 and adhesion quantified after 3 h (Caco-2 cells are a colonic intestinal cell line also used in bacterial adhesion assays). FIG. 54 is similar to the prior experiment, no reduction in adherence was observed, instead, a slight increase was observed in FIV-50-treated samples. This data was obtained after 3 h of incubation and it is possible that the effect on these cells require longer incubation times. $1\times10^6$ Caco-2 cells were infected with $1\times10^7$ bacteria +/−FIV-50 and adhesion quantified after 3 h.

Comparing FIV-50 treatment (FIV-50 only by the oral or i.p. routes; defining toxicity): To evaluate whether the presence of FIV-50 in the intestine produce any toxic effect on the tissue, animals receiving ETEC only, FIV-50 only, ETEC+FIV-50 (oral route only), and ETEC+FIV-50 (i.p. route only) were compared. 32 animals were used (8 animals per group), (1) CD-1 mice receiving ETEC only; (2) CD-1 mice receiving FIV-50 only; (3) CD-1 mice receiving ETEC+FIV-50 only oral; (4) CD-1 mice receiving ETEC+FIV-50 only i.p. Animals received ETEC ($1\times10^8$)+/−FIV-50 (0.1 mM) at time 0h (oral or i.p.). One group only received FIV-50 orally (no ETEC) FIV-50 i.p. or oral boosters were administered at 12, 24, 36, 48 and 60 h. Animals were euthanized at 24 and 72 h. Data obtained at 24 h (4 mice per group) and 72 h (4 mice per group) post infection were analyzed for physical signs of toxicity (inflammation, fluid accumulation, bleeding, etc) and bacterial counts were determined at both time points. Data was analyzed by a two-tailed Student's t-test for independent samples.

No signs of bleeding or inflammation were observed in any of the conditions tested. Fluid accumulation was observed at 24 h (ETEC+FIV-50 oral infection) as reported in prior experiments. Intestinal tissue was normal as compared to control animals (no infected or receiving FIV-50). Bacterial counts were recovered in animals infected with ETEC and reduction in the bacterial counts were obtained in mice treated with FIV-50 (FIG. 55). No bacteria were recovered in animals receiving only FIV-50.

The diet-restricted, antibiotic-treated mouse model and performed studies with FIV-50 and $PGE_2$-imidazole were optimize as shown here. Also, it was confirmed that FIV-50 inhibits intestinal fluid loss during experimental infection with enterotoxigenic *E. coli*, but this compound increase fluid accumulation early during infection probably due to mode of administration. FIV-50 had an effect on the ability of ETEC to colonize the small intestine. Further, histological and microscopical data confirmed that treatment with FIV-50 does not damage the intestinal architecture. In vitro adhesion assays confirmed that FIV-50 affects ETEC binding but does not exhibit similar effect in other pathogens.

Example 17

Mouse Studies of Formula 1 Type Compounds with Cholera Toxin

Summary of the experimental procedure and overall results. Cholera toxin (CT), when inoculated into the ligated intestinal loop of mice, caused marked distension due to fluid accumulation. In order to determine whether $PGE_2$-L-histidine or other compounds reduce CT-induced $PGE_2$ activity, the murine model of experimental cholera was used. The mouse intestinal ligated loop assay was performed in adult Swiss-Webster mice (6-8 weeks old) which were purchased and housed in a pathogen-free animal facility. Briefly, mice were given water without food for 18 h before surgery to reduce the food content of the small intestine. A ventral midline incision was made under isoflurane: ethanol mixture anesthesia to expose the small intestine. A single 5-8 cm segment of the small intestine, ligated with 00 Vicryl suture, was created in each mouse. Intestinal challenge was accomplished by injecting CT (1 μg) with or without 200 μM $PGE_2$ in 100 μl of phosphate buffer saline (PBS and bovine serum albumin (BSA) or 100-200 μM of the different compounds tested (FI-3, FI-2, FI-1, FIV-50, and FII-1) in 100l of PBS+ BSA. Control groups included animals inoculated with $PGE_2$-imidazole or the different analogue compounds tested in PBS/BSA or with 1% dimethyl sulfoxide (DMSO; used to get the different compounds into solution). After 6 h of observation, the animals were euthanized by cervical dislocation and the intestinal loops were removed. In some of the experiments, the animals received an intraperitoneal injection of 100-200 μM of $PGE_2$-imidazole or the different analogue compounds as pre-treatment prior to the surgery. The amount of luminal fluid was measured and expressed as μl/cm. Fluid accumulation data was analyzed by a two tailed Student's t-test for independent samples or by Dunnett's Multiple Group Comparison test.

Summary of the changes elicited by $PGE_2$ imidazole and $PGE_2$ imidazole analogues in a murine model of experimental cholera is shown in Table 6.

TABLE 6

| Compound tested | Experimental conditions | Reduction of fluid accumulation | Toxicity |
|---|---|---|---|
| $PGE_2$-imidazole | No pre-incubation | Yes | No |
| | 4 h pre-incubation with compound | Yes | No |
| FI-3 | No pre-incubation | Yes | No |
| | 4 h pre-incubation with compound | Yes | Yes |
| FI-2 | No pre-incubation | Yes | No |
| | 4 h pre-incubation with compound | Yes | No |
| FI-1 | No pre-incubation | No | Yes |
| FIV-50 | No pre-incubation | Yes | No |
| | 4 h pre-incubation with compound | Yes | No |
| FII-1 | No pre-incubation | No* | No |

Optimizing the murine model, $PGE_2$-imidazole confers protection against intestinal fluid loss during experimental infection with CT. The studies in the murine model of infection with CT using $PGE_2$-imidazole were performed for further optimization.

As shown in FIG. 56, $PGE_2$-imidazole effectively reduced the intestinal fluid loss after experimental CT infection. This experiment was repeated at least two times and a representative experiment is displayed in FIG. 56. As control experiments, infections were performed with the $PGE_2$-imidazole alone or PBS+BSA and confirmed that these compounds in absence of CT do not cause fluid accumulation in the experimental set up.

It was then determined whether pre-incubation with $PGE_2$-imidazole enhanced the anti-secretory effect of the compound. Forty μg of $PGE_2$-imidazole in 200 μl PBS were administered via the intraperitoneal route 4 hours prior to challenge. As shown in FIG. 57, pre-incubation with $PGE_2$-imidazole caused a significant reduction in the accumulation of intestinal fluid after experimental infection with CT. The results are representative of two independent experiments performed on two different days.

These results indicated that $PGE_2$-imidazole significantly inhibits cholera toxin induced intestinal secretion and that the experimental model was optimize to test which of the analogues identified for having increase activity in vitro are more effective during the in vivo infection.

FI-3 also confers protection against intestinal fluid loss during experimental infection with CT but displayed toxic effects. The first analogue tested was FI-3, which has been shown previously to have a dose-dependent activity and reduced extracellular cAMP accumulation in vitro caused by *Bacillus anthracis* Edema toxin.

Similar to the results obtained with $PGE_2$-imidazole, FI-3 caused an effective and significant reduction in the accumulation of intestinal fluid after experimental infection with CT (FIG. 58, representative of two independent experiments). However, it was observed that several animals treated with the CT+FI-3 mixture died before the end of the experiment at 6 h. Furthermore, in the surviving animals, it was observed that the ligated loops became inflamed and blood was collected from the intestinal lumen. In some cases, blood clots and fluid accumulation was observed in the loop.

An additional experiment was performed where animals treated with FI-3 at the time of infection with those receiving an I.P. dose of FI-3 4 hours before the infection were compared. As shown in FIG. 59, a statistical significant difference in the different treatment groups regardless of the pre-incubation time was not observed. Again, animals died before the end point of the experiment and several animals receiving FI-3 treatments displayed edema, blood and fluid accumulation.

The next compound tested was FI-2, another $PGE_2$-imidazole analogue which showed cAMP inhibitory activity in vitro with minimal cytotoxic effect. Initial analysis showed that FI-2 could be a promising compound that was effective in reducing the accumulation of intestinal fluid after experimental infection with CT (FIG. 60). Edema with FI-2 was not commonly present, however, blood accumulation in the loop and in the peritoneal cavity was observed. FI-2 was protective against intestinal fluid loss but was highly toxic to the animals.

One aspect to keep in mind is that FI-2 required the addition of DMSO to get in solution and this solvent could be potentially toxic in vivo. As demonstrated in FIG. 60, injection of ligated loops with 1% DMSO caused slight accumulation of fluid (however, further experimentation demonstrated that DMSO was not the source of the toxicity.

Similar to the studies with FI-3, animals treated with CT at the time of infection with those receiving an I.P were compared. As shown in FIG. 61, reduction of fluid accumulation was observed (although no statistically significant) when the pre-treated animals were compared with CT-controls. However, the number of animals surviving the full 6 hour of the incubation was reduced by half, which was not due to the surgery of the anathetic but was associated with the toxic effect of the compound. The surviving animals that received FI-2 treatments displayed bloody intestines, destruction of the microvasculature and in some cases fluid accumulation.

Further studies were initiated to investigate the toxic effect observed in the animals treated with FI-2. Animals were pretreated with FI-2, with 1% DMSO alone or with CT/FI-2 and then sacrificed at different time points to observe and record changes in the intestinal architecture, fluid accumulation, and damage to the peritoneal cavity due to the pretreatment with FI-2 via the intraperitoneal route (i.p.). As observed in FIG. 62, panel A, the color of the intestine ("pinkish") and the intact blood supply (veins and arteries) represent an intact mouse intestine. In contrast, intestines obtained from animals pre-treated with FI-2, 4 h prior to the intestinal loop surgery, became fragile and bleeding was observed even before the surgery (panel B) and extensive bleeding was observed post-ligation (panel C). To rule out the possibility that the DMSO used to solubilize FI-2 was responsible for the bleeding, mice were injected i.p. with 1% DMSO and incubated for 4 h (panel D) or 7 h (panel E). The integrity of the intestines remained intact and no toxicity was observed. In contrast, mice intestines injected with FI-2 and incubated for 5.5 h (panel F) or 7 h (panel G) displayed drastic changes in the coloration and texture of the intestine. Further, the blood supply was disrupted and even the feces displayed a "greenish/yellowish" discoloration (panel F).

To confirm that the experiment worked, a control animal intestine was ligated and cholera toxin (CT) was injected in the loop. After 3 h post-surgery, fluid accumulation was observed in the loop (panel h). In contrast, animals pre-treated with FI-2 and then injected with a solution containing both CT-FI-2 displayed a reduction in fluid accumulation, but massive bleeding and destruction of the intestinal architecture was observed. Further, blood was observed in the intraperitoneal and pulmonary cavity (panel I). Overall, the experiment confirmed that while FI-2 is effective in reducing fluid accumulation induced by CT, it was also toxic to the animals.

FI-1, a compound analogue to FI-2, did not reduce fluid accumulation and was still toxic. To determine whether the toxicity observed with FI-2 was caused by the structure of the compound, an analogue compound, FI-1, was tested in the loop model (FIG. 63).

In contrast to the FI-2 compound, FI-1 did not cause a reduction in fluid accumulation and instead, produced a slight increase. Further, toxic effects similar to FI-2 were observed in those animals injected with this compound. The results suggest that similar compound structures might produce a similar toxic effect in the intestinal cavity and in the intestinal loop but they do not display the same effectiveness regarding fluid accumulation.

FIV-50 was protective against intestinal fluid loss and did not display any apparent toxic effect in the animals. The compounds found by in vivo that were effective inhibitors of both Edema Toxin and Cholera toxin were tested in vitro. The first compound tested was FIV-50, which was extremely effective in the experiments in vitro with no obvious cytotoxic effect.

The first set of experiments showed that FIV-50 effectively reduced the accumulation of intestinal fluid after experimental infection with CT (FIG. 64). Edema was not present in animals treated with FIV-50 alone, indicating that this compound was not toxic under the conditions tested. In some animals, blood accumulation was observed in the intestinal loop.

Subsequent experiments were performed where animals were pre-treated with compound FIV-50 prior to ligation of the loop, because previous compounds that were not apparently toxic in the first experiment, display toxicity if they were used to pre-treatment using the i.p route. As shown in FIG. 65, significant reduction of fluid accumulation was observed when the pre-treated animals were compared with CT-controls. Almost all the animals survived the full 6 hour of the incubation and no signs of toxic effect associated with the compound pre-treatment was observed. Several of the surviving animals that received FIV-50 pre-treatment displayed bloody intestines and blood accumulation in the loop was more common than in the control animals treated with CT alone.

FII-1 produced a slight reduction in intestinal fluid loss but was not really effective because it came out of solution when the compound was mixed with buffer used to adjust the volume to inject. A second compound identified from in vivo studies tested was FII-1. This compound was also effective in the experiments in vitro with no obvious cytotoxic effect.

FII-1 did not cause a significant reduction in fluid accumulation and instead, produced a slight increase in fluid accumulation when the animals received the compound alone (FIG. 66). Toxic effects were observed; however, it is important to note that the FII-1 compound came out of solution when it was mixed with the loading buffer (PBS and BSA).

The murine model of experimental cholera and perform studies with $PGE_2$-imidazole and other analogues was optimized. It is confirmed that $PGE_2$-imidazole confers protection against intestinal fluid loss during experimental infection with CT. Furthermore, it was demonstrated that FI-3 and FI-2 can also reduced intestinal fluid loss. The compound FIV-50 is a promising analogue effective in the murine loop model. Finally, studies were initiated with FII-1 and results indicated that this compound is also an inhibitor.

Example 18

Exemplary Compounds and Synthesis of the Invention

The molecules that were originally found to be active were amine adducts of a cyclopentenone, $PGA_2$. This was the first structure that lead to the synthesis of a series of simple amine adducts of cyclic enones (FIG. 67). While active, adducts of this type were found to be unstable with regard to their reverse reaction. Consequently, a new series of compounds was developed where the carbon-nitrogen bond was replaced with a carbon-carbon bond that would not be susceptible to the unwanted elimination reaction. These molecules were designed to contain a heterocyclic ring much like the original imidazole adducts. Once chemistry was developed for their synthesis, these structures constituted one of the first sets of compounds synthesized and tested. A number of compounds with activities approaching that found with the original lead were discovered.

New heterocyclics linked bC-N bonds: The molecules that were originally found to be active were amine adducts of a cyclopentenone, $PGA_2$. This was the first structure that lead to the synthesis of a series of simple amine adducts of cyclic enones (FIG. 67). While active, adducts of this type were found to be unstable with regard to their reverse reaction. Consequently, a new series of compounds was developed where the carbon-nitrogen bond was replaced with a carbon-carbon bond that would not be susceptible to the unwanted elimination reaction. These molecules were designed to contain a heterocyclic ring much like the original imidazole adducts. Once chemistry was developed for their synthesis, these structures constituted one of the first sets of compounds synthesized and tested. A number of compounds with activities approaching that found with the original lead were discovered. This work has been discussed in previous reports.

Another approach to the synthesis of heterocyclic adducts that are stable was undertaken. Since the original adducts were unstable to elimination, a set of molecules was designed that attached the heterocycle to a sp2 hybridized carbon. It is not possible for these compounds possessing a C—N bond to a sp2 hybridized carbon to undergo elimination since such a reaction would form an alkyne in a small, five or six member ring. Both cyclopentenone and cyclohexenone adducts were synthesized and assayed. Interestingly, these compounds were inactive in the inhibition of anthrax edema factor and cholera toxin.

Tricyclic structures The structure types originally tested were very simple. Given that the assay results appear to plateau in the 10 μmol range, it was decided to synthesize a series of compounds that have a second ring attached to the parent cyclic ketone, while maintaining the best pharmacophores found in the earlier screens. These molecules possess a second ring attached to the cyclohexenone core at the 5 position (FIG. 68). The fluorobenzene and furan cyclohex-1,3-cyclodiones were purchased and chemistry was developed that converted them to the desired molecules in two steps. In the initial assay the parafluorophenyl derivative demonstrated activity that appeared promising. However, in the intestinal loop assay it was found to be toxic.

New leads based on computation. In conjunction with the medicinal chemistry being carried out, molecular modeling was done on the enzyme active site in an attempt to find new structure types that will have potential as inhibitors. A compound that came out of the molecular modeing was assayed and found to have promising activity. Based on that lead three new compounds were synthesized (FIG. 69). In one embodiment, these structures provide access to new compounds with better activity and physiological properties.

Attempting to find derivatives with better solubility, a series of molecules was synthesized based on the fluorenone lead. The goal in synthesizing these molecules is to improve activity, solubility and learn more about the structure activity relationship of the molecule. The benzamides (FI-10 and FI-11) were synthesized primarily to improve solubility of the system. The biphenyl versions were synthesized to improve solubility as while retaining a hydrophobic character more similar to the fluorenone. Molecules were synthesized that take advantage of the original pharmacophore while possessing additional functionality. The goal of this approach was to identify compounds that have increased activity through interaction with a second binding site. While effective in the assay, they proved to be toxic. Additionally, through a molecular modeling approach, two structure types were identified that demonstrated promising activity in the in vivo assays.

Example 19

Methods for Example 20

General Methods: All the solvents used in the reactions were dried prior to use unless reported. Thin-layer chromatography was performed using silica gel 60 $F_{24}$ precoated plates (250 μm thickness). Column chromatography was performed using 230-400 mesh silica gel 60. NMR spectra were obtained on a Varian 300 MHz spectrometer; chemical shifts are reported in δ units relative to the tetramethylsilane (TMS) signal at 0.00 ppm. Coupling constants are reported in Hz. High-resolution mass spectroscopy was provided by the mass spectrometry & proteomics facility of Ohio State University.

General Procedure for the Synthesis of the Bromoenones 16 and 21: Triphenylphosphine (14.4 g, 55 mmol, 1.1 equiv.) was diluted in 80 mL of anhydrous benzene. The solution was cooled to 0° C. in an ice bath and a solution of 1M $Br_2$ in benzene (55 mmol, 1.1 equiv.) was added dropwise employing an addition funnel. Upon bromine addition, the mixture was allowed to warm to room temperature and triethylamine (7.8 mL, 55 mmol, 1.1 equiv.) was added via syringe followed by the quick addition of a suspension of the 1,3-dione (7.0 g, 50 mmol, 1.0 equiv.) in methylene chloride. The mixture then was allowed to stir overnight at room temperature. The solvent was removed on a rotary evaporator and the residue was diluted in $CH_2Cl_2$ and adsorbed in silica gel prior to flash chromatography eluding with 0-50% ethyl acetate-hexane affording the bromoenone in good yields.

General Procedure for the Suzuki Coupling: A microwave vial was charged with a stir bar, bromoenone (100 mg, 1 equiv.), boronic acid or ester (1.2 equiv.) and ethanol (4 mL). To the solution was added 1M $K_2CO_3$ (1.2 equiv.) followed by the addition of the polymer supported palladium (FC 1001, 0.8 mol % Pd) catalyst. The reaction was subjected to the following microwave conditions: Power 250 W, Temperature 110° C., Ramp Time 1:00 min, Time holds 5 min, Power Max on (continuous air cooling). The reaction was then cooled to room temperature and filtered through a plug of celite eluding with ethyl acetate or methylene chloride. The solvent was evaporated on a rotary evaporator. The residue was diluted in methylene chloride and washed with brine. The organic layers were dried over $MgSO_4$ and the residue was purified by automated silica gel chromatography affording the desired product in moderate to good yields.

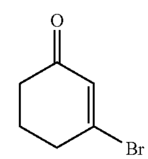

3-Bromocyclohex-2-enone. To a 250 mL round bottom flask containing a stir bar under nitrogen atmosphere was added 17.72 g of triphenylphosphine (67.57 mmol) and 60 mL of anhydrous benzene. The reaction was stirred and cooled to 0° C. in an ice-water bath. Bromine (3.50 mL, 68.11 mmol) was added dropwise to the well-stirred solution over a 30 min. period. Following addition, the reaction was stirred an additional hour at room temperature and 9.5 mL of triethylamine (67.60 mmol) was added by syringe followed by a solution of 1,3-cyclohexanedione (5.125 g in 25 mL of $CHCl_3$, 45.71 mmol). The reaction was stirred for 12 hours at room temperature under nitrogen. The reaction was worked up by passing the mixture through a filter funnel containing 3 cm of silica gel and washing with ether (50 mL). The filtrate was concentrated and purified by flash chromatography on the Biotage system, eluting 0% to 50% ethyl acetate/hexanes. The product fractions were collected and concentrated to yield a colorless oil (5.634 g, 70%). (Ref. *JOC* 1982, 47, 2829.) $^1H$ NMR ($CDCl_3$, 300 MHz): δ 2.07 (quintet, J=6.3 Hz, 2H), 2.41 (t, J=6.3 Hz, 2H), 2.81 (t, J=6.3 Hz, 2H), 6.46 (t, J=1.8 Hz, 1H). $^{13}C$ NMR ($CDCl_3$, 75 MHz): δ 23.0, 36.3, 36.4, 132.4, 150.0, 196.0.

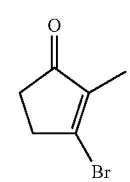

3-Bromo-2-methylcyclopent-2-enone. A 250 mL round bottom flask was dried in the oven and cooled under vacuum. To the flask was added 25.03 g of $PPh_3Br_2$ (59.31 mmol), and the flask was placed under nitrogen atmosphere. Anhydrous benzene (150 mL) was added by syringe, and the solution was stirred for 20 min. before the addition of Et₃N (8.40 mL, 59.76 mmol). Following addition, 2-methyl-cyclopentanedione (5.23 g, 46.66 mmol) was added to the stirred solution. The reaction was stirred for 12 hours and worked up by passing the pale orange reaction mixture through a filter funnel packed with silica gel. The filtrate was collected in a round bottom flask and the silica gel was washed with an additional 20 mL of ether. The solvent was removed under reduced pressure and the compound was purified by vacuum distillation (42-43° C., 0.1 mm Hg) yielding a pale yellow oil (4.10 g, 50%). (Ref. Synthetic Communications 1975, 5 (3), 193-199). $^1$H NMR (CDCl$_3$, 300 MHz): δ 1.79 (t, J=2.4 Hz, 3H), 2.54-2.57 (m, 2H), 2.90-2.95 (m, 2H). $^{13}$C NMR (CDCl$_3$, 75 MHz): δ 10.0, 35.1, 35.8, 141.3, 156.1, 204.0.

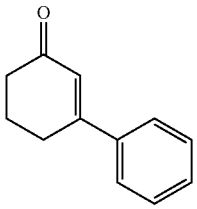

3-Phenylcyclohex-2-enone (FI-4). A microwave vial was charged with a stir bar, 3-bromocyclohex-2-enone (65 mg, 1 equiv., 0.37 mmol), phenyl boronic acid (55 mg, 1.2 equiv., 0.45 mmol) and ethanol (4 mL). To the solution was added 1M K$_2$CO$_3$ (1.2 equiv., 0.45 mmol) followed by the addition of the polymer supported palladium FC 1001 (27 mg, 3 mol % Pd) catalyst. The reaction was subjected to the following microwave conditions: Power 250 W, Temperature 110° C., ramp time 1:00 min, time holds 5 min, Power Max on (continuous air cooling). The reaction was then cooled to room temperature and filtered through a plug of celite eluding with ethyl acetate. The solvent was evaporated on a rotary evaporator. The residue was diluted in methylene chloride and washed with brine. The organic layers were dried over MgSO$_4$ and the residue was purified by automated silica gel chromatography using gradient elution (0 to 20% ethyl acetate/hexanes) affording the desired product as a white solid (48 mg, 75% yield). $^1$H NMR (300 MHz, CDCl$_3$): δ 7.50-7.53 (m, 2H), 7.36-7.41 (m, 3H), 6.40 (t, J=1.4 Hz, 1H), 2.76 (td, J=6.9, 1.2 Hz, 2H), 2.48 (t, J=6.9 Hz, 2H), 2.14 (quintet, J=6.9 Hz, 2H). $^{13}$C (75 MHz, CDCl$_3$): 199.6, 159.6, 138.6, 129.8, 128.6, 125.9, 125.3, 37.3, 28.1, 22.9. LCMS (ESI): mass calcd for (C$_{12}$H$_{12}$O) m/z 172.09; measured [M+H]$^+$: m/z 173.17.

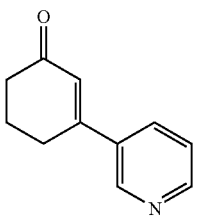

3-Pyridin-3-yl-cyclohex-2-enone (FI-5). Prepared as described above from 3-bromocyclohex-2-enone and 3-pyridinylboronic acid. Purification by automated flash chromatography using gradient elution (20 to 60% ethyl acetate/hexanes) yielded the product (42 mg, 54%) as a dark orange solid. $^1$H NMR (300 MHz, CDCl$_3$): δ 7.80 (ddd, J=7.8, 2.4, 1.5 Hz, 1H), 7.34 (ddd, J=7.8, 4.5, 0.6 Hz, 1H), 6.41 (t, J=1.5 Hz, 1H), 2.78 (t, J=5.8 Hz, 2H), 2.51 (t, J=6.6 Hz, 2H), 2.19 (quintet, J=6.2 Hz, 2H). $^{13}$C (75 MHz, CDCl$_3$): 199.2, 156.5, 150.8, 147.3, 133.4, 126.6, 123.6, 37.4, 28.0, 22.9. LCMS (ESI): mass calcd for (C$_{11}$H$_{11}$NO) m/z 173.08; measured [M+H]$^+$: m/z 174.16.

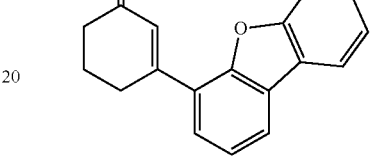

3-Dibenzofuran-4-yl-cyclohex-2-enone. Synthesized from 3-bromocyclohex-2-enone and dibenzofuran-4-boronic acid according to the general procedure described for the Suzuki coupling. Purification by automated flash chromatography using gradient elution (0 to 20% ethyl acetate/hexanes) yielded the product (141 mg, 83%) as a white solid. $^1$H NMR (300 MHz, CDCl$_3$): δ 7.91 (d, J=6.9 Hz, 2H), 7.30-7.58 (m, 5H), 6.90 (s, 1H), 2.97 (t, J=4.7 Hz, 2H), 2.56 (t, J=6.1 Hz, 2H), 2.21 (quintet, J=5.8 Hz, 2H). $^{13}$C (75 MHz, CDCl$_3$): 200.1, 156.2, 155.9, 153.3, 128.6, 127.7, 125.6, 125.3, 124.0, 123.5, 123.2, 123.0, 122.0, 120.7, 111.9, 37.7, 29.0, 23.2. HRMS (LCT Electrospray): mass calcd for (C$_{18}$H$_{14}$O$_2$+Na) m/z 285.0891; measured [M+Na]$^+$: m/z 285.0895.

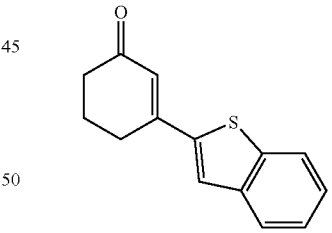

3-Benzo[b]thiophen-2-yl-cyclohex-2-enone. Synthesized from 3-bromocyclohex-2-enone and benzothiophene-2-boronic acid according to the general procedure described for the Suzuki coupling. Purification by automated flash chromatography yielded the product (134 mg, 89%) as a white solid. $^1$H NMR (300 MHz, CDCl$_3$): δ 7.73-7.82 (m, 2H), 7.58 (s, 1H), 7.31-7.39 (m, 2H), 6.46 (s, 1H), 2.87 (td, J=5.9, 1.2 Hz, 2H), 2.51 (t, J=6.3 Hz, 2H), 2.18 (quintet, J=6.3 Hz, 2H). $^{13}$C (75 MHz, CDCl$_3$): 199.3, 152.5, 142.6, 140.2, 139.8, 126.3, 125.04, 125.0, 124.9, 124.6, 122.5, 37.6, 27.9, 22.8. HRMS (LCT Electrospray): mass calcd for (C$_{14}$H$_{12}$OS+Na) m/z 251.0507; measured [M+Na]$^+$: m/z 251.0501.

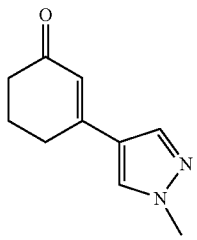

3-(1-Methyl-1H-pyrazol-4-yl)-cyclohex-2-enone. To a 50 mL round bottom flask containing a stir bar was added 0.152 g of 3-bromocyclohex-2-enone (0.868 mmol), 0.216 g of 1-methyl-4-(4,4,5,5-tetramethyl-1,3,2-dioxaborolan-2-yl)-1H-pyrazole (1.04 mmol), 5 mL of THF, 4.0 mL of an aqueous solution of 2.0 M KF solution, and 0.139 g of 5% Pd on activated charcoal (Degussa type E105 CA/W, 7.5 mol %). The reaction was stirred, placed under nitrogen, and heated to 60° C. in an oil bath overnight. The reaction was not complete by TLC so the temperature was raised to 80° C. and heated an additional 18 hours. The reaction was worked up by filtering the crude mixture through a celite plug and extraction with methylene chloride (2 times with 5 mL). The organic phases were combined, dried with sodium sulfate, filtered, and concentrated under reduced pressure. The mixture was passed through a Fisher Prep Sep SCX column eluting with 8 mL of $CH_2Cl_2$ followed by 5 mL of methanol/ammonia (7N). The fractions were not pure so purification was accomplished using flash chromatography on the Biotage system utilizing gradient elution (0% to 80% ethyl acetate/hexanes). The product fractions were combined and concentrated to give a white powder (45 mg, 29%). $^1$H NMR (CDCl$_3$, 300 MHz): δ 2.09 (quintet, J=6.3 Hz, 2H), 2.41-2.46 (m, 2H), 2.63 (t, J=6.3 Hz, 2H), 3.92 (s, 3H), 6.26 (t, J=2.4 Hz, 1H), 7.57 (s, 1H), 7.69 (s, 1H). $^{13}$C NMR (CDCl$_3$, 75 MHz): δ 22.5, 27.9, 37.4, 39.4, 121.5, 128.6, 137.6, 151.9, 199.3. LCMS (ESI): mass calcd for ($C_{10}H_{12}N_2O$) m/z 176.09; measured [M+H]$^+$: m/z 177.08.

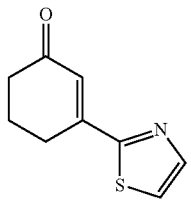

3-Thiazol-2-yl-cyclohex-2-enone. To a 100 mL round bottom flask containing a stir bar was added 0.185 g of zinc dust (2.83 mmol) and 3 mL of N,N-dimethylacetamide. The flask was placed under nitrogen and 0.08 mL of TMS-chloride (0.63 mmol) and 0.05 mL of 1,2-dibromoethane (0.58 mmol) were added by syringe. The reaction was stirred for 5 min. and 0.09 mL of 2-bromothiazole (0.998 mmol) was added by syringe. The reaction was stirred for 1 hour at room temperature under nitrogen. To a separate 100 mL round bottom flask containing a stir bar was added 0.124 g of 3-bromocyclohex-2-enone (0.708 mmol) and 0.024 g of Pd(PPh$_3$)$_2$Cl$_2$ (4.8 mol %), and 10 mL of anhydrous THF. The previously prepared organozinc species was added to the enone solution dropwise with removal of excess zinc using a syringe fitted with a cotton plug. The reaction was heated overnight at 60° C. in an oil bath with stirring under nitrogen atmosphere. The reaction was worked up by transferring the solution to a vial containing 10 mL of saturated ammonium chloride solution, and the product was extracted with ethyl acetate (2 times with 8 mL). The organic layer was dried with sodium sulfate, filtered, and solvent was concentrated under reduced pressure. The product was purified by flash chromatography using the Biotage system utilizing gradient elution (0% to 80% ethyl acetate/hexanes). Product fractions were combined and concentrated to yield a pale yellow solid (35 mg, 28%). $^1$H NMR (CDCl$_3$, 300 MHz): δ 2.17 (quintet, J=6.3 Hz, 2H), 2.52 (t, J=6.3 Hz, 2H), 2.97 (td, J=6.3, 1.5 Hz, 2H), 6.69 (br s, 1H), 7.45 (d, J=3.0 Hz, 1H), 7.93 (d, J=3.0 Hz, 1H). $^{13}$C NMR (CDCl$_3$, 75 MHz): δ 22.4, 27.0, 37.8, 121.4, 126.6, 144.4, 151.7, 166.7, 199.4. LCMS (ESI): mass calcd for ($C_9H_9NOS$) m/z 179.04; measured [M+H]$^+$: m/z 180.03.

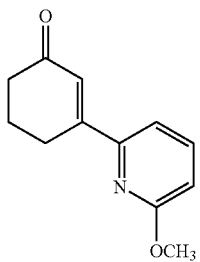

3-(6-Methoxy-pyridin-2-yl)-cyclohex-2-enone. Synthesized from 3-bromocyclohex-2-enone and 6-methoxy-2-pyridineboronic acid N-phenyldiethanolamine ester according to the general procedure described for the Suzuki coupling. Purification by automated flash chromatography using gradient elution (0 to 80% ethyl acetate/hexanes) yielded the product (156 mg, 89%) as a white powder. $^1$H NMR (CDCl$_3$, 300 MHz): δ 2.15 (quintet, J=6.3 Hz, 2H), 2.50 (t, J=6.3 Hz, 2H), 2.86 (td, 6.3, 1.5 Hz, 2H), 3.95 (s, 3H), 6.75 (dd, J=8.4, 0.6 Hz, 1H), 6.91 (t, J=1.5 Hz, 1H), 7.18 (dd, J=7.5, 0.6 Hz, 1H), 7.59 (td, J=7.5, 0.6 Hz, 1H). $^{13}$C NMR (CDCl$_3$, 75 MHz): δ 22.7, 26.2, 37.7, 53.3, 112.2, 114.1, 126.1, 138.8, 152.6, 157.7, 163.2, 200.5. LCMS (ESI): mass calcd for ($C_{12}H_{13}NO_2$) m/z 203.09; measured [M+H]$^+$: m/z 204.05.

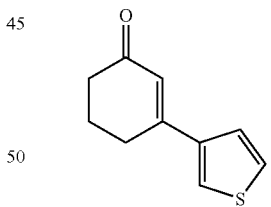

3-Thiophen-3-yl-cyclohex-2-enone. Synthesized from 3-bromocyclohex-2-enone and 3-thiophene boronic acid according to the general procedure described for the Suzuki coupling. The product was purified by automated flash chromatography using gradient elution (0 to 50% ethyl acetate/hexanes). A yellow solid was isolated after collection of fractions and recrystallized from hexanes and ethyl acetate to give 0.086 g of colorless needles (72%). $^1$H NMR (CDCl$_3$, 300 MHz): δ 2.13 (quintet, J=6.3 Hz, 2H), 2.47 (t, J=6.3 Hz, 2H), 2.76 (dd, J=6.3, 1.2 Hz, 2H), 6.39 (t, J=1.2 Hz, 1H), 7.31-7.36 (m, 2H), 7.55 (dd, J=2.7, 1.5 Hz, 1H). $^{13}$C NMR (CDCl$_3$, 75 MHz): δ 22.6, 27.8, 37.4, 123.8, 124.9, 125.0, 126.6, 140.5, 153.3, 199.9. LCMS (ESI): mass calcd for ($C_{10}H_{10}OS$) m/z 178.05; measured [M+H]$^+$: m/z 179.04.

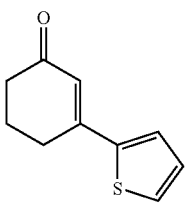

3-Thiophen-2-yl-cyclohex-2-enone. Synthesized from 3-bromocyclohex-2-enone and 2-thiophene boronic acid according to the general procedure described for the Suzuki coupling. The product was purified by passing the product through a small silica gel plug eluting with methylene chloride and recrystallization from hexanes and ethyl acetate to yield a pale yellow crystalline solid (125 mg, 83%). $^1$H NMR (CDCl$_3$, 300 MHz): δ 7.42 (d, J=5.4 Hz, 1H), 7.36 (d, J=3.3 Hz, 1H), 7.08 (t, J=3.9 Hz, 1H), 6.41 (s, 1H), 2.79 (t, J=6.3 Hz, 2H), 2.46 (t, J=6.3 Hz, 2H), 2.14 (quintet, J=6.3 Hz, 2H). $^{13}$C NMR (CDCl$_3$, 75 MHz): δ 199.2, 152.3, 142.6, 128.7, 128.2, 127.2, 122.7, 37.3, 28.1, 22.5. LCMS (ESI): mass calcd for (C$_{10}$H$_{10}$OS) m/z 178.05; measured [M+H]$^+$: m/z 179.04.

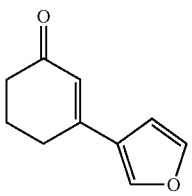

3-Furan-3-yl-cyclohex-2-enone. Synthesized from 3-bromocyclohex-2-enone and furan-3-boronic acid according to the general procedure described for the Suzuki coupling. Purification by silica gel column chromatography using gradient elution (0 to 30% ether/hexanes) yielded the product (13 mg, 16%) as a white solid. $^1$H NMR (300 MHz, CDCl$_3$): δ 7.70 (s, 1H), 7.44 (t, J=1.9 Hz, 1H), 6.59 (t, J=1.1 Hz, 1H), 6.24 (s, 1H), 2.63 (td, J=5.7, 1.1 Hz, 2H), 2.46 (t, J=6.3 Hz, 2H), 2.11 (quintet, J=6.3 Hz, 2H). $^{13}$C (75 MHz, CDCl$_3$): 200.1, 152.0, 144.6, 142.4, 126.0, 123.3, 107.6, 37.6, 27.5, 22.7. HRMS (LCT Electrospray): mass calcd for (C$_{10}$H$_{10}$O$_2$+Na) m/z 185.0578; measured [M+Na]$^+$: m/z 185.0574.

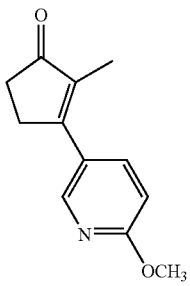

3-(6-Methoxy-pyridin-3-yl)-2-methyl-cyclopent-2-enone. Synthesized from 3-bromo-2-methylcyclopent-2-enone and 6-methoxypyridine-3-boronic acid according to the general procedure described for the Suzuki coupling. Purification by automated flash chromatography yielded the product (138 mg, 92%) as a white solid. $^1$H NMR (300 MHz, CDCl$_3$): δ 8.41 (d, J=2.2 Hz, 1H), 7.77 (dd, J=8.5, 2.5 Hz, 1H), 6.83 (d, J=8.5 Hz, 1H), 3.99 (s, 3H), 2.92-2.87 (m, 2H), 2.56-2.53 (m, 2H), 1.99 (t, J=1.9 Hz, 3H). $^{13}$C (75 MHz, CDCl$_3$): δ 208.9, 164.4, 162.6, 146.4, 137.4, 135.9, 125.4, 110.9, 53.8, 33.8, 28.7, 10.2. LCMS (ESI): mass calcd for (C$_{12}$H$_{13}$NO$_2$) m/z 203.09; measured [M+H]$^+$: m/z 204.09.

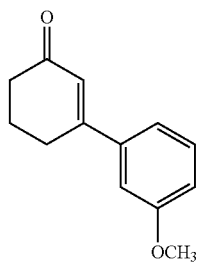

3-(3-Methoxy-phenyl)-cyclohex-2-enone (FI-15). Synthesized from 3-bromocyclohex-2-enone and 3-methoxyphenylboronic acid according to the general procedure described for the Suzuki coupling. Purification by automated flash chromatography using gradient elution (0 to 80% ethyl acetate/hexanes) yielded the product (141 mg, 88%) as a pale yellow solid. $^1$H NMR (300 MHz, CDCl$_3$): δ 7.30 (t, J=8.0 Hz, 1H), 7.10 (dd, J=8.0, 0.8 Hz, 1H), 7.03 (t, J=2.2 Hz, 1H), 6.93 (dd, J=8.3, 2.5 Hz, 1H), 6.39 (bs, 1H), 3.82 (s, 3H), 2.75 (td, J=6.1, 0.8 Hz, 2H), 2.48 (t, J=6.3 Hz, 2H), 2.14 (quintet, J=6.1 Hz, 2H).

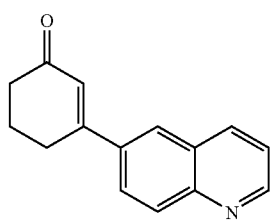

3-Quinolin-6-yl-cyclohex-2-enone. Synthesized from 3-bromocyclohex-2-enone and 6-(4,4,5,5-tetramethyl-1,3,2-dioxaborolan-2-yl)quinoline according to the general procedure described for the Suzuki coupling. Purification by automated flash chromatography using gradient elution (40 to 100% ethyl acetate/hexanes) yielded the product (164 mg, 88%) as a white powder. $^1$H NMR (CDCl$_3$, 300 MHz): δ 8.92 (dd, J=4.2, 1.5 Hz, 1H), 8.17 (d, J=7.8 Hz, 1H), 8.11 (d, J=9.0 Hz, 1H), 7.95 (d, J=2.1 Hz, 1H), 7.86 (dd, J=9.0, 2.4 Hz, 1H), 7.43 (dd, J=8.4, 4.5 Hz, 1H), 6.54 (s, 1H), 2.89 (t, J=6.3 Hz, 2H), 3.53 (t, J=6.3 Hz, 2H), 2.21 (pent, J=6.3 Hz, 2H). $^{13}$C NMR (CDCl$_3$, 75 MHz): δ 199.4, 158.3, 151.2, 148.6, 136.7, 136.5, 129.9, 127.8, 126.8, 126.3, 125.7, 121.7, 37.3, 28.2, 22.8. LCMS (ESI): mass calcd for (C$_{15}$H$_{13}$NO) m/z 223.10; measured [M+H]$^+$: m/z 224.80.

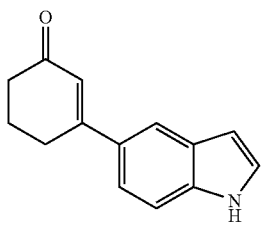

3-(1H-Indol-5-yl)-cyclohex-2-enone. Synthesized from 3-bromocyclohex-2-enone and indole-5-boronic acid pinacol ester according to the general procedure described for the Suzuki coupling. Purification by automated flash chromatography using gradient elution yielded the product (151 mg, 83%) as a pale yellow solid. $^1$H NMR (300 MHz, CDCl$_3$): δ 8.68 (bs, 1H), 7.86 (d, J=0.3 Hz, 1H), 7.37-7.44 (m, 2H), 7.25 (dd, J=3.3, 2.5 Hz, 1H), 6.59 (t, J=2.5 Hz, 1H), 6.51 (t, J=1.1 Hz, 1H), 2.88 (td, J=6.3, 1.4 Hz, 2H), 2.51 (t, J=6.3 Hz, 2H), 2.18 (quintet, J=6.0 Hz, 2H). $^{13}$C (75 MHz, CDCl$_3$): 200.1, 161.5, 136.7, 130.1, 127.9, 125.4, 123.7, 120.2, 119.1, 111.3, 103.3, 37.3, 28.5, 23.0. HRMS (LCT Electrospray): mass calcd for (C$_{14}$H$_{13}$NO+Na) m/z 234.0895; measured [M+Na]$^+$: m/z 234.0897.

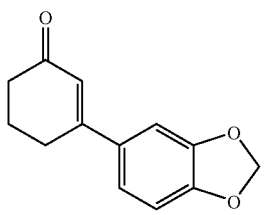

3-Benzo[1,3]dioxol-5-yl-cyclohex-2-enone. Synthesized from 3-bromocyclohex-2-enone and 3,4-methylenedioxyphenylboronic acid according to the general procedure described for the Suzuki coupling. Purification by automated flash chromatography using gradient elution (0 to 80% ethyl acetate/hexanes) yielded the product (164 mg, 85%) as a white solid. $^1$H NMR (300 MHz, CDCl$_3$): δ 7.07-7.00 (m, 2H), 6.81 (d, J=8.0 Hz, 2H), 6.31 (s, 1H), 5.99 (s, 2H), 2.70 (t, J=5.5 Hz, 2H), 2.45 (t, J=6.3 Hz, 2H), 2.12 (quintet, J=6.3 Hz, 2H). $^{13}$C (75 MHz, CDCl$_3$): 199.7, 159.0, 149.2, 148.2, 132.8, 124.2, 120.7, 108.4, 106.3, 101.6, 37.4, 28.3, 23.0. LCMS (ESI): mass calcd for (C$_{13}$H$_{12}$O$_3$) m/z 216.08; measured [M+H]$^+$: m/z 216.95.

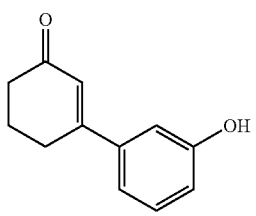

3-(3-Hydroxy-phenyl)-cyclohex-2-enone. Synthesized from 3-bromocyclohex-2-enone and 3-hydroxyphenylboronic acid according to the general procedure described for the Suzuki coupling. Purification by automated flash chromatography yielded the product (83 mg, 64%) as a pale yellow solid. $^1$H NMR (300 MHz, CD$_3$OD): δ 7.22 (t, J=7.8 Hz 1H), 7.05 (ddd, J=7.8, 1.5, 0.9 Hz, 1H), 6.98 (t, J=1.5 Hz, 1H), 6.83 (ddd, J=8.1, 2.4, 1.2 Hz, 1H), 6.31 (t, J=1.2 Hz, 1H), 2.79 (td, J=6.0, 1.5 Hz, 2H), 2.46 (t, J=6.0 Hz, 2H), 2.12 (quintet, J=6.6 Hz, 2H). $^{13}$C (75 MHz, CD$_3$OD): 202.5, 163.4, 158.8, 141.3, 130.7, 125.2, 118.4, 118.2, 113.8, 38.1, 29.2, 23.9. LCMS (ESI): mass calcd for (C$_{12}$H$_{12}$O$_2$) m/z 188.08; measured [M+H]$^+$: m/z 189.0.

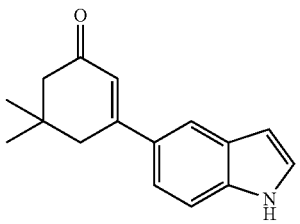

3-(1H-Indol-5-yl)-5,5-dimethyl-cyclohex-2-enone. Synthesized from 3-Bromo-5,5-dimethyl-cyclohex-2-enone and indole-5-boronic acid pinacol ester according to the general procedure described for the Suzuki coupling. Purification by automated flash chromatography using gradient elution (0 to 80% ethyl acetate/hexanes) yielded the product (177 mg, 95%) as an off-white solid. $^1$H NMR (300 MHz, CDCl$_3$): δ 8.97 (bs, 1H), 7.84 (s, 1H), 7.39 (d, J=1.2 Hz, 2H), 7.22 (dd, J=3.0, 2.1 Hz, 1H), 6.56 (dd, J=3.0, 2.1 Hz, 1H), 6.49 (t, J=1.5 Hz, 1H), 2.74 (d, J=1.2 Hz, 2H), 2.35 (s, 2H), 1.25 (s, 3H), 1.14 (s, 3H). $^{13}$C (75 MHz, CDCl$_3$): 200.4, 159.5, 136.8, 130.2, 127.9, 125.5, 122.4, 120.1, 119.1, 111.3, 103.1, 50.9, 42.6, 33.8, 28.4, 24.9. HRMS (LCT Electrospray): mass calcd for (C$_{16}$H$_{17}$NO+Na) m/z 262.1208; measured [M+Na]$^+$: m/z 262.1204.

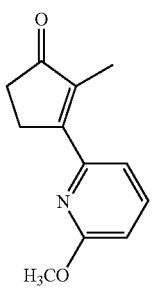

3-(6-Methoxy-pyridin-2-yl)-2-methyl-cyclopent-2-enone. Synthesized from 3-bromo-2-methylcyclopent-2-enone and 6-methoxy-2-pyridineboronic acid N-phenyldiethanolamine ester according to the general procedure described for the Suzuki coupling. Purification by automated flash chromatography using gradient elution (0 to 50% ethyl acetate/hexanes) yielded the product (94 mg, 69%) as a pale yellow solid. $^1$H NMR (CDCl$_3$, 300 MHz): δ 7.64 (dd, J=8.4, 7.5 Hz, 1H), 7.17 (d, J=7.2 Hz, 1H), 6.75 (d, J=8.1 Hz, 1H), 3.97 (s, 3H), 3.00-2.95 (m, 2H), 2.56-2.53 (m, 2H), 2.20 (t, J=2.1 Hz, 3H). $^{13}$C NMR (CDCl$_3$, 75 MHz): δ 210.2, 163.2, 152.0, 138.8, 138.6, 129.1, 116.1, 111.7, 53.6, 33.9, 27.7, 10.6. LCMS (ESI): mass calcd for (C$_{12}$H$_{13}$NO$_2$) m/z 203.09; measured [M+H]$^+$: m/z 204.04.

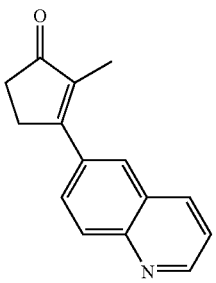

2-Methyl-3-quinolin-6-yl-cyclopent-2-enone. Synthesized from 3-bromo-2-methylcyclopent-2-enone and indole-5-boronic acid pinacol ester according to the general procedure described for the Suzuki coupling. Purification by automated flash chromatography using gradient elution (40 to 100% ethyl acetate/hexanes) yielded the product (146 mg, 78%) as a white solid. $^1$H NMR (CDCl$_3$, 300 MHz): δ 8.95 (dd, J=4.2, 1.5 Hz, 1H), 8.21 (d, J=7.5 Hz, 1H), 8.16 (d, J=8.7 Hz, 1H), 7.95 (d, J=2.1 Hz, 1H), 7.86 (dd, J=8.7, 1.8 Hz, 1H), 7.45 (dd, J=8.1, 4.2 Hz, 1H), 3.01-3.05 (m, 2H), 2.59-2.62 (m, 2H), 2.05 (t, J=2.1 Hz, 3H). $^{13}$C NMR (CDCl$_3$, 75 MHz): δ 209.3, 165.2, 151.3, 148.1, 137.4, 136.4, 134.6, 129.8, 128.4, 127.9, 127.0, 121.8, 34.1, 29.5, 10.2. LCMS (ESI): mass calcd for (C$_{15}$H$_{13}$NO) m/z 223.10; measured [M+H]$^+$: m/z 223.74.

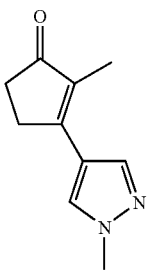

2-Methyl-3-(1-methyl-1H-pyrazol-4-yl)-cyclopent-2-enone. Synthesized from 3-bromo-2-methylcyclopent-2-enone and 1-methyl-4-(4,4,5,5-tetramethyl-1,3,2-dioxaborolan-2-yl)-1H-pyrazole according to the general procedure described for the Suzuki coupling. Purification by automated flash chromatography using gradient elution (0 to 100% ethyl acetate/hexanes) and further recrystallization yielded the product (21 mg, 16%) as a white solid. $^1$H NMR (CDCl$_3$, 300 MHz): δ 7.80 (s, 1H), 7.70 (s, 1H), 2.84-2.80 (m, 2H), 2.52-2.48 (m, 2H), 1.95 (t, J=2.1 Hz, 3H). LCMS (ESI): mass calcd for (C$_{10}$H$_{12}$N$_2$O) m/z 176.09; measured [M+H]$^+$: m/z 177.09.

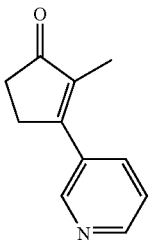

2-Methyl-3-pyridin-3-yl-cyclopent-2-enone. Synthesized from 3-bromo-2-methylcyclopent-2-enone and 3-pyridine boronic acid according to the general procedure described for the Suzuki coupling. Purification by automated flash chromatography using gradient elution (0 to 100% ethyl acetate/hexanes) and further recrystallization yielded the product (38 mg, 31%) as a brown oil. $^1$H NMR (CDCl$_3$, 300 MHz): δ 8.78 (s, 1H), 8.63 (br d, J=3.6 Hz, 1H), 7.82 (dt, J=8.1, 2.1 Hz, 1H), 7.40 (dd, J=8.1, 4.8 Hz, 1H), 2.91-2.96 (m, 2H), 2.56-2.59 (m, 2H), 1.98 (t, J=2.1 Hz, 3H). $^{13}$C NMR (CDCl$_3$, 75 MHz): δ 208.8, 162.5, 150.1, 148.3, 137.9, 134.5, 129.1, 123.4, 33.9, 29.0, 9.9. LCMS (ESI): mass calcd for (C$_{11}$H$_{11}$NO) m/z 173.08; measured [M+H]$^+$: m/z 174.07.

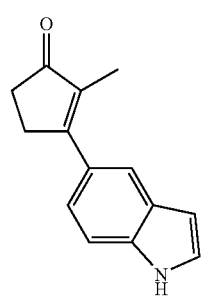

3-(1H-Indol-5-yl)-2-methyl-cyclopent-2-enone. Synthesized from 3-bromo-2-methylcyclopent-2-enone and 5-(4,4,5,5-tetramethyl-1,3,2-dioxaborolan-2-yl)-1H-indole according to the general procedure described for the Suzuki coupling. Purification by automated flash chromatography using gradient elution (0 to 100% ethyl acetate/hexanes) and further recrystallization yielded the product (138 mg, 92%) as pale yellow solid. $^1$H NMR (CDCl$_3$, 300 MHz): δ 7.86 (s, 1H), 7.47-7.39 (m, 2H), 7.27 (t, J=3.0 Hz, 1H), 6.62 (t, J=2.1 Hz, 1H), 3.02-2.97 (m, 2H), 2.57-2.54 (m, 2H), 2.05 (t, 3H, J=1.8). $^{13}$C NMR (CDCl$_3$, 75 MHz): δ 210.0, 168.3, 136.2, 134.5, 128.2, 127.8, 125.3, 121.9, 120.6, 111.1, 103.4, 34.2, 29.7, 10.5. LCMS (ESI): mass calcd for (C$_{14}$H$_{13}$NO) m/z 211.10; measured [M+H]$^+$: m/z 212.03.

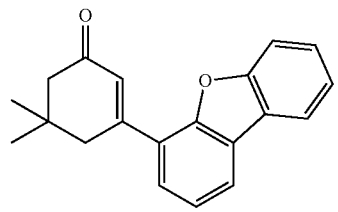

3-Dibenzofuran-4-yl-5,5-dimethyl-cyclohex-2-enone. Synthesized from 3-bromo-5,5-dimethylcyclohex-2-enon and dibenzofuran-4-boronic acid according to the general procedure described for the Suzuki coupling. Purification by automated flash chromatography yielded the product (192 mg, 96%) as a white solid. $^1$H NMR (300 MHz, CDCl$_3$): δ 7.93 (dd, J=7.4, 1.1 Hz, 1H), 7.92 (ddd, J=7.7, 0.8, 0.6 Hz, 1H), 7.59 (d, J=8.3 Hz, 1H), 7.51-7.43 (m, 2H), 7.34 (t, J=7.7 Hz, 1H), 7.33 (t, J=7.4 Hz, 1H), 6.91 (t, J=1.4 Hz, 1H), 2.85 (d, J=1.4 Hz, 2H), 2.42 (s, 2H), 1.19 (s, 6H). $^{13}$C (75 MHz, CDCl$_3$): δ 200.3, 156.0, 153.9, 153.4, 127.7, 127.6, 125.6, 125.3, 124.3, 123.6, 123.2, 123.0, 122.0, 120.7, 112.0, 51.3, 43.0, 34.2, 28.7. HRMS (LCT Electrospray): mass calcd for (C$_{20}$H$_{18}$O$_2$+Na) m/z 313.1204; measured [M+Na]$^+$: m/z 313.1201.

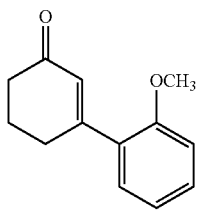

3-(2-Methoxy-phenyl)-cyclohex-2-enone. Synthesized from 3-bromocyclohex-2-enone and 2-methoxyphenylboronic acid according to the general procedure described for the Suzuki coupling. Purification by automated flash chromatography using gradient elution (0 to 80% ethyl acetate/hexanes) yielded the product (166 mg, 98%) as a pale yellow oil. $^1$H NMR (300 MHz, $CDCl_3$): δ 7.32 (ddd, J=8.3, 7.4, 1.9 Hz, 1H), 7.18 (dd, J=7.7, 1.9 Hz, 1H), 6.96 (dd, J=7.4, 1.1 Hz, 1H), 6.91 (d, J=8.5 Hz, 1H), 6.18 (t, J=1.8 Hz, 1H), 3.83 (s, 3H), 2.73 (td, J=6.1, 1.4 Hz, 2H), 2.48 (t, J=6.3 Hz, 2H), 2.14-2.06 (m, 2H).

Example 20

Synthesis and Screening of Small Molecule Inhibitors

These molecules are derived from the initial discovery that histidine and imidazole adducts of the prostaglandin $PGE_2$ reduce the net secretory response of cholera toxin-challenged mice and act directly on the action of anthrax edema factor, a calmodulin-dependent adenylyl cyclase. The simple enones examined here were prepared by palladium-catalyzed Suzuki reaction.

The initial lead for the development of the molecules reported here came from the report by Peterson that histidine and imidazole adducts of prostaglandin $E_2$ ($PGE_2$) (FIG. 70) reduced the net secretory response of the small intestine of mice challenged with cholera toxin (CT) (Peterson et al., 2001). It was reported that upon in vitro incubation of $PGE_2$ with either L-histidine or imidazole, a covalent adduct formed, presumably with $PGA_2$ as the intermediate (FIG. 67). These adducts were found to be responsible for the observed antisecretory activity. Subsequent studies revealed that not only were the imidazole-prostaglandin adducts active against mammalian adenylyl cyclases, but also the edema factor of anthrax. With these derivatives as the lead compounds, an effort has been made to develop novel small molecule inhibitors of EF through the synthesis of a series of related compounds.

With $PGE_2$-L-histidine, and $PGE_2$-imidazole in mind, a series of simple enone adducts of imidazole were examined. One problem that had to be considered in the development of new inhibitor molecules was that the initial lead compounds were unstable to elimination of the amine at the β-position with the subsequent reformation of $PGA_2$ (FIG. 67). While it was understood that the reversible nature of the amine adducts would present a problem, the decision was made to examine such adducts, since they were readily available. Interestingly, a number of these very simple compounds (FIG. 68) exhibited adenylyl cyclase inhibition activity in the same potency range as the $PGE_2$ imidazole adducts (100-500 μM). In the initial experiments the cyclohexenone adducts appeared to be more active than the five-member ring compounds. However, these observations were not conclusive, since they may be biased by the fact that the six member ring adducts appeared to be more stable to elimination of imidazole than the five-member ring derivatives.

Because of the labile nature of the amine adducts, the decision was made to examine molecules with the heterocycle attached via a carbon-carbon bond. There were a number of methods that could have been used in the synthesis of such molecules. The addition of the imidazolium cuprate was attempted on cyclohexenone (Tatsuta et al., 1995; Krik, 1978). However our initial use of cuprate chemistry demonstrated that each cuprate addition required its own set of reaction conditions. This precluded it as a method to provide ready access to a number of different derivates. Attempts to use the Heck reaction also proved problematic. The Heck reaction between cyclohexenone and vinyl or arylbromides often provided mixtures of saturated and unsaturated products. These materials proved to be difficult to separate and consequently this approach was not considered appropriate for a system where ready access to a variety of compounds was desired.

A number of select compounds were synthesized and assayed. It was observed that the unsaturated versions of these molecules had inhibitory activities comparable to the saturated adducts. Consequently it was decided to synthesize unsaturated versions of the primary target. This allowed the use of the Suzuki reaction for their synthesis (FIG. 68). For ensembles of the desired molecules, the Suzuki reaction appeared to be a good choice. There are over 500 commercially available boronic acids and esters and the necessary vinyl bromo enones are available from 1,3-diones in a single step (FIG. 71) (Piers and NAgakura, 1975). The ready availability of the two principal starting materials allowed for a variety of different structural types to be synthesized and tested (Table 7).

TABLE 7

YIELD AND SELECT ACTIVITY DATA FOR ENONE ADDUCTS

| Cpd # | Structure | Yield[a] | IC-50 |
|---|---|---|---|
| FI-4 | 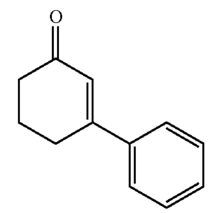  | 75% | >100 μm |
| FI-5 | 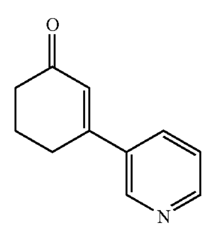  | 54% | >100 μm |
| FI-6 | 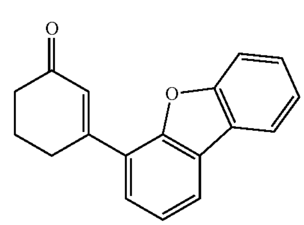  | 83% | >100 μm |

TABLE 7-continued

YIELD AND SELECT ACTIVITY DATA FOR ENONE ADDUCTS

| Cpd # | Structure | Yield[a] | IC-50 |
|---|---|---|---|
| FI-7 | (benzothiophene enone) | 89% | * |
| FI-8 | (1-methylpyrazole enone) | 29% | >100 μm |
| FI-9 | (6-methoxypyridin-2-yl enone) | 89% | >100 μm |
| FI-10 | (thiazol-2-yl enone) | 28% | >100 μm |
| FI-11 | (thiophen-3-yl enone) | 72% | >100 μm |
| FI-12 | (thiophen-2-yl enone) | 83% | >100 μm |
| FI-13 | (furan-3-yl enone) | 16% | >100 μm |
| FI-14 | (2-methyl-3-(6-methoxypyridin-3-yl)cyclopentenone) | 92% | 24 μm |
| FI-15 | (3-methoxyphenyl enone) | 88% | 30 μm |
| FI-16 | (quinolin-6-yl enone) | 88% | >100 μm |
| FI-17 | (indol-5-yl enone) | 83% | 56 μm |
| FI-18 | (benzo[d][1,3]dioxol-5-yl enone) | 85% | 53 μm |
| FI-19 | (3-hydroxyphenyl enone) | 64% | >100 μm |

TABLE 7-continued

YIELD AND SELECT ACTIVITY DATA FOR ENONE ADDUCTS

| Cpd # | Structure | Yield[a] | IC-50 |
|---|---|---|---|
| FI-20 | 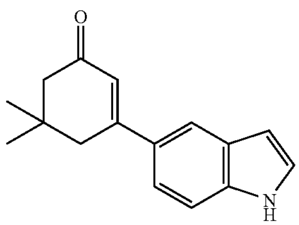 | 95% | >100 μm |
| FI-21 | 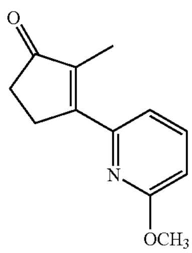 | 69% | 30 μm |
| FI-22 | 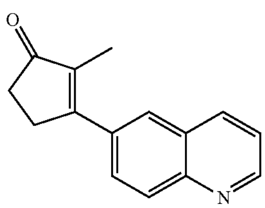 | 78% | * |
| FI-23 | 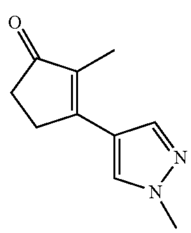 | 16% | * |
| FI-24 | 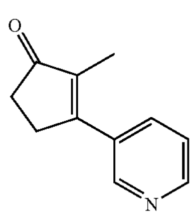 | 31% | * |
| FI-25 | 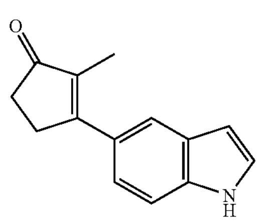 | 92% | * |
| FI-26 | | 96% | >100 μm |
| FI-27 | | 98% | 35 μm |

*IC-50 was not determined a.) spectral data for compounds the purification information is available in the previous example.

In previous work twenty four enones were synthesized. The Suzuki reaction was catalyzed by a variety of different palladium catalysts with FC1007 providing the most consistent results (Wang and Sauer, 2004; Sauer et al., 2003). The reactions where conducted under microwave conditions (250 Watts at 110° C. for 10 minutes). The yields ranged from low to quite good with no attempt to optimize the reaction conditions. In all cases the samples were purified by column chromatography to remove any metal-based contaminates and other impurities.

The molecules were tested in whole cells to determine their ability to inhibit the production of cAMP by anthrax edema factor. As can be seen methoxypyridine adducts of 2-methyl-cyclopentenone (FI-14 and FI-21) had good activity, while the analogous adduct of cyclohexenone (FI-9) was not active. The indole adduct of cyclohexenone (FI-17) also exhibited comparable activity to the best compounds.

This example establishes structure activity relationships. It was determined that only cyclic ketone and enone adducts are active. Acyclic versions of active structures are not. The ketone functionality appears to be necessary in that molecules where the ketone has been reduced to an alcohol are inactive. Additionally, only aromatic heterocyclic adducts are active. The addition of simple amines did not provide inhibitors.

The Suzuki reaction of β-bromoenones with boronic acids provided the desired compounds for screening. Additional versions of these molecules can be synthesized using the same methods.

Another example of a method of synthesis is found in FIG. 72.

REFERENCES

All patents and publications cited herein are hereby incorporated by reference in their entirety herein. Full citations for the references cited herein are provided in the following list.

U.S. Pat. No. 5,466,468
U.S. Pat. No. 5,629,001
U.S. Pat. No. 6,613,308
U.S. Pat. No. 5,466,468
U.S. Pat. No. 5,543,158
U.S. Pat. No. 5,641,515
U.S. Pat. No. 5,399,363

U.S. Pat. No. 5,466,468
U.S. Pat. No. 5,756,353
U.S. Pat. No. 5,804,212
U.S. Pat. No. 5,725,871
U.S. Pat. No. 5,780,045
U.S. Pat. No. 5,641,515
U.S. Pat. No. 5,580,579
U.S. Pat. No. 5,792,451
Abrami L, Reig N, van der Goot F G. Anthrax toxin: the long and winding road that leads to the kill. Trends Microbiol 2005; 13(2):72-78.
Abramova, F A, L M Grinberg, O V Yampolskaya, and D H Walker. 1993 Pathology of inhalational anthrax in 42 cases from the Sverdlovsk outbreak of 1979. Proc. Natl. Acad. Sci. 90:2291-94.
Ahuja, N.; Kumar, P.; Bhatnagar, R., The adenylate cyclase toxins. Crit. Rev. Microbiol. 2004, 30, (3), 187-196.
Ascenzi, P.; Visca, P.; Ippolito, G.; Spallarossa, A.; Bolognesi, M.; Montecucco, C., Anthrax toxin: a tripartite lethal combination. FEBS Lett. 2002, 531, (3), 384-388.
Bissantz, C.; Folkers, G.; Rognan, D., Protein-based virtual screening of chemical databases. 1. Evaluation of different docking/scoring combinations. J. Med. Chem. 2000, 43, (25), 4759-4767.
Bohm, H. J., Prediction of binding constants of protein ligands: a fast method for the prioritization of hits obtained from de novo design or 3D database search programs. J. Comput. Aided Mol. Des. 1998, 12, (4), 309-323.
Bohm, H. J., LUDI: rule-based automatic design of new substituents for enzyme inhibitor leads. Comput. Aided Mol. Des. 1992, 6, (6), 593-606.
Bohm, H. J., Computational tools for structure-based ligand design. Prog. Biophys. Mol. Biol. 1996, 66, (3), 197-210.
Bohm, H. J., The development of a simple empirical scoring function to estimate the binding constant for a protein-ligand complex of known three-dimensional structure. J. Comput. Aided Mol. Des. 1994, 8, (3), 243-256.
Bohm, H. J., Prediction of binding constants of protein ligands: a fast method for the prioritization of hits obtained from de novo design or 3D database search programs. J. Comput. Aided Mol. Des. 1998, 12, (4), 309-323.
Brachman, P. S. 1972. Anthrax. In: Infectious Diseases, chapter 80, pp 757-762, ed. P. D. Hoeprich. Harper & Rowe, New York.
Brisson, M.; Nguyen, T.; Vogt, A.; Yalowich, J.; Giorgianni, A.; Tobi, D.; Bahar, I.; Stephenson, C. R. J.; Wipf, P.; Lazo, J. S., Discovery and characterization of novel small molecule inhibitors of human Cdc25B dual specificity phosphatase. Molecular Pharmacology 2004, 66, (4), 824-833.
Brooijmans, N.; Kuntz, I. D., Molecular recognition and docking algorithms. Annu. Rev. Biophys. Biomol. Struct. 2003, 32, 335-373.
Brossier, F, M Weber-Levy, M Mock, and J Sirard. 2000. Role of toxin functional domains in anthrax pathogenesis. Infect. Immun. 68:1781-86.
Chen, D. L.; Menche, G.; Power, T. D.; Sower, L.; Peterson, J. W.; Schein, C. H., Accounting for ligand-bound metal ions in docking small molecules on adenylyl cyclase toxins. Proteins-Structure Function and Bioinformatics 2007, 67, (3), 593-605.
Chopra, A. K.; Gorenstein, D. Biochimica et Biophys Acta 2001, 1537, 27-41.
Cozzini, P.; Fomabaio, M.; Marabotti, A.; Abraham, D. J.; Kellogg, G. E.; Mozzarelli, A., Simple, intuitive calculations of free energy of binding for protein-ligand complexes. 1. Models without explicit constrained water. J. Med. Chem. 2002, 45, (12), 2469-2483.
Cummings R T, S P Salowe, B R Cunningham, J Wiltsie, Y W Park, L M Sonatore, D Wisniewski, C M Douglas, J D Hermes, and E M Scolnick. 2002. A peptide-based fluorescence resonance energy transfer assay for Bacillus anthracis lethal factor protease. PNAS. 99:10: 6603-6606.
Dessauer, C. W.; Gilman, A. G., The catalytic mechanism of mammalian adenylyl cyclase. Equilibrium binding and kinetic analysis of P-site inhibition. J. Biol. Chem. 1997, 272, (44), 27787-27795.
Drum, C. L.; Yan, S. Z.; Bard, J.; Shen, Y. Q.; Lu, D.; Soelaiman, S.; Grabarek, Z.; Bohm, A.; Tang, W. J., Structural basis for the activation of anthrax adenylyl cyclase exotoxin by calmodulin. Nature 2002, 415, (6870), 396-402.
Drysdale M, Heninger S, Hutt J, Chen Y H, Lyons C R, Koehler T M. Capsule synthesis by Bacillus anthracis is required for dissemination in murine inhalation anthrax. Embo Journal 2005; 24(1):221-227.
Erwin, J. L., L. M. DaSilva, S. Bavari, S. F. Little, A. M. Friedlander, and T. C. Chanh. 2001. Macrophagederived cell lines do not express proinflammatory cytokines after exposure to Bacillus anthracis lethal toxin. Infect. Immun. 69:1175-1177.
Firoved, A M, G F Miller, M Moayeri, R Kakkar, Y Shen, J F Wiggins, E M McNally, W-J Tang, and S H Leppla. 2005. Bacillus anthracis edema toxin causes extensive tissue lesions and rapid lethality in mice. Amer. J. Path. 167:5: 1309-1320.
Fornabaio, M.; Cozzini, P.; Mozzarelli, A.; Abraham, D. J.; Kellogg, G. E., Simple, intuitive calculations of free energy of binding for protein-ligand complexes. 2. Computational titration and pH effects in molecular models of neuraminidase-inhibitor complexes. J. Med. Chem. 2003, 46, (21), 4487-4500.
Fornabaio, M.; Spyrakis, F.; Mozzarelli, A.; Cozzini, P.; Abraham, D. J.; Kellogg, G. E., Simple, intuitive calculations of free energy of binding for protein-ligand complexes. 3. The free energy contribution of structural water molecules in HIV-1 protease complexes. J. Med. Chem. 2004, 47, (18), 4507-4516.
Friedlander, A. M, S. L. Welkos, M. L. Pitt, J. W. Ezzell, P. L. Worsham, K. J. Rose, B. E. Ivins, J. R. Lowe, G. B. Howe, P. Mikesell, et al. 1993. Postexposure prophylaxis against experimental inhalation anthrax. J. Infect. Dis. 167:1239-1243.
Friesner, R. A.; Banks, J. L.; Murphy, R. B.; Halgren, T. A.; Klicic, J. J.; Mainz, D. T.; Repasky, M. P.; Knoll, E. H.; Shelley, M.; Perry, J. K.; Shaw, D. E.; Francis, P.; Shenkin, P. S., Glide: a new approach for rapid, accurate docking and scoring. 1. Method and assessment of docking accuracy. J. Med. Chem. 2004, 47, (7), 1739-1749.
T. W. Greene, P. G. M. Wuts: Protective Groups in Organic Synthesis, $2^{nd}$ Edition, John Wiley & Sons, NY, 1991
Gehlhaar, D. K.; Verkhivker, G. M.; Rejto, P. A.; Sherman, C. J.; Fogel, D. B.; Fogel, L. J.; Freer, S. T., Molecular recognition of the inhibitor AG-1343 by HIV-1 protease: conformationally flexible docking by evolutionary programming. Chem. Biol. 1995, 2, (5), 317-324.
Gille, A.; Lushington, G. H.; Mou, T. C.; Doughty, M. B.; Johnson, R. A.; Seifert, R., Differential inhibition of adenylyl cyclase isoforms and soluble guanylyl cyclase by purine and pyrimidine nucleotides. J. Biol. Chem. 2004, 279, (19), 19955-19969.
Gottle, M.; Dove, S.; Steindel, P.; Shen, Y.; Tang, W.-J.; Geduhn, J.; Konig, B.; Seifert, R., Molecular Analysis of the Interaction of Bordetella pertussis Adenylyl Cyclase with Fluorescent Nucleotides. Mol Pharmacol 2007, 72, (3), 526-535.

Grinberg, L M, F A Abramova, O V Yampolskaya, D H Walker, and J H Smith. 2001. Quantitative pathology of inhalational anthrax 1: quantitative microscopic findings. *Mod. Pathol.* 14:482-95.

Guidi-Rontani, C.; Weber-Levy, M.; Mock, M.; Cabiaux, V., Translocation of *Bacillus anthracis* lethal and oedema factors across endosome membranes. *Cell Microbiol.* 2000, 2, (3), 259-264.

Guo, Q.; Shen, Y.; Zhukovskaya, N. L.; Florian, J.; Tang, W. J., Structural and kinetic analyses of the interaction of anthrax adenylyl cyclase toxin with reaction products cAMP and pyrophosphate. *J. Biol. Chem.* 2004, 279, (28), 29427-29435.

Halgren, T. A.; Murphy, R. B.; Friesner, R. A.; Beard, H. S.; Frye, L. L.; Pollard, W. T.; Banks, J. L., Glide: a new approach for rapid, accurate docking and scoring. 2. Enrichment factors in database screening. *J. Med. Chem.* 2004, 47, (7), 1750-1759.

Hanoune, J. and N. Defer. 2001. Regulation and role of adenylyl cyclase isoforms. *Annu. Rev. Pharmacol. Toxicol.* 41:145-174.

Hewlett E L, Underhill L H, Cook G H, Manclark C R, Wolff J. A protein activator for the adenylate cyclase of *Bordetella pertussis*. J Biol Chem 1979; 254(13):5602-5605.

Hewlett E L, Urban M A, Manclark C R, Wolff J. Extracytoplasmic adenylate cyclase of *Bordetella pertussis*. Proc Natl Acad Sci USA 1976; 73(6):1926-1930.

Hu, X.; Shelver, W. H., Docking studies of matrix metalloproteinase inhibitors: zinc parameter optimization to improve the binding free energy prediction. *J. Mol. Graph. Model.* 2003, 22, (2), 115-126.

Hu, X.; Balaz, S.; Shelver, W. H., A practical approach to docking of zinc metalloproteinase inhibitors. *J. Mol. Graph. Model.* 2004, 22, (4), 293-307.

Inglesby, T V, et al. 1999. Anthrax as a biological weapon: medical and public health management. Working Group on Civilian Biodefense. *JAMA*, 281:1735-1745.

Irwin, J. J.; Shoichet, B. K., ZINC—A Free Database of Commercially Available Compounds for Virtual Screening. *J. Chem. Inf Model.* 2005, 45, 177-182.

Irwin, J. J.; Raushel, F. M.; Shoichet, B. K., Virtual screening against metalloenzymes for inhibitors and substrates. *Biochemistry* 2005, 44, (37), 12316-12328.

Kellogg, G. E.; Chen, D. L., The Importance of Being Exhaustive. Optimization of Bridging Structural Water Molecules and Water Networks in Models of Biological Systems. *Chem. & Biodivers.* 2004, 1, (1), 98-105.

Kirk, K. L. *J. Org. Chem.* 1978, 43, 4381-3.

Johnson, R. A.; Shoshani, I., Inhibition of *Bordetella pertussis* and *Bacillus anthracis* adenylyl cyclases by polyadenylate and "P"-site agonists. *J. Biol. Chem.* 1990, 265, (31), 19035-19039.

Johnson, R. A.; Desaubry, L.; Bianchi, G.; Shoshani, I.; Lyons, E., Jr.; Taussig, R.; Watson, P. A.; Cali, J. J.; Krupinski, J.; Pieroni, J. P.; Iyengar, R., Isozyme-dependent sensitivity of adenylyl cyclases to P-site-mediated inhibition by adenine nucleosides and nucleoside 3'-polyphosphates. *J. Biol. Chem.* 1997, 272, (14), 8962-8966.

Jones, G.; Willett, P.; Glen, R. C.; Leach, A. R.; Taylor, R., Development and validation of a genetic algorithm for flexible docking. *J. Mol. Biol.* 1997, 267, (3), 727-748.

Lacy D B, Collier R J. Structure and function of anthrax toxin. Curr Top Microbiol Immunol 2002; 271:61-85.

Lacy, D. B.; Mourez, M.; Fouassier, A.; Collier, R. J., Mapping the anthrax protective antigen binding site on the lethal and edema factors. *J. Biol. Chem.* 2002, 277, (4), 3006-3010.

Leppla, S. H., Anthrax toxin edema factor: a bacterial adenylate cyclase that increases cyclic AMP concentrations of eukaryotic cells. *Proc. Natl. Acad. Sci. USA* 1982, 79, (10), 3162-3166.

Leppla, S H. 2000. Anthrax toxin, vol 145, pp 445-472 In *Handbook of Experimental Pathology*, Springer, NY Lin, Z. P.; Zhu, Y.-L.; Johnson, D. R.; Rice, K. P.; Nottoli, T.; Hains, B. C.; McGrath, J.; Waxman, S. G.; Sartorelli, A. C., Disruption of cAMP and Prostaglandin E2 Transport by Multidrug Resistance Protein 4 Deficiency Alters cAMP-Mediated Signaling and Nociceptive Response. *Mol Pharmacol* 2008, 73, (1), 243-251.

March's Advanced Organic Chemistry: Reactions, Mechanisms, and Structures, 5$^{th}$ Edition John Wiley and Sons by Michael B. Smith and Jerry March Morris, G. M.; Goodsell, D. S.; Halliday, R. S.; Huey, R.; Hart, W. E.; Belew, R. K.; Olson, A. J., Automated docking using a Lamarckian genetic algorithm and an empirical binding free energy function. *J. Comput. Chem.* 1998, 19, (14), 1639-1662.

Morris, G. M.; Goodsell, D. S.; Huey, R.; Olson, A. J., Distributed automated docking of flexible ligands to proteins: parallel applications of AutoDock 2.4. *J. Comput. Aided Mol. Des.* 1996, 10, (4), 293-304.

Milne J C, S R Blanke, P C Hanna, R J Collier. 1995. Protective antigen-binding domain of anthrax lethal factor mediates translocation of a heterologous protein fused to its amino- or carboxy-terminus. Mol. Microbiol. 15: 4: 661-6.

Muegge, I.; Martin, Y. C., A general and fast scoring function for protein-ligand interactions: a simplified potential approach. *J. Med. Chem.* 1999, 42, (5), 791-804.

Munier H, Bouhss A, Krin E, Danchin A, Gilles A M, Glaser P, Barzu O. The role of histidine 63 in the catalytic mechanism of *Bordetella pertussis* adenylate cyclase. J Biol Chem 1992; 267(14):9816-9820.

Onda, T.; Hashimoto, Y.; Nagai, M.; Kuramochi, H.; Saito, S.; Yamazaki, H.; Toya, Y.; Sakai, I.; Homcy, C. J.; Nishikawa, K.; Ishikawa, Y., Type-specific regulation of adenylyl cyclase. Selective pharmacological stimulation and inhibition of adenylyl cyclase isoforms. *J. Biol. Chem.* 2001, 276, (51), 47785-47793.

Patel T. B., Z. Du, S. Pierre, L. Cartin, and K. Scholich. 2001. Molecular biological approaches to unravel adenylyl cyclase signaling and function. *Gene* 269:13-25.

Pellizzari, R., C. Guidi-Rontani, G. Vitale, M. Mock, and C. Montecucco. 1999. Anthrax lethal factor cleaves MKK3 in macrophages and inhibits the LPS/IFNg-induced release of NO and TNF☐. *FEBS Letters* 462:199-204.

Pellizzari, R., C. Guidi-Rontani, G. Vitale, M. Mock, and C. Montecucco. 2000. Lethal factor of *Bacillus anthracis* cleaves the N-terminus of MAPKKs: Analysis of the intracellular consequences in macrophages. *Int. J. Med. Microbiol.* 290:421-427.

Peterson, J. W.; King, D.; Ezell, E. L.; Rogers, M.; Gessell, D.; Hoffpauer, J.; Reuss, L.; Chopra, A. K.; Gorenstein, D., Cholera toxin-induced PGE(2) activity is reduced by chemical reaction with L-histidine. *Biochim. Biophys. Acta.* 2001, 1537, (1), 27-41.

Peterson J W, N C Molina, C W Houston and R C Fader. 1983. Elevated cAMP in intestinal epithelial cells during experimental cholera and salmonellosis. *Toxicon.* 21: 761-775.

Peterson J W, W D Berg, and L G Ochoa 1988. Indomethacin inhibits cholera toxin-induced cyclic AMP accumulation in Chinese hamster ovary cells. *FEMS Microbiol. Letts.* 49: 187-192.

Peterson J W, L G Ochoa, and W D Berg 1988. Inhibitory effect of ibuprofen on cholera toxins induced cyclic AMP formation in Chinese hamster ovary cells. FEMS Microbiol. Letts. 56: 139-144.

Peterson J W, and L G Ochoa. 1989. Role of prostaglandins and cAMP in the secretory effects of cholera toxin, *Science.* 245: 857-859.

Peterson, J. W.; King, D.; Ezell, E. L.; Rogers, M.; Gessell, D.; Hoffpauer, J.; Reuss, L.; Piers, E.; Nagakura, I. *Sny. Commun.* 1975, 5, 193-199.

Peterson, J. W.; J. E. Comer; D. M. Noffsinger; A. Wenglikowski; K. G. Walberg; B. M. Chatuev; A. K. Chopra; L. R. Stanberry; A. S. Kang; W. W. Scholz; Sircar., J., Human monoclonal anti-protective antigen antibody completely protects rabbits and is synergistic with ciprofloxacin in protecting mice and guinea pigs against inhalation anthrax. *Infect. Immun.* 2006, 74, 1016-24.

Peterson, J. W., J. E. Comer, W. B. Baze, D. M. Noffsinger, A. Wenglikowski, K. G. Walberg, J. Hardcastle, J. Pawlik, K. Bush, S. Moen, J. Thomas, B. M. Chatuev, L. Sower, A. K. Chopra, L. R. Stanberry, R. Sawada, W. W. Scholz, and J. Sircar., Human monoclonal antibody (AVP-21D9) to protective antigen reduces the dissemination of *Bacillus anthracis* Ames strain from the lungs in a rabbit model. *Infect. Immun.* 2007, 75, 3414-3424.

Peterson, J. W.; King, D.; Ezell, E. L.; Rogers, M.; Gessell, D.; Hoffpauer, J.; Reuss, L.; Chopra, A. K.; Gorenstein, D., Cholera toxin-induced PGE(2) activity is reduced by chemical reaction with L-histidine. *Biochim. Biophys. Acta.* 2001, 1537, (1), 27-41.

Rarey, M.; Wefing, S.; Lengauer, T., Placement of medium-sized molecular fragments into active sites of proteins. *J. Comput. Aided Mol. Des.* 1996, 10, (1), 41-54.

Recommendations on the use of anthrax vaccine in the US, 2000. MMWR Weekly Reports, vol 49, CDC, Atlanta Remington's Pharmaceutical Sciences, 18th Ed. Mack Printing Company, 1990.

de Rooij, J.; Zwartkruis, F. J.; Verheijen, M. H.; Cool, R. H.; Nijman, S. M.; Wittinghofer, A.; Bos, J. L., Epac is a Rap1 guanine-nucleotide-exchange factor directly activated by cyclic AMP. *Nature* 1998, 396, (6710), 474-477.

Sauer, D. R.; Kalvin, D.; Phelan, K. M. *Org. Lett.* 2003, 5, 4721-4724.

Shen, Y.; Guo, Q.; Zhukovskaya, N. L.; Drum, C. L.; Bohm, A.; Tang, W. J., Structure of anthrax edema factor-calmodulin-adenosine 5'-(alpha,beta-methylene)-triphosphate complex reveals an alternative mode of ATP binding to the catalytic site. *Biochem. Biophys. Res. Commun.* 2004, 317, (2), 309-314.

Shen, Y.; Lee, Y. S.; Soelaiman, S.; Bergson, P.; Lu, D.; Chen, A.; Beckingham, K.; Grabarek, Z.; Mrksich, M.; Tang, W. J., Physiological calcium concentrations regulate calmodulin binding and catalysis of adenylyl cyclase exotoxins. *EMBO J.* 2002, 21, (24), 6721-6732.

Shen, Y.; Zhukovskaya, N. L.; Zimmer, M. I.; Soelaiman, S.; Bergson, P.; Wang, C. R.; Gibbs, C. S.; Tang, W. J., Selective inhibition of anthrax edema factor by adefovir, a drug for chronic hepatitis B virus infection. *Proc. Natl. Acad. Sci. USA* 2004, 101, (9), 3242-3247.

Shen, Y.; Zhukovskaya, N. L.; Guo, Q.; Florian, J.; Tang, W. J., Calcium-independent calmodulin binding and two-metal-ion catalytic mechanism of anthrax edema factor. *EMBO J.* 2005, 24, (5), 929-941.

W L Shoop, Y Xiong, J Wiltsie, A Woods, J Guo, J V Pivnichny, T Felcetto, B F Michael, A Bansal, R T Cummings, B R Cunningham, A M Friedlander, C M Douglas, S B Patel, D Wisniewski, G Scapin, S P Salowe, D M Zaller, K T Chapman, E M Scolnick, D M Schmatz, K Bartizal, M MacCoss, and JD Hermes. 2005. Anthrax lethal factor inhibition. *Proc. Natl. Acad. Sci. USA.* 102: 22: 7958-7963.

Simonds, W. F. 1999. G protein regulation of adenylyl cyclase. *TiPS* 20:66-73.

Soelaiman, S.; Wei, B. Q.; Bergson, P.; Lee, Y. S.; Shen, Y.; Mrksich, M.; Shoichet, B. K.; Tang, W. J., Structure-based inhibitor discovery against adenylyl cyclase toxins from pathogenic bacteria that cause anthrax and whooping cough. *J. Biol. Chem.* 2003, 278, (28), 25990-25997.

Sunahara, R. K., A. Beuve, J. J. G. Tesmer, S. R. Sprang. 1998. Exchange of substrate and inhibitor specificities between adenylyl and guanylyl cyclases. *J. Biol. Chem.* 273:16332-16338.

Tatsuta, K.; Miura, S.; Ohta, S.; Gunji, H. *J. Antibiotics* 1995, 48, 286-8.

Tesmer, J. J.; Sunahara, R. K.; Johnson, R. A.; Gosselin, G.; Gilman, A. G.; Sprang, S. R., Two-metal-Ion catalysis in adenylyl cyclase. *Science* 1999, 285, (5428), 756-760.

Vitale, G., R. Pellizzari, C. Recchi, G. Napolitani, M. Mock, and C. Montecucco. 1998. Anthrax lethal factor cleaves the N-terminus of MAPKKs and induces tyrosine/threonine phosphorylation of MAPKs in cultured macrophages. *Biochem. Biophys. Res. Commun.* 248:706-711.

Vitale, G., L. Bernardi, G. Napolitani, M. Mock, and C. Montecucco. 2000. Susceptibility of mitogen-activated protein kinase kinase family members to proteolysis by anthrax lethal factor. *Biochem. J.* 352:739-745.

Wang, R.; Lu, Y.; Fang, X.; Wang, S., An extensive test of 14 scoring functions using the PDBbind refined set of 800 protein-ligand complexes. *J. Chem. Inf. Comput. Sci.* 2004, 44, (6), 2114-2125.

Wang, R. X.; Lu, Y. P.; Wang, S. M., Comparative evaluation of 11 scoring functions for molecular docking. *J. Med. Chem.* 2003, 46, (12), 2287-2303.

Wang, Y.; Sauer, D. R. *Org. Lett.* 2004, 6, 2793-2796.

Wang, J. L.; Guo, J. X.; Zhang, Q. Y.; Wu, J. J. Q.; Seifert, R.; Lushington, G. H., A conformational transition in the adenylyl cyclase catalytic site yields different binding modes for ribosyl-modified and unmodified nucleotide inhibitors. *Bioorganic & Medicinal Chemistry* 2007, 15, (8), 2993-3002.

Welkos S L, T J Keener, and P H Gibbs. 1986. Differences in susceptibility of inbred mice to *Bacillus anthracis. Infect. Immunol* 51:795-800.

Wu, A. G.; Alibek, D.; Li, Y. L.; Bradburne, C.; Bailey, C. L.; Alibek, K., Anthrax toxin induces hemolysis: an indirect effect through polymorphonuclear cells. *J. Infect. Dis.* 2003, 188, (8), 1138-1141.

Venkatachalam, C. M.; Jiang, X.; Oldfield, T.; Waldman, M., LigandFit: a novel method for the shape-directed rapid docking of ligands to protein active sites. *J. Mol. Graph. Model.* 2003, 21, (4), 289-307.

de Vos, V. 1994. Anthrax, vol. 2, pp 1262-1289. In: *Infectious Disease of Livestock.* ed. Oxford Univ. Press. NY.

Xiong Y S, Wiltsie J, Woods A, Guo J, Pivnichny J V, Tang W, Bansal A, Cummings R T, Cunningham B R, Friedlander A M, Douglas C M, Salowe S P, Zaller D M, Scolnick E M, Schmatz D M, Bartizal K, Hermes J D, MacCoss M, Chapman K T. The discovery of a potent and selective lethal factor inhibitor for adjunct therapy of anthrax infection. Bioorganic & Medicinal Chemistry Letters 2006; 16(4): 964-968.

Young J A, and R J Collier. 2007. Anthrax Toxin: Receptor Binding, Internalization, Pore Formation and Translocation. Annu. Rev. Biochem. 17: 17.1-17.23

Zhang, C.; Liu, S.; Zhu, Q. Q.; Zhou, Y. Q., A knowledge-based energy function for protein-ligand, protein-protein, and protein-DNA complexes. *J. Med. Chem.* 2005, 48, (7), 2325-2335.

Zmuda, J. F.; Zhang, L.; Richards, T.; Pham, Q.; Zukauskas, D.; Pierre, J. L.; Laird, M. W.; Askins, J.; Choi, G. H., Development of an edema factor-mediated cAMP-induction bioassay for detecting antibody-mediated neutralization of anthrax protective antigen. *J. Immunol. Methods* 2005, 298, (1-2), 47-60.

What is claimed is:

1. A method of treating intestinal fluid loss in a subject, the method comprising administering to the subject a composition comprising a therapeutically effective amount of a compound or a pharmaceutically acceptable salt thereof wherein a therapeutically effective amount of a compound reduces cyclic adenosine monophosphate levels, and wherein the formula of the compound is selected from the group consisting of:

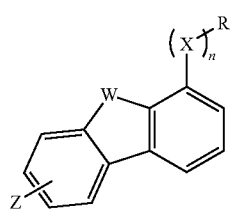

Formula IV and any combination thereof wherein,

R is an optionally substituted cyclic or bicyclic ring structure; wherein R is selected from the group consisting of phenyl, pyranyl, pyridyl, imidazolyl, 1,8-naphthridinyl and N-oxide pyridyl X is an alkyl, oxygen, an ester, an amine, or an amide Z is selected from the group consisting of hydrogen, alkenyl, alkynyl, phenyl, benzyl, halo, fluoro, chloro, bromo, iodo, hydroxy, keto, oxo, aldo, carbonate, carboxy, alkoxy, ester, carboxamido, amino, ammonio, imino, imido, azido, azo, cyanato, isocyano, isocyanato, isothiocyanato, nitroxy, cyano, nitrosooxy, nitro, nitroso, 4-pyridyl, 3-pyridyl, 2-pyridyl, thioether, sulfonyl, sulfo, sulfinyl, mercapto, sulfanyl, sulfhydryl, sulfonamino, thiocyanato, alkyl amino, hydroxyamic acid, methyl, ethyl, 1,3-dioxylanyl, propyl, iso-propyl, butyl, tert-butyl, alkyl, (C1-C3) alkenyl, aryl, alkylaryl;

W is selected from the group consisting of CO, NH, methylene, sulfur atom, oxygen atom and thionyl; and, n is 0 or 1 wherein the intestinal fluid loss is the result of a bacterial infection of a pathogen, wherein the pathogen is selected from a group consisting of *B. antracis, V. cholerae, E. coli, S. typhimurium, Y. pestis* and any combination thereof.

2. The method of claim 1, wherein R is mono, di, tri, tetra, or app

133
-continued
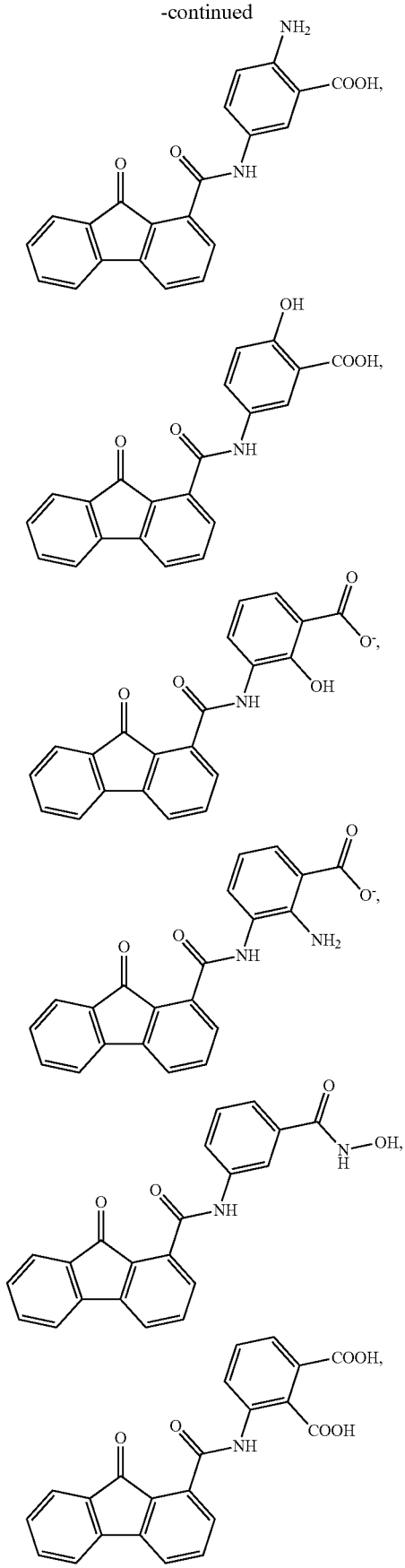
134
-continued
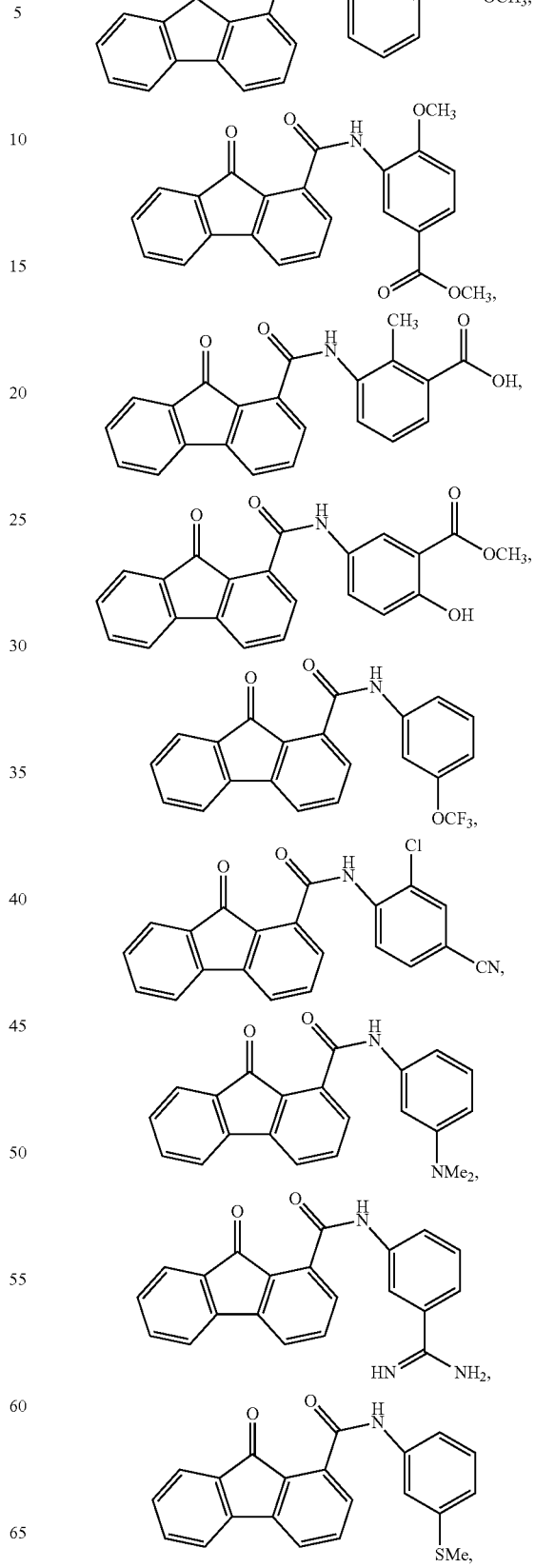

-continued

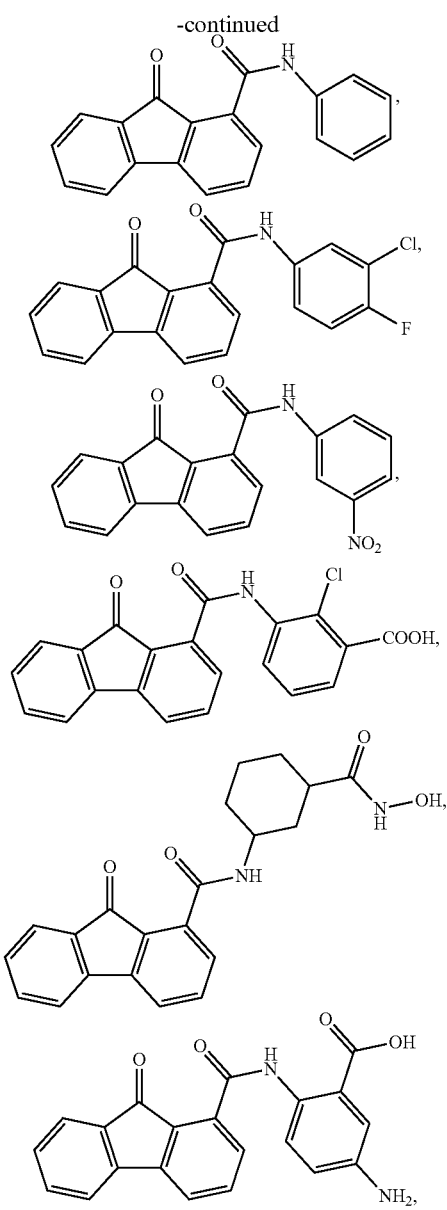

-continued

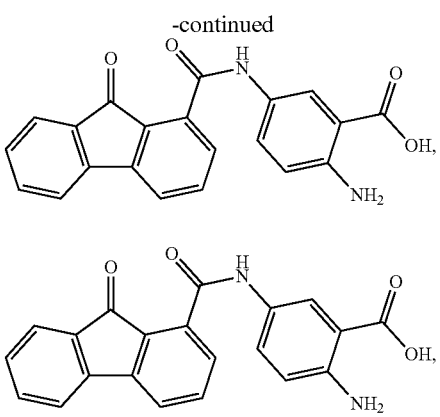

and any combination thereof.

4. The method of claim 1, wherein the method comprises inhibiting adenylyl cyclase, edema factor, CTA1, or any combination thereof.

5. The method of claim 1, wherein the intestinal fluid loss is caused by an increase in 3',5'-adenosine monophosphate levels in the subject's tissue.

6. The method of claim 1, wherein the composition is administered in combination with one or more other drugs.

7. The method of claim 1, wherein the composition further comprises an antibiotic or an anti-inflammatory.

8. The method of claim 1, wherein the composition comprises a pharmaceutically acceptable carrier.

9. The method of claim 1, wherein the compound is delivered at dosages between 0.001 mM and 10 mM.

10. The method of claim 9, wherein the compound is delivered at dosages between 0.1 mM and 1 mM.

11. The method of claim 1, wherein the subject is a human.

12. The method of claim 1, wherein the composition is administered through a route selected from the group consisting of alimentary, parenteral, topical, mucosal, inhalation and any combination thereof.

* * * * *